(12) United States Patent
Takamuro et al.

(10) Patent No.: US 7,384,952 B2
(45) Date of Patent: Jun. 10, 2008

(54) PYRAZOLOPYRIMIDINE COMPOUND AND A PROCESS FOR PREPARING THE SAME

(75) Inventors: Iwao Takamuro, Osaka (JP); Yasuo Sekine, Osaka (JP); Yasunori Tsuboi, Osaka (JP); Kouji Nogi, Osaka (JP); Hiroyuki Taniguchi, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 348 days.

(21) Appl. No.: 10/542,081

(22) PCT Filed: Jan. 23, 2004

(86) PCT No.: PCT/JP2004/000617

§ 371 (c)(1),
(2), (4) Date: Jul. 13, 2005

(87) PCT Pub. No.: WO2004/064721

PCT Pub. Date: Aug. 5, 2004

(65) Prior Publication Data

US 2006/0135525 A1 Jun. 22, 2006

(30) Foreign Application Priority Data

| Jan. 24, 2003 | (JP) | ............................. 2003-016770 |
| Aug. 1, 2003 | (JP) | ............................. 2003-205341 |
| Nov. 14, 2003 | (JP) | ............................. 2003-385399 |

(51) Int. Cl.
C07D 487/04 (2006.01)
C07D 519/00 (2006.01)
A61K 31/519 (2006.01)

(52) U.S. Cl. .................... 514/262.1; 544/262
(58) Field of Classification Search ................ 544/262; 514/262.1
See application file for complete search history.

(56) References Cited

U.S. PATENT DOCUMENTS 5,866,562 A 2/1999 Schohe-Loop et al.

FOREIGN PATENT DOCUMENTS

| WO | WO-97/48705 A1 | 12/1997 |
| WO | WO-00/01676 A1 | 1/2000 |
| WO | WO-02/079189 A2 | 10/2002 |

OTHER PUBLICATIONS

Waterman et al., Journal of Physiology, vol. 477.3, 1994, pp. 459-468.
Spencer et al., Journal of Physiology, vol. 517.3, 1999, pp. 889-898.
Ikonen et al., European Journal of Pharmacology, vol. 347, 1998, pp. 13-21.
Ghelardini et al., British Journal of Pharmacology, vol. 123, 1998, pp. 1079-1084.
Galeotti et al., British Journal of Pharmacology, vol. 126, 1999, pp. 1653-1659.
Nature, vol. 319, 1986, pp. 678-680.
Behrens et al., Muscle & Nerve, vol. 17, 1994, pp. 1264-1270.
Science, vol. 289, 2000, pp. 1942-1946.

*Primary Examiner*—Bruck Kifle
(74) *Attorney, Agent, or Firm*—Birch, Stewart, Kolasch & Birch, LLP

(57) ABSTRACT

The present invention provides a novel pyrazolopyrimidine compound of the formula [I]: wherein R' is (A) a substituted aryl group, (B) an optionally substituted nitrogen-containing aliphatic heteromonocyclic group, (C) a substituted cyclo-lower alkyl group, (D) an optionally substituted amino group, or (E) a substituted heteroaryl group, $R^2$ is (a) an optionally substituted heteroaryl group or (b) an optionally substituted aryl group, Y is a single bond, a lower alkylene group or a lower alkenylene group, Z is a group of the formula: —CO—, —CH2-, —SO2- or a group of the formula [II]: Q is a lower alkylene group, and q is an integer of 0 or 1 or a pharmaceutically acceptable salt thereof, which has a small conductance potassium channel (SK channel) blocking activity and is useful as a medicament and a process for preparing the same

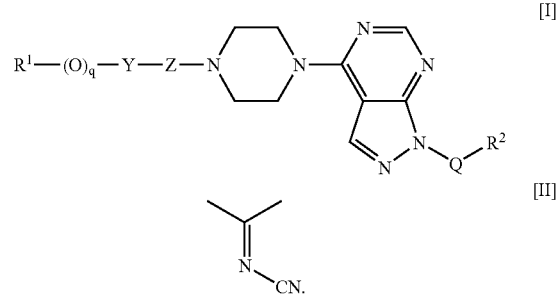

14 Claims, No Drawings

PYRAZOLOPYRIMIDINE COMPOUND AND A PROCESS FOR PREPARING THE SAME

TECHNICAL FIELD

This invention relates to a novel pyrazolopyrimidine compound, which has a small-conductance potassium channel (SK) blocking activity and is useful as a medicament and a method for preparing the same.

BACKGROUND ART $Ca^{2+}$-activated potassium (K) channels consist of at least three subtypes: Big- (BK), Intermediate- (IK) and Small-conductance K channel. These channels are activated by increase in intracellular $Ca^{2+}$ level. Although BK and IK channels are sensitive to changes in membrane voltage and increase in intracellular $Ca^{2+}$ level, SK channels are not significantly sensitive to the change in membrane voltage. Besides, SK channels are characterized in that the channels have a low conductance of 6 to 20 pS to single channel and a higher sensitivity to apamin. SK channels are present not only in excitable cells such as nerve cells and muscle cells but also in other kinds of cells such as liver cells or blood cells, and may be responsible for various cell functions including chemokine release, muscle contraction and secretion.

Apamin is a well-known selective SK channel blocker, and it has been reported that this agent activates gastrointestinal peristaltic function (S. A. Waterman and M. Costa, J. Physiology 477, 459-468, 1994; N. Spencer et al., J. Physiology 517, 889-898, 1999), improves cognitive/acquisition deficits (S. Ikonen et al., Eur. J. Pharmacol. 347, 13-21, 1998; C. Ghelardini et al., Br. J. Pharmacol. 123, 1079-1084, 1998) and decreases immobility time in mouse forced swimming test (N. Galeotti et al., Br. J. Pharmacol. 126, 1653-1659, 1999). Moreover, it is reported that a specific receptor for apamin exists in skeletal muscle cells and administration of this agent alleviates the symptoms in patients with myotonic muscle dystrophy (J. F. Renaud et al., Nature 319, 678-680, 1986; M. I Behrens et al., Muscle & Nerve 17, 1264-1270, 1994). Furthermore, it was reported that mice showed abnormal respiratory responses to hypoxia under conditional overexpression of SK subtype (SK3) (C. T. Bond et al., Science 289, 1942-1946, 2000).

As compounds having a SK channel-blocking activity, bis(benzimidazol) compounds such as 1,1'-(α,α'-p-xylene)-3,3'-(α,α'-m-xylene)-bis(benzimidazolium), cyclophan compounds such as 7,18-diaza-3,4(1,4)-dibenzena-1,6(1,4)-diquinolin-acyclooctadecaphan 3 trifluoroacetate hydrate, cross-linked bisquinoline compounds such as 1,4-bis-(2-methyl-quinolin-4-yl)-[1,4]-diazepane and compounds having a cyclohexane-1,1'(2'H)-spiroisoquinoline moiety are disclosed in International Patent Publication WO00/01676, WO97/48705, the U.S. Pat. No. 5,866,562 and WO02/79189, respectively.

SUMMARY OF THE INVENTION

The object of the present invention is to provide a novel pyrazolopyrimidine compound as a medicament having an excellent SK channel blocking activity and a method for preparing the same.

The present invention relates to a pyrazolopyrimidine compound of the formula [I]:

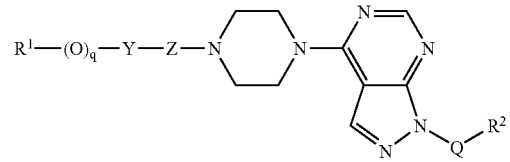

wherein $R^1$ is
(A) a substituted aryl group,
(B) an optionally substituted nitrogen-containing aliphatic heteromonocyclic group,
(C) a substituted cyclo-lower alkyl group,
(D) an optionally substituted amino group, or
(E) a substituted heteroaryl group,
$R^2$ is (a) an optionally substituted heteroaryl group or (b) an optionally substituted aryl group,
Y is a single bond, a lower alkylene group or a lower alkenylene group,
Z is a group of the formula: —CO—, —CH$_2$—, —SO$_2$— or

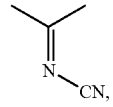

Q is a lower alkylene group, and q is an integer of 0 or 1 or a pharmaceutically acceptable salt thereof.

DETAILED DESCRIPTION OF THE PREFERRED EMBODIMENTS

In case that $R^1$ in the compound [I] is (A) a substituted aryl group, the substituent may be the same or different one to three groups selected from the group consisting of
(i) a hydroxyl group; (ii) a halogen atom; (iii) a lower alkyl group; (iv) an amino group optionally substituted by one or two groups selected from a lower alkyl group optionally substituted by a hydroxyl group, a lower alkoxy-lower alkyl group, an amino-lower alkanoyl group optionally substituted by a group selected from a lower alkyl group, a lower alkoxycarbonyl group and a group of the formula:

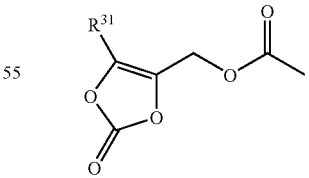

in which $R^{31}$ is a lower alkyl group at the amino moiety, a (mono- or di-lower alkyl)amino-lower alkyl group, a (mono- or di-lower alkyl)carbamoyl group, a lower alkanoyl group optionally substituted by a hydroxyl group, a cyclo-lower alkylcarbonyl group, a lower alkoxy-lower alkanoyl group, a lower alkoxy-lower alkoxycarbonyl group, a cyclo-lower alkyl-lower alkyl group, a lower alkylsulfonyl group, an aryl-lower alkyl group optionally substituted by a (mono- or di-lower alkyl)amino group, a lower alkenoyl group, a thiocarbamoyl group optionally substituted by a lower alkyl group, a heteroarylcarbonyl group, a nitrogen-containing aliphatic heteromonocyclic group-substituted lower alkyl group, a nitrogen-containing aliphatic heteromonocyclic group-substituted lower alkanoyl group, an arylsulfonyl group optionally substituted by a (mono- or di-lower alkyl) amino group at the aryl moiety; a group of the formula:

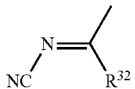

in which $R^{32}$ is a lower alkoxy group and a nitrogen-containing aliphatic heteromonocyclic group optionally substituted by a lower alkyl group, (v) a lower alkoxy group optionally substituted by a group selected from an amino group optionally substituted by a group(s) selected from a lower alkyl group and an aryl-lower alkyl group, a heteroaryl group optionally substituted by a lower alkyl group and a nitrogen-containing aliphatic heteromonocyclic group optionally substituted by a lower alkyl group; (vi) an amino-lower alkyl group optionally substituted by a group selected from a lower alkyl group optionally substituted by a hydroxyl group, a lower alkanoyl group, a (mono- or di-lower alkyl)amino-lower alkyl group, a (mono- or di-lower alkyl)amino-lower alkoxycarbonyl group, a lower alkoxy-lower alkanoyl group, a (mono- or di-lower alkyl)carbamoyl group, a lower alkoxy-lower alkoxycarbonyl group, a lower alkoxy-lower alkyl group, a cyclo-lower alkylcarbonyl group, an aryl-lower alkyl group, a cyclo-lower alkyl group, a cyclo-lower alkyl-lower alkyl group, a nitrogen-containing aliphatic heteromonocyclic group-substituted lower alkoxycarbonyl group and a group of the formula:

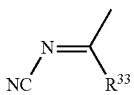

in which $R^{33}$ is an amino group, a (mono- or di-lower alkyl)amino group or a (mono- or di-lower alkyl)amino-lower alkylamino group; (vii) a nitrogen-containing aliphatic heteromonocyclic group-substituted lower alkyl group optionally substituted by a group selected from a hydroxyl group, a lower alkyl group optionally substituted by a hydroxyl group, a lower alkoxy-lower alkyl group and a carbamoyl group; (viii) a carbamoyl group optionally substituted by a group selected from a lower alkyl group, a (mono- or di-lower alkyl)amino-lower alkyl group, a heteroaryl group-substituted lower alkyl group and a nitrogen-containing aliphatic heteromonocyclic group-substituted lower alkyl group; (ix) a nitrogen-containing aliphatic heteromonocyclic group optionally substituted by a lower alkyl group (said nitrogen-containing aliphatic heteromonocyclic group may bond to the aryl moiety via an oxygen atom); (x) a nitro group; (xi) a cyclo-lower alkyloxy group optionally substituted by a (mono- or di-lower alkyl)amino group; (xii) a lower alkenyl group optionally substituted by a group selected from a (mono- or di-lower alkyl)amino group and a nitrogen-containing aliphatic heteromonocyclic group; (xiii) a lower alkynyl group optionally substituted by a group(s) selected from a (mono- or di-lower alkyl)amino group and a nitrogen-containing aliphatic heteromonocyclic group; (xiv) a lower alkylthio group optionally substituted by a (mono- or di-lower alkyl)amino group; and (xv) a cyclo-lower alkyl-lower alkoxy group optionally substituted by a (mono- or di-lower alkyl)amino group at the cyclo-lower alkyl moiety.

In case that $R^1$ in the compound [I] is (B) an optionally substituted nitrogen-containing aliphatic heteromonocyclic group, the substituent may be the group(s) selected from a lower alkyl group, a nitrogen-containing aliphatic heteromonocyclic group-substituted lower alkanoyl group, a (mono- or di-lower alkyl)amino-lower alkanoyl group, a lower alkoxy-lower alkyl group, a (mono- or di-lower alkyl) amino-lower alkyl group, a cyclo-lower alkyl group, a heteroaryl group, a nitrogen-containing aliphatic heteromonocyclic group optionally containing one or more double bond in the ring and optionally substituted by a group(s) selected from a lower alkyl group, a lower alkoxy-lower alkyl group, a carbamoyl group and a lower alkanoyl-amino group and an amino group optionally substituted by a group(s) selected from a lower alkyl group, a (mono- or di-lower alkyl)amino group, a cyclo-lower alkyl-carbonyl group, a lower alkenoyl group, a heteroarylcarbonyl group, a lower alkoxy-lower alkyl group, a lower alkanoyl group and a nitrogen-containing aliphatic heteromonocyclic group.

In case that $R^1$ in the compound [I] is (C) a substituted cyclo-lower alkyl group, the substituent may be a group(s) selected from a group consisting of (i) an amino group optionally substituted by a group selected from a lower alkyl group, a (mono- or di-lower alkyl)amino-lower alkanoyl group, a nitrogen-containing aliphatic heteromonocyclic group-substituted lower alkanoyl group, a (mono- or di-lower alkyl)amino-lower alkyl group, a lower alkanoyl group, a cyclo-lower alkylcarbonyl group, a lower alkenoyl group, a heteroarylcarbonyl group, an arylcarbonyl group optionally substituted by a halogen atom(s), a lower alkyl-thiocarbamoyl group, a lower alkoxycarbonyl group, a cyclo-lower alkyl group, a group of the formula:

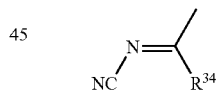

in which $R^{34}$ is a (mono- or di-lower alkyl)amino group, a cyclo-lower alkyl-lower alkyl group and a lower alkylsulfonyl group; (ii) an amino-lower alkyl group optionally substituted by a group selected from a lower alkyl group optionally substituted by a hydroxyl group, a (mono- or di-lower alkyl)amino-lower alkanoyl group, a nitrogen-containing aliphatic heteromonocyclic group-substituted lower alkanoyl group, a nitrogen-containing aliphatic heteromonocyclic group-substituted lower alkyl group, a (mono- or di-lower alkyl)amino-lower alkyl group, a heteroaryl group-substituted lower alkyl group, a lower alkoxy-lower alkyl group, a lower alkanoyl group, a heteroarylcarbonyl group (the heteroaryl moiety of said group is optionally substituted by a lower alkyl group), a cyclo-lower alkylcarbonyl group, an aryl-lower alkyl group, a cyclo-lower alkyl group, a cyclo-lower alkyl-lower alkyl group, a lower alkylsulfonyl group, a lower alkoxycarbonyl group, a mono- or di-lower alkylcarbamoyl group and an arylcarbonyl group optionally substituted by a group(s) selected from a halogen atom and a lower alkoxy group, a lower alkoxy-lower alkanoyl group and a lower alkanoyl group; (iii) a nitrogen-containing aliphatic heteromonocyclic group optionally substituted by a group(s) selected from a hydroxyl group, a lower alkyl group, a lower alkanoyl group and a lower alkoxy-lower alkyl group; (iv) a nitrogen-containing aliphatic heteromonocyclic group-substituted lower alkyl group (said nitrogen-containing aliphatic heteromonocyclic group is optionally fused to a benzene ring and optionally substituted by a group selected from a lower alkyl group, a carbamoyl (or thiocarbamoyl) group, a hydroxyl group, a lower alkoxy-lower alkyl group, a lower alkanoyl group and a (mono- or di-lower alkyl)amino group); (v) a mono- or di-lower alkylamino-lower alkoxy group; and (vi) a carbamoyl group optionally substituted by a group(s) selected from a nitrogen-containing aliphatic heteromonocyclic group-substituted lower alkyl group optionally substituted by a lower alkyl group, a (mono- or di-lower alkyl)amino group and a lower alkyl group.

In case that $R^1$ in the compound [I] is (D) an optionally substituted amino group, the substituent may be a lower alkyl group.

In case that $R^1$ in the compound [I] is (E) a substituted heteroaryl group, the substituent may be a group(s) selected from (i) an amino-lower alkyl group optionally substituted by a group(s) selected from a lower alkyl group and a lower alkoxy-lower alkyl group; (ii) an amino group optionally substituted by a group selected from a cyclo-lower alkyl-carbonyl group, a (mono- or di-lower alkyl)amino-lower alkyl group, a lower alkanoyl group, a lower alkenoyl group, a (mono- or di-lower alkyl)thiocarbamoyl group, a (mono- or di-lower alkyl)carbamoyl group and a lower alkyl group; (iii) a carbamoyl group optionally substituted by a group selected from a lower alkyl group, a nitrogen-containing aliphatic heteromonocyclic group-substituted lower alkyl group and a (mono- or di-lower alkyl)amino-lower alkyl group; (iv) a lower alkyl group optionally substituted by a halogen atom(s); (v) a (mono- or di-lower alkyl)amino-lower alkoxy group; (vi) an oxo group; and (vii) a group of the formula:

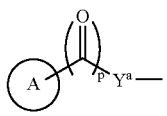

wherein ring A is a nitrogen-containing aliphatic heteromonocyclic group optionally substituted by a lower alkyl group and optionally fused to a benzene ring, $Y^a$ is a single bond, a lower alkylene group or a lower alkenylene group and p is an integer of 0 or 1.

In case that $R^2$ in the compound [I] is (a) an optionally substituted heteroaryl group, the substituent may be the same or different one to three groups selected from a lower alkyl group, a lower alkoxy group and a (mono- or di-lower alkyl)amino group. In case that $R^2$ in the compound [I] is (b) an optionally substituted aryl group, the substituent may be the same or different one to three groups selected from a lower alkyl group, a halogen atom, a halogeno-lower alkoxy group, a (mono- or di-lower alkyl)amino group, a lower alkoxy group, a nitro group, a lower alkoxy-lower alkyl group, a hydroxyl group, a lower alkanoyl group and a lower alkoxycarbonyl group.

Examples of the aryl group in $R^1$ and $R^2$ include a 6- to 10-membered, mono- or bi-cyclic aryl group such as a phenyl group and a naphthyl group.

Examples of the nitrogen-containing aliphatic heteromonocyclic group in $R^1$ and $R^2$ include a 4- to 8-membered (preferably 5- or 6-membered) nitrogen-containing aliphatic heteromonocyclic group (said cyclic group optionally contain one or more double bond in the ring) such as an azetidinyl group, a pyrrolidinyl group, an imidazolidinyl group, a pyrazolidinyl group, a piperidyl group, a piperazinyl group, an azepinyl group, a diazepinyl group, an azeocinyl group, a diazeocinyl group, a 3-pyrrolinyl group or a morpholinyl group.

Examples of the heteroaryl group in $R^1$ and $R^2$ include a 5- to 14-membered (preferably 5- to 10-membered) mono- or bi-cyclic heteroaryl group having at least one heteroatom selected from nitrogen atom, sulfur atom and oxygen atom. Such heteroaryl group may be a nitrogen-containing heteroaryl group selected from a pyrrolyl group, an imidazolyl group, a pyrazolyl group, an oxazolyl group, a thiazolyl group, an isothiazolyl group, an isoxazolyl group, a pyridyl group, a dihydropyridyl group, a pyrazinyl group, a pyrimidinyl group, a tetrahydropyrimidinyl group, a furopyrimidinyl group, a pyridazinyl group, an imidazolidinyl group, an indolyl group, a quinolyl group, an isoquinolyl group, a purinyl group, a 1H-indazolyl group, a quinazolinyl group, a cinnolinyl group, a quinoxalinyl group, a phthalazinyl group and a pteridinyl group or an oxygen- or sulfur-containing heteroaryl group selected from a furyl group, a pyranyl group, a thienyl group, a benzofuryl group and a benzothienyl group.

Examples of the lower alkylene group and the lower alkenylene group in Y includes an alkylene group having one to eight carbon atoms (e.g., methylene group, ethylene group or propylene group) and an alkenylene group having two to eight carbon atoms (e.g., vinylene group or propenylene group), respectively.

Among the objective compounds [I] of the present invention, preferred examples are (1) those in which Y is a single bond, a lower alkylene group or a lower alkenylene group, Z is —CO—, $R^2$ is a phenyl group substituted by a group selected from a lower alkyl group, a lower alkoxy group and a halogen atom, a lower alkoxy-substituted heteroaryl group or a lower alkyl-substituted heteroaryl group and q is an integer of 0, or (2) those in which Y is a single bond, Z is —CH$_2$—, $R^2$ is a lower alkoxyphenyl group and q is an integer of 0.

Among the objective compounds [I] of the present invention, more preferred examples are those in which $R^1$ is (a) a phenyl group substituted by a group selected from (i) a lower alkoxy group substituted by a group selected from a (mono- or di-lower alkyl)amino group and a nitrogen-containing aliphatic heteromonocyclic group, (ii) a lower allyl group substituted by a group selected from a (mono- or di-lower alkyl)-amino group and a nitrogen-containing aliphatic heteromonocyclic group, and (iii) an amino group substituted by a group selected from a lower alkyl group, a cyclo-lower alkylcarbonyl group, a (mono- or di-lower alkyl)amino-lower alkyl group, a lower alkoxy-lower alkoxycarbonyl group, a nitrogen-containing aliphatic heteromonocyclic group-substituted lower alkyl group, a lower alkanoyl group and a lower alkenoyl group, (b) a cyclo-lower alkyl group substituted by a group selected from (i) an amino-lower alkyl group optionally substituted by a group selected from a lower alkyl group, a hydroxy-lower alkyl group, a (mono- or di-lower alkyl)amino-lower alkyl group, a lower alkanoyl group, a cyclo-lower alkylcarbonyl group and a lower alkoxy-lower alkyl group; (ii) a nitrogen-containing aliphatic heteromonocyclic group optionally substituted by a hydroxyl group; and (iii) an amino group substituted by a group selected from a lower alkyl group, a cyclo-lower alkylcarbonyl group, a (mono- or di-lower alkyl)amino-lower alkyl group, a lower alkanoyl group, a heteroarylcarbonyl group, a lower alkylsulfonyl group and a lower alkyl-thiocarbamoyl group, or (c) a nitrogen-containing aliphatic heteromonocyclic group substituted by a group selected from (i) a lower alkyl group, (ii) an amino group optionally substituted by a group selected from a lower alkyl group, a (mono- or di-lower alkyl)amino-lower alkyl group and a cyclo-lower alkylcarbonyl group and (iii) a nitrogen-containing aliphatic heteromonocyclic group substituted by a lower alkyl group, $R^2$ is a phenyl group substituted by a group selected from a halogen atom and a lower alkoxy group, a lower alkyl group-substituted heteroaryl group or a lower alkoxy-substituted heteroaryl group and Q is methylene group.

Among the more preferred compounds [I] mentioned above, further preferred compound are those in which the group of the formula: $R^1$—(O)$_q$—Y-Z- is a 4-(mono- or di-lower alkylamino-lower alkyl)benzoyl group; a 4-(pyrrolidino-lower alkyl)benzoyl group; a 4-(di-lower alkylamino-lower alkoxy)benzoyl group; a 3-(di-lower alkylamino-lower alkoxy)-4-(di-lower alkylamino-lower alkoxy)benzoyl group; a 4-(piperidino-lower alkoxy)benzoyl group; a 4-[N-lower alkyl-N-(di-lower alkylamino-lower alkyl)-amino]benzoyl group; a 4-[N-lower alkanoyl-N-(di-lower alkylamino-lower alkyl)-amino]benzoyl group; a 4-[N-lower alkenoyl-N-(di-lower alkylamino-lower alkyl)-amino]benzoyl group; a 4-[N-(cyclo-lower alkylcarbonyl)-N-(di-lower alkylamino-lower alkyl)amino]benzoyl group; a 4-[N-(lower alkoxy-lower alkoxycarbonyl)-N-(di-lower alkylamino-lower alkyl)amino]benzoyl group; a 4-[N-lower alkanoyl-N-(pyrrolidino-lower alkyl)amino]benzoyl group; a [1-(lower alkyl)piperidin-4-yl]-carbonyl group; a 4-[N-lower alkyl-N-(di-lower alkylamino-lower alkyl)amino]-piperidinocarbonyl group; a 4-[N-(cyclo-lower alkylcarbonyl)-N-(di-lower alkylamino-lower alkyl)amino]-piperidinocarbonyl group; a 4-[4-(di-lower alkyl)piperidino]-piperidinocarbonyl group; a [1-(lower alkyl)piperidin-4-yl]lower alkanoyl group; a [1-(lower alkyl)piperidin-4-yl]lower alkenoyl group; a 4-(di-lower alkylamino-lower alkyl)cyclohexylcarbonyl group; a 4-(mono- or di-lower alkylamino)cyclohexylcarbonyl group; a 4-[N-lower alkanoyl-N-(di-lower alkylamino-lower alkyl)amino]-cyclohexylcarbonyl group; a 4-[N-lower alkenoyl-N-(di-lower alkylamino-lower alkyl)-amino]cyclohexylcarbonyl group; a 4-[N-heteroarylcarbonyl-N-(di-lower alkylamino-lower alkyl)amino]cyclohexyl-carbonyl group; a 4-[N-lower alkylthiocarbamoyl-N-(di-lower alkylamino-lower alkyl)amino]cyclohexylcarbonyl group; a 4-[N-(di-lower alkylamino-lower alkyl)-N-(lower alkylsulfonyl)amino]cyclohexylcarbonyl group; a 4-[[N-lower alkyl-N-(hydroxy-lower alkyl)amino]lower alkyl]cyclohexylcarbonyl group; a 4-[[N-lower alkyl-N-lower alkoxy-lower alkyl)amino]lower alkyl]cyclohexylcarbonyl group; a 4-[[N-lower alkanoyl-N-(di-lower alkylamino-lower alkyl)amino]-lower alkyl]cyclohexylcarbonyl group; a 4-[[N-(cyclo-lower alkylcarbonyl)-N-(di-lower alkylamino-lower alkyl)amino]lower alkyl]cyclohexylcarbonyl group; a 4-(pyrrolidino)-cyclohexylcarbonyl group; a 4-(hydroxypyrrolidino)cyclohexylcarbonyl group; or a 4-(piperidino)cyclohexylcarbonyl group, and $R^2$ is a phenyl group substituted by one or two groups selected from an ethoxy group and a fluorine atom, an ethoxypyridyl group, a propylpyridyl group or a propylthiazolyl group.

Among the further preferred compounds [I] of the present invention mentioned above, particularly preferred examples are those in which R2 is 3-ethoxyphenyl group, 6-propylpyridin-2-yl group, 6-ethoxypyridin-2-yl group, 2-propyl-1,3-thiazol-4-yl group or 3-ethoxy-2-fluorophenyl group.

The concrete examples of the particularly preferred compound include 1-(3-ethoxybenzyl)-4-[4-[4-[2-(dimethylamino)ethoxy]benzoyl]piperazin-1-yl]-1H-pyrazolo[3,4-d]pyrimidine;

1-(3-ethoxybenzyl)-4-[4-[4-[2-(1-piperidyl)ethoxy]benzoyl]piperazin-1-yl]-1H-pyrazolo[3,4-d]pyrimidine;

1-(3-ethoxybenzyl)-4-[4-[4-(dimethylaminomethyl)benzoyl]piperazin-1-yl]-1H-pyrazolo[3,4-d]pyrimidine;

1-(3-ethoxybenzyl)-4-[4-[4-(diethylaminomethyl)benzoyl]piperazin-1-yl]-1H-pyrazolo-[3,4-d]pyrimidine;

1-(3-ethoxybenzyl)-4-[4-[4-(1-pyrrolidinylmethyl)benzoyl]piperazin-1-yl]-1H-pyrazolo[3,4-d]pyrimidine;

1-(3-ethoxybenzyl)-4-[4-[4-[N-(cyclopropylcarbonyl)-N-[2-(dimethylamino)ethyl]-amino]benzoyl]piperazin-1-yl]-1H-pyrazolo[3,4-d]pyrimidine;

1-(3-ethoxybenzyl)-4-[4-[4-[N-[(2-methoxyethoxy)carbonyl]-N-[2-(dimethylamino)-ethyl]amino]benzoyl]piperazin-1-yl]-1H-pyrazolo[3,4-d]pyrimidine;

1-(3-ethoxybenzyl)-4-[4-[4-[N-isobutyl-N-[2-(dimethylamino)ethyl]amino]benzoyl]-piperazin-1-yl]-1H-pyrazolo[3,4-d]pyrimidine;

1-(3-ethoxybenzyl)-4-[4-[(1-propylpiperidin-4-yl)carbonyl]piperazin-1-yl]-1H-pyrazolo[3,4-d]pyrimidine;

1-(3-ethoxybenzyl)-4-[4-[3-(1-isopropylpiperidin-4-yl)propionyl]piperazin-1-yl]-1H-pyrazolo[3,4-d]pyrimidine;

1-(3-ethoxybenzyl)-4-[4-[[trans-4-(dimethylaminomethyl)cyclohexyl]carbonyl]-piperazin-1-yl]-1H-pyrazolo[3,4-d]pyrimidine;

1-(3-ethoxybenzyl)-4-[4-[[trans-4-(1-pyrrolidinyl)cyclohexyl]carbonyl]piperazin-1-yl]-1H-pyrazolo[3,4-d]pyrimidine;

1-(3-ethoxybenzyl)-4-[4-[(E)-3-(1-isopropylpiperidin-4-yl)acryloyl]piperazin-1-yl]-1H-pyrazolo[3,4-d]pyrimidine;

1-(3-ethoxybenzyl)-4-[4-[4-[3-(dimethylamino)-2,2-dimethylpropyloxy]benzoyl]-piperazin-1-yl]-1H-pyrazolo[3,4-d]pyrimidine;

1-[(6-propylpyridin-2-yl)methyl]-4-[4-[4-[3-(dimethylamino)-2,2-dimethylpropyloxy]-benzoyl]piperazin-1-yl]-1H-pyrazolo[3,4-d]pyrimidine;

1-(3-ethoxybenzyl)-4-[4-[4-[N-acetyl-N-[2-(1-pyrrolidinyl)ethyl]amino]benzoyl]-piperazin-1-yl]-1H-pyrazolo[3,4-d]pyrimidine;

1-(3-ethoxybenzyl)-4-[4-[4-[N-acetyl-N-[2-(dimethylamino)ethyl]amino]benzoyl]-piperazin-1-yl]-1H-pyrazolo[3,4-d]pyrimidine;

1-(3-ethoxybenzyl)-4-[4-[4-(ethylaminomethyl)benzoyl]piperazin-1-yl]-1H-pyrazolo-[3,4-d]pyrimidine;

1-(3-ethoxybenzyl)-4-[4-[(trans-4-piperidinocyclohexyl)carbonyl]piperazin-1-yl]-1H-pyrazolo[3,4-d]pyrimidine;

1-(3-ethoxybenzyl)-4-[4-[[trans-4-((3S)-3-hydroxy-1-pyrrolidinyl)cyclohexyl]-carbonyl]piperazin-1-yl]-1H-pyrazolo[3,4-d]pyrimidine;

1-(3-ethoxybenzyl)-4-[4-[[trans-4-[N-acetyl-N-[2-(dimethylamino)ethyl]amino]-cyclohexyl]carbonyl]piperazin-1-yl]-1H-pyrazolo[3,4-d]pyrimidine;

1-(3-ethoxybenzyl)-4-[4-[[trans-4-[N-(2-furoyl)-N-[2-(dimethylamino)ethyl]amino]-cyclohexyl]carbonyl]piperazin-1-yl]-1H-pyrazolo[3,4-d]pyrimidine;

1-(3-ethoxybenzyl)-4-[4-[[trans-4-[N-(crotonoyl)-N-[2-(dimethylamino)ethyl]amino]-cyclohexyl]carbonyl]piperazin-1-yl]-1H-pyrazolo[3,4-d]pyrimidine;

1-(3-ethoxybenzyl)-4-[4-[[trans-4-[N-(methylthiocarbamoyl)-N-[2-(dimethylamino)-ethyl]amino]cyclohexyl]carbonyl]piperazin-1-yl]-1H-pyrazolo[3,4-d]pyrimidine;

1-[(2-propyl-1,3-thiazol-4-yl)methyl]-4-[4-[4-[N-crotonoyl-N-[2-(dimethylamino)-ethyl]amino]benzoyl]piperazin-1-yl]-1H-pyrazolo[3,4-d]pyrimidine;

1-[(6-ethoxypyridin-2-yl)methyl]-4-[4-[[trans-4-(1-pyrrolidinyl)cyclohexyl]carbonyl]-piperazin-1-yl]-1H-pyrazolo[3,4-d]pyrimidine;

1-[(6-propylpyridin-2-yl)methyl]-4-[4-[[trans-4-(1-pyrrolidinyl)cyclohexyl]carbonyl]-piperazin-1-yl]-1H-pyrazolo[3,4-d]pyrimidine;

1-[(6-propylpyridin-2-yl)methyl]-4-[4-[[trans-4-(diethylaminomethyl)cyclohexyl]-carbonyl]piperazin-1-yl]-1H-pyrazolo[3,4-d]pyrimidine;

1-[(6-propylpyridin-2-yl)methyl]-4-[4-[[trans-4-[N-isopropyl-N-(2-methoxyethyl)-aminomethyl]cyclohexyl]carbonyl]piperazin-1-yl]-1H-pyrazolo[3,4-d]pyrimidine;

1-[(2-propyl-1,3-thiazol-4-yl)methyl]-4-[4-[4-[2,2-dimethyl-3-(dimethylamino)-propyloxy]benzoyl]piperazin-1-yl]-1H-pyrazolo[3,4-d]pyrimidine;

1-[(6-propylpyridin-2-yl)methyl]-4-[4-[[trans-4-(dipropylamino)cyclohexyl]carbonyl]-piperazin-1-yl]-1H-pyrazolo[3,4-d]pyrimidine;

1-[(2-propyl-1,3-thiazol-4-yl)methyl]-4-[4-[[trans-4-(dipropylamino)cyclohexyl]-carbonyl]piperazin-1-yl]-1H-pyrazolo[3,4-d]pyrimidine;

1-[(6-propylpyridin-2-yl)methyl]-4-[4-[[trans-4-(1-piperidyl)cyclohexyl]carbonyl]-piperazin-1-yl]-1H-pyrazolo[3,4-d]pyrimidine;

1-[(6-ethoxypyridin-2-yl)methyl]-4-[4-[[trans-4-(1-piperidyl)cyclohexyl]carbonyl]-piperazin-1-yl]-1H-pyrazolo[3,4-d]pyrimidine;

1-[(2-propyl-1,3-thiazol-4-yl)methyl]-4-[4-[[trans-4-(1-piperidyl)cyclohexyl]carbonyl]-piperazin-1-yl]-1H-pyrazolo[3,4-d]pyrimidine;

1-(3-ethoxybenzyl)-4-[4-[[trans-4-(ethylamino)cyclohexyl]carbonyl]piperazin-1-yl]-1H-pyrazolo[3,4-d]pyrimidine;

1-(3-ethoxybenzyl)-4-[4-[3-[2-(diisopropylamino)ethoxy]-4-[3-(dimethylamino)-2,2-(dimethyl)propyloxy]benzoyl]piperazin-1-yl]-1H-pyrazolo[3,4-d]pyrimidine;

1-(3-ethoxybenzyl)-4-[4-[4-[N-(cyclopropanecarbonyl)-N-[2-(dimethylamino)ethyl]-amino]piperidinocarbonyl]piperazin-1-yl]-1H-pyrazolo[3,4-d]pyrimidine;

1-(3-ethoxybenzyl)-4-[4-[4-(3,3-dimethylpiperadino)piperidinocarbonyl]piperazin-1-yl]-1H-pyrazolo[3,4-d]pyrimidine;

1-(3-ethoxybenzyl)-4-[4-[4-[N-ethyl-N-[2-(dimethylamino)ethyl]amino]piperidino-carbonyl]piperazin-1-yl]-1H-pyrazolo[3,4-d]pyrimidine;

1-[(6-propylpyridin-2-yl)methyl]-4-[4-[[trans-4-[[N-(t-butyl)-N-ethylamino]methyl]-cyclohexyl]carbonyl]piperazin-1-yl]-1H-pyrazolo[3,4-d]pyrimidine;

1-[(6-propylpyridin-2-yl)methyl]-4-[4-[[trans-4-[[N-(t-butyl)-N-[2-(methoxy)ethyl]-amino]methyl]cyclohexyl]carbonyl]piperazin-1-yl]-1H-pyrazolo[3,4-d]pyrimidine;

1-[(6-ethoxypyridin-2-yl)methyl]-4-[4-[[trans-4-[[N-(t-butyl)-N-[2-(methoxy)ethyl]-amino]methyl]cyclohexyl]carbonyl]piperazin-1-yl]-1H-pyrazolo[3,4-d]pyrimidine;

1-(3-ethoxybenzyl)-4-[4-[[trans-4-[[N-(t-butyl)-N-[2-(methoxy)ethyl]amino]methyl]-cyclohexyl]carbonyl]piperazin-1-yl]-1H-pyrazolo[3,4-d]pyrimidine;

1-[(2-propyl-1,3-thiazol-4-yl)methyl]-4-[4-[[trans-4-[[N-(t-butyl)-N-[2-(methoxy)-ethyl]amino]methyl]cyclohexyl]carbonyl]piperazin-1-yl]-1H-pyrazolo[3,4-d]-pyrimidine;

1-(3-ethoxybenzyl)-4-[4-[[trans-4-[[N-(t-butyl)-N-[2-(hydroxy)ethyl]amino]methyl]-cyclohexyl]carbonyl]piperazin-1-yl]-1H-pyrazolo[3,4-d]-pyrimidine;

1-[(6-propylpyridin-2-yl)methyl]-4-[4-[[trans-4-[N-[2-(dimethylamino)ethyl]-N-(methanesulfonyl)amino]cyclohexyl]carbonyl]piperazin-1-yl]-1H-pyrazolo[3,4-d]-pyrimidine;

1-[(6-ethoxypyridin-2-yl)methyl]-4-[4-[[trans-4-[N-[2-(dimethylamino)ethyl]-N-(methanesulfonyl)amino]cyclohexyl]carbonyl]piperazin-1-yl]-1H-pyrazolo[3,4-d]-pyrimidine;

1-[(2-propyl-1,3-thiazol-4-yl)methyl]-4-[4-[[trans-4-[N-[2-(dimethylamino)ethyl]-N-(methanesulfonyl)amino]cyclohexyl]carbonyl]piperazin-1-yl]-1H-pyrazolo[3,4-d]-pyrimidine;

1-[(6-propylpyridin-2-yl)methyl]-4-[4-[[trans-4-[[N-[2-(dimethylamino)ethyl]-N-pivaloylamino]methyl]cyclohexyl]carbonyl]piperazin-1-yl]-1H-pyrazolo[3,4-d]-pyrimidine;

1-[(6-propylpyridin-2-yl)methyl]-4-[4-[[trans-4-[[N-(cyclopropanecarbonyl)-N-[2-(dimethylamino)ethyl]amino]methyl]cyclohexyl]carbonyl]piperazin-1-yl]-1H-pyrazolo-[3,4-d]pyrimidine;

1-(3-ethoxybenzyl)-4-[4-[[trans-4-[N-[2-(dimethylamino)ethyl]-N-propionylamino]-cyclohexyl]carbonyl]piperazin-1-yl]-1H-pyrazolo[3,4-d]pyrimidine;

1-(3-ethoxy-2-fluorobenzyl)-4-[4-[(trans-4-piperidin-1-yl-cyclohexyl)carbonyl]-piperazin-1-yl]-1H-pyrazolo[3,4-d]pyrimidine;

1-(3-ethoxy-2-fluorobenzyl)-4-[4-[[trans-4-[[N-(t-butyl)-N-[2-(methoxy)ethyl]amino]-methyl]cyclohexyl]carbonyl]piperazin-1-yl]-1H-pyrazolo[3,4-d]pyrimidine;

1-(3-ethoxy-2-fluorobenzyl)-4-[4-[4-(ethylaminomethyl)benzoyl]piperazin-1-yl]-1H-pyrazolo[3,4-d]pyrimidine;

1-(3-ethoxy-2-fluorobenzyl)-4-[4-[4[N-acetyl-N-[2-(dimethylamino)ethyl]amino]-benzoyl]piperazin-1-yl]1H-pyrazolo[3,4-d]pyrimidine;

or a pharmaceutically acceptable salt thereof.

When the compound [I] of the present invention has an asymmetric carbon atom(s) at the substituent in $R^1$ and/or $R^2$, it may exist in the form of a stereoisomer thereof (diastereoisomers, optical isomers) owing to said asymmetric carbon atom(s) thereof, and the present invention also includes these stereoisomers and a mixture thereof.

A compound [I] of the present invention or a pharmaceutically acceptable salt thereof shows a significant antagonizing activity against apamin, which is known as a selective SK channel blocker, in a competitive binding assay. For example, as a result of the assay conducted in the same manner as described in WO02/079189 (Experiment 1), a compound of the present invention, 1-(3-ethoxybenzyl)-4-[4-[4-[N-(cyclopropyl-carbonyl)-N-[2-(dimethylamino)ethyl]amino]benzoyl]piperazin-1-yl]-1H-pyrazolo[3,4-d]pyrimidine, showed an excellent apamin-binding inhibitory activity ($IC_{50}$: 0.05 μM. Therefore, the compounds [I] or a pharmaceutically acceptable salt thereof is useful as a SK channel blocker which is applicable to treatment and/or prophylaxis of SK-channel-related diseases such as gastrointestinal motility disorders (e.g., constipation, irritable bowel syndrome, gastroesophageal reflux disease, postoperative ileus), central nervous system disorders (e.g., memory and learning disorders including Arzheimer's disease, depression), emotional disorders, myotonic muscular dystrophy or sleep apnea.

Moreover, the compound of the present invention shows a low toxicity and are safe as medicaments.

The compound [I] of the present invention can be clinically used either in the free form or in the form of a pharmaceutically acceptable salt thereof. The pharmaceutically acceptable salt of the compound [I] includes a salt with an inorganic acid such as hydrochloride, sulfate, phosphate or hydrobromide, or a salt with an organic acid such as oxalate, citrate, methanesulfonate, benzenesulfonate, tosylate or maleate. Besides, when the compounds [I] of the present invention has a carboxyl group(s) and the like in its molecule, examples of the pharmaceutically acceptable salt include, salts with a base such as alkaline metal (e.g., sodium salt, potassium salt), or alkaline earth metal (e.g., calcium salt).

The compound [I], a salt thereof, or its intermediate or a salt thereof includes either intramolecular salt or an additive thereof, and solvates or hydrates thereof.

The present compound [I] or a pharmaceutically acceptable salt thereof can be administered either orally or parenterally, and can be formulated into a conventional pharmaceutical preparation such as tablets, granules, fine granules, capsules, powders, injections or inhalants.

The dose of the compounds [I] of the present invention or a pharmaceutically acceptable salt thereof may vary in accordance with the administration routes, and the ages, weights and conditions of the patients. For example, when administered in an injection preparation, it is usually in the range of about 0.0001 to 1 mg/kg/day, preferably in the range of about 0.001 to 0.1 mg/kg/day. When administered in an oral preparation, it is usually in the range of about 0.001 to 100 mg/kg/day, preferably in the range of 0.01 to 10 mg/kg/day.

BEST MODE FOR CARRYING OUT THE INVENTION

The pyrazolopyrimidine compounds [I] of the present invention may be prepared by the following manners.

Process A:

Among the compounds [I] of the present invention, the compound of the following formula [I-A]:

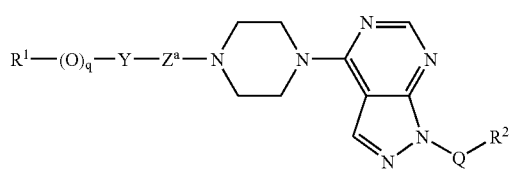

[I-A]

wherein $Z^a$ is a group of the formula: —CO—, —SO$_2$— or =C=N—CN and other symbols are the same as defined above, can be prepared by reacting a compound of the formula [II]:

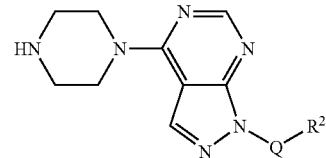

[II]

wherein the symbols are the same as defined above or a salt thereof with a compound of the formula [III]:

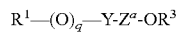

$R^1$—(O)$_q$—Y-Z$^a$-OR$^3$ [III]

wherein $R^3$ is a hydrogen atom, a lower alkyl group or benzyl group and other symbols are the same as defined above or a salt thereof.

When $R^3$ is a hydrogen atom, the above-mentioned reaction can be carried out in a solvent in the presence of a condensing agent, and in the presence or absence of an activating agent and a base. Examples of the solvent include any solvent which does not disturb the reaction, such as methylene chloride, chloroform, N,N-dimethylformaide, N,N-dimethylacetamide, tetrahydrofuran, dioxane, toluene, benzene, 1,2-dichloroethane, 1-methyl-2-pyrrolidinone, 1,2-dimethoxyethane and the like.

The condensing agent includes, for example, dicyclohexylcarbodiimide (DCC), 1-ethyl-3-(3-dimethylaminopropyl)carbodiimide•hydrochloride (WSC.HCl), diphenylphosphoryl azide (DPPA), carbonyldiimidazole (CDI), diethylcyano-phosphonate (DEPC), diisopropylcarbodiimide (DIPCI), benzotriazol-1-yloxy-trispyrrolidinophosphonium hexafluorophosphate (PyBOP), carbonylditriazole, N-cyclohexylcarbodiimide-N'-propyloxymethylpolystylene (PS-carbodiimide), N-ethoxy-carbonyl-2-ethoxy-1,2-dihydroquinoline (EEDQ), 2-(7-azabenzotriazol-1-yl)-1,1,3,3-tetramethyluronium hexafluorophosphate (HATU), 2-(1H-benzotriazol-1-yl-1,1,3,3-tetramethyluronium (HBTU), bromotrispyrrolidinophosphonium hexafluorophosphate (PyBroP), 2-(1H-benzotriazol-1-yl)-1,1,3,3-tetramethyluronium tetrafluoroborate (TBTU), chloro-1,1,3,3-tetramethyluronium chloroantimonate (ACTU) and the like.

Examples of the activating agent include 1-hydroxybenzotriazole (HOBt), 1-hydroxysuccinimide (HOSu), dimethylaminopyridine (DMAP), 1-hydroxy-7-azabenzotriazole (HOAt), hydroxyphthalimide (HOPht), pentafluorophenol (Pfp-OH), 1-hydroxybenzotriazole-6-sulfonamidomethylpolystylene (PS-HOBt) and the like.

The base includes, for example, pyridine, triethylamine, diisopropylethylamine, 4-methylmorpholine, 1,8-diazabicyclo[5,4,0]-7-undecene (BU) and the like.

In the above-mentioned process, the compound [II] can be used in an amount of 0.3 to 10 moles, preferably 0.5 to 2 moles per mole of the compound [III]. The condensing agent can be used in an amount of 1 to 10 moles, preferably 1.5 to 4 moles per one mole of the compound [II] or [III]. The base can be used in an amount of 1 to 10 moles, preferably 2 to 4 moles per one mole of the compound [II] or [III]. The activating agent can be used in an amount of 1 to 10 moles, preferably 1.5 to 4 moles per one mole of the compound [II] or [III]. The reaction can be carried out at −20 to 80° C., preferably 0 to 30° C.

Concomitantly, when $R^3$ in the compound [III] is hydrogen atom, the reaction process A to prepare the compound [I-A] can be carried out by converting the compound to a reactive derivative at the carboxyl group and the like (e.g., an acid halide, a mixed acid anhydride) and reacting the reactive derivative with the compound [II] in the presence of the base in the solvent or without solvent.

When $R^3$ in the compound [III] is a lower alkyl group or a benzyl group, the reaction process A can be also carried out by converting the compound to a corresponding carboxylic acid (sulfonic acid or imino acid) compound by a conventional method such as hydrolysis, acidolysis using hydrochloric acid, formic acid, trifluoroacetic acid and the like or hydrogenation and reacting the carboxylic acid compound with the compound [II] by the above-mentioned method.

Furthermore, when $R^3$ in the compound [III] is a lower alkyl group or a benzyl group, the reaction process A can be also carried out by directly reacting the ester compound [II] with the compound [III] in the presence of a base in a solvent or without solvent. The solvent includes any solvent which does not disturb the reaction, such as methylene chloride, chloroform, N,N-dimethylformamide, N,N-dimethylacetamide, tetrahydrofuran, dioxane, toluene, benzene, 1,2-dichloroethane, 1-methyl-2-pyrrolidinone, methanol, ethanol, isopropanol and the like. The base includes, for example, triethylamine, diisopropylethylamine, 4-methylmorpholine, 1,8-diazabicyclo-[5,4,0]undecene (DBU), dimethylaminopyridine (DMAP) and the like.

In the above-mentioned process, the compound [III] can be used in an amount of 0.3 to 10 moles, preferably 0.5 to 2 moles per mole of the compound [II]. The base can be used in an amount of 1 to 10 moles, preferably 1 to 4 moles per one mole of the compound [II] or [III]. The reaction can be carried out at 25 to 150° C., preferably 60 to 100° C.

Process B:

Among the compounds [I] of the present invention, the compound in which Z is —$CH_2$— of the following formula [I-B]:

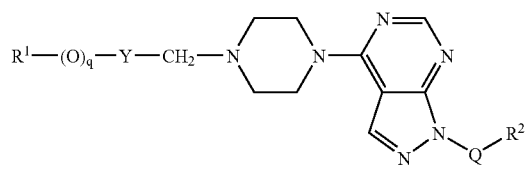

[I-B]

wherein the symbols are the same as defined above, can be prepared by reacting a compound [II] or a salt thereof with an aldehyde compound (a lower alkanal or an aryl-lower alkanal) of the formula [IV]:

[IV]

wherein the symbols are the same as defined above in the presence of a reducing agent in a solvent.

The solvent includes any solvent which does not disturb the reaction, such as methylene chloride, chloroform, 1,2-dichloroethane, N,N-dimethylformamide, N,N-dimethylacetamide, 1-methyl-2-pyrrolidinone, tetrahydrofuran, 1,2-dimethoxyethane, dioxane, toluene, benzene, methanol, ethanol, isopropanol, acetic acid and the like. The reducing agent includes, for example, macroporous triethylammonium-methyl-polystelene cyanoborohydride (MP-Cyanoborohydride), sodium borohydride, sodium triacetoxyborohydride, sodium cyanoborohydride and the like. The reducing agent can be used in an amount of 1 to 10 moles, preferably 1 to 4 moles per one mole of the compound [II]. The reaction can be carried out at −20 to 100° C., preferably 0 to 40° C.

Process C:

Among the compounds [I] of the present invention, the compound of the formula [I-C]:

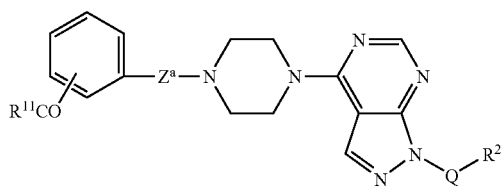

[I-C]

wherein $R^{11}$ is an amino group optionally substituted by a group selected from a lower alkyl group, a (mono- or di-lower alkyl)amino-lower alkyl group and a nitrogen-containing aliphatic heteromonocyclic group-substituted lower alkyl group, $Z^a$ is a group of the formula: —CO—, —$SO_2$— or =C=N—CN and other symbols are the same as defined above, can be prepared by reacting a carboxylic acid compound of the formula [V]:

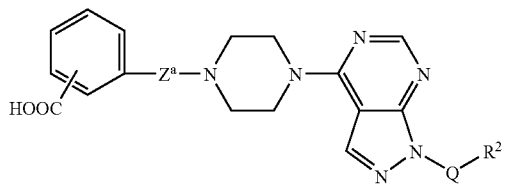

[V]

wherein the symbols are the same as defined above or a salt thereof with an amine compound of the formula [VI]:

[VI]

wherein $R^{11}$ is the same as defined above or a salt thereof. The reaction can be carried out in a solvent in the presence of a condensing agent and in the presence or absence of an activating agent and a base. Examples of the solvent, condensing agent, activating agent and base include those as exemplified in the Process A.

The compound [V] can be used in an amount of 0.5 to 3 moles, preferably 1 to 2 moles per one mole of the compound [VI]. The condensing agent can be used in an amount of 1 to 10 moles, preferably 1.5 to 4 moles per one mole of the compound [V] or [VI]. The base can be used in an amount of 1 to 10 moles, preferably 2 to 4 moles per one mole of the compound [V] or [VI]. The activating agent can be used in an amount of 1 to 10 moles, preferably 1.5 to 4 moles per one mole of the compound [V] or [VI]. The reaction can be carried out at −20 to 80° C., preferably 0 to 30° C.

Process D:

Among the compounds [I] of the present invention, the compound of the formula [I-D]:

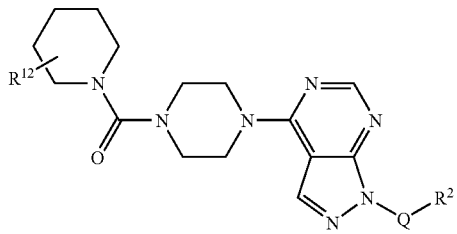

wherein $R^{12}$ is an optionally substituted nitrogen-containing aliphatic heteromonocyclic group or an optionally substituted amino group and other symbols are the same as defined above can be prepared by reacting a compound of the formula [VII]:

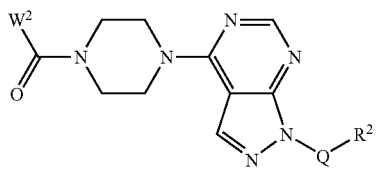

wherein $W^2$ is a reactive residue and other symbols are the same as defined above with a compound of the formula [VIII]:

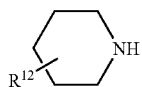

wherein the symbol is the same as defined above or a salt thereof, or reacting a compound of the formula [II]:

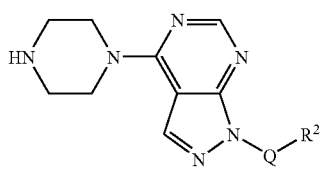

wherein the symbols are the same as defined above or a salt thereof with a compound of the formula [IX]:

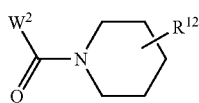

wherein the symbol is the same as defined above.

The reaction for preparing the compound [I-D] from the compound [VII] and [VIII] or the compound [II] and [IX] can be carried out in a solvent in the presence of a base. The solvent includes any solvent which does not disturb the reaction, such as chloroform, methylene chloride, 1,2-dichloroethane, tetrahydrofuran, dioxane, ethyl acetate, N,N-dimethylformamide, N,N-dimethylacetamide, 1-methyl-2-pyrrolidinone, dimethylsulfoxide, toluene and the like. The base includes, for example, triethylamine, diisopropylethylamine, N-methylmorpholine, pyridine and the like. The compound [VIII] or [II] can be used in an amount of 0.8 to 3 moles, preferably 1 to 1.5 moles per one mole of the compound [VII] or [IX]. The base can be used in an amount of 1 to 4 moles, preferably 2 to 3 moles per one mole of the compound [II] or [IX]. The reaction can be carried out at 25 to 150° C., preferably 60 to 120° C.

Meanwhile, the compound [IX] can be prepared by reacting the compound [II] with a compound of the formula [X] (phosgen, a phosgen precursor, a phosgen equivalent and the like):

wherein $W^1$ and $W^2$ are a reactive residue.

Besides, the compound [IX] can be prepared by reacting the compound [VIII] with the compound [X]. In the compound [X], the reactive residue represented as $W^1$ or $W^2$ may be a halogen atom, phenoxy group, p-nitrophenoxy group, a lower alkoxy group or a nitrogen-containing aromatic heteromonocyclic group (e.g., a 5- or 6-membered heteroaryl group containing at least one nitrogen atom such as pyridyl group).

The reaction for preparing the compound [VII] or [IX] can be carried out in a solvent in the presence of a base. The solvent and the base include those used in the reaction for preparing the compound [I-D] from the compound [VII] and [VIII] or the compound [II] and [IX]. The phosgen precursor is, for example, triphosgen, diphosgen (phosgen dimer) and the like. The phosgen equivalent includes, for example, p-nitrophenyl chloroformate, diethyl carbonate, 1,1'-carbonyldiimidazole, diphenyl chlorocarbonate, diethyl carbonate, N,N'-disuccinimidyl carbonate, dipyridin-2-yl carbonate and the like.

The compound [X] can be used in an amount of 0.2 to 4 moles, preferably 0.4 to 2 moles per one mole of the compound [II] or [VIII]. The base can be used in an amount of 3 to 6 moles, preferably 3 to 4 moles per one mole of the compound [II] or [VIII]. The reaction can be carried out at −4 to 60° C., preferably 0 to 30° C.

The aforementioned reactions for preparing the compound [I-D] from the compound [VIII] via the compound [VII] or [IX] can be also carried out without isolating the intermediate compound [VII] or [IX].

The objective compound [I] of the present invention can be also prepared by intramolecularly converting the substituent(s) in $R^1$ of the compounds [I] as obtained above to the other desired substituent(s) within the scope the present invention. The intramolecular conversion processes can be selected according to the kinds of the objective substituents, and may be carried out, for example, by the following methods (a) to (e).

Method (a):

An objective compound [I] of the present invention having a substituent(s) containing a substituted lower alkoxy group in $R^1$ can be prepared by reacting a compound [I] having a substituent(s) containing a hydroxyl group in $R^1$ with a lower alkyl halide having a corresponding substituent(s) in the presence of a base (e.g., sodium hydride, potassium carbonate), or by reacting a compound [I] having a substituent(s) containing a hydroxyl group in $R^1$ with a lower alkanol having a corresponding substituent(s) in an appropriate solvent in the presence of triphenylphosphine and isopropyl azodicarboxylate.

Method (b):

An objective compound [I] of the present invention having a substituent(s) containing a lower alkylamino group in $R^1$ can be prepared by reacting a corresponding compound [I] having a substituent(s) containing a primary or secondary amino group with a corresponding lower alkyl halide in an appropriate solvent in the presence of a base.

Method (c):

An objective compound [I] of the present invention having a substituent(s) containing an acylamino group such as a lower alkanoylamino group in $R^1$ can be prepared by reacting a corresponding compound [I] having a substituent(s) containing a primary or secondary amino group in $R^1$ with a corresponding carboxylic acid or thiocarboxylic acid compound in the same manner as described in the above Process A.

Method (d):

An objective compound [I] of the present invention having a substituent(s) containing a group of the formula:

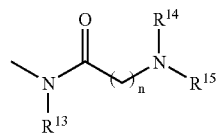

wherein $R^{13}$ is a hydrogen atom or a lower alkyl group, $R^{14}$ and $R^{15}$ are a lower alkyl group which may be combined each other to form a ring group and n is an integer of 1 or 2 in $R^1$, can be prepared by reacting a corresponding compound [I] having a substituent(s) containing a primary or secondary amino group in $R^1$ with a compound of the formula [X']:

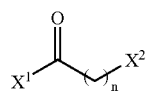

[X']

wherein $X^1$ and $X^2$ is a halogen atom and the other symbols are the same as defined above in an appropriate solvent in the presence of a base and then reacting the resultant product with an amine compound of the formula [XI]:

  $(R^{14})(R^{15})NH$ [XI]

wherein the symbols are the same as defined above. Meanwhile, the reaction can be also carried out in a single reaction vessel without isolating an intermediate.

Method (e):

An objective compound [I] of the present invention having a substituent(s) containing a group of the formula:

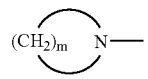

wherein m is an integer of 5 or 6 in $R^1$ can be prepared by reacting a corresponding compound [I] having a substituent(s) containing an amino group(s) with a compound of the formula [XII]:

  $X^3$—$(CH_2)m$-$X^4$ [XII]

wherein $X^3$ and $X^4$ are a halogen atom and the other symbols are the same as defined above in an appropriate solvent in the presence of a base.

In conducting the above mentioned Processes A to C and Methods (a) to (e), when the starting materials or intermediate compounds have a functional group(s), if necessary, the protection of the functional groups and the following deprotection thereof may be carried out in accordance with a conventional method.

An intermediate compound [II] for preparation of the objective compounds [I] of the present invention can be obtained, for example, in accordance with the following method as described in WO02/79189, reacting a compound [XIII] with a compound [XIV] to prepare a compound [II-A], reacting the product with a compound [XV] to prepare a compound [II-B] and removing an amino-protecting group (G) from the resultant product in a conventional manner.

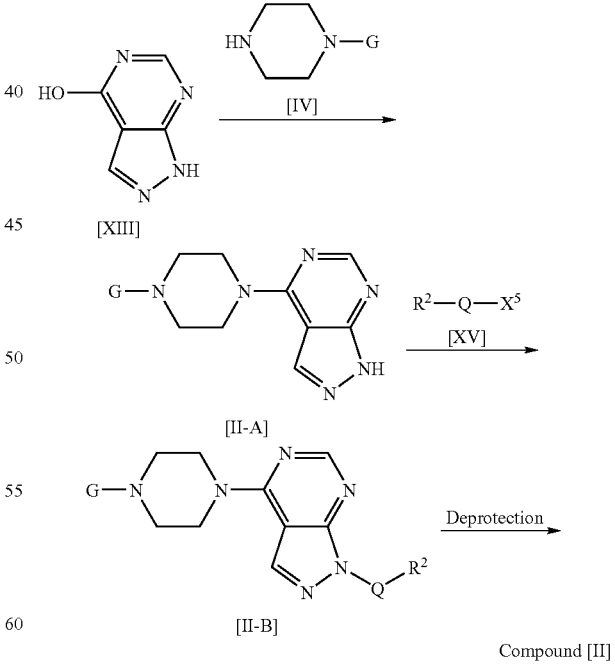

Compound [II]

In the above scheme, G is an amino-protecting group and the other symbols are the same as defined above.

The reaction process to prepare the compound [II-A] can be carried out in a solvent or without solvent in the presence or absence of an activating agent and an additive. The solvent includes any solvent which does not disturb the reaction, for example, xylene, chloroform and the like. Examples of the activating agent include hexamethyldisilazane, N,O-bistrimethylsilylacetamide, chlorotrimethylsilane. The additives include ammonium sulfate, chlorotrimethylsilane, triethylamine hydrochloride, pyridine hydrochloride, triethylamine and the like.

The compound [II-B] can be prepared by reacting a compound [II-A] with a lower alkanol or a compound having a leaving group of the formula [XV]:

   [XV]

wherein $X^5$ is hydroxyl group or a leaving group and the other symbols are the same as defined above in an appropriate solvent in the presence of an dehydrating agent or a base. The solvent includes, for example, methylene chloride, chloroform, 1,2-dichloroethane, N,N-dimethylformamide, N,N-dimethylacetamide, 1-methyl-pyrrolidinone, tetrahydrofuran, 1,2-dimethoxyethane, 1,4-dioxane, toluene, benzene and the like. The dehydrating agent for the compound in which $X^5$ is a hydroxyl group includes, for example, a combination of a diester of azodicarboxylic acid and a tri-substituted phosphine or phosphorane and the like. The base for the compound in which $X^5$ is a leaving group such as a halogen atom, a lower alkylsulfonyloxy group or an arylsulfonyloxy group includes, for example, an alkaline metal hydroxide such as lithium hydroxide, an alkali metal hydride, an alkali metal carbonate, an alkali metal lower alkoxide, lithium diisopropylamide (LDA) and the like.

In the above compound [II-B], amino-protecting group G includes, for example, benzyl group, a lower alkoxycarbonyl group and the protecting group can be removed in a conventional manner.

The intermediate compound [V] of the present invention can be prepared by reacting a compound [III] with a compound of the formula [XVI]:

   [XVI]

wherein $R^{16}$ is a phenyl group substituted by a protected or esterified carboxyl group or its reactive derivative such as a corresponding acid halide (e.g., an acid chloride) and removing the protecting group or ester residue from the resultant product in accordance with a conventional manner.

The objective compound [I] and the starting materilas [III] or [IV] of the present invention can be also prepared by intramolecularly converting the substituent(s) in $R^1$ and/or $R^2$ of the compound as obtained above to the other desired substituent(s) within the scope the present invention. The method of such conversion can be selected according to the kind of the desired substituent and includes, for example, O-alkylation, reductive amination and the like.

If necessary, the compounds [I] of the present invention obtained in the aforementioned Processes A to D or Methods (a) to (e) can be converted to a pharmaceutically acceptable salt thereof by a conventional manner.

Throughout the present description and claims, the "lower alkyl group" or "lower alkoxy group" means a straight or branched chain alkyl or alkoxy group having 1 to 6 carbon atoms, preferably 1 to 4 carbon atoms. The "lower alkanoyl group" means a straight or branched chain alkanoyl group having 2 to 7 carbon atoms, preferably 2 to 5 carbon atoms. The "cyclo-lower alkyl group" means a cycloalkyl having 3 to 8 carbon atoms, preferably 3 to 6 carbon atoms. The "lower alkenyl group" means a straight or branched chain alkenyl group having 2 to 8 carbon atoms, preferably 2 to 4 carbon atoms. The "lower alkynyl group" means a straight or branched chain alkynyl group having 2 to 8 carbon atoms, preferably 2 to 4 carbon atoms. The "lower alkylene group" means a straight or branched chain alkylene group having 1 to 6 carbon atoms, preferably 1 to 5 carbon atoms. The "lower alkenylene group" means a straight or branched chain alkenylene group having 2 to 8 carbon atoms, preferably 2 to 4 carbon atoms. Moreover, "halogen atom" means fluorine, chlorine, bromine or iodine atom. The "lower alkenoyl group" means a straight or branched chain alkenoyl group having 2 to 8 carbon atoms, preferably 3 to 6 carbon atoms. The "heteroaryl group" means a 5- to 14-membered heteroaryl group containing at least one heteroatom selected from nitrogen atom, sulfur atom or oxygen atom, particularly a 5- to 10-membered, mono- or bi-cyclic heteroaryl group containing at least one nitrogen atom as a heteroatom.

The present invention is illustrated in more detail by the following Examples and Reference Examples but should not be construed to be limited thereto.

EXAMPLE 1

To a solution of ethyl 4-[N-(cyclopropylcarbonyl)-N-[2-(dimethylamino)ethyl]-amino]benzoate (106 mg; compound obtained in Reference Example 11) in ethanol (3 mL) is added 2N sodium hydroxide solution (21 µL) and the mixture is stirred at room temperature overnight. To the reaction mixture is added 2N HCl (42 µL) and the mixture is concentrated to give a crude carboxylic acid compound. To the compound is added successively methylene chloride (2 mL), 1-(3-ethoxybenzyl)-4-piperazin-1-yl-1H-pyrazolo [3,4-d]pyrimidine dihydrochloride (105 mg, compound described in WO02/79189), 1-hydroxybenzotriazole (51.7 mg), triethylamine (124.5 µL) and 1-ethyl-3-(3-dimethylaminopropyl)carbodiimide hydrochloride (73.4 mg) and the mixture is stirred at room temperature for 19 hours. The reaction mixture is diluted with chloroform (5 mL) and thereto is added a saturated sodium hydrogencarbonate solution (10 mL). After stirring, the organic layer is separated and concentrated. The resultant crude product is purified by flash column chromatography on NH-silica gel (Chromatorex NH silica gel; Fuji Silicia Chemical Ltd., Solvent; ethyl acetate:chloroform=1:0→0:1) to give 1-(3-ethoxybenzyl)-4-[4-[4-[N-(cyclopropyl-carbonyl)-N-[2-(dimethylamino)ethyl]amino]benzoyl]piperazin-1-yl]-1H-pyrazolo[3,4-d]pyrimidine (127 mg, yield; 84%) as an amorphous powder. MS (APCI) m/z: 597 [M+H]+

EXAMPLE 2

To trans-4-(1-pyrrolidinyl)cyclohexanecarboxylate hydrochloride (26 mg; compound obtained in Reference example 87(2)) is added successively methylene chloride (3.5 mL), 1-(3-ethoxybenzyl)-4-piperazin-1-yl-1H-pyrazolo [3,4-d]pyrimidine dihydrochloride (30 mg), 0.5M 1-hydroxybenzotriazole in N,N-dimethylformamide (219 µL), triethylamine (35.6 µL) and N-cyclohexylcarbodiimide-N'-propyloxymethylpolystyrene (310.4 mg, PS-Carbodiimide, 0.94 mmol/g, Argonaut Technology) and the mixture is stirred at room temperature for 24 hours by using a parallel synthesizer (Quest 210; Argonaut Technology). To the reaction mixture is added macroporous triethylammoniummethylpolystyrene carbonate (120 mg, MP-Carbonate 3.04 mmol/g; Argonaut Technology) and the mixture is stirred at room temperature for 3 hours. The liquid layer is separated from the reaction mixture and the residual resin is washed successively with chloroform and methanol. The liquid layer and the washings are combined and concentrated by centrifugal concentrator. The resultant crude product is purified by HPLC (XTerra PerpMS C18 column; Waters Inc., Solvent; 10 mM ammonium carbonate:methanol=1:1→5:95) to give 1-(3-ethoxybenzyl)-4-[4-[[trans-4-(1-pyrrolidinyl)cyclohexyl]carbonyl]piperazin-1-yl]-1H-pyrazolo[3,4-d]-pyrimidine (27 mg, yield; 71%) as an amorphous powder.

MS (APCI) m/z: 518 [M+H]$^+$

IR(Nujol) cm$^{-1}$; 1634, 1596, 1555, 1459

EXAMPLE 3

To 4-[2-(dimethylamino)ethoxy]benzoic acid hydrochloride (66 mg, compound obtained in Reference example 78(2)) is added successively methylene chloride (2 mL), 1-(3-ethoxybenzyl)-4-piperazin-1-yl-1H-pyrazolo[3,4-d]pyrimidine dihydrochloride (100 mg), 1-hydroxybenzotriazole (49.3 mg), triethylamine (118.6 µL) and 1-ethyl-3-[3-(dimethylamino)propyl]carbodiimide hydrochloride (70 mg) and the mixture is stirred at room temperature for 17 hours. The reaction mixture is diluted with chloroform (5 mL) and thereto is added a saturated sodium hydrogencarbonate solution (10 mL). After stirring, the organic layer is separated and concentrated. The resultant crude product is purified by flash column chromatography on NH-silica gel (Solvent; ethyl acetate:chloroform=1:0→0:1) to give 1-(3-ethoxybenzyl)-4-[4-[2-(dimethylamino)ethoxy]benzoyl]piperazin-1-yl]-1H-pyrazolo[3,4-d]pyrimidine (103 mg, yield; 69%) as an amorphous powder. MS (APCI) m/z: 530 [M+H]$^+$

EXAMPLE 4

(1) To a suspension of 1-(3-ethoxybenzyl)-4-piperazin-1-yl]-1H-pyrazolo[3,4-d]pyrimidine dihydrochloride (2 g) and triethylamine (2.18 mL) in methylene chloride (20 mL) is added dropwise a solution of terephthalic acid mono-methyl ester chloride (970 mg) in methylene chloride (10 mL) under ice-cooling and the mixture is stirred at room temperature for one day. The reaction mixture is diluted with water and stirred for 30 minutes. The methylene chloride layer is separated and the aqueous layer is extracted with chloroform. The chloroform layer and the methylene chloride layer are combined, washed with saturated brine, dried over anhydrous sodium sulfate, and concentrated. The crude product is purified by flash column chromatography on silica gel (Biotage Flush 40M; Solvent; ethyl acetate:n-hexane=1:1) to give 1-(3-ethoxybenzyl)-4-[4-[4-(methoxycarbonyl)benzoyl]piperazin-1-yl]-1H-pyrazolo[3,4-d]-pyrimidine (2.4 g, yield; 98%) as an amorphous powder. MS (APCI) m/z: 501 [M+H]$^+$ (2) To a suspension of the compound obtained in the above step (1) (2.4 g) in ethanol/tetrahydofuran (1:1, 25 mL) is added dropwise 10% aqueous sodium hydroxide solution (10 mL) and the mixture is stirred at room temperature for 19 hours. The reaction mixture is diluted with chloroform, neutralized with 10% aqueous citric acid solution and extracted with chloroform (×2). The extract is washed with saturated brine, dried over anhydrous sodium sulfate and concentrated. To the resultant crude carboxylic acid compound (50 mg) is added successively N,N-diethylethylenediamine (35.8 mg), 0.5 M 1-hydroxybenzotriazole in N,N-dimethylformamide (308 µL) and N-cyclohexylcarbodiimide-N'-propyloxymethylpolystylene (328 mg, PS-carbodiimide 0.94 mmol/g). The mixture is stirred at room temperature for 24 hour by using a parallel synthesizer (Quest 210). To the reaction mixture is added macroporous triethylammoniummethylpolystylenecarbonate (MP-Carbonate 3.04 mmol/g, 120 mg) and the mixture is stirred at room temperature for 1 hour. The liquid layer is separated and the resin is washed successively with chloroform and methanol. The washing and the reaction solution are combined and concentrated. The resultant crude product is purified by HPLC (XTerra PrepMS C18 column, Solvent; 10 mM ammonium carbonate:methanol=80:20→5:95) to give 1-(3-ethoxybenzyl)-4-[4-[4-[2-(diethylamino)ethylcarbamoyl]benzoyl]piperazin-1-yl]-1H-pyrazolo[3,4-d]-pyrimidine (15.6 mg, yield; 19%) as an amorphous powder. MS (APCI) m/z: 585 [M+H]$^+$ (3) The compound obtained in the above step (2) is dissolved in ethanol (1 mL) and thereto is added 2N hydrochloric acid (16 µL). The mixture is evaporated to remove solvent and the residue is dissolved in water and lyophilized to give 1-(3-ethoxybenzyl)-4-[4-[4-[2-(diethylamino)ethylcarbamoyl]benzoyl]piperazin-1-yl]-1H-pyrazolo[3,4-d]pyrimidine hydrochloride as an amorphous powder. MS (APCI) m/z: 585 [M+H]$^+$

EXAMPLE 5

(1) The compound obtained in Reference Example 1(3) is treated in the same manner as described in Example 1 to give 1-(3-ethoxybenzyl)-4-[4-[4-[N-[3-(dimethylamino)propionyl]-N-[2-(dimethylamino)ethyl]amino]benzoyl]piperazin-1-yl]-1H-pyrazolo[3,4-d]pyrimidine as an amorphous powder.

(2) A mixture of the compound obtained in the above step (1) (131 mg) and fumaric acid 24.2 mg is dissolved in water and lyophilized to give 1-(3-ethoxybenzyl)-4-[4-[4-[N-[3-(dimethylamino)propionyl]-N-[2-(dimethylamino)ethyl]amino]benzoyl]-piperazin-1-yl]-1H-pyrazolo[3,4-d]pyrimidine fumarate as powder.

MS (APCI) m/z: 628 [M+H]$^+$

EXAMPLE 6

To 4-[N-[(2-methoxyethoxy)carbonyl]-N-[2-(dimethylamino)ethyl]amino]-benzaldehyde (90 mg, compound obtained in Reference Example 97) is added successively tetrahydrofuran (1.5 mL), 1-(3-ethoxybenzyl)-4-(1-piperazinyl)-1H-pyrazolo[3,4-d]pyrimidine dihydrochloride (100 mg), triethylamine (90 µL), acetic acid (73 µL) and macroporous triethylammoniummethylpolystylenecyanoborohydride (MP-Cyanoborohydride 2.04 mmol/g, Argonaut Technology). The mixture is shaken at room temperature for 18 hours by using a parallel synthesizer (MiniBlock; Mettler Toledo). The reaction mixture is separated and the residual resin is washed with tetrahydrofuran (×3). The washings and the reaction solution are combined and concentrated. The resultant crude product is purified by flash column chromatography on silica gel (Solvent; ethyl acetate:chloroform=1:0→0:1) to give 1-(3-ethoxybenzyl)-4-[4-[4-[N-[(2-methoxyethoxy)carbonyl]-N-[2-(dimethylamino)ethyl]-amino]benzyl]piperazin-1-yl]-1H-pyrazolo[3,4-d]pyrimidine (159 mg, yield; 38%) as an amorphous powder. MS (APCI) m/z: 617 [M+H]$^+$

EXAMPLES 7 TO 83

The corresponding materials are treated in the same manner as described in Example 1, or Examples 1 and 4(2) to give the compounds as shown in the following Table 1.

TABLE 1

(No. 1)

| Ex. Nos. | R¹ | Physicochemical properties etc. |
|---|---|---|
| 7* | O=C(Me)-N(CH₂CH₂NMe₂)(4-methylphenyl) | amorphous powder MS (APCI) 571 [M + H]+ |
| 8* | O=C(CH₂Me)-N(CH₂CH₂NMe₂)(4-methylphenyl) | amorphous powder MS (APCI) 599 [M + H]+ |
| 9* | O=C(CHMe₂)-N(CH₂CH₂NMe₂)(4-methylphenyl) | amorphous powder MS (APCI) 599 [M + H]+ |
| 10* | O=C(t-Bu)-N(CH₂CH₂NMe₂)(4-methylphenyl) | amorphous powder MS (APCI) 613 [M + H]+ |
| 11* | O=C(CH=CHMe)-N(CH₂CH₂NMe₂)(4-methylphenyl) | amorphous powder MS (APCI) 597 [M + H]+ |
| 12* | O=C(CH₂OH)-N(CH₂CH₂NMe₂)(4-methylphenyl) | amorphous powder MS (APCI) 587 [M + H]+ |

*hydrochloride
Me: methyl group, Et: ethyl group, t-Bu: tert-butyl group

TABLE 1

(No. 2)

| Ex. Nos. | R¹ | Physicochemical properties etc. |
|---|---|---|
| 13* | O=C(C(Me)=CMe₂)-N(CH₂CH₂NMe₂)(4-methylphenyl) | amorphous powder MS (APCI) 611 [M + H]+ |
| 14 | O=C(2-thienyl)-N(CH₂CH₂NMe₂)(4-methylphenyl) | amorphous powder MS (APCI) 639 [M + H]+ |
| 15 | O=C(2-furyl)-N(CH₂CH₂NMe₂)(4-methylphenyl) | amorphous powder MS (APCI) 623 [M + H]+ |
| 16* | O=C(CH₂-t-Bu)-N(CH₂CH₂NMe₂)(4-methylphenyl) | amorphous powder MS (APCI) 627 [M + H]+ |
| 17* | O=C(cyclopentyl)-N(CH₂CH₂NMe₂)(4-methylphenyl) | amorphous powder MS (APCI) 625 [M + H]+ |

*hydrochloride
Me: methyl group, Et: ethyl group, t-Bu: tert-butyl group

TABLE 1
(No. 3)

| Ex. Nos. | R¹ | Physicochemical properties etc. |
|---|---|---|
| 18* | S=C(NHMe)–N(CH₂CH₂NMe₂)(p-tolyl) | amorphous powder MS (APCI) 602 [M + H]+ |
| 19* | S=C(NH-n-Bu)–N(CH₂CH₂NMe₂)(p-tolyl) | amorphous powder MS (APCI) 644 [M + H]+ |
| 20* | S=C(NH-iBu)–N(CH₂CH₂NMe₂)(p-tolyl) | amorphous powder MS (APCI) 644 [M + H]+ |
| 21 | O=C(CH₂CH₂NEt₂)–N(CH₂CH₂NMe₂)(p-tolyl) | amorphous powder MS (APCI) 656 [M + H]+ |
| 22 | Me₂NCH₂CH₂–NH–(methyl-pyridyl) | amorphous powder MS (APCI) 529 [M + H]+ |
| 23 | O=C(Et)–N(CH₂CH₂NMe₂)(p-tolyl) | amorphous powder MS (APCI) 585 [M + H]+ |

*hydrochloride
Me: methyl group, Et: ethyl group

TABLE 1
(No. 4)

| Ex. Nos. | R¹ | Physicochemical properties etc. |
|---|---|---|
| 24 | O=C(CH₂CH₂CH₂Me)–N(CH₂CH₂NMe₂)(p-tolyl) | amorphous powder MS (APCI) 613 [M + H]+ |
| 25 | O=C(CH₂OMe)–N(CH₂CH₂NMe₂)(p-tolyl) | amorphous powder MS (APCI) 601 [M + H]+ |
| 26 | O=C(OCH₂CH₂OMe)–N(CH₂CH₂NMe₂)(p-tolyl) | amorphous powder MS (APCI) 631 [M + H]+ |
| 27 | O=C(NH-n-Bu)–N(CH₂CH₂NMe₂)(p-tolyl) | amorphous powder MS (APCI) 628 [M + H]+ |

Me: methyl group, Et: ethyl group

TABLE 1-continued (No. 5)

| Ex. Nos. | R¹ | Physicochemical properties etc. |
|---|---|---|
| 28* | benzyl-N-(4-methylphenyl)-C(=O)-CH₂-pyrrolidine | amorphous powder MS (APCI) 659 [M + H]+ |
| 29* | benzyl-N-(4-methylphenyl)-C(=O)-CH₂-NEt₂ | amorphous powder MS (APCI) 661 [M + H]+ |
| 30* | benzyl-N-(4-methylphenyl)-C(=O)-CH₂CH₂-NMe₂ | amorphous powder MS (APCI) 647 [M + H]+ |
| 31* | benzyl-N-(4-methylphenyl)-C(=O)-CH₂CH₂-pyrrolidine | amorphous powder MS (APCI) 673 [M + H]+ |
| 32* | benzyl-N-(4-methylphenyl)-C(=O)-CH₂CH₂-NEt₂ | amorphous powder MS (APCI) 675 [M + H]+ |
| 33* | benzyl-N-(4-methylphenyl)-C(=O)-CH₂-NMe₂ | amorphous powder MS (APCI) 633 [M + H]+ |

*hydrochloride
Me: methyl group, Et: ethyl group

TABLE 1-continued (No. 6)

| Ex. Nos. | R¹ | Physicochemical properties etc. |
|---|---|---|
| 34* | n-propyl-N-(4-methylphenyl)-C(=O)-CH₂CH₂-pyrrolidine | amorphous powder MS (APCI) 625 [M + H]+ |
| 35* | n-propyl-N-(4-methylphenyl)-C(=O)-CH₂CH₂-NMe₂ | amorphous powder MS (APCI) 599 [M + H]+ |
| 36* | n-propyl-N-(4-methylphenyl)-C(=O)-CH₂CH₂-NEt₂ | amorphous powder MS (APCI) 627 [M + H]+ |
| 37 | EtOCH₂CH₂-N-(4-methylphenyl)-C(=O)-CH₂CH₂-NMe₂ | amorphous powder MS (APCI) 629 [M + H]+ |
| 38 | EtOCH₂CH₂-N-(4-methylphenyl)-C(=O)-CH₂CH₂-NEt₂ | amorphous powder MS (APCI) 657 [M + H]+ |
| 39 | EtOCH₂CH₂-N-(4-methylphenyl)-C(=O)-CH₂-NMe₂ | amorphous powder MS (APCI) 615 [M + H]+ |

*hydrochloride
Me: methyl group, Et: ethyl group

TABLE 1

(No. 7)

| Ex. Nos. | R¹ | Physicochemical properties etc. |
|---|---|---|
| 40 | O=C(CH₂NEt₂)–N(CH₂CH₂OEt)(p-tolyl) | amorphous powder MS (APCI) 643 [M + H]+ |
| 41 | O=C(CH₂CH₂NMe₂)–NH(p-tolyl) | amorphous powder MS (APCI) 557 [M + H]+ |
| 42 | O=C(CH₂CH₂NEt₂)–NH(p-tolyl) | amorphous powder MS (APCI) 585 [M + H]+ |
| 43 | O=C(Et)–N(CH₂CH₂NMe₂)(CH₂-p-tolyl) | amorphous powder MS (APCI) 599 [M + H]+ |
| 44 | O=C(cPr)–N(CH₂CH₂NMe₂)(CH₂-p-tolyl) | amorphous powder MS (APCI) 611 [M + H]+ |

Me: methyl group, Et: ethyl group

TABLE 1

(No. 8)

| Ex. Nos. | R¹ | Physicochemical properties etc. |
|---|---|---|
| 45 | Me₂N–CH₂CH₂–N(C(O)CH₂CH₂CH₂Me)(CH₂-p-tolyl) | amorphous powder MS (APCI) 627 [M + H]+ |
| 46 | Me₂N–CH₂CH₂–N(C(O)CH₂OMe)(CH₂-p-tolyl) | amorphous powder MS (APCI) 615 [M + H]+ |
| 47 | Me₂N–CH₂CH₂–N(C(O)NMe₂)(CH₂-p-tolyl) | amorphous powder MS (APCI) 614 [M + H]+ |
| 48 | Me₂N–CH₂CH₂–N(C(O)OCH₂CH₂OMe)(CH₂-p-tolyl) | amorphous powder MS (APCI) 645 [M + H]+ |
| 49 | Me₂N–CH₂CH₂–N(C(O)NH–CH₂CH₂CH₂Me)(CH₂-p-tolyl) | amorphous powder MS (APCI) 642 [M + H]+ |

Me: methyl group, Et: ethyl group

TABLE 1

(No. 9)

| Ex. Nos. | R¹ | Physicochemical properties etc. |
|---|---|---|
| 50 | Me₂N-CH₂-(3-methylphenyl) | amorphous powder MS (APCI) 500 [M + H]+ |
| 51 | Me-CH₂CH₂CH₂-N(Me)-CH₂-(3-methylphenyl) | amorphous powder MS (APCI) 542 [M + H]+ |
| 52 | MeO-CH₂CH₂-N(CH(Me)₂)-CH₂-(3-methylphenyl) | amorphous powder MS (APCI) 572 [M + H]+ |
| 53 | Me-N(piperazine)-CH₂-(3-methylphenyl) | amorphous powder MS (APCI) 555 [M + H]+ |
| 54 | pyrrolidinyl-CH₂-(3-methylphenyl) | amorphous powder MS (APCI) 526 [M + H]+ |
| 55 | piperidinyl-CH₂-(3-methylphenyl) | amorphous powder MS (APCI) 540 [M + H]+ |

Me: methyl group, Et: ethyl group

TABLE 1

(No. 10)

| Ex. Nos. | R¹ | Physicochemical properties etc. |
|---|---|---|
| 56 | Me₂N-CH₂CH₂-N(Me)-(4-methylphenyl) | amorphous powder MS (APCI) 571 [M + H]+ |
| 57 | Me₂N-CH₂CH₂-N(CH₂CH(Me)₂)-(4-methylphenyl) | amorphous powder MS (APCI) 585 [M + H]+ |
| 58 | Me₂N-CH₂CH₂-N(CH₂-cyclohexyl)-(4-methylphenyl) | amorphous powder MS (APCI) 625 [M + H]+ |

Me: methyl group, Et: ethyl group

TABLE 1

(No. 11)

| Ex. Nos. | R¹ | Physicochemical properties etc. |
|---|---|---|
| 59 | Me₂N-CH₂CH₂-N(Me)-CH₂-(4-methylphenyl) | amorphous powder MS (APCI) 557 [M + H]+ |
| 60 | Me₂N-CH₂CH₂-N(CH₂CH₂Me)-CH₂-(4-methylphenyl) | amorphous powder MS (APCI) 585 [M + H]+ |

TABLE 1-continued

(No. 11)

Structure: R¹-C(=O)-N(piperazine)-N-[pyrazolo[3,4-d]pyrimidine]-N-CH₂-C₆H₄-OEt (3-position)

| Ex. Nos. | R¹ | Physicochemical properties etc. |
|---|---|---|
| 61 | Me₂N-CH₂CH₂-N(CH(Me)Me-)-CH₂-C₆H₄-Me (4-) (isobutyl branch with Me, Me) | amorphous powder MS (APCI) 599 [M + H]+ |
| 62 | Me₂N-CH₂CH₂-N(CH₂-cyclohexyl)-CH₂-C₆H₄-Me (4-) | amorphous powder MS (APCI) 639 [M + H]+ |
| 63 | Et₂N-CH₂-C₆H₄-Me (4-) | amorphous powder MS (APCI) 528 [M + H]+ |

Me: methyl group, Et: ethyl group

TABLE 1

(No. 12)

Structure: R¹-C(=O)-N(piperazine)-N-[pyrazolo[3,4-d]pyrimidine]-N-CH₂-C₆H₄-OEt (3-position)

| Ex. Nos. | R¹ | Physicochemical properties etc. |
|---|---|---|
| 64 | Me-CH₂CH₂CH₂-N(Me)-CH₂-C₆H₄-Me (4-) | amorphous powder MS (APCI) 542 [M + H]+ |
| 65 | Me-CH₂CH₂CH₂-N(Et)-CH₂-C₆H₄-Me (4-) | amorphous powder MS (APCI) 556 [M + H]+ |
| 66 | MeO-CH₂CH₂-N(CH(Me)Me)-CH₂-C₆H₄-Me (4-) | amorphous powder MS (APCI) 572 [M + H]+ |

TABLE 1-continued

(No. 12)

| Ex. Nos. | R¹ | Physicochemical properties etc. |
|---|---|---|
| 67 | PhCH₂-N(Et)-CH₂-C₆H₄-Me (4-) | amorphous powder MS (APCI) 590 [M + H]+ |
| 68 | cyclohexyl-N(Me)-CH₂-C₆H₄-Me (4-) | amorphous powder MS (APCI) 568 [M + H]+ |
| 69 | pyrrolidin-1-yl-CH₂-C₆H₄-Me (4-) | amorphous powder MS (APCI) 526 [M + H]+ |
| 70 | piperidin-1-yl-CH₂-C₆H₄-Me (4-) | amorphous powder MS (APCI) 540 [M + H]+ |
| 71 | 4-(H₂N-C(=O))-piperidin-1-yl-CH₂-C₆H₄-Me (4-) | amorphous powder MS (APCI) 583 [M + H]+ |

Me: methyl group, Et: ethyl group

TABLE 1

(No. 13)

Structure: R¹-C(=O)-N(piperazine)-N-[pyrazolo triazine]-N-CH₂-C₆H₄-OEt (3-position)

| Ex. Nos. | R¹ | Physicochemical properties etc. |
|---|---|---|
| 72 | MeO-CH₂CH₂-N(Me)-CH₂-C₆H₄-Me (4-) | amorphous powder MS (APCI) 544 [M + H]+ |

TABLE 1-continued (No. 13)

[Structure: R¹-C(=O)-piperazine-pyrazolo[3,4-d]pyrimidine with N-CH₂-(3-ethoxyphenyl) substituent]

| Ex. Nos. | R¹ | Physicochemical properties etc. |
|---|---|---|
| 73 | -C(=O)-CH₂-NHBoc with N(Me₂NCH₂CH₂)(4-methylphenyl) | amorphous powder MS (APCI) 686 [M + H]+ |
| 74 | Et₂N-CH₂CH₂-N(SO₂Me)-(2-MeO-5-methylphenyl) | amorphous powder MS (APCI) 665 [M + H]+ |
| 75 | Me₂N-CH₂-(5-methylpyridin-2-yl) | amorphous powder MS (APCI) 501 [M + H]+ |
| 76* | Et-N(Me)-CH₂-(5-methylpyridin-2-yl) | amorphous powder MS (APCI) 515 [M + H]+ |

*hydrochloride,
Me: methyl group, Et: ethyl group, Boc: tert-butoxycarbonyl group

TABLE 1

(No. 14)

[Structure: R¹-C(=O)-piperazine-pyrazolo[3,4-d]pyrimidine with N-CH₂-(3-ethoxyphenyl) substituent]

| Ex. Nos. | R¹ | Physicochemical properties etc. |
|---|---|---|
| 77* | Et₂N-CH₂-(5-methylpyridin-2-yl) | amorphous powder MS (APCI) 529 [M + H]+ |
| 78* | pyrrolidin-1-yl-CH₂-(5-methylpyridin-2-yl) | amorphous powder MS (APCI) 527 [M + H]+ |

TABLE 1-continued (No. 14)

| Ex. Nos. | R¹ | Physicochemical properties etc. |
|---|---|---|
| 79* | piperidin-1-yl-CH₂-(5-methylpyridin-2-yl) | amorphous powder MS (APCI) 541 [M + H]+ |
| 80* | 4-methylpiperazin-1-yl-CH₂-(5-methylpyridin-2-yl) | amorphous powder MS (APCI) 556 [M + H]+ |
| 81* | MeO-CH₂CH₂-N(iPr)-CH₂-(5-methylpyridin-2-yl) | amorphous powder MS (APCI) 572 [M + H]+ |
| 82* | Me-N(iPr)-CH₂-(5-methylpyridin-2-yl) | amorphous powder MS (APCI) 529 [M + H]+ |
| 83* | isoindolin-2-yl-CH₂-(5-methylpyridin-2-yl) | amorphous powder MS (APCI) 575 [M + H]+ |

*hydrochloride
Me: methyl group, Et: ethyl group

EXAMPLES 84 TO 92

The corresponding materials are treated in the same manner as described in Example 2 to give the compounds as shown in the following Table 2.

TABLE 2

[Structure: R¹-Y-C(=O)-piperazine-pyrazolo[3,4-d]pyrimidine with N-CH₂-(3-ethoxyphenyl) substituent]

| Ex. Nos. | R¹ | Physicochemical properties etc. |
|---|---|---|
| 84 | Me-CH(-)-CH₂-piperidin-1-yl (4-methylpiperidine with ethyl linker) | amorphous powder MS (APCI) 492 [M + H]+ |

TABLE 2-continued

[Structure: R¹—Y—C(=O)—piperazine—pyrazolo[3,4-d]pyrimidine with N-benzyl-3-OEt substituent]

| Ex. Nos. | R¹ | Physicochemical properties etc. |
|---|---|---|
| 85 | 1-(1-methylethyl)-4-methylpiperidinyl | amorphous powder MS (APCI) 492 [M + H]+ |
| 86 | 4-(pyridin-4-yl)-4-ethylpiperidinyl | amorphous powder MS (APCI) 541 [M + H]+ |
| 87 | Me₂N-propyl | amorphous powder MS (APCI) 452 [M + H]+ |
| 88 | 1-(1-methylethyl)-4-ethylpiperidinyl | amorphous powder MS (APCI) 506 [M + H]+ |
| 89 | 1-(1-methylethyl)-4-propylpiperidinyl | amorphous powder MS (APCI) 520 [M + H]+ |
| 90 | Me₂N-CH₂-cyclohexyl (trans) | amorphous powder MS (APCI) 506 [M + H]+ |
| 91 | Me₂N-cyclohexyl (trans) | amorphous powder MS (APCI) 492 [M + H]+ |
| 92 | morpholinyl-cyclohexyl (trans) | amorphous powder MS (APCI) 534 [M + H]+ |

Me: methyl group, Et: ethyl group

EXAMPLES 93 TO 129

The corresponding materials are treated in the same manner as described in Example 3, or Examples 3 and 5(2) to give the compounds as shown in the following Table 3.

TABLE 3

(No. 1)

[Structure: carbamate with NMe₂-propyl-O-C(=O)-N(CH₂CH₂NMe₂)-CH₂-phenyl-C(=O)-piperazine-pyrazolo[3,4-d]pyrimidine-N-Q-R²]

| Ex. Nos. | R¹ | Physicochemical properties etc. |
|---|---|---|
| 93* | 2-chlorophenyl (ethyl) | amorphous powder MS (APCI) 662 [M + H]+ |
| 94* | 2-methyl-6-ethylpyridinyl | amorphous powder MS (APCI) 643 [M + H]+ |
| 95* | 2-ethyl-6-ethylpyridinyl | amorphous powder MS (APCI) 657 [M + H]+ |
| 96* | 3-methylphenyl (ethyl) | amorphous powder MS (APCI) 642 [M + H]+ |
| 97* | 2-ethoxy-6-ethylpyridinyl | amorphous powder MS (APCI) 673 [M + H]+ |
| 98* | 3-ethoxyphenyl (ethyl) | amorphous powder MS (APCI) 672 [M + H]+ |
| 99* | 3-trifluoromethoxyphenyl (ethyl) | amorphous powder MS (APCI) 712 [M + H]+ |

*fumarate
Me: methyl group, Et: ethyl group

TABLE 3
(No. 2)

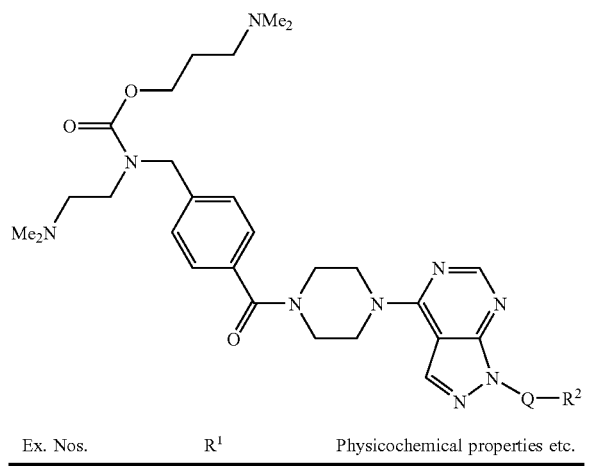

| Ex. Nos. | R¹ | Physicochemical properties etc. |
|---|---|---|
| 100* | 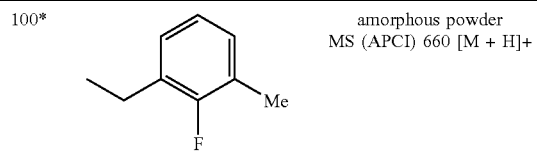 | amorphous powder<br>MS (APCI) 660 [M + H]+ |
| 101* | 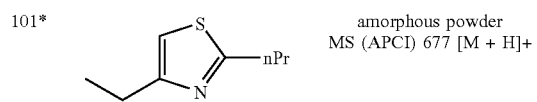 | amorphous powder<br>MS (APCI) 677 [M + H]+ |
| 102* | 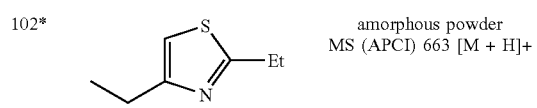 | amorphous powder<br>MS (APCI) 663 [M + H]+ |
| 103* | 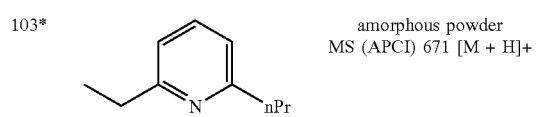 | amorphous powder<br>MS (APCI) 671 [M + H]+ |
| 104* |  | amorphous powder<br>MS (APCI) 671 [M + H]+ |
| 105* | 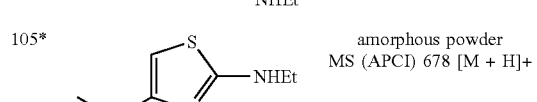 | amorphous powder<br>MS (APCI) 678 [M + H]+ |

*fumarate
Me: methyl group, Et: ethyl group, nPr: n-propyl group

TABLE 3
(No. 3)

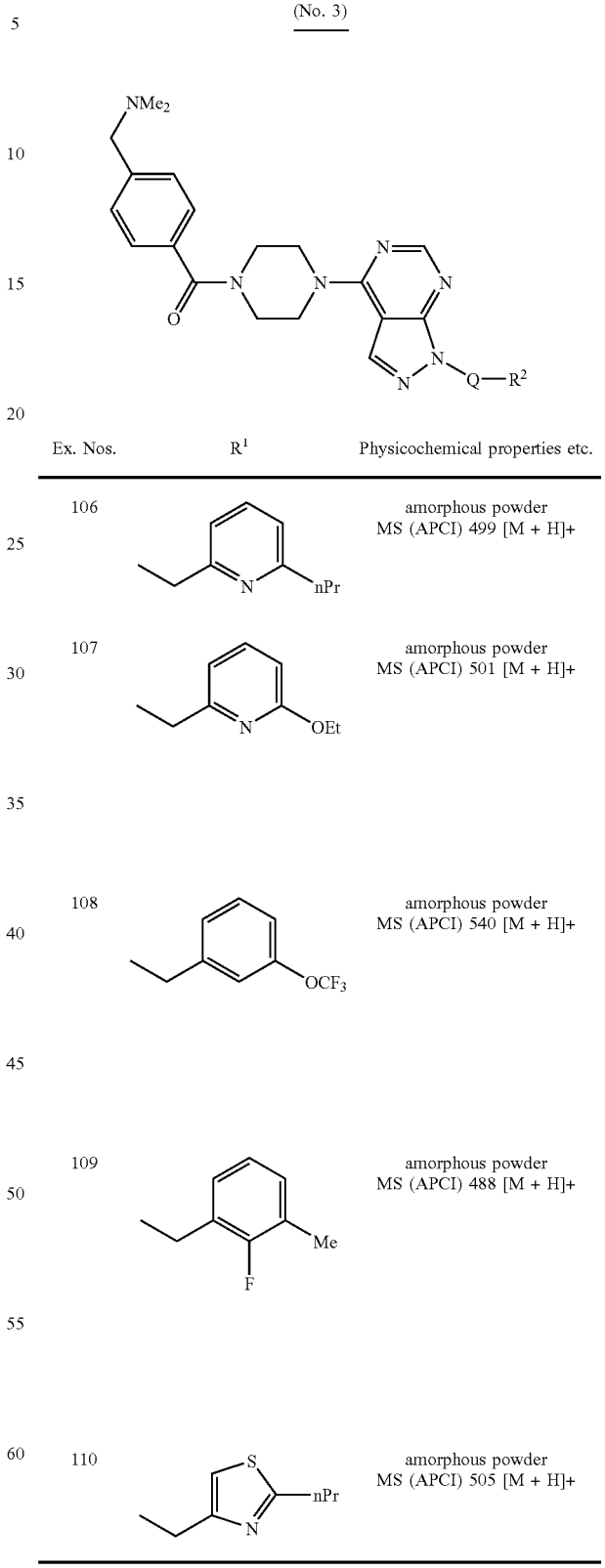

Me: methyl group, Et: ethyl group, nPr: n-propyl group

TABLE 3

(No. 4)

[Structure: para-substituted benzamide with N-(2-dimethylaminoethyl) and 3-(dimethylamino)propanoyl groups on aniline nitrogen; benzoyl-piperazine linked to pyrazolo[3,4-d]pyrimidine bearing N-Q-R²]

| Ex. Nos. | R¹ | Physicochemical properties etc. |
|---|---|---|
| 111* | 2-chlorophenyl | amorphous powder MS (APCI) 618 [M + H]+ |
| 112* | 6-ethyl-pyridin-2-yl | amorphous powder MS (APCI) 613 [M + H]+ |
| 113* | 6-methyl-pyridin-2-yl | amorphous powder MS (APCI) 599 [M + H]+ |
| 114* | 6-n-propyl-pyridin-2-yl | amorphous powder MS (APCI) 627 [M + H]+ |
| 115* | 2-fluoro-3-methylphenyl | amorphous powder MS (APCI) 616 [M + H]+ |
| 116* | 6-ethoxy-pyridin-2-yl | amorphous powder MS (APCI) 629 [M + H]+ |
| 117* | 3-methylphenyl | amorphous powder MS (APCI) 598 [M + H]+ |

*fumarate
Me: methyl group, Et: ethyl group, nPr: n-propyl group

TABLE 3

(No. 5)

[Structure: analogous para-substituted benzamide, piperazine-pyrazolopyrimidine-N-Q-R²]

| Ex. Nos. | R¹ | Physicochemical properties etc. |
|---|---|---|
| 118* | 3-(trifluoromethoxy)phenyl | amorphous powder MS (APCI) 668 [M + H]+ |
| 119* | 3-(ethylamino)phenyl | amorphous powder MS (APCI) 627 [M + H]+ |
| 120* | 2-(ethylamino)thiazol-4-yl | amorphous powder MS (APCI) 634 [M + H]+ |
| 121* | 2-ethyl-thiazol-4-yl | amorphous powder MS (APCI) 619 [M + H]+ |
| 122* | 2-n-propyl-thiazol-4-yl | amorphous powder MS (APCI) 633 [M + H]+ |

*fumarate
Me: methyl group, Et: ethyl group, nPr: n-propyl group

TABLE 3

(No. 6)

[Structure: R¹-Y-C(O)-piperazine-pyrazolo[3,4-d]pyrimidine-N-CH₂-(3-ethoxyphenyl)]

| Ex. Nos. | R¹—Y— | Physicochemical properties etc. |
|---|---|---|
| 123 | Me₂N-CH₂CH₂-O-(4-propenylphenyl) | amorphous powder MS (APCI) 556 [M + H]+ |

TABLE 3-continued (No. 6)

R¹—Y—[piperazine-N]—[pyrazolopyrimidine]—N—CH₂—C₆H₄—OEt

| Ex. Nos. | R¹—Y— | Physicochemical properties etc. |
|---|---|---|
| 124 | Me₂N-(CH₂)₃-O-C₆H₄-CH=CH- | amorphous powder MS (APCI) 570 [M + H]+ |
| 125 | morpholine-N-CH₂CH₂-O-C₆H₃(OMe)-CH=CH-Me | amorphous powder MS (APCI) 628 [M + H]+ |
| 126 | Me₂N-CH₂CH₂-O-C₆H₄(m-Me) | amorphous powder MS (APCI) 530 [M + H]+ |
| 127 | piperidine-N-CH₂CH₂-O-C₆H₄(p-Me) | amorphous powder MS (APCI) 570 [M + H]+ |
| 128 | Me₂N-CH₂-C₆H₄(p-Me) | amorphous powder MS (APCI) 500 [M + H]+ |
| 129 | Me-N(piperazine)N-C₆H₄(p-Me) | amorphous powder MS (APCI) 541 [M + H]+ |

Me: methyl group, Et: ethyl group

EXAMPLES 130 TO 133

The corresponding materials are treated in the same manner as described in Examples 4 and 5(2) to give the compounds as shown in the following Table 4.

TABLE 4

R¹—C(O)—[piperazine]—[pyrazolopyrimidine]—N—CH₂—C₆H₄—OEt

| Ex. Nos. | R¹ | Physicochemical properties etc. |
|---|---|---|
| 130* | piperidine-N-CH₂CH₂-NH-C(=O)-C₆H₄(p-Me) | amorphous powder MS (APCI) 597 [M + H]+ |
| 131* | pyrrolidine-N-CH₂CH₂-NH-C(=O)-C₆H₄(p-Me) | amorphous powder MS (APCI) 583 [M + H]+ |
| 132* | piperidine-N-CH₂CH₂-N(Me)-C(=O)-C₆H₄(p-Me) | amorphous powder MS (APCI) 611 [M + H]+ |
| 133* | Et₂N-CH₂CH₂-N(Me)-C(=O)-C₆H₄(p-Me) | amorphous powder MS (APCI) 599 [M + H]+ |

*hydrochloride
Me: methyl group, Et: ethyl group

EXAMPLES 134 TO 139

The corresponding materials are treated in the same manner as described in Example 6 to give the compounds as shown in the following Table 5.

TABLE 5

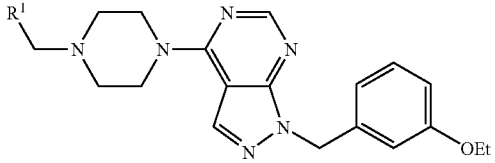

| Ex. Nos. | R¹ | Physicochemical properties etc. |
|---|---|---|
| 134 | 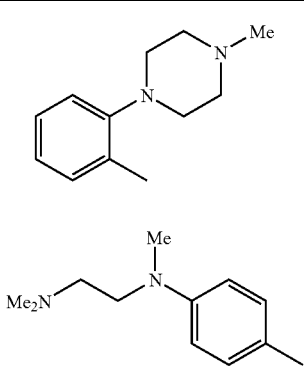 | amorphous powder MS (APCI) 527 [M + H]+ |
| 135 | 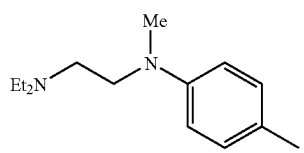 | amorphous powder MS (APCI) 529 [M + H]+ |
| 136 | 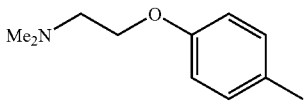 | amorphous powder MS (APCI) 557 [M + H]+ |
| 137 | 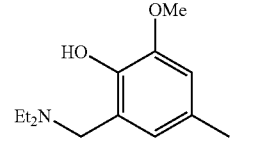 | amorphous powder MS (APCI) 530 [M + H]+ |
| 138 | 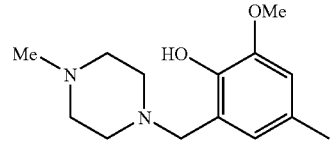 | amorphous powder MS (APCI) 560 [M + H]+ |
| 139 | 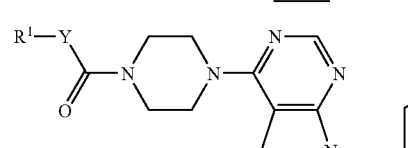 | amorphous powder MS (APCI) 587 [M + H]+ |

Me: methyl group, Et: ethyl group

EXAMPLES 140 TO 181

The corresponding materials are treated in the same manner as described in either one of Examples 1 to 6 to give the compounds as shown in the following Table 6.

TABLE 6 (No. 1)

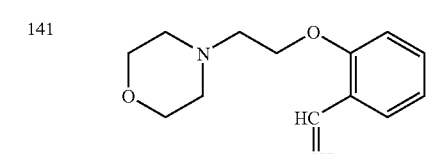

| Ex. Nos. | R¹—Y— | Physicochemical properties etc. |
|---|---|---|
| 140 | 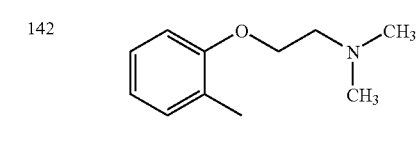 | amorphous powder MS (APCI) 628 [M + H]+ |
| 141 | 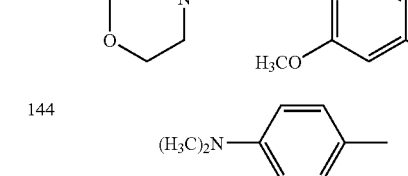 | amorphous powder MS (APCI) 598 [M + H]+ |
| 142 | 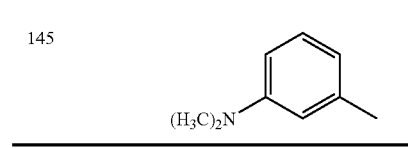 | amorphous powder MS (APCI) 530 [M + H]+ |
| 143 | 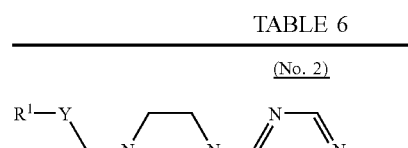 | amorphous powder MS (APCI) 602 [M + H]+ |
| 144 | (H₃C)₂N—⟨benzene⟩—CH₃ | amorphous powder MS (APCI) 486 [M + H]+ |
| 145 | (H₃C)₂N—⟨benzene⟩—CH₃ | amorphous powder MS (APCI) 486 [M + H]+ |

TABLE 6 (No. 2)

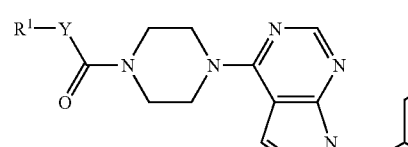

| Ex. Nos. | R¹—Y— | Physicochemical properties etc. |
|---|---|---|
| 146 | (H₃C)₂N—⟨benzene⟩—Et | amorphous powder MS (APCI) 500 [M + H]+ |

TABLE 6-continued

(No. 2)

R¹—Y— substituted piperazine-pyrazolo[3,4-d]pyrimidine with 1-(3-ethoxybenzyl) group

| Ex. Nos. | R¹—Y— | Physicochemical properties etc. |
|---|---|---|
| 147 | 6-(dimethylamino)-2-naphthyl (with methyl) | amorphous powder MS (APCI) 536 [M + H]+ |
| 148 | 4-(dimethylamino)styryl | amorphous powder MS (APCI) 512 [M + H]+ |
| 149 | N-(2-ethoxyethyl)-N-(4-methylphenyl)amino | amorphous powder MS (APCI) 530 [M + H]+ |
| 150 | 2-(pyrimidin-2-yl)-4-methylpiperidin-1-yl | amorphous powder MS (APCI) 528 [M + H]+ |
| 151 | piperidin-1-yl-CH₂CH₂— | colorless liquid MS (APCI) 478 [M + H]+ |

TABLE 6

(No. 3)

| Ex. Nos. | R¹—Y— | Physicochemical properties etc. |
|---|---|---|
| 152 | H₃C-CH₂CH₂CH₂-N(CH₃)-CH₂-(3-methylphenyl) | amorphous powder MS (APCI) 542 [M + H]+ |
| 153 | H₃C-O-CH₂CH₂-N(CH₃)-CH₂-(3-methylphenyl) | amorphous powder MS (APCI) 544 [M + H]+ |
| 154 | morpholino-CH₂-(3-methylphenyl) | amorphous powder MS (APCI) 542 [M + H]+ |

TABLE 6-continued

(No. 3)

| Ex. Nos. | R¹—Y— | Physicochemical properties etc. |
|---|---|---|
| 155 | morpholino-CH₂-(4-methylphenyl) | amorphous powder MS (APCI) 542 [M + H]+ |

TABLE 6

(No. 4)

| Ex. Nos. | R¹—Y— | Physicochemical properties etc. |
|---|---|---|
| 156 | 4-(pyrimidin-4-yl)piperidin-1-yl-propyl | amorphous powder MS (APCI) 556 [M + H]+ |
| 157 | N-benzyl-N-(4-methylphenyl)-2-morpholinoacetamide | colorless liquid MS (APCI) 675 [M + H]+ |
| 158 | N-benzyl-N-(4-methylphenyl)-3-morpholinopropanamide | amorphous powder MS (APCI) 689 [M + H]+ |

TABLE 6-continued

(No. 4)

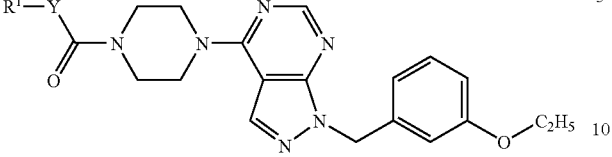

| Ex. Nos. | R¹—Y— | Physicochemical properties etc. |
|---|---|---|
| 159 | 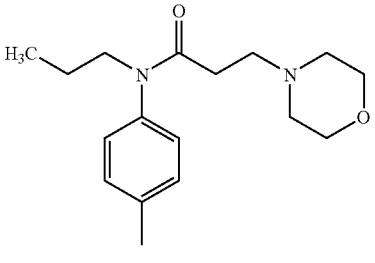 | colorless liquid MS (APCI) 641 [M + H]+ |
| 160* | 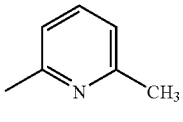 | amorphous powder MS (APCI) 599 [M + H]+ |

*hydrochloride

TABLE 6

(No. 5)

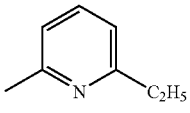

| Ex. Nos. | R² | Physicochemical properties etc. |
|---|---|---|
| 161 | 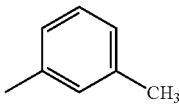 | amorphous powder MS (APCI) 471 [M + H]+ |
| 162 | 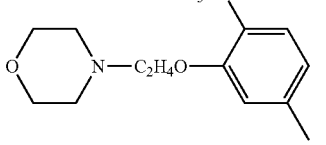 | amorphous powder MS (APCI) 485 [M + H]+ |
| 163 | 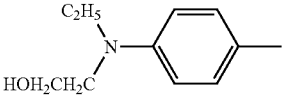 | amorphous powder MS (APCI) 470 [M + H]+ |
| 164 | 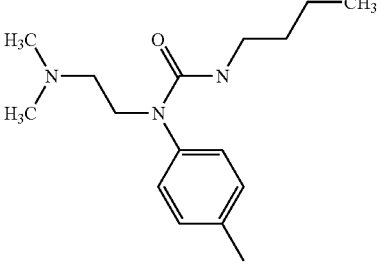 | amorphous powder MS (APCI) 491 [M + H]+ |

TABLE 6

(No. 6)

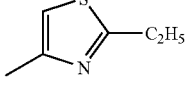

| Ex. Nos. | R¹ | Physicochemical properties etc. |
|---|---|---|
| 165 | (morpholine-$C_2H_4O$-, $H_3CO$, methyl-phenyl) | amorphous powder MS (APCI) 587 [M + H]+ |
| 166 | ($C_2H_5$, $HOCH_2CH_2$)N-(p-tolyl) | amorphous powder MS (APCI) 516 [M + H]+ |
| 167 | 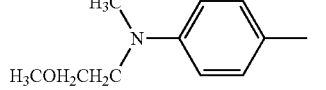 | amorphous powder MS (APCI) 614 [M + H]+ |
| 168 | ($H_3C$, $H_3COCH_2CH_2$)N-(p-tolyl) | amorphous powder MS (APCI) 516 [M + H]+ |

TABLE 6-continued (No. 6)

| Ex. Nos. | R¹ | Physicochemical properties etc. |
|---|---|---|
| 169 | H₃C, HOH₂CH₂C-N-C₆H₄-CH₃ | amorphous powder MS (APCI) 502 [M + H]+ |

TABLE 6

(No. 7)

| Ex. Nos. | R¹ | Physicochemical properties etc. |
|---|---|---|
| 170 | C₂H₅-C(=O)-N(C₆H₄-CH₃)-CH₂CH₂-N(CH₃)₂ | amorphous powder MS (APCI) 571 [M + H]+ |
| 171 | cyclopropyl-C(=O)-N(C₆H₄-CH₃)-CH₂CH₂-N(CH₃)₂ | amorphous powder MS (APCI) 583 [M + H]+ |
| 172 | CH₃CH₂CH₂CH₂-C(=O)-N(C₆H₄-CH₃)-CH₂CH₂-N(CH₃)₂ | amorphous powder MS (APCI) 599 [M + H]+ |
| 173 | CH₃O-CH₂-C(=O)-N(C₆H₄-CH₃)-CH₂CH₂-N(CH₃)₂ | amorphous powder MS (APCI) 587 [M + H]+ |

TABLE 6-continued (No. 7)

| Ex. Nos. | R¹ | Physicochemical properties etc. |
|---|---|---|
| 174 | 2-methylphenyl-O-CH₂CH₂-morpholine | amorphous powder MS (APCI) 558 [M + H]+ |
| 175 | 4-methyl-2-methoxyphenyl-O-CH₂CH₂-morpholine | amorphous powder MS (APCI) 588 [M + H]+ |

TABLE 6

(No. 8)

| Ex. Nos. | R¹ | Physicochemical properties etc. |
|---|---|---|
| 176 | 3-methylphenyl-O-CH₂CH₂-morpholine | amorphous powder MS (APCI) 558 [M + H]+ |
| 177 | (H₃C)₂N-C₆H₄-CH₃ | amorphous powder MS (APCI) 472 [M + H]+ |
| 178 | (C₂H₅)₂N-C₆H₄-CH₃ | amorphous powder MS (APCI) 500 [M + H]+ |
| 179 | morpholine-N-C₆H₄-CH₃ | amorphous powder MS (APCI) 514 [M + H]+ |
| 180 | 2-HO-3-H₃CO-5-methylphenyl-CH₂-morpholine | amorphous powder MS (APCI) 574 [M + H]+ |

TABLE 6-continued (No. 8)

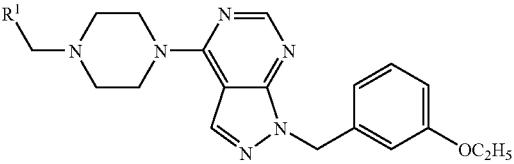

| Ex. Nos. | R¹ | Physicochemical properties etc. |
|---|---|---|
| 181 | HO, H₃CO, with CH₂N(CH₃)₂ and CH₃ substituents | amorphous powder MS (APCI) 532 [M + H]+ |

EXAMPLES 182 TO 341

The corresponding materials are treated in the same manner as described in Example 1, or Examples 1 and 4(3) to give the compounds as shown in the following Table 7.

TABLE 7

(No. 1)

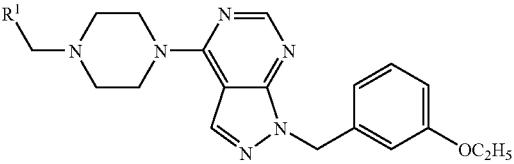

| Ex. Nos. | R¹ | Physicochemical properties etc. |
|---|---|---|
| 182 | HN−CH₂CH₂−NMe₂ benzoyl with p-methyl | amorphous powder MS (APCI) 557 [M + H]+ |
| 183 | MeN−CH₂CH₂−NMe₂ benzoyl with p-methyl | amorphous powder MS (APCI) 571 [M + H]+ |
| 184 | HN−CH₂CH₂CH₂−NMe₂ benzoyl with p-methyl | amorphous powder MS (APCI) 571 [M + H]+ |

TABLE 7-continued (No. 1)

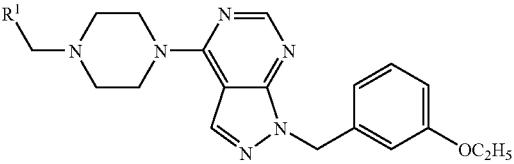

| Ex. Nos. | R¹ | Physicochemical properties etc. |
|---|---|---|
| 185 | HN−CH₂CH₂CH₂−imidazolyl benzoyl with p-methyl | amorphous powder MS (APCI) 594 [M + H]+ |

Me: methyl group, Et: ethyl group

TABLE 7

(No. 2)

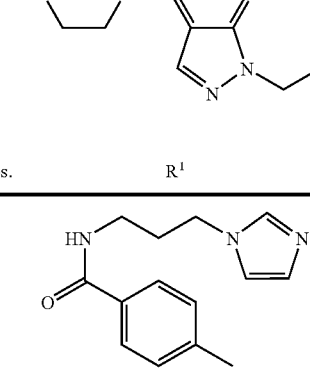

| Ex. Nos. | R¹ | Physicochemical properties etc. |
|---|---|---|
| 186 | HN−CH₂CH₂−NMe₂ benzoyl with p-methyl | amorphous powder MS (APCI) 571 [M + H]+ |
| 187 | MeN−CH₂CH₂−NMe₂ benzoyl with p-methyl | amorphous powder MS (APCI) 585 [M + H]+ |
| 188 | HN−CH₂CH₂CH₂−NMe₂ benzoyl with p-methyl | amorphous powder MS (APCI) 585 [M + H]+ |
| 189 | HN−CH₂CH₂CH₂−imidazolyl benzoyl with p-methyl | amorphous powder MS (APCI) 608 [M + H]+ |

TABLE 7-continued (No. 2)

| Ex. Nos. | R¹ | Physicochemical properties etc. |
|---|---|---|

Me: methyl group, nPr: n-propyl group

TABLE 7

(No. 3)

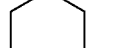

| Ex. Nos. | R¹ | Physicochemical properties etc. |
|---|---|---|
| 190* |  | amorphous powder MS (APCI) 665 [M + H]+ |
| 191* | 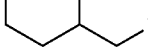 | amorphous powder MS (APCI) 653 [M + H]+ |
| 192* | 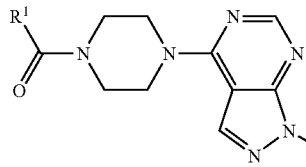 | amorphous powder MS (APCI) 679 [M + H]+ |
| 193* | 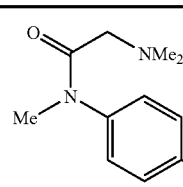 | amorphous powder MS (APCI) 681 [M + H]+ |

TABLE 7-continued (No. 3)

| Ex. Nos. | R¹ | Physicochemical properties etc. |
|---|---|---|
| 194* | 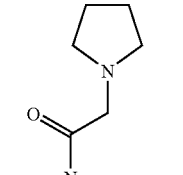 | amorphous powder MS (APCI) 557 [M + H]+ |
| 195* | | amorphous powder MS (APCI) 583 [M + H]+ |

*hydrochloride
Me: methyl group, Et: ethyl group

TABLE 7

(No. 4)

| Ex. Nos. | R¹ | Physicochemical properties etc. |
|---|---|---|
| 196* | | amorphous powder MS (APCI) 571 [M + H]+ |
| 197* | | amorphous powder MS (APCI) 597 [M + H]+ |

TABLE 7-continued

(No. 4)

[Structure: R¹-C(=O)-N(piperazine)-N-(pyrazolo[3,4-d]pyrimidine)-N-CH₂-(3-ethoxyphenyl)]

| Ex. Nos. | R¹ | Physicochemical properties etc. |
|---|---|---|
| 198* | C(=O)-N(Me)-(4-methylphenyl), CH₂CH₂-NEt₂ | amorphous powder MS (APCI) 599 [M + H]+ |
| 199 | C(=O)-N(CH₂-cyclohexyl)-(4-methylphenyl), CH₂-NMe₂ | amorphous powder MS (APCI) 639 [M + H]+ |
| 200* | C(=O)-N(CH₂-cyclohexyl)-(4-methylphenyl), CH₂-NEt₂ | amorphous powder MS (APCI) 667 [M + H]+ |

*hydrochloride
Me: methyl group, Et: ethyl group

TABLE 7

(No. 5)

[Structure: R¹-C(=O)-N(piperazine)-N-(pyrazolo[3,4-d]pyrimidine)-N-CH₂-(3-ethoxyphenyl)]

| Ex. Nos. | R¹ | Physicochemical properties etc. |
|---|---|---|
| 201** | Me₂N-CH₂-(2-bromo-4-methylphenyl) | amorphous powder MS (APCI) 578/580 [M + H]+ |
| 202** | Et₂N-CH₂-(2-bromo-4-methylphenyl) | amorphous powder MS (APCI) 606/608 [M + H]+ |
| 203** | pyrrolidinyl-CH₂-(2-bromo-4-methylphenyl) | amorphous powder MS (APCI) 604/606 [M + H]+ |

TABLE 7-continued

(No. 5)

[Structure: R¹-C(=O)-N(piperazine)-N-(pyrazolo[3,4-d]pyrimidine)-N-CH₂-(3-ethoxyphenyl)]

| Ex. Nos. | R¹ | Physicochemical properties etc. |
|---|---|---|
| 204** | Me₂N-CH₂-(2-methyl-4-methylphenyl) | amorphous powder MS (APCI) 514 [M + H]+ |

**dihydrochloride
Me: methyl group, Et: ethyl group

TABLE 7

(No. 6)

[Structure: R¹-Y-C(=O)-N(piperazine)-N-(pyrazolo[3,4-d]pyrimidine)-N-CH₂-(3-ethoxyphenyl)]

| Ex. Nos. | R¹—Y— | Physicochemical properties etc. |
|---|---|---|
| 205** | Me₂N-CH₂-C(=O)-N(4-methylpiperidinyl) | amorphous powder MS (APCI) 535 [M + H]+ |
| 206 | Me₂N-CH₂CH₂-C(=O)-N(4-methylpiperidinyl) | amorphous powder MS (APCI) 549 [M + H]+ |
| 207** | Et₂N-CH₂CH₂-C(=O)-N(4-methylpiperidinyl) | amorphous powder MS (APCI) 577 [M + H]+ |
| 208** | Me₂N-CH₂-C(=O)-N(4-ethylpiperidinyl) | amorphous powder MS (APCI) 549 [M + H]+ |
| 209** | Et₂N-CH₂-C(=O)-N(4-ethylpiperidinyl) | amorphous powder MS (APCI) 577 [M + H]+ |

TABLE 7-continued

(No. 6)

Core structure: R¹—Y—C(O)—piperazine—[pyrazolo[3,4-d]pyrimidine]—N-CH₂—(3-ethoxyphenyl)

| Ex. Nos. | R¹—Y— | Physicochemical properties etc. |
|---|---|---|
| 210** | pyrrolidin-1-yl-CH₂-C(O)-(4-ethylpiperidin-1-yl) | amorphous powder MS (APCI) 575 [M + H]+ |
| 211** | Me₂N-CH₂CH₂-C(O)-(4-ethylpiperidin-1-yl) | amorphous powder MS (APCI) 563 [M + H]+ |
| 212** | Et₂N-CH₂CH₂-C(O)-(4-ethylpiperidin-1-yl) | amorphous powder MS (APCI) 591 [M + H]+ |

**dihydrochloride
Me: methyl group, Et: ethyl group

TABLE 7

(No. 7)

| Ex. Nos. | R¹—Y— | Physicochemical properties etc. |
|---|---|---|
| 213 | Me₂N-CH₂-C(O)-(4-propylpiperidin-1-yl) | amorphous powder MS (APCI) 563 [M + H]+ |
| 214 | Et₂N-CH₂-C(O)-(4-propylpiperidin-1-yl) | amorphous powder MS (APCI) 591 [M + H]+ |
| 215 | pyrrolidin-1-yl-CH₂-C(O)-(4-propylpiperidin-1-yl) | amorphous powder MS (APCI) 589 [M + H]+ |

TABLE 7-continued

(No. 7)

| Ex. Nos. | R¹—Y— | Physicochemical properties etc. |
|---|---|---|
| 216** | pyrrolidin-1-yl-CH₂CH₂-C(O)-(4-propylpiperidin-1-yl) | amorphous powder MS (APCI) 603 [M + H]+ |
| 217 | Me₂N-CH₂-C(O)-NH-CH₂-(trans-cyclohexyl) | amorphous powder MS (APCI) 563 [M + H]+ |
| 218 | Et₂N-CH₂-C(O)-NH-CH₂-(trans-cyclohexyl) | amorphous powder MS (APCI) 591 [M + H]+ |
| 219 | pyrrolidin-1-yl-CH₂-C(O)-NH-CH₂-(trans-cyclohexyl) | amorphous powder MS (APCI) 589 [M + H]+ |

**dihydrochloride
Me: methyl group, Et: ethyl group

TABLE 7

(No. 8)

| Ex. Nos. | R¹—Y— | Physicochemical properties etc. |
|---|---|---|
| 220** | Et₂N-CH₂-(4-ethylphenyl) | amorphous powder MS (APCI) 542 [M + H]+ |
| 221** | pyrrolidin-1-yl-CH₂-(4-ethylphenyl) | amorphous powder MS (APCI) 540 [M + H]+ |

TABLE 7-continued

(No. 8)

| Ex. Nos. | R¹—Y— | Physicochemical properties etc. |
|---|---|---|
| 222** | piperidin-1-yl-CH₂-(4-methylphenyl) | amorphous powder MS (APCI) 554 [M + H]+ |
| 223** | Me₂CH-N(Me)-CH₂-(4-methylphenyl) | amorphous powder MS (APCI) 542 [M + H]+ |
| 224** | Me₂N-CH₂CH₂-(4-methylphenyl) | amorphous powder MS (APCI) 514 [M + H]+ |
| 225** | Et-N(Me)-CH₂CH₂-(4-methylphenyl) | amorphous powder MS (APCI) 528 [M + H]+ |
| 226** | Et₂N-CH₂CH₂-(4-methylphenyl) | amorphous powder MS (APCI) 542 [M + H]+ |

**dihydrochloride
Me: methyl group, Et: ethyl group

TABLE 7

(No. 9)

| Ex. Nos. | R¹ | Physicochemical properties etc. |
|---|---|---|
| 227** | pyrrolidin-1-yl-CH₂CH₂-(4-methylphenyl) | amorphous powder MS (APCI) 540 [M + H]+ |
| 228** | piperidin-1-yl-CH₂CH₂-(4-methylphenyl) | amorphous powder MS (APCI) 554 [M + H]+ |
| 229* | 2,5-dimethylpyrrolidin-1-yl-CH₂-(4-methylphenyl) | amorphous powder MS (APCI) 554 [M + H]+ |
| 230* | 2-(hydroxymethyl)pyrrolidin-1-yl-CH₂-(4-methylphenyl) | amorphous powder MS (APCI) 556 [M + H]+ |
| 231* | 2-(methoxymethyl)pyrrolidin-1-yl-CH₂-(4-methylphenyl) | amorphous powder MS (APCI) 570 [M + H]+ |
| 232* | 4-hydroxypiperidin-1-yl-CH₂-(4-methylphenyl) | amorphous powder MS (APCI) 556 [M + H]+ |
| 233* | 4-methylpiperazin-1-yl-CH₂-(4-methylphenyl) | amorphous powder MS (APCI) 555 [M + H]+ |

*hydrochloride,
**dihydrochloride
Me: methyl group, Et: ethyl group

TABLE 7

(No. 10)

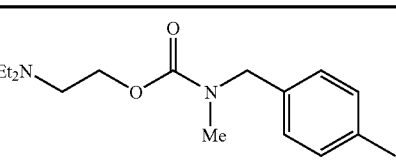

| Ex. Nos. | R¹ | Physicochemical properties etc. |
|---|---|---|
| 234* | Et₂N—CH₂CH₂—O—C(=O)—N(Me)—CH₂—(4-Me-C₆H₄) | amorphous powder MS (APCI) 629 [M + H]+ |
| 235* | pyrrolidinyl—CH₂CH₂—O—C(=O)—N(Me)—CH₂—(4-Me-C₆H₄) | amorphous powder MS (APCI) 627 [M + H]+ |
| 236** | pyrrolidinyl—CH₂—(2-Me,4-Me-C₆H₃) | amorphous powder MS (APCI) 540 [M + H]+ |
| 237** | Me₂N—CH₂CH₂—C(=O)—NH—CH₂—(trans-4-Me-cyclohexyl) | amorphous powder MS (APCI) 577 [M + H]+ |
| 238** | Et₂N—CH₂—(2-Me,4-Me-C₆H₃) | amorphous powder MS (APCI) 542 [M + H]+ |

*hydrochloride, **dihydrochloride
Me: methyl group, Et: ethyl group

TABLE 7-continued (No. 11)

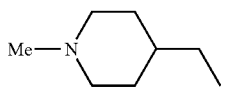

| Ex. Nos. | R¹—Y— | Physicochemical properties etc. |
|---|---|---|
| 239* | Me—N(4-ethylpiperidinyl)— | amorphous powder MS (APCI) 478 [M + H]+ |
| 240* | cyclopentyl—N(4-ethylpiperidinyl)— | amorphous powder MS (APCI) 532 [M + H]+ |

TABLE 7-continued

(No. 11)

R¹—Y—[piperazine-C(=O)]—[pyrazolo[3,4-d]pyrimidine]—N—CH₂—(3-ethoxyphenyl)

| Ex. Nos. | R¹—Y— | Physicochemical properties etc. |
|---|---|---|
| 241* | nPr-N-(piperidine)-CH₂CH₂- | amorphous powder MS (APCI) 520 [M + H]+ |
| 242* | MeO-CH₂CH₂-N-(piperidine)-CH₂CH₂- | amorphous powder MS (APCI) 522 [M + H]+ |
| 243* | nBu-N-(piperidine)-CH₂CH₂- | amorphous powder MS (APCI) 534 [M + H]+ |
| 244* | cyclopentyl-N-(piperidine)-CH₂CH₂- | amorphous powder MS (APCI) 546 [M + H]+ |
| 245* | Et₂CH-N-(piperidine)-CH₂CH₂- | amorphous powder MS (APCI) 534 [M + H]+ |

*hydrochloride
Me: methyl group, Et: ethyl group, nPr: n-propyl group, nBu: n-butyl group

TABLE 7

(No. 12)

R¹—Y—[piperazine-C(=O)]—[pyrazolo[3,4-d]pyrimidine]—N—CH₂—(3-ethoxyphenyl)

| Ex. Nos. | R¹—Y— | Physicochemical properties etc. |
|---|---|---|
| 246* | Me-N-(piperidine)-CH₂CH₂CH₂- | amorphous powder MS (APCI) 492 [M + H]+ |
| 247* | Et-N-(piperidine)-CH₂CH₂CH₂- | amorphous powder MS (APCI) 506 [M + H]+ |
| 248* | Me₂N-CH₂CH₂-N-(piperidine)-CH₂CH₂CH₂- | amorphous powder MS (APCI) 549 [M + H]+ |

TABLE 7-continued

(No. 12)

| Ex. Nos. | R¹—Y— | Physicochemical properties etc. |
|---|---|---|
| 249* | MeO-CH₂CH₂-N-(piperidine)-CH₂CH₂- | amorphous powder MS (APCI) 536 [M + H]+ |
| 250* | Me₂N-CH₂CH₂-N-(piperidine)-CH₂CH₂- | amorphous powder MS (APCI) 535 [M + H]+ |
| 251* | Et₂CH-N-(piperazine)-Et | amorphous powder MS (APCI) 535 [M + H]+ |
| 252* | nBu-N-(piperidine)-Et | amorphous powder MS (APCI) 520 [M + H]+ |

*hydrochloride
Me: methyl group, Et: ethyl group, nBu: n-butyl group

TABLE 7

(No. 13)

R¹—Y—[piperazine-C(=O)]—[pyrazolo[3,4-d]pyrimidine]—N—CH₂—(3-ethoxyphenyl)

| Ex. Nos. | R¹—Y— | Physicochemical properties etc. |
|---|---|---|
| 253* | Me₂N-CH₂CH₂-N-(3-methylpiperidine)- | amorphous powder MS (APCI) 521 [M + H]+ |
| 254* | Me₂CH-N-(piperazine)-Et | amorphous powder MS (APCI) 507 [M + H]+ |
| 255* | cyclopentyl-N-(piperazine)-Et | amorphous powder MS (APCI) 533 [M + H]+ |
| 256* | MeO-CH₂CH₂-N-(4-methylpiperidine)- | amorphous powder MS (APCI) 508 [M + H]+ |

TABLE 7-continued

(No. 13)

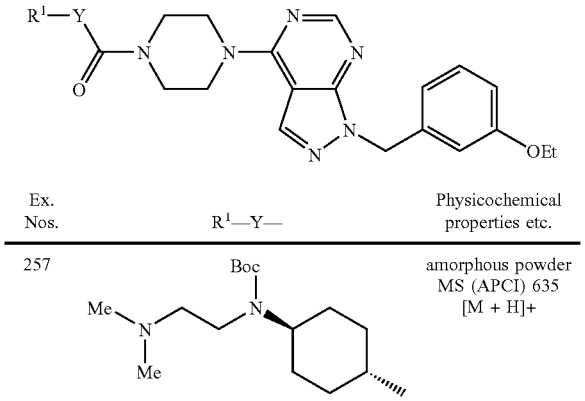

| Ex. Nos. | R¹—Y— | Physicochemical properties etc. |
|---|---|---|
| 257 | Me₂N-CH₂CH₂-N(Boc)-cyclohexyl-Me | amorphous powder MS (APCI) 635 [M + H]+ |

*hydrochloride
Me: methyl group, Et: ethyl group, Boc: tert-butoxycarbonyl group

TABLE 7

(No. 14)

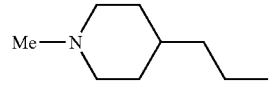

| Ex. Nos. | R¹—Y— | Physicochemical properties etc. |
|---|---|---|
| 258* | cyclopentyl-piperidine-ethyl | amorphous powder MS (APCI) 520 [M + H]+ |
| 259* | nPr-N-piperidine-ethyl | amorphous powder MS (APCI) 508 [M + H]+ |
| 260* | MeO-CH₂-piperidine-ethyl | amorphous powder MS (APCI) 510 [M + H]+ |
| 261* | Et₂CH-piperidine-ethyl | amorphous powder MS (APCI) 536 [M + H]+ |
| 262* | nBu-N-piperidine-propyl | amorphous powder MS (APCI) 522 [M + H]+ |
| 263* | Me₂N-CH₂CH₂-piperidine-propyl | amorphous powder MS (APCI) 537 [M + H]+ |
| 264* | Et₂CH-piperidine-ethyl | amorphous powder MS (APCI) 522 [M + H]+ |

TABLE 7-continued

(No. 14)

| Ex. Nos. | R¹—Y— | Physicochemical properties etc. |
|---|---|---|
| 265* | Me-N-piperidine-propyl | amorphous powder MS (APCI) 480 [M + H]+ |

*hydrochloride
Me: methyl group, Et: ethyl group, nPr: n-propyl group, nBu: n-butyl group

TABLE 7

(No. 15)

| Ex. Nos. | R¹—Y— | Physicochemical properties etc. |
|---|---|---|
| 266* | Et-N-piperidine-ethyl | amorphous powder MS (APCI) 494 [M + H]+ |
| 267* | cyclopentyl-piperidine-ethyl | amorphous powder MS (APCI) 534 [M + H]+ |
| 268* | MeO-CH₂-piperidine-ethyl | amorphous powder MS (APCI) 524 [M + H]+ |
| 269* | Me₂N-CH₂-piperidine-ethyl | amorphous powder MS (APCI) 523 [M + H]+ |
| 270* | Me₂CH-piperazine-Et | amorphous powder MS (APCI) 495 [M + H]+ |
| 271* | Et₂CH-piperazine-Et | amorphous powder MS (APCI) 523 [M + H]+ |

TABLE 7-continued (No. 15)

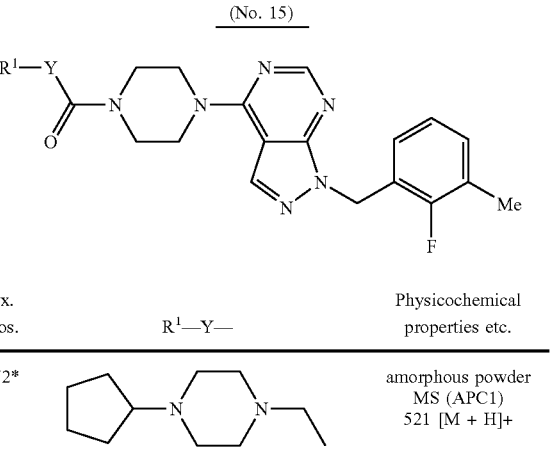

| Ex. Nos. | R¹—Y— | Physicochemical properties etc. |
|---|---|---|
| 272* | cyclopentyl-N-piperazine-ethyl | amorphous powder MS (APC1) 521 [M + H]+ |

*hydrochloride
Me: methyl group, Et: ethyl group

TABLE 7

(No. 16)

| Ex. Nos. | R¹—Y— | Physicochemical properties etc. |
|---|---|---|
| 273* | cyclopentyl-N-piperidine-ethyl | amorphous powder MS (APCI) 537 [M + H]+ |
| 274* | nPr—N-piperidine-ethyl | amorphous powder MS (APCI) 525 [M + H]+ |
| 275* | Et₂CH—N-piperidine-propyl | amorphous powder MS (APCI) 553 [M + H]+ |
| 276* | nBu—N-piperidine-ethyl | amorphous powder MS (APCI) 539 [M + H]+ |
| 277* | cyclopentyl-N-piperidine-propyl | amorphous powder MS (APCI) 551 [M + H]+ |
| 278* | Et₂CH—N-piperidine-ethyl | amorphous powder MS (APCI) 539 [M + H]+ |
| 279* | Me—N-piperidine-ethyl | amorphous powder MS (APCI) 497 [M + H]+ |

TABLE 7-continued (No. 16)

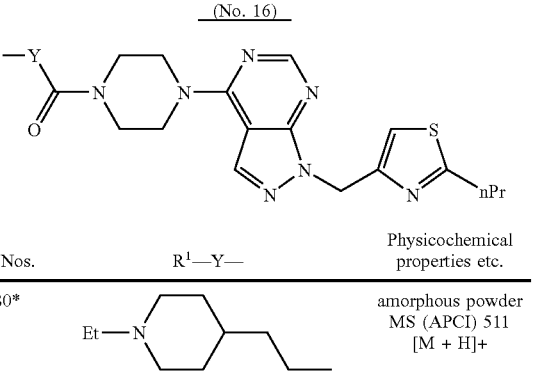

| Ex. Nos. | R¹—Y— | Physicochemical properties etc. |
|---|---|---|
| 280* | Et—N-piperidine-propyl | amorphous powder MS (APCI) 511 [M + H]+ |

*hydrochloride
Me: methyl group, Et: ethyl group, nPr: n-propyl group, nBu: n-butyl group

TABLE 7

(No. 17)

| Ex. Nos. | R¹—Y— | Physicochemical properties etc. |
|---|---|---|
| 281* | MeO-ethyl-N-piperidine-ethyl | amorphous powder MS (APCI) 541 [M + H]+ |
| 282* | Me₂N-ethyl-N-piperidine-ethyl | amorphous powder MS (APCI) 540 [M + H]+ |
| 283* | Et₂CH—N-piperazine-ethyl | amorphous powder MS (APCI) 540 [M + H]+ |
| 284* | nBu—N-piperidine-ethyl | amorphous powder MS (APCI) 525 [M + H]+ |
| 285* | Me₂CH—N-piperazine-ethyl | amorphous powder MS (APCI) 512 [M + H]+ |
| 286* | cyclopentyl-N-piperidine-ethyl | amorphous powder MS (APCI) 538 [M + H]+ |
| 287* | Me₂N-ethyl-N-piperidine-ethyl | amorphous powder MS (APCI) 554 [M + H]+ |

*hydrochloride
Me: methyl group, Et: ethyl group, nPr: n-propyl group, nBu: n-butyl group

TABLE 7

(No. 18)

R¹—Y—C(=O)—[piperazine]—[pyrazolo[3,4-d]pyrimidine]—N-CH₂—[pyridine]-nPr

| Ex. Nos. | R¹—Y— | Physicochemical properties etc. |
|---|---|---|
| 288* | cyclopentyl-N(piperidine)-4-ethyl | amorphous powder MS (APCI) 531 [M + H]+ |
| 289* | Et₂CH-N(piperidine)-4-nPr | amorphous powder MS (APCI) 547 [M + H]+ |
| 290* | nBu-N(piperidine)-4-nPr | amorphous powder MS (APCI) 533 [M + H]+ |
| 291* | nPr-N(piperidine)-4-nPr | amorphous powder MS (APCI) 519 [M + H]+ |
| 292* | cyclopentyl-N(piperidine)-4-nPr | amorphous powder MS (APCI) 545 [M + H]+ |
| 293* | Et₂CH-N(piperidine)-4-Et | amorphous powder MS (APCI) 533 [M + H]+ |
| 294* | Me-N(piperidine)-4-Et | amorphous powder MS (APCI) 491 [M + H]+ |

*hydrochloride
Me: methyl group, Et: ethyl group, nPr: n-propyl group, nBu: n-butyl group

TABLE 7

(No. 19)

R¹—Y—C(=O)—[piperazine]—[pyrazolo[3,4-d]pyrimidine]—N-CH₂—[pyridine]-nPr

| Ex. Nos. | R¹—Y— | Physicochemical properties etc. |
|---|---|---|
| 295* | Et-N(piperidine)-4-nPr | amorphous powder MS (APCI) 505 [M + H]+ |
| 296* | Me₂N-CH₂CH₂-N(piperidine)-4-nPr | amorphous powder MS (APCI) 548 [M + H]+ |
| 297* | MeO-CH₂CH₂-N(piperidine)-4-Et | amorphous powder MS (APCI) 535 [M + H]+ |
| 298* | Et₂CH-N(piperazine)-Et | amorphous powder MS (APCI) 534 [M + H]+ |
| 299* | nBu-N(piperidine)-4-Et | amorphous powder MS (APCI) 519 [M + H]+ |
| 300* | MeO-CH₂CH₂-N(piperidine)-4-Et | amorphous powder MS (APCI) 521 [M + H]+ |
| 301* | cyclopentyl-N(piperazine)-Et | amorphous powder MS (APCI) 532 [M + H]+ |

*hydrochloride
Me: methyl group, Et: ethyl group, nPr: n-propyl group, nBu: n-butyl group

TABLE 7

(No. 20)

R¹—C(=O)—[piperazine]—[pyrazolo[3,4-d]pyrimidine]—N-CH₂—[phenyl]-OEt

| Ex. Nos. | R¹ | Physicochemical properties etc. |
|---|---|---|
| 302* | (Me₂CH)₂N-CH₂-[4-methylphenyl] | amorphous powder MS (APCI) 556 [M + H]+ |

TABLE 7-continued (No. 20)

| Ex. Nos. | R¹ | Physicochemical properties etc. |
|---|---|---|
| 303** | HO-CH₂CH₂-N(Me)-CH₂-(4-methylphenyl) | amorphous powder MS (APCI) 530 [M + H]+ |
| 304* | cyclopropyl-C(O)-N(CH₂CH₂NMe₂)-(5-methylfuran-2-yl) | amorphous powder MS (APCI) 587 [M + H]+ |
| 305* | Me-C(O)-N(CH₂CH₂NMe₂)-(4-methylthiophen-2-yl) | amorphous powder MS (APCI) 577 [M + H]+ |
| 306* | cyclopropyl-C(O)-N(CH₂CH₂NMe₂)-(4-methylthiophen-2-yl) | amorphous powder MS (APCI) 603 [M + H]+ |

*hydrochloride,
**dihydrochloride
Me: methyl group, Et: ethyl group

TABLE 7

(No. 21)

| Ex. Nos. | R¹ | Physicochemical properties etc. |
|---|---|---|
| 307* | Me-CH=CH-C(O)-N(CH₂CH₂NMe₂)-(4-methylthiophen-2-yl) | amorphous powder MS (APCI) 603 [M + H]+ |
| 308* | Me-(CH₂)₃-NH-C(O)-N(CH₂CH₂NMe₂)-(4-methylthiophen-2-yl) | amorphous powder MS (APCI) 634 [M + H]+ |
| 309* | Me-NH-C(S)-N(CH₂CH₂NMe₂)-(4-methylthiophen-2-yl) | amorphous powder MS (APCI) 608 [M + H]+ |
| 310* | (5-methylthiophen-2-yl)-C(O)-N(Me)-CH₂CH₂-piperidin-1-yl | amorphous powder MS (APCI) 617 [M + H]+ |
| 311* | (5-methylthiophen-2-yl)-C(O)-NH-CH₂CH₂-NMe₂ | amorphous powder MS (APCI) 563 [M + H]+ |

TABLE 7-continued (No. 21)

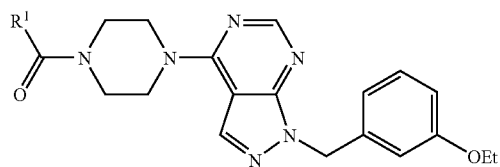

| Ex. Nos. | R¹ | Physicochemical properties etc. |
|---|---|---|
| 312* | 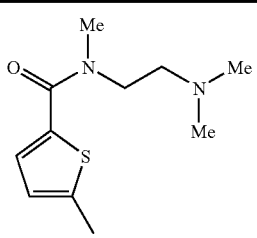 | amorphous powder MS (APCI) 577 [M + H]+ |

*hydrochloride
Me: methyl group, Et: ethyl group

TABLE 7

(No. 22)

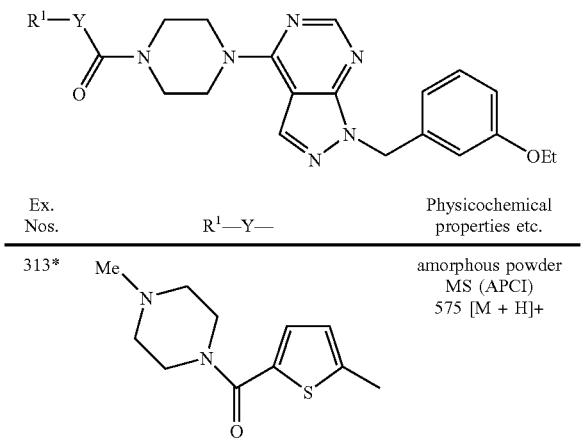

| Ex. Nos. | R¹—Y— | Physicochemical properties etc. |
|---|---|---|
| 313* | 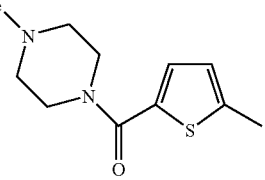 | amorphous powder MS (APCI) 575 [M + H]+ |
| 314* | 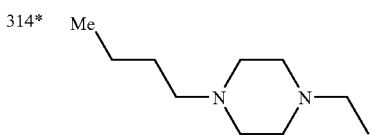 | amorphous powder MS (APCI) 521 [M + H]+ |
| 315 | 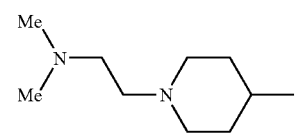 | amorphous powder MS (APCI) 521 [M + H]+ |
| 316* | 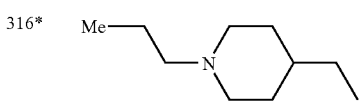 | amorphous powder MS (APCI) 506 [M + H]+ |

TABLE 7-continued (No. 22)

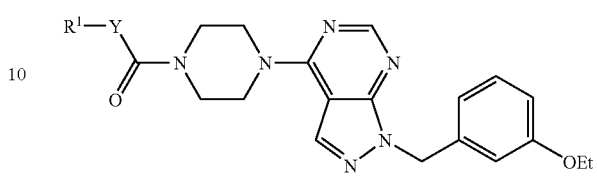

| Ex. Nos. | R¹—Y— | Physicochemical properties etc. |
|---|---|---|
| 317* | 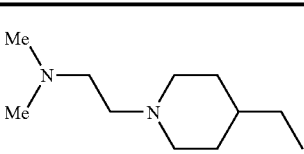 | amorphous powder MS (APCI) 536.5 [M + H]+ |
| 318 | 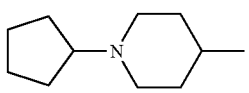 | amorphous powder MS (APCI) 518 [M + H]+ |

*hydrochloride
Me: methyl group, Et: ethyl group

TABLE 7

(No. 23)

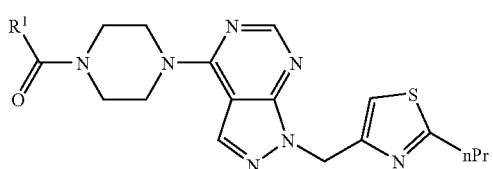

| Ex. Nos. | R¹ | Physicochemical properties etc. |
|---|---|---|
| 319* | 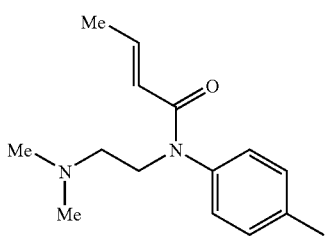 | amorphous powder MS (APCI) 602 [M + H]+ |
| 320* | 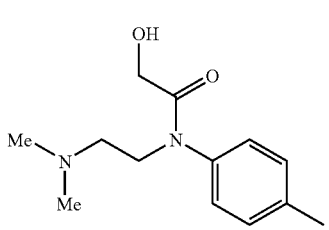 | amorphous powder MS (APCI) 592 [M + H]+ |

TABLE 7-continued (No. 23)

[Structure: R¹-C(=O)-piperazine-pyrazolo[3,4-d]pyrimidine with N-CH₂-thiazole-nPr substituent]

| Ex. Nos. | R¹ | Physicochemical properties etc. |
|---|---|---|
| 321* | furan-2-carbonyl with N,N-dimethylaminoethyl-N-(p-tolyl) group | amorphous powder MS (APCI) 628 [M + H]+ |
| 322* | acetyl with N,N-dimethylaminoethyl-N-(p-tolyl) group | amorphous powder MS (APCI) 576 [M + H]+ |
| 323* | N-methylthiourea with N,N-dimethylaminoethyl-N-(p-tolyl) group | amorphous powder MS (APCI) 607 [M + H]+ |
| 324* | cyclopropanecarbonyl with N,N-dimethylaminoethyl-N-(p-tolyl) group | amorphous powder MS (APCI) 602 [M + H]+ |

*hydrochloride
Me: methyl group, Et: ethyl group, nPr: n-propyl group

TABLE 7

(No. 24)

[Structure: R¹-C(=O)-piperazine-pyrazolo[3,4-d]pyrimidine with N-CH₂-pyridine-OEt substituent]

| Ex. Nos. | R¹ | Physicochemical properties etc. |
|---|---|---|
| 325* | (E)-2-butenoyl with N,N-dimethylaminoethyl-N-(p-tolyl) group | amorphous powder MS (APCI) 598 [M + H]+ |
| 326* | hydroxyacetyl with N,N-dimethylaminoethyl-N-(p-tolyl) group | amorphous powder MS (APCI) 588 [M + H]+ |
| 327* | furan-2-carbonyl with N,N-dimethylaminoethyl-N-(p-tolyl) group | amorphous powder MS (APCI) 624 [M + H]+ |
| 328* | acetyl with N,N-dimethylaminoethyl-N-(p-tolyl) group | amorphous powder MS (APCI) 572 [M + H]+ |
| 329* | N-methylthiourea with N,N-dimethylaminoethyl-N-(p-tolyl) group | amorphous powder MS (APCI) 603 [M + H]+ |
| 330* | cyclopropanecarbonyl with N,N-dimethylaminoethyl-N-(p-tolyl) group | amorphous powder MS (APCI) 598 [M + H]+ |

TABLE 7-continued

(No. 24)

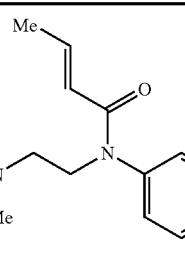

| Ex. Nos. | R[1] | Physicochemical properties etc. |
|---|---|---|

*hydrochloride
Me: methyl group, Et: ethyl group

TABLE 7
(No. 25)

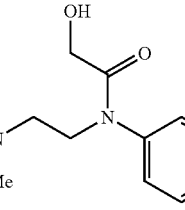

| Ex. Nos. | R[1] | Physicochemical properties etc. |
|---|---|---|
| 331* | 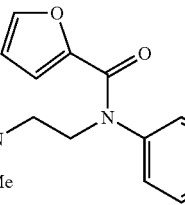 | amorphous powder MS (APCI) 596 [M + H]+ |
| 332* | 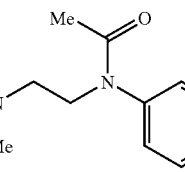 | amorphous powder MS (APCI) 586 [M + H]+ |
| 333* | 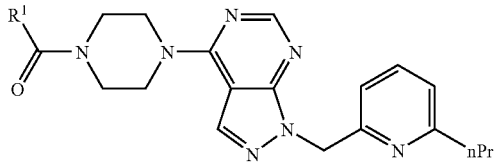 | amorphous powder MS (APCI) 622 [M + H]+ |
| 334* | 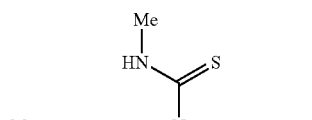 | amorphous powder MS (APCI) 570 [M + H]+ |

TABLE 7-continued

(No. 25)

| Ex. Nos. | R[1] | Physicochemical properties etc. |
|---|---|---|
| 335* | 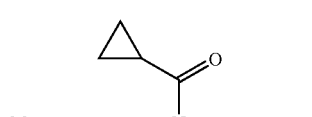 | amorphous powder MS (APCI) 601 [M + H]+ |
| 336* | 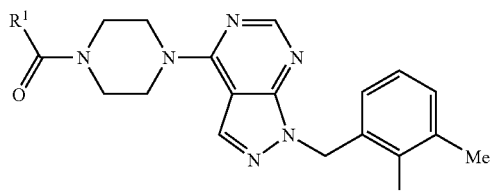 | amorphous powder MS (APCI) 596 [M + H]+ |

*hydrochloride
Me: methyl group, Et: ethyl group, nPr: n-propyl group

TABLE 7
(No. 26)

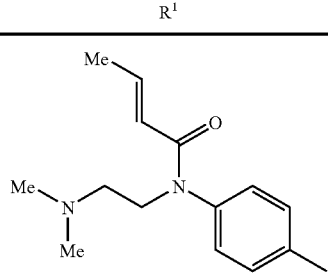

| Ex. Nos. | R[1] | Physicochemical properties etc. |
|---|---|---|
| 337* | Me(acryloyl) | amorphous powder MS (APCI) 585 [M + H]+ |

TABLE 7-continued (No. 26)

| Ex. Nos. | R¹ | Physicochemical properties etc. |
|---|---|---|
| 338* | OH-CH₂-C(=O)– (hydroxyacetyl) with Me₂N-CH₂CH₂-N(p-tolyl)– | amorphous powder MS (APCI) 575 [M + H]+ |
| 339* | Me-C(=O)– (acetyl) with Me₂N-CH₂CH₂-N(p-tolyl)– | amorphous powder MS (APCI) 559 [M + H]+ |
| 340* | MeHN-C(=S)– (methylthiourea) with Me₂N-CH₂CH₂-N(p-tolyl)– | amorphous powder MS (APCI) 590 [M + H]+ |
| 341* | cyclopropyl-C(=O)– with Me₂N-CH₂CH₂-N(p-tolyl)– | amorphous powder MS (APCI) 585 [M + H]+ |

*hydrochloride
Me: methyl group

EXAMPLE 342

The corresponding materials are treated in the same manner as described in Example 2 to give the compound as shown in the following Table 8.

TABLE 8

| Ex. Nos. | R¹—Y— | Physicochemical properties etc. |
|---|---|---|
| 342 | Me₂CH-N(piperidin-4-yl with CH=CH-Me)– | amorphous powder MS (APCI) 518 [M + H]+ |

Me: methyl group, Et: ethyl group

EXAMPLES 343 TO 365

The corresponding materials are treated in the same manner as described in Examples 3, Examples 3 and 4(3) to give the compounds as shown in the following Table 9.

TABLE 9

(No. 1)

| Ex. Nos. | —Q—R² | Physicochemical properties etc. |
|---|---|---|
| 343 | 6-ethyl-2-nPr-pyridin-yl-CH₂– | oil MS (APCI) 529 [M + H]+ |
| 344 | 6-ethyl-2-Me-pyridin-yl-CH₂– | amorphous powder MS (APCI) 501 [M + H]+ |
| 345 | 6-ethyl-2-Et-pyridin-yl-CH₂– | amorphous powder MS (APCI) 515 [M + H]+ |

TABLE 9-continued (No. 1)

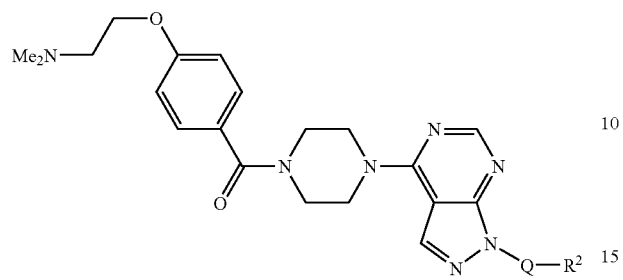

| Ex. Nos. | —Q—R² | Physicochemical properties etc. |
|---|---|---|
| 346 | 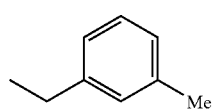 | amorphous powder<br>MS (APCI) 500 [M + H]+ |
| 347 | 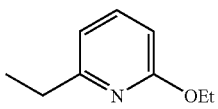 | amorphous powder<br>MS (APCI) 531 [M + H]+ |
| 348 | 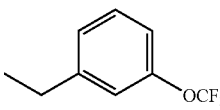 | amorphous powder<br>MS (APCI) 570 [M + H]+ |
| 349 | 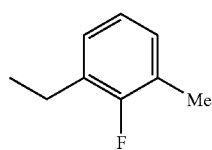 | amorphous powder<br>MS (APCI) 518 [M + H]+ |

Me: methyl group, Et: ethyl group, nPr: n-propyl group

TABLE 9

(No. 2)

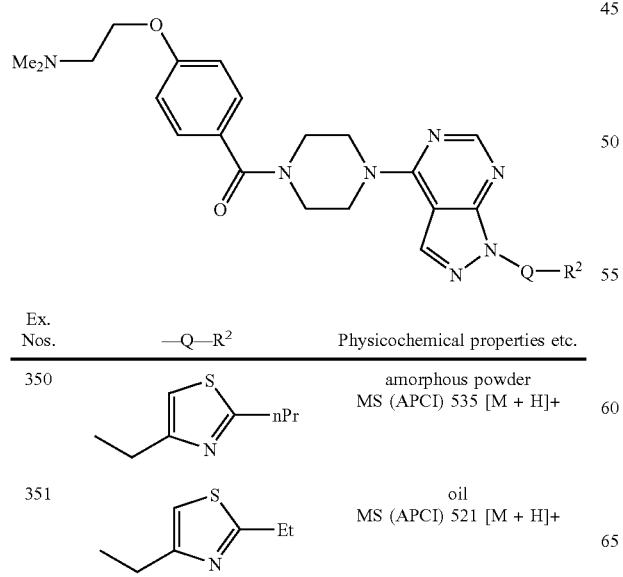

| Ex. Nos. | —Q—R² | Physicochemical properties etc. |
|---|---|---|
| 350 | 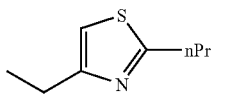 | amorphous powder<br>MS (APCI) 535 [M + H]+ |
| 351 | 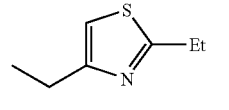 | oil<br>MS (APCI) 521 [M + H]+ |
| 352 | 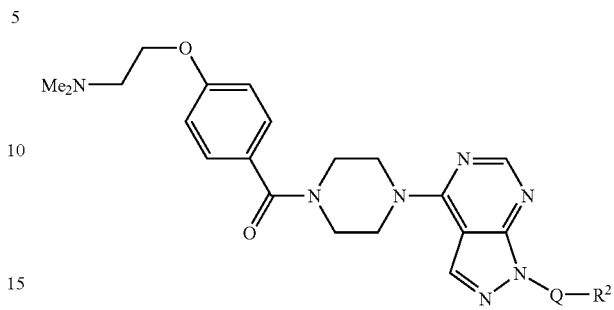 | oil<br>MS (APCI) 544 [M + H]+ |

Me: methyl group, Et: ethyl group, nPr: n-propyl group

TABLE 9

(No. 3)

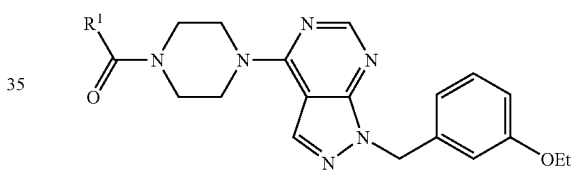

| Ex. Nos. | R¹ | Physicochemical properties etc. |
|---|---|---|
| 353** | Me₂N—CH₂—(2-OMe, 4-Me-C₆H₃) | amorphous powder<br>MS (APCI) 530 [M + H]+ |
| 354** | EtN(Me)—CH₂—(2-OMe, 4-Me-C₆H₃) | amorphous powder<br>MS (APCI) 544 [M + H]+ |
| 355** | Et₂N—CH₂—(2-OMe, 4-Me-C₆H₃) | amorphous powder<br>MS (APCI) 558 [M + H]+ |
| 356** | pyrrolidinyl-CH₂—(2-OMe, 4-Me-C₆H₃) | amorphous powder<br>MS (APCI) 556 [M + H]+ |

TABLE 9-continued (No. 3)

| Ex. Nos. | R¹ | Physicochemical properties etc. |
|---|---|---|
| 357** | (piperidinyl-CH2- with 2-OMe, 4-Me phenyl) | amorphous powder MS (APCI) 570 [M + H]+ |
| 358** | (Me)2CH-N(Me)-CH2- with 2-OMe, 4-Me phenyl | amorphous powder MS (APCI) 558 [M + H]+ |

**dihydrochloride
Me: methyl group, Et: ethyl group

TABLE 9

(No. 4)

| Ex. Nos. | R¹ | Physicochemical properties etc. |
|---|---|---|
| 359** | Me2N-CH2-(thiophene-Me) | amorphous powder MS (APCI) 506 [M + H]+ |
| 360** | Et2N-CH2-(thiophene-Me) | amorphous powder MS (APCI) 534 [M + H]+ |
| 361** | pyrrolidinyl-CH2-(thiophene-Me) | amorphous powder MS (APCI) 532 [M + H]+ |
| 362** | Me2N-CH2-(furan-Me) | amorphous powder MS (APCI) 490 [M + H]+ |
| 363** | Et2N-CH2-(furan-Me) | amorphous powder MS (APCI) 518 [M + H]+ |
| 364** | pyrrolidinyl-CH2-(furan-Me) | amorphous powder MS (APCI) 516 [M + H]+ |

TABLE 9-continued (No. 4)

| Ex. Nos. | R¹ | Physicochemical properties etc. |
|---|---|---|

**dihydrochloride,
Me: methyl group, Et: ethyl group

TABLE 9

(No. 5)

| Ex. Nos. | R¹ | Physicochemical properties etc. |
|---|---|---|
| 365** | Me2N-CH2-(2-OMe, 4-Me phenyl) | amorphous powder MS (APCI) 518 [M + H]+ |

**dihydrochloride,
Me: methyl group

EXAMPLE 366

To a solution of tert-butyl 4-[N-acetyl-N-[2-(1-pyrrolidinyl)ethyl]amino]-benzoic acid (37 mg, compound obtained in Reference Example 107) in methylene chloride (0.2 mL) is added trifluoroacetic acid (0.2 mL), and the mixture is shaken at room temperature for one day. The reaction mixture is concentrated and the residue is subjected to azeotropic distillation successively with chloroform, 4N HCl-dioxane and chloroform to give 4-[N-acetyl-N-[2-(1-pyrrolidinyl)ethyl]amino]benzoate hydrochloride. The product and 1 (3-ethoxybenzyl)-4-piperazin-1-yl-1H-pyrazolo[3,4-d]pyrimidine dihydrochloride are treated in the same manner (condensation reaction) as described in Example 3 and then the resultant product is treated in the same manner as described in Example 4(3) to give 1-(3-ethoxybenzyl)-4-[4-[4-[N-acetyl-N-[2-(1-pyrrolidinyl)ethyl]amino]benzoyl]piperazin-1-yl]-1H-pyrazolo[3,4-d]pyrimidine hydrochloride (15 mg, yield; 21%) as an amorphous powder. MS (APCI) m/z; 597 [M+H]+

EXAMPLES 367 TO 380

The corresponding materials are treated in the same manner as describe in Example 366 to give the compounds as shown in the following Table 9.1.

TABLE 9.1

(No. 1)

[Structure: R¹-C(=O)-N(piperazine)N-[pyrazolo[3,4-d]pyrimidine]-N(CH₂-phenyl-3-OEt)]

| Ex. Nos. | R¹ | Physicochemical properties etc. |
|---|---|---|
| 367 | furan-2-yl-C(=O)-N(CH₂CH₂CH₂NMe₂)-(4-methylphenyl) | amorphous powder MS (APCI) 637 [M + H]+ |
| 368* | MeO-CH₂-C(=O)-N(CH₂CH₂-pyrrolidin-1-yl)-(4-methylphenyl) | amorphous powder MS (APCI) 627 [M + H]+ |
| 369* | Me-CH₂CH₂CH₂-C(=O)-N(CH₂CH₂-pyrrolidin-1-yl)-(4-methylphenyl) | amorphous powder MS (APCI) 639 [M + H]+ |
| 370* | cyclopropyl-C(=O)-N(CH₂CH₂-pyrrolidin-1-yl)-(4-methylphenyl) | amorphous powder MS (APCI) 623 [M + H]+ |
| 371* | MeO-CH₂-C(=O)-N(CH₂CH₂NEt₂)-(4-methylphenyl) | amorphous powder MS (APCI) 629 [M + H]+ |
| 372* | Me-C(=O)-N(CH₂CH₂NEt₂)-(4-methylphenyl) | amorphous powder MS (APCI) 599 [M + H]+ |

*hydrochloride
Me: methyl group, Et: ethyl group

TABLE 9.1

(No. 2)

[Structure: R¹-C(=O)-N(piperazine)N-[pyrazolo[3,4-d]pyrimidine]-N(CH₂-phenyl-3-OEt)]

| Ex. Nos. | R¹ | Physicochemical properties etc. |
|---|---|---|
| 373* | furan-2-yl-C(=O)-N(CH₂CH₂-pyrrolidin-1-yl)-(4-methylphenyl) | amorphous powder MS (APCI) 649 [M + H]+ |
| 374* | Me-C(=O)-N(CH₂CH₂CH₂NMe₂)-(4-methylphenyl) | amorphous powder MS (APCI) 585 [M + H]+ |
| 375* | Me-CH₂CH₂CH₂-C(=O)-N(CH₂CH₂CH₂NMe₂)-(4-methylphenyl) | amorphous powder MS (APCI) 627 [M + H]+ |
| 376* | cyclopropyl-C(=O)-N(CH₂CH₂CH₂NMe₂)-(4-methylphenyl) | amorphous powder MS (APCI) 611 [M + H]+ |
| 377* | MeO-CH₂-C(=O)-N(CH₂CH₂CH₂NMe₂)-(4-methylphenyl) | amorphous powder MS (APCI) 615 [M + H]+ |
| 378* | Me-CH₂CH₂CH₂-C(=O)-N(CH₂CH₂NEt₂)-(4-methylphenyl) | amorphous powder MS (APCI) 641 [M + H]+ |

*hydrochloride
Me: methyl group, Et: ethyl group

TABLE 9.1

(No. 3)

R¹-C(=O)-N(piperazine)-N-[pyrazolo[3,4-d]pyrimidine]-N-CH₂-C₆H₄-OEt

| Ex. Nos. | R¹ | Physicochemical properties etc. |
|---|---|---|
| 379 | cyclopropyl-C(=O)-N(Et₂NCH₂CH₂-)-(4-methylphenyl) | amorphous powder MS (APCI) 625 [M + H]+ |
| 380 | 2-furyl-C(=O)-N(Et₂NCH₂CH₂-)-(4-methylphenyl) | amorphous powder MS (APCI) 651 [M + H]+ |

Me: methyl group, Et: ethyl group

EXAMPLE 381

(1) To 4-hydroxybenzoic acid (1.06 g) is added successively methylene chloride (30 mL), 1-(3-ethoxybenzyl)-4-piperazin-1-yl-1H-pyrazolo[3,4-d]pyrimidine dihydrochloride (3.02 g), 1-hydroxybenzotriazole (1.25 g), triethylamine (3.7 mL) and 1-ethyl-3-(3-dimethylaminopropyl)carbodiimide hydrochloride (1.78 g). The mixture is stirred at room temperature for 17 hours. The reaction mixture is diluted with chloroform and thereto is added a saturated sodium hydrogencarbonate solution. After stirring, the organic layer is separated and evaporated to remove solvent. The resultant residue is purified by flash column chromatography on silica gel (Solvent; chloroform:methanol=50:1) to give 1-(3-ethoxybenzyl)-4-[4-(4-hydroxybenzoyl)piperazin-1-yl]-1H-pyrazolo[3,4-d]pyrimidine (2.70 g, yield; 80%) as an amorphous powder. MS (APCI) m/z: 459 [M+H]+

(2) To a solution of the compound obtained in the above step (1) (250 mg), 3-dimethylamino-2,2-dimethyl-1-propanol (215 mg), and triphenylphosphine (429 mg) in tetrahydrofuran (4.0 mL) is added dropwise diisopropyl azodicarboxylate (330 mg) under ice-cooling and the mixture is stirred at room temperature overnight. The reaction mixture is diluted with methylene chloride (4 mL) and treated with cation-exchange resin (ISOLUTE SCX; IST Ltd., Solvent; methanol:methylene chloride=1:1→1N ammonia/methanol). The resultant crude product is purified by flash column chromatography on silica gel (Solvent; chloroform:methanol=10:1) and then the product is treated in the same manner as described in Example 4(3) to give 1-(3-ethoxybenzyl)-4-[4-[4-[3-(dimethylamino)-2,2-dimethylpropyloxy]benzoyl]piperazin-1-yl]-1H-pyrazolo[3,4-d]pyrimidine hydrochloride (257 mg, yield; 78%) as an amorphous powder. MS (APCI) m/z: 572 [M+H]+

EXAMPLES 382 TO 403

The corresponding materials are treated in the same manner as described in Example 381 to give the compounds as shown in the following Table 10.

TABLE 10

(No. 1)

R¹-C(=O)-N(piperazine)-N-[pyrazolo[3,4-d]pyrimidine]-N-CH₂-C₆H₄-OEt

| Ex. Nos. | R¹ | Physicochemical properties etc. |
|---|---|---|
| 382* | Et₂N-CH₂CH₂-O-(4-methylphenyl) | amorphous powder MS (APCI) 558 [M + H]+ |
| 383* | Me₂N-C(Me)₂-CH₂-O-(4-methylphenyl) | amorphous powder MS (APCI) 558 [M + H]+ |
| 384* | Et₂N-CH₂CH₂CH₂-O-(4-methylphenyl) | amorphous powder MS (APCI) 572 [M + H]+ |

TABLE 10-continued (No. 1)

[Structure: R¹-C(=O)-N(piperazine)N-[pyrazolo[3,4-d]pyrimidine]-N(CH₂-phenyl-OEt)]

| Ex. Nos. | R¹ | Physicochemical properties etc. |
|---|---|---|
| 385* | pyrrolidine-CH₂CH₂-O-(4-methylphenyl) | amorphous powder<br>MS (APCI) 556 [M + H]+ |
| 386* | morpholine-CH₂CH₂-O-(4-methylphenyl) | amorphous powder<br>MS (APCI) 572 [M + H]+ |
| 387* | (N-Me-pyrrolidin-2-yl)-CH₂-O-(4-methylphenyl) | amorphous powder<br>MS (APCI) 556 [M + H]+ |
| 388* | (N-iPr-piperidin-4-yl)-CH₂CH₂-O-(4-methylphenyl) | amorphous powder<br>MS (APCI) 612 [M + H]+ |

*hydrochloride
Me: methyl group, Et: ethyl group

TABLE 10 (No. 2)

[Structure: R¹-C(=O)-N(piperazine)N-[pyrazolo[3,4-d]pyrimidine]-N(CH₂-phenyl-OEt)]

| Ex. Nos. | R¹ | Physicochemical properties etc. |
|---|---|---|
| 389* | PhCH₂-N(Me)-CH₂CH₂-O-(4-methylphenyl) | amorphous powder<br>MS (APCI) 606 [M + H]+ |
| 390* | (N-Me-piperidin-2-yl)-CH₂-O-(4-methylphenyl) | amorphous powder<br>MS (APCI) 570 [M + H]+ |
| 391* | (1-(1-methylethyl)-piperidin-4-yl)-CH₂-O-(4-methylphenyl) | amorphous powder<br>MS (APCI) 598 [M + H]+ |
| 392* | (1-methyl-imidazol-2-yl)-CH₂-O-(4-methylphenyl) | amorphous powder<br>MS (APCI) 553 [M + H]+ |

TABLE 10-continued (No. 2)

| Ex. Nos. | R¹ | Physico-chemical properties etc. |
|---|---|---|
| 393* | Me₂N-CH₂CH₂CH₂-O-C₆H₄-Me (NMe₂-propyl-O-tolyl) | amorphous powder MS (APCI) 544 [M + H]+ |
| 394* | (iPr)₂N-CH₂CH₂-O-C₆H₄-Me | amorphous powder MS (APCI) 586 [M + H]+ |
| 395* | Et₂N-C(Me)₂-CH₂-O-C₆H₄-Me | amorphous powder MS (APCI) 586 [M + H]+ |

*hydrochloride
Me: methyl group, Et: ethyl group

TABLE 10

(No. 3)

| Ex. Nos. | R¹ | Physicochemical properties etc. |
|---|---|---|
| 396* | Et₂N-CH₂CH₂-O-C₆H₄-Me | amorphous powder MS (APCI) 557 [M + H]+ |
| 397* | Et₂N-CH₂CH₂CH₂-O-C₆H₄-Me | amorphous powder MS (APCI) 571 [M + H]+ |
| 398* | (iPr)₂N-CH₂CH₂-O-C₆H₄-Me | amorphous powder MS (APCI) 585 [M + H]+ |

TABLE 10-continued (No. 3)

| Ex. Nos. | R¹ | Physicochemical properties etc. |
|---|---|---|
| 399* | pyrrolidinyl-CH₂CH₂-O-C₆H₄-Me | amorphous powder MS (APCI) 555 [M + H]+ |
| 400* | morpholinyl-CH₂CH₂-O-C₆H₄-Me | amorphous powder MS (APCI) 571 [M + H]+ |
| 401* | N-methyl-pyrrolidin-2-yl-CH₂-O-C₆H₄-Me | amorphous powder MS (APCI) 555 [M + H]+ |

*hydrochloride
Me: methyl group, Et: ethyl group, nPr: n-propyl group

TABLE 10

(No. 4)

| Ex. Nos. | R¹ | Physicochemical properties etc. |
|---|---|---|
| 402* | Me₂N-C(Me)₂-CH₂-O-C₆H₄-Me | amorphous powder MS (APCI) 557 [M + H]+ |
| 403* | Me₂N-CH₂-C(Me)₂-CH₂-O-C₆H₄-Me | amorphous powder MS (APCI) 571 [M + H]+ |

*hydrochloride
Me: methyl group, nPr: n-propyl group

EXAMPLE 404

(1) The corresponding compound is treated in the same manner as described in Example 381 to give 1-(3-ethoxybenzyl)-4-[4-[4-[[1-(tert-butoxycarbonyl)piperidin-4-yl ]oxy]benzoyl]piperazin-1-yl]-1H-pyrazolo[3,4-d]pyrimidine (34 mg, yield; 61%) as an amorphous powder. MS (APCI) m/z: 642 [M+H]$^+$ (2) To a solution of the compound obtained in the above step (1) (34 mg) in methanol (0.5 mL) is added 4N HCl-dioxane (0.1 mL) and the mixture is stirred at room temperature overnight. The reaction mixture is evaporated to remove solvent. The resultant residue is dissolved in water and lyophilized to give 1-(3-ethoxybenzyl)-4-[4-[4-(4-piperidyloxy)benzoyl]piperazin-1-yl]-1H-pyrazolo[3,4-d]pyrimidine 2hydrochloride (27 mg, yield; 79%) as an amorphous powder. MS (APCI) m/z: 542 [M+H]$^+$

EXAMPLES 405 TO 406

The corresponding materials are treated in the same manner as described in Example 404 to give the compounds as shown in the following Table 11.

TABLE 11

| Ex. Nos. | R$^1$ | Physicochemical properties etc. |
|---|---|---|
| 405** | (pyrrolidinyl-CH-O-C$_6$H$_4$-Me) | amorphous powder MS (APCI) 542 [M + H]+ |
| 406** | MeNH-CH$_2$CH$_2$CH$_2$-O-C$_6$H$_4$-Me | amorphous powder MS (APCI) 530 [M + H]+ |

**dihydrochloride
Me: methyl group, Et: ethyl group

EXAMPLE 407

(1) Methyl 4-[[N-ethyl-N-(tert-butoxycarbonyl)]aminomethyl]benzoate (230 mg, compound obtained in Reference Example 81) is treated in the same manner as described in Example 1 to give 1-(3-ethoxybenzyl)-4-[4-[4-[[N-ethyl-N-(tert-butoxy-carbonyl)]aminomethyl]benzoyl]piperazin-1-yl]-1H-pyrazolo[3,4-d]pyrimidine (330 mg, 2 steps yield; 70%) as an amorphous powder. MS (APCI) m/z: 600 [M+H]$^+$ (2) To a solution of the compound obtained in the above step (1) (330 mg) in dioxane (2 mL) is added 4N HCl-dioxane (4 mL) and the mixture is stirred at room temperature for 6 hours. To the reaction mixture is added diisopropylether (6 mL,), and after stirring, the supernatant is removed (Such washing procedure is repeated again). The precipitate is dissolved in water (2 mL) and thereto is added a saturated sodium hydrogencarbonate solution (3 mL) and chloroform (3 mL). After standing, the organic layer is separated and concentrated. The resultant crude product is purified by flash column chromatography on NH-silica gel (Purif 8 Hi-flush/L, MORITEX Inc.; Solvent; n-hexane: ethyl acetate=65:35→0:100) to give 1-(3-ethoxybenzyl)-4-[4-[4-(ethylaminomethyl)benzoyl]piperazin-1-yl]-1H-pyrazolo[3,4-d]pyrimidine (121 mg, yield; 44%) as an amorphous powder. MS (APCI) m/z: 500 [M+H]$^+$ (3) To a suspension of the compound obtained in the above step (2) (110 mg) in water (500 μL) is added 2N HCl (220 μL) and the mixture is lyophilized to give 1-(3-ethoxybenzyl)-4-[4-[4-(ethylaminomethyl)benzoyl]piperazin-1-yl]-1H-pyrazolo[3,4-d]-pyrimidine dihydrochloride as an amorphous powder. MS (APCI) m/z: 500 [M+H]$^+$

EXAMPLES 408 TO 415

The corresponding materials are treated in the same manner as described in Example 407 to give the compounds as shown in the following Table 12.

TABLE 12

| Ex. Nos. | R$^1$—Y— | Physicochemical properties etc. |
|---|---|---|
| 408** | H$_2$N-CH$_2$-(4-methylphenyl) | amorphous powder MS (APCI) 472 [M + H]+ |
| 409** | H$_2$N-CH$_2$-cyclohexyl | amorphous powder MS (APCI) 478 [M + H]+ |
| 410** | MeHN-cyclohexyl | amorphous powder MS (APCI) 478 [M + H]+ |
| 411** | H$_2$N-cyclohexyl | amorphous powder MS (APCI) 464 [M + H]+ |
| 412** | HN-piperidinyl-Me | amorphous powder MS (APCI) 450 [M + H]+ |
| 413** | HN-piperidinyl-Et | amorphous powder MS (APCI) 464 [M + H]+ |
| 414** | HN-piperidinyl-CH$_2$CH$_2$- | amorphous powder MS (APCI) 478 [M + H]+ |
| 415*** | Me$_2$N-CH$_2$CH$_2$-NH-cyclohexyl | amorphous powder MS (APCI) 535 [M + H]+ |

**dihydrochloride,
***trihydrochloride
Me: methyl group, Et: ethyl group

EXAMPLE 416

To a solution of the compound obtained in Example 415 (50 mg) and triethylamine (50 mg) in methylene chloride is added acetyl chloride (10 mg) and the mixture is stirred at room temperature for 18 hours. The reaction mixture is diluted with a saturated sodium hydrogencarbonate solution and extracted with chloroform. The extract is evaporated to remove solvent and the resultant crude product is purified by HPLC (Solvent; 10 mM ammonium carbonate:methanol=80:20→5:95) and then the resultant product (1-(3-ethoxybenzyl)-4-[4-[[trans-4-[N-acetyl-N-[2-(dimethylamino)ethyl]amino]cyclohexyl]carbonyl]piperazin-1-yl]-1H-pyrazolo[3,4-d]pyrimidine) is treated in the same manner as described in Example 4(3) to give 1-(3-ethoxybenzyl)-4-[4-[[trans-4-(N-acetyl-N-[2-(dimethylamino)ethyl]amino]cyclohexyl]-carbonyl]piperazin-1-yl]-1H-pyrazolo[3,4-d]pyrimidine dihydrochloride (20 mg, yield; 40%) as an amorphous powder. MS (APCI) m/z: 577 [M+H]$^+$

EXAMPLES 417 TO 421

The corresponding materials are treated in the same manner as described in Example 416 to give the compounds as shown in the following Table 13.

TABLE 13

| Ex. Nos. | R$^1$ | Physicochemical properties etc. |
|---|---|---|
| 417** | cyclopropyl-C(O)- with Me₂N-CH₂CH₂-N-cyclohexyl | amorphous powder MS (APCI) 603 [M + H]+ |
| 418** | Me-CH=CH-C(O)- with Me₂N-CH₂CH₂-N-cyclohexyl | amorphous powder MS (APCI) 603 [M + H]+ |
| 419** | 2-furyl-C(O)- with Me₂N-CH₂CH₂-N-cyclohexyl | amorphous powder MS (APCI) 629 [M + H]+ |
| 420** | Ph-C(O)- with Me₂N-CH₂CH₂-N-cyclohexyl | amorphous powder MS (APCI) 639 [M + H]+ |
| 421** | Me-NH-C(S)- with Me₂N-CH₂CH₂-N-cyclohexyl | amorphous powder MS (APCI) 608 [M + H]+ |

**dihydrochloride
Me: methyl group, Et: ethyl group

EXAMPLE 422

To a suspension of the compound obtained in Example 410 (40 mg) in tetrahydrofuran (1 mL) is added successively potassium carbonate (35 mg) and ethyl iodide (9 μL), and the mixture is stirred at room temperature overnight. The reaction mixture is diluted with chloroform (5 mL) and thereto is added a saturated sodium hydrogencarbonate solution. After stirring, the organic layer is separated and concentrated. The resultant crude product is purified by HPLC (Solvent; 10 mM ammonium carbonate:methanol=80:20→5:95) and then the resultant product is treated in the same manner as described in Example 4(3) to give 1-(3-ethoxybenzyl)-4-[4-[[trans-4-(N-ethyl-N-methylamino)cyclohexyl]carbonyl]piperazin-1-yl]-1H-pyrazolo[3,4-d]pyrimidine dihydrochloride (13 mg, yield; 31%) as an amorphous powder. MS (APCI) m/z: 506 [M+H]$^+$

EXAMPLES 423 TO 424

The corresponding materials are treated in the same manner as described in Example 422 to give the compounds as shown in the following Table 14.

TABLE 14

| Ex. Nos. | R¹ | Physicochemical properties etc. |
|---|---|---|
| 423** | iPr-N(Me)-cyclohexyl (trans) | amorphous powder MS (APCI) 520 [M + H]+ |
| 424** | nPr-N(Me)-cyclohexyl (trans) | amorphous powder MS (APCI) 520 [M + H]+ |

**dihydrochloride
Me: methyl group, Et: ethyl group, nPr: n-propyl group, iPr: isopropyl group

EXAMPLE 425

(1) To a suspension of the compound obtained in Example 411 (50 mg) in dichloromethane (1 mL) is added successively triethylamine (44 μL) and chloroacetyl chloride (9 μL), and the mixture is stirred for 2 hours under ice-cooling. To the mixture is added 2M dimethylamine in tetrahydrofuran (0.3 mL) under ice-cooling and the mixture is stirred at room temperature overnight. The reaction mixture is diluted with chloroform (3 mL) and thereto is added a saturated sodium hydrogencarbonate solution (5 mL). After stirring, the organic layer is separated and concentrated. The resultant crude product is purified by HPLC (Solvent; 10 mM ammonium carbonate:methanol=80:20→5:95) to give 1-(3-ethoxybenzyl)-4-[4-[[trans-4-[N,N-(dimethylglycyl)amino]cyclohexyl]carbonyl]piperazin-1-yl]-1H-pyrazolo[3,4-d]-pyrimidine (20.4 mg, yield; 40%) as an amorphous powder. MS (ESI) m/z: 549 [M+H]+

(2) The compound obtained in the above step (1) is treated in the same manner as described in Example 4(3) to give 1-(3-ethoxybenzyl)-4-[4-[[trans-4-[N,N-(dimethyl-glycyl)amino]cyclohexyl]carbonyl]piperazin-1-yl]-1H-pyrazolo[3,4-d]pyrimidine 2 hydrochloride (21.5 mg, yield; 93%) as an amorphous powder. MS (APCI) m/z: 549 [M+H]+

EXAMPLES 426 TO 433

The corresponding materials are treated in the same manner as described in Example 425 to give the compounds as shown in the following Table 15.

TABLE 15 (No. 1)

| Ex. Nos. | R¹ | Physicochemical properties etc. |
|---|---|---|
| 426** | Et-N(Et)-CH₂-C(O)NH-cyclohexyl | amorphous powder MS (APCI) 577 [M + H]+ |
| 427** | pyrrolidinyl-CH₂-C(O)NH-cyclohexyl | amorphous powder MS (APCI) 575 [M + H]+ |
| 428** | Me-N(Me)-CH₂CH₂-C(O)NH-cyclohexyl | amorphous powder MS (APCI) 563 [M + H]+ |
| 429** | Et-N(Et)-CH₂CH₂-C(O)NH-cyclohexyl | amorphous powder MS (APCI) 591 [M + H]+ |
| 430** | pyrrolidinyl-CH₂CH₂-C(O)NH-cyclohexyl | amorphous powder MS (APCI) 589 [M + H]+ |

**dihydrochloride
Me: methyl group, Et: ethyl group

TABLE 15 (No. 2)

| Ex. Nos. | R¹ | Physicochemical properties etc. |
|---|---|---|
| 431 | Et-N(Et)-CH₂-C(O)N(Me)-cyclohexyl | amorphous powder MS (APCI) 591 [M + H]+ |

TABLE 15-continued (No. 2)

[Structure: R¹-C(=O)-piperazine-pyrazolo[3,4-d]pyrimidine-N-CH₂-phenyl-OEt]

| Ex. Nos. | R¹ | Physico-chemical properties etc. |
|---|---|---|
| 432 | Me₂N-CH₂-CH₂-N(Me)- | amorphous powder MS (APCI) 577 [M + H]+ |
| 433 | pyrrolidinyl-CH₂-CH₂-N(Me)- | amorphous powder MS (APCI) 603 [M + H]+ |

Me: methyl group  Et: ethyl group

EXAMPLE 434

(1) To a suspension of the compound obtained in Example 411 (40 mg) in tetrahydrofuran (1 mL) is added successively dimetylacetamide (0.2 mL), 1,5-diiodopentane (16.6 µL), and sodium carbonate (28 mg). The mixture is stirred at 70° C. for 23 hours. After cooling, the reaction mixture is diluted with chloroform (3 mL) and thereto is added a saturated sodium hydrogencarbonate solution (5 mL). After stirring, the organic layer is separated and concentrated. The resultant crude product is purified by HPLC (Solvent; 10 mM ammonium carbonate:methanol=80:20→5:95) to give 1-(3-ethoxybenzyl)-4-[4-[[trans-4-(1-piperidyl)cyclohexyl]-carbonyl]piperazin-1-yl]-1H-pyrazolo[3,4-d]pyrimidine (12.9 mg, yield: 34%). MS (ESI) m/z: 532 [M+H]⁺

(2) The compound obtained in the above step (1) is treated in the same manner as described in Example 4(3) to give 1-(3-ethoxybenzyl)-4-[4-[[trans-4-(1-piperidyl)-cyclohexyl]carbonyl]piperazin-1-yl]-1H-pyrazolo[3,4-d]pyrimidine dihydrochloride (15.4 mg, yield; quantitatively) amorphous powder. MS (APCI) m/z: 532 [M+H]⁺

EXAMPLE 435

The corresponding materials are treated in the same manner as described in Example 434 to give the compound as shown in the following Table 16.

TABLE 16

[Structure: R¹-C(=O)-piperazine-pyrazolo[3,4-d]pyrimidine-N-CH₂-phenyl-OEt]

| Ex. Nos. | R¹ | Physicochemical properties etc. |
|---|---|---|
| 435* | HO-(3-hydroxypyrrolidinyl)-cyclohexyl- | amorphous powder MS (APCI) 534 [M + H]+ |

*fumarate
Et: ethyl group

EXAMPLES 436 TO 442

The corresponding materials are treated in the same manner as described in Example 407 to give the compounds as shown in the following Table 17.

TABLE 17

(No. 1)

[Structure: EtHN-CH₂-phenyl-C(=O)-piperazine-pyrazolo[3,4-d]pyrimidine-N-CH₂-R²]

| Ex. Nos. | R² | Physicochemical properties etc. |
|---|---|---|
| 436** | 4-methyl-2-n-propyl-thiazolyl | amorphous powder MS (APCI) 505 [M + H]+ |
| 437** | 3-fluoro-2,4-dimethyl-phenyl | amorphous powder MS (APCI) 488 [M + H]+ |
| 438** | 6-methyl-2-n-propyl-pyridyl | amorphous powder MS (APCI) 499 [M + H]+ |

**dihydrochloride
Me: methyl group, Et: ethyl group, nPr: n-propyl group

TABLE 17

(No. 2)

[Structure: RHN-cyclohexyl-C(=O)-piperidine-N-pyrazolo[3,4-d]pyrimidine-N-CH2-phenyl-OEt]

| Ex. Nos. | R | Physicochemical properties etc. |
|---|---|---|
| 439** | cyclopentyl | amorphous powder<br>MS (APCI) 532 [M + H]+ |
| 440** | iPr | amorphous powder<br>MS (APCI) 506 [M + H]+ |
| 441** | nPr | amorphous powder<br>MS (APCI) 506 [M + H]+ |
| 442** | Et | amorphous powder<br>MS (APCI) 492 [M + H]+ |

**dihydrochloride,
Et: ethyl group, nPr: n-propyl group, iPr: isopropyl group

EXAMPLE 443 TO 500

The corresponding materials are treated in the same manner as described in Example 3 to give compounds as shown in the following Table 18.

TABLE 18

(No. 1)

[Structure: pyrrolidine-cyclohexyl-C(=O)-piperazine-N-pyrazolo[3,4-d]pyrimidine-N-CH2-R²]

| Ex. Nos. | R² | Physicochemical properties etc. |
|---|---|---|
| 443 | 6-methyl-2-ethoxy-pyridin-3-yl | amorphous powder<br>MS (ESI) 519 [M + H]+ |
| 444 (1)(2)* | 6-methyl-2-n-propyl-pyridin-3-yl | amorphous powder<br>MS (APCI) 517 [M + H]+ |

TABLE 18-continued (No. 1)

| Ex. Nos. | R² | Physicochemical properties etc. |
|---|---|---|
| 445* | 4-fluoro-2,3-dimethylphenyl | amorphous powder<br>MS (APCI) 506 [M + H]+ |
| 446* | 3-(trifluoromethoxy)phenyl (with methyl) | amorphous powder<br>MS (APCI) 558 [M + H]+ |
| 447* | 2-fluoro-3,6-dimethylphenyl | amorphous powder<br>MS (APCI) 506 [M + H]+ |
| 448* | 3-chlorophenyl (with methyl) | amorphous powder<br>MS (APCI) 508/510 [M + H]+ |
| 449 | 2-ethyl-4-methyl-thiazol-5-yl | amorphous powder<br>MS (ESI) 509 [M + H]+ |
| 450 | 3-(n-propoxy)phenyl (with methyl) | amorphous powder<br>MS (ESI) 532 [M + H]+ |
| 451 | 3-(isopropoxy)phenyl (with methyl) | amorphous powder<br>MS (ESI) 532 [M + H]+ |

*hydrochloride
Me: methyl group, Et: ethyl group, nPr: n-propyl group, iPr: isopropyl group

TABLE 18

(No. 2)

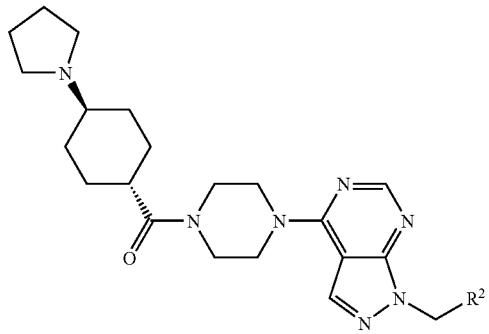

| Ex. Nos. | R² | Physicochemical properties etc. |
|---|---|---|
| 452** | 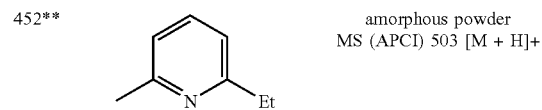 | amorphous powder MS (APCI) 503 [M + H]+ |
| 453** | 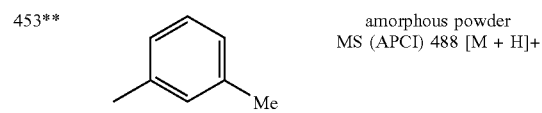 | amorphous powder MS (APCI) 488 [M + H]+ |
| 454** | 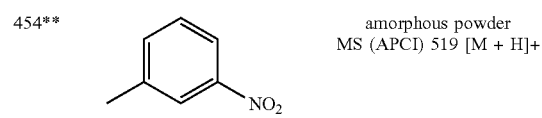 | amorphous powder MS (APCI) 519 [M + H]+ |
| 455** | 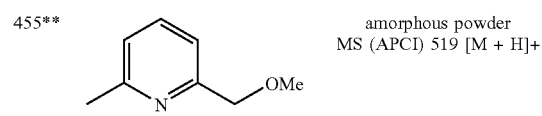 | amorphous powder MS (APCI) 519 [M + H]+ |

**dihydrochloride
Me: methyl group, Et: ethyl group

TABLE 18

(No. 3)

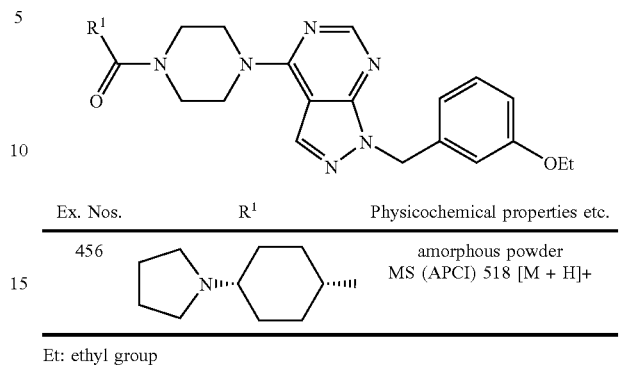

| Ex. Nos. | R¹ | Physicochemical properties etc. |
|---|---|---|
| 456 | 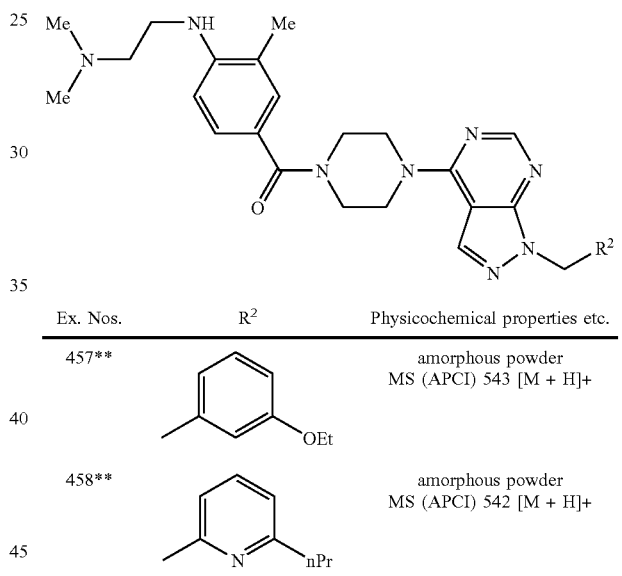 | amorphous powder MS (APCI) 518 [M + H]+ |

Et: ethyl group

TABLE 18

(No. 4)

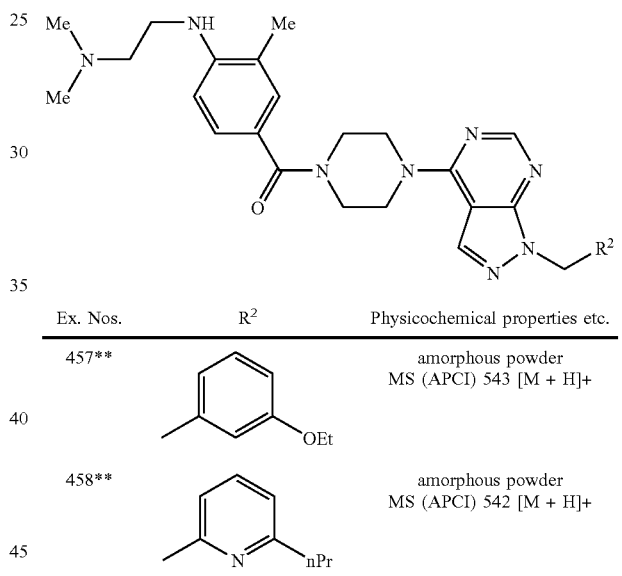

| Ex. Nos. | R² | Physicochemical properties etc. |
|---|---|---|
| 457** | 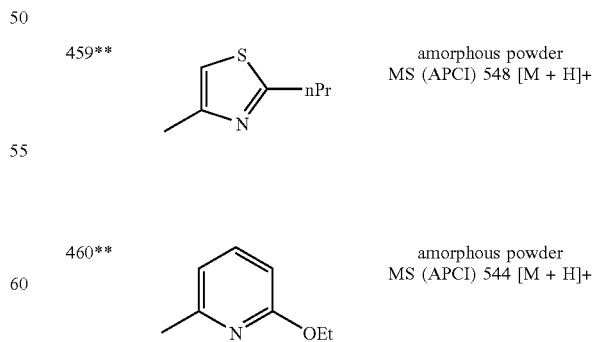 | amorphous powder MS (APCI) 543 [M + H]+ |
| 458** | 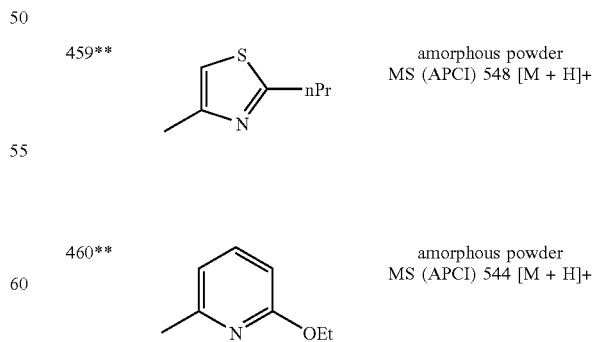 | amorphous powder MS (APCI) 542 [M + H]+ |
| 459** | 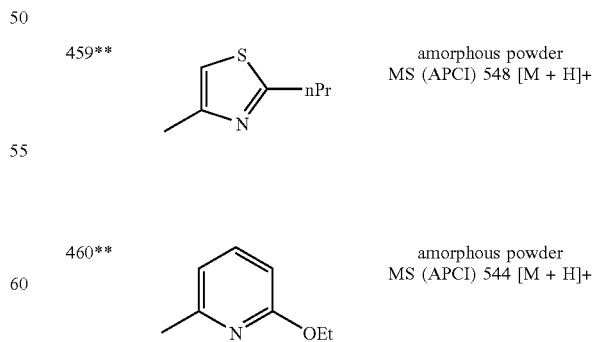 | amorphous powder MS (APCI) 548 [M + H]+ |
| 460** | 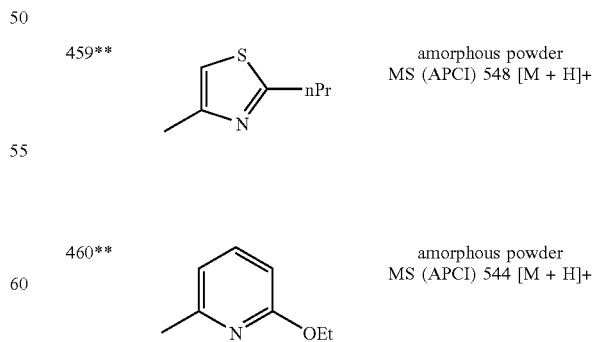 | amorphous powder MS (APCI) 544 [M + H]+ |

**dihydrochloride
Me: methyl group, Et: ethyl group, nPr: n-propyl group

TABLE 18
(No. 5)
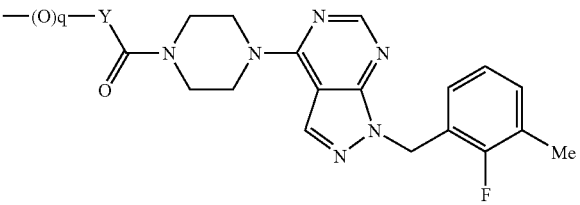
| Ex. Nos. | R¹—(O)q—Y— | Physicochemical properties etc. |
|---|---|---|
| 461* | 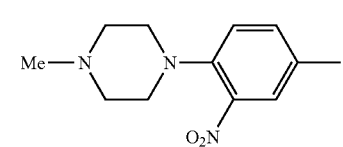 | amorphous powder<br>MS (APCI) 588 [M + H]+ |
| 462* | 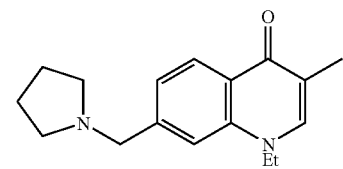 | amorphous powder<br>MS (APCI) 574 [M + H]+ |
| 463* | 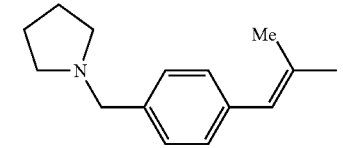 | amorphous powder<br>MS (APCI) 609 [M + H]+ |
| 464* | 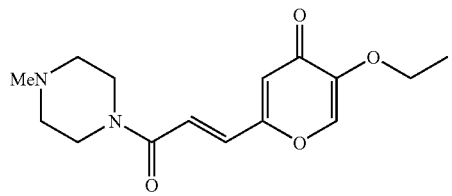 | E-isomer<br>amorphous powder<br>MS (APCI) 554 [M + H]+ |
| 465* | 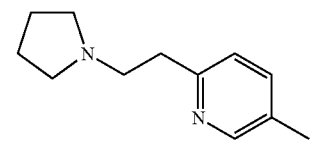 | E-isomer<br>amorphous powder<br>MS (APCI) 631 [M + H]+ |
| 466* | | amorphous powder<br>MS (APCI) 529 [M + H]+ |
*hydrochloride
Me: methyl group, Et: ethyl group

TABLE 18

(No. 6)

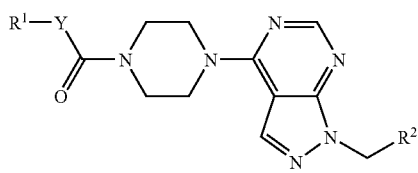

| Ex. Nos. | R¹—Y— | R² | Physicochemical properties etc. |
|---|---|---|---|
| 467* | pyrrolidine-CH₂-C₆H₄-CH=C(Me)- | 4-methyl-2-nPr-thiazol-5-yl | amorphous powder<br>MS (APCI) 571 [M + H]+ |
| 468* | pyrrolidine-CH₂CH₂-(5-methylpyridin-2-yl)- | 4-methyl-2-nPr-thiazol-5-yl | amorphous powder<br>MS (APCI) 546 [M + H]+ |
| 469* | Me-piperazine-(4-methyl-2-nitrophenyl)- | 3-OEt-phenyl | amorphous powder<br>MS (APCI) 586 [M + H]+ |
| 470* | pyrrolidine-CH₂-C₆H₄-CH=C(Me)- | 3-OEt-phenyl | amorphous powder<br>MS (APCI) 566 [M + H]+ |
| 471* | pyrrolidine-CH₂CH₂-(5-methylpyridin-2-yl)- | 3-OEt-phenyl | amorphous powder<br>MS (APCI) 541 [M + H]+ |
| 472* | Me-piperazine-(4-methyl-2-nitrophenyl)- | 6-methyl-2-nPr-pyridin-3-yl | amorphous powder<br>MS (APCI) 585 [M + H]+ |
| 473* | pyrrolidinylmethyl-(1-Et-3-methyl-4-oxo-quinolin-7-yl)- | 6-methyl-2-nPr-pyridin-3-yl | amorphous powder<br>MS (APCI) 620 [M + H]+ |
| 474* | pyrrolidine-CH₂-C₆H₄-CH=C(Me)- | 6-methyl-2-nPr-pyridin-3-yl | amorphous powder<br>MS (APCI) 565 [M + H]+ |

*hydrochloride
Me: methyl group, Et: ethyl group, nPr: n-propyl group

TABLE 18

(No. 7)

| Ex. Nos. | R¹—(O)q—Y— | R² | Physicochemical properties etc. |
|---|---|---|---|
| 475* | 1-methylpiperazinyl-C(O)-CH=CH-(5-ethoxy-4-oxo-4H-pyran-2-yl) | 6-methyl-2-n-propyl-pyridin-yl | amorphous powder MS (APCI) 642 [M + H]+ |
| 476* | pyrrolidin-1-yl-CH₂CH₂-(5-methylpyridin-2-yl) | 6-methyl-2-n-propyl-pyridin-yl | amorphous powder MS (APCI) 540 [M + H]+ |
| 477* | pyrrolidin-1-yl-CH₂-(5-ethoxy-4-oxo-4H-pyran-2-yl) | 3-ethoxyphenyl | amorphous powder MS (APCI) 574 [M + H]+ |

*hydrochloride
Me: methyl group, Et: ethyl group, nPr: n-propyl group

TABLE 18

(No. 8)

| Ex. Nos. | R² | Physicochemical properties etc. |
|---|---|---|
| 478 | 6-methyl-2-ethoxy-pyridin-yl | amorphous powder MS (APCI) 573 [M + H]+ |
| 479* | 3-fluoro-2-methyl-phenyl (dimethylphenyl with F, Me) | amorphous powder MS (APCI) 560 [M + H]+ |
| 480 | 6-methyl-2-ethyl-pyridin-yl | amorphous powder MS (APCI) 557 [M + H]+ |
| 481 | 4-methyl-2-n-propyl-thiazol-yl | amorphous powder MS (APCI) 577 [M + H]+ |

TABLE 18-continued (No. 8)

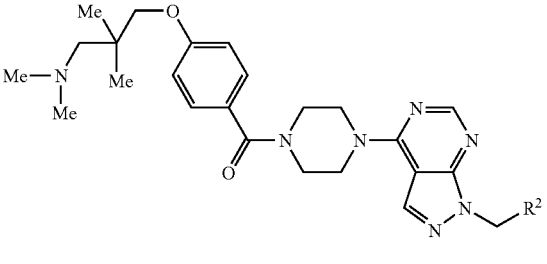

| Ex. Nos. | R² | Physicochemical properties etc. |
|---|---|---|
| 482* | (3-methyl-2-fluoro-phenyl OMe) | amorphous powder MS (APCI) 576 [M + H]+ |

*hydrochloride
Me: methyl group, Et: ethyl group, nPr: n-propyl group

TABLE 18

(No 9)

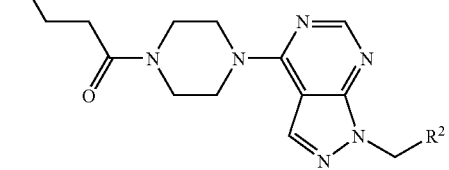

| Ex. Nos. | R² | Physicochemical properties etc. |
|---|---|---|
| 483 | (3-methylphenyl O—iPr) | amorphous powder MS (APCI) 534 [M + H]+ |
| 484* | (6-methylpyridin-2-yl Et) | amorphous powder MS (APCI) 505 [M + H]+ |
| 485 | (4-methylthiazol-2-yl NHEt) | amorphous powder MS (APCI) 526 [M + H]+ |
| 486* | (F, Me phenyl) | amorphous powder MS (APCI) 508 [M + H]+ |

TABLE 18-continued (No 9)

| Ex. Nos. | R² | Physicochemical properties etc. |
|---|---|---|
| 487 | (6-methylpyridin-2-yl OEt) | amorphous powder MS (APCI) 521 [M + H]+ |
| 488 | (2-fluoro-3-methylphenyl Me) | amorphous powder MS (APCI) 508 [M + H]+ |
| 489* | (4-methylthiazol-2-yl nPr) | amorphous powder MS (APCI) 525 [M + H]+ |
| 490* | (6-methylpyridin-2-yl NHMe) | amorphous powder MS (APCI) 506 [M + H]+ |
| 491 | (3-methyl-2-fluoro-phenyl OMe) | amorphous powder MS (APCI) 524 [M + H]+ |

*hydrochloride
Me: methyl group, Et: ethyl group, nPr: n-propyl group, iPr: isopropyl group

TABLE 18
(No.10)

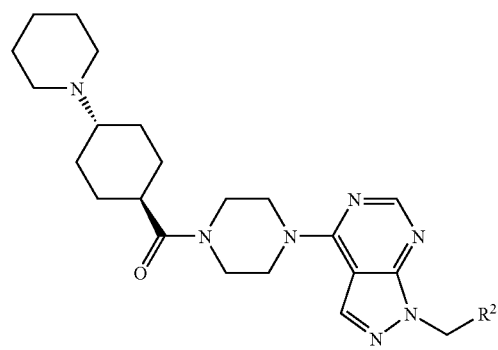

| Ex. Nos. | $R^2$ | Physicochemical properties etc. |
|---|---|---|
| 492 | 6-methyl-2-nPr-pyridin-3-yl | amorphous powder MS (APCI) 531 [M + H]+ |
| 493 | 6-methyl-2-OEt-pyridin-3-yl | amorphous powder MS (APCI) 533 [M + H]+ |
| 494 | 3-methyl-5-(OCF$_3$)-phenyl | amorphous powder MS (APCI) 572 [M + H]+ |
| 495 | 3-methyl-2-F-6-Me-phenyl | amorphous powder MS (APCI) 520 [M + H]+ |
| 496 | 4-methyl-2-nPr-thiazol-5-yl | amorphous powder MS (APCI) 537 [M + H]+ |
| 497 | 3-methyl-5-(O-nPr)-phenyl | amorphous powder MS (APCI) 546 [M + H]+ |

TABLE 18-continued
(No.10)

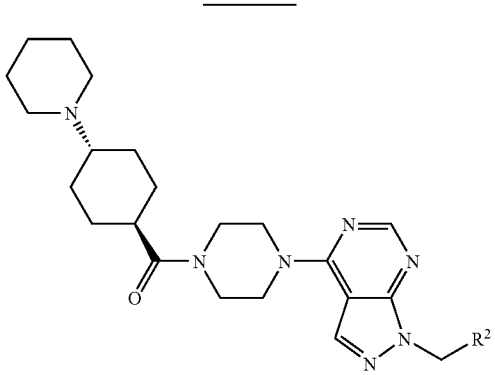

| Ex. Nos. | $R^2$ | Physicochemical properties etc. |
|---|---|---|
| 498 | 3-Cl-phenyl | amorphous powder MS (APCI) 522/524 [M + H]+ |
| 499 | 3-methyl-2-F-6-OMe-phenyl | amorphous powder MS (APCI) 536 [M + H]+ |

Me: methyl group, Et: ethyl group, nPr: n-propyl group

TABLE 18
(No. 11)

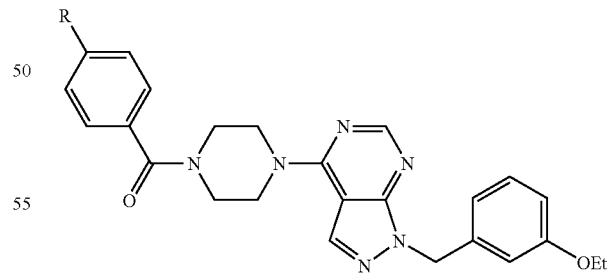

| Ex. Nos. | R | Physicochemical properties etc. |
|---|---|---|
| 500 | Me$_2$N-CH$_2$CH$_2$-N(Me)- with SMe | amorphous powder MS (APCI) 546 [M + H]+ |

**dihydrochloride
Me: methyl group, Et: ethyl group

TABLE 19

(No. 1)

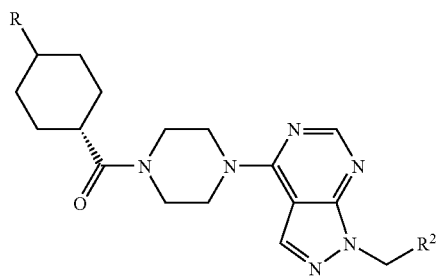

| Ex. Nos. | R | R² | Physicochemical properties etc. |
|---|---|---|---|
| 501 | MeN(piperazine)-CH₂- | 6-methyl-2-n-Pr-pyridin-3-yl | amorphous powder<br>MS (ESI) 560 [M + H]+ |
| 502 | (Me)₂CH-N(Me)-CH₂- | 6-methyl-2-n-Pr-pyridin-3-yl | amorphous powder<br>MS (ESI) 533 [M + H]+ |
| 503 | MeN(piperazine)-CH₂CH₂- | 3-OEt-phenyl | amorphous powder<br>MS (ESI) 561 [M + H]+ |
| 504 | MeN(homopiperazine)-CH₂- | 3-OEt-phenyl | amorphous powder<br>MS (ESI) 575 [M + H]+ |
| 505 | pyrrolidin-1-yl-CH₂- | 6-methyl-2-n-Pr-pyridin-3-yl | amorphous powder<br>MS (ESI) 531 [M + H]+ |
| 506 | Et₂N-CH₂- | 6-methyl-2-n-Pr-pyridin-3-yl | amorphous powder<br>MS (ESI) 533 [M + H]+ |
| 507 | MeO-CH₂CH₂-N(Me)-CH₂- | 6-methyl-2-n-Pr-pyridin-3-yl | amorphous powder<br>MS (ESI) 529 [M + H]+ |
| 508 | pyrrolidin-1-yl-CH₂- | 3-OEt-phenyl | amorphous powder<br>MS (ESI) 532 [M + H]+ |

Me: methyl group, Et: ethyl group, n-Pr: n-propyl group

TABLE 19 (No. 2)

Structure: R-cyclohexyl-C(O)-piperazine-pyrazolopyrimidine-N-CH2-pyridine-n-Pr

| Ex. Nos. | R | Physicochemical properties etc. |
|---|---|---|
| 509 | piperidine-CH2CH2-N(Me)(Et) | amorphous powder MS (ESI) 602 [M + H]+ |
| 510 | Me2N-CH2CH2-N(Me)(vinyl) | amorphous powder MS (ESI) 562 [M + H]+ |
| 511 | Et2N-CH2CH2-N(Me)(vinyl) | amorphous powder MS (ESI) 590 [M + H]+ |
| 512 | 2-pyridyl-CH2CH2-N(Me)(Et) | amorphous powder MS (ESI) 596 [M + H]+ |
| 513 | Me-N(homopiperazine)-Et | amorphous powder MS (ESI) 574 [M + H]+ |
| 514 | MeO-CH2CH2-N(Et)(CH(Me)2) | amorphous powder MS (ESI) 577 [M + H]+ |
| 515 | H2N-C(O)-piperidine-vinyl | amorphous powder MS (ESI) 588 [M + H]+ |

Me: methyl group, Et: ethyl group, n-Pr: n-propyl group

TABLE 19 (No. 3)

Structure: R-cyclohexyl-C(O)-piperazine-pyrazolopyrimidine-N-CH2-phenyl-OEt

| Ex. Nos. | R | Physicochemical properties etc. |
|---|---|---|
| 516 | Et2N-CH2-N(Et) | amorphous powder MS (ESI) 534 [M + H]+ |
| 517 | Me2CH-N(Me)(vinyl) | amorphous powder MS (ESI) 534 [M + H]+ |
| 518 | MeO-CH2CH2-N(Me)(vinyl) | amorphous powder MS (ESI) 550 [M + H]+ |

Me: methyl group, Et: ethyl group

TABLE 19 (No. 4)

Structure: R-cyclohexyl-C(O)-piperazine-pyrazolopyrimidine-N-CH2-phenyl-OEt

| Ex. Nos. | R | Physicochemical properties etc. |
|---|---|---|
| 519 | piperidine-CH2CH2-N(Me)(Et) | amorphous powder MS (ESI) 603 [M + H]+ |
| 520 | Et2N-CH2CH2-N(Me)(vinyl) | amorphous powder MS (ESI) 591 [M + H]+ |
| 521 | 2-pyridyl-CH2CH2-N(Me)(vinyl) | amorphous powder MS (ESI) 597 [M + H]+ |

TABLE 19-continued (No. 4)

[Structure: R-cyclohexyl-C(O)-piperazine-pyrazolopyrimidine-N-CH2-phenyl-OEt]

| Ex. Nos. | R | Physicochemical properties etc. |
|---|---|---|
| 522 | MeO-CH2CH2-N(CH=CH2)-CH(Me)2 | amorphous powder MS (ESI) 578 [M + H]+ |
| 523 | 1-ethyl-piperidine-4-C(O)NH2 | amorphous powder MS (ESI) 589 [M + H]+ |

Me: methyl group, Et: ethyl group

TABLE 19

(No. 5)

[Structure: Me2N-CH2CH2-N(Me)-pyrimidine(CF3)-C(O)-piperazine-pyrazolopyrimidine-N-CH2-R2]

| Ex. Nos. | R² | Physicochemical properties etc. |
|---|---|---|
| 524* | 6-methyl-2-n-Pr-pyridine | amorphous powder MS (APCI) 612 [M + H]+ |
| 525* | 3-methyl-phenyl-OEt | amorphous powder MS (APCI) 613 [M + H]+ |
| 526* | 4-methyl-2-n-Pr-thiazole | amorphous powder MS (APCI) 618 [M + H]+ |

*hydrochloride
Me: methyl group, Et: ethyl group, n-Pr: n-propyl group

TABLE 19

(No. 6)

[Structure: R'-phenyl-C(O)-piperazine-pyrazolopyrimidine-N-CH2-R2]

| Ex. Nos. | R' | R² | Physicochemical properties etc. |
|---|---|---|---|
| 527* | (Z)- Me2N-CH2-CH=CH- | 6-methyl-2-n-Pr-pyridine | amorphous powder MS (APCI) 525 [M + H]+ |
| 528* | (Z)- Me2N-CH2-CH=CH- | 3-methyl-phenyl-OEt | amorphous powder MS (APCI) 526 [M + H]+ |

TABLE 19-continued (No. 6)

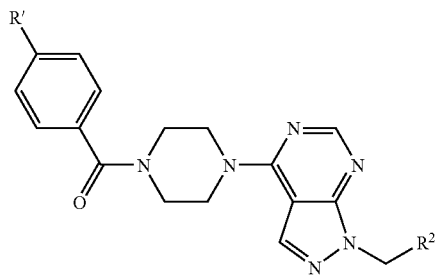

| Ex. Nos. | R' | R² | Physicochemical properties etc. |
|---|---|---|---|
| 529* | pyrrolidinyl-CH₂-C≡CH | 3-methyl-phenyl-OEt | amorphous powder MS (APCI) 550 [M + H]+ |
| 530* | (Z)- Et₂N-CH₂-CH=CH- | 3-methyl-phenyl-OEt | amorphous powder MS (APCI) 554 [M + H]+ |
| 531* | (Z)- pyrrolidinyl-CH₂-CH=CH- | 3-methyl-phenyl-OEt | amorphous powder MS (APCI) 552 [M + H]+ |

*hydrochloride
Me: methyl group, Et: ethyl group, n-Pr: n-propyl group

TABLE 19

(No. 7)

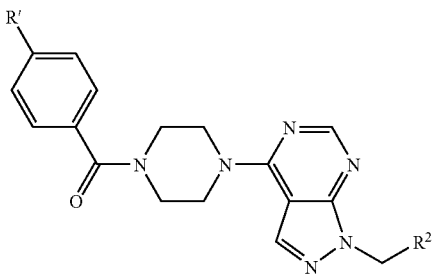

| Ex. Nos. | R' | R² | Physicochemical properties etc. |
|---|---|---|---|
| 532* | Me₂N-(CH₂)₃- | 6-methyl-2-n-Pr-pyridin-yl | amorphous powder MS (APCI) 527 [M + H]+ |
| 533* | Me₂N-(CH₂)₃- | 3-methyl-phenyl-OEt | amorphous powder MS (APCI) 528 [M + H]+ |
| 534* | Me₂N-(CH₂)₃- | 4-methyl-2-n-Pr-thiazol-yl | amorphous powder MS (APCI) 533 [M + H]+ |

TABLE 19-continued (No. 7)

| Ex. Nos. | R' | R² | Physicochemical properties etc. |
|---|---|---|---|
| 535* | Et-N(Et)(n-butyl) | 3-OEt-benzyl | amorphous powder MS (APCI) 556 [M + H]+ |
| 536* | pyrrolidin-1-yl-butyl | 3-OEt-benzyl | amorphous powder MS (APCI) 554 [M + H]+ |

*hydrochloride
Me: methyl group, Et: ethyl group, n-Pr: n-propyl group

TABLE 19

(No. 8)

| Ex. Nos. | R² | Physicochemical properties etc. |
|---|---|---|
| 537 | 6-n-Pr-pyridin-2-yl | amorphous powder MS (ESI) 547 [M + H]+ |
| 538* | 3-OEt-phenyl | amorphous powder MS (ESI) 548 [M + H]+ |
| 539 | 4-methyl-2-n-Pr-thiazol-5-yl | amorphous powder MS (ESI) 553 [M + H]+ |

*hydrochloride
Et: ethyl group, n-Pr: n-propyl group

TABLE 19

(No. 9)

| Ex. Nos. | R' | Physicochemical properties etc. |
|---|---|---|
| 540* | Me₂N— | amorphous powder MS (APCI) 656/658 [M + H]+ |
| 541* | Et₂N— | amorphous powder MS (APCI) 684/686 [M + H]+ |
| 542* | pyrrolidin-1-yl— | amorphous powder MS (APCI) 682/684 [M + H]+ |

*: hydrochloride
Me: methyl group, Et: ethyl group

TABLE 19 (No. 10)

| Ex. Nos. | R' | R² | Physicochemical properties etc. |
|---|---|---|---|
| 543** | Et(Me)N— | 6-methyl-2-n-Pr-pyridin-3-yl | amorphous powder MS (APCI) 513 [M + H]+ |
| 544** | cyclopentyl(Me)N— | 6-methyl-2-n-Pr-pyridin-3-yl | amorphous powder MS (APCI) 553 [M + H]+ |
| 545** | Et(Me)N— | 3-OEt-phenyl (methyl) | amorphous powder MS (APCI) 514 [M + H]+ |
| 546** | cyclopentyl(Me)N— | 3-OEt-phenyl (methyl) | amorphous powder MS (APCI) 554 [M + H]+ |
| 547** | Et(Me)N— | 2-F-3-Me-phenyl (methyl) | amorphous powder MS (APCI) 502 [M + H]+ |
| 548** | cyclopentyl(Me)N— | 2-F-3-Me-phenyl (methyl) | amorphous powder MS (APCI) 542 [M + H]+ |
| 549** | Et(Me)N— | 4-methyl-2-n-Pr-thiazol-5-yl | amorphous powder MS (APCI) 519 [M + H]+ |
| 550** | cyclopentyl(Me)N— | 4-methyl-2-n-Pr-thiazol-5-yl | amorphous powder MS (APCI) 559 [M + H]+ |

**dihydrochloride
Me: methyl group, Et: ethyl group, n-Pr: n-propyl group

TABLE 19 (No. 11)

| Ex. Nos. | R' | R'' | Physicochemical properties etc. |
|---|---|---|---|
| 551** | Et₂N— | Me | amorphous powder MS (APCI) 585 [M + H]+ |
| 552** | Me(Me)N— | benzyl | amorphous powder MS (APCI) 661 [M + H]+ |
| 553** | pyrrolidin-1-yl— | benzyl | amorphous powder MS (APCI) 687 [M + H]+ |
| 554** | piperidin-1-yl— | benzyl | amorphous powder MS (APCI) 701 [M + H]+ |
| 555** | Et₂N— | benzyl | amorphous powder MS (APCI) 689 [M + H]+ |

**dihydrochloride
Me: methyl group, Et: ethyl group

TABLE 19 (No. 12)

| Ex. Nos. | R' | R² | Physicochemical properties etc. |
|---|---|---|---|
| 556* | pyrrolidin-1-yl— | 6-methyl-2-n-Pr-pyridin-3-yl | amorphous powder MS (APCI) 701 [M + H]+ |
| 557* | morpholin-4-yl— | 6-methyl-2-n-Pr-pyridin-3-yl | amorphous powder MS (APCI) 717 [M + H]+ |

TABLE 19-continued (No. 12)

| Ex. Nos. | R' | R² | Physicochemical properties etc. |
|---|---|---|---|
| 558* | Me-N(Me)-CH₂CH₂- | 6-methyl-2-n-Pr-pyridin-yl | amorphous powder MS (APCI) 689 [M + H]+ |
| 559* | pyrrolidin-1-yl-ethyl | 6-methyl-2-n-Pr-pyridin-yl | amorphous powder MS (APCI) 715 [M + H]+ |
| 560* | N-methylpyrrolidinyl | 3-OEt-phenyl-methyl | amorphous powder MS (APCI) 702 [M + H]+ |
| 561* | morpholinomethyl | 3-OEt-phenyl-methyl | amorphous powder MS (APCI) 718 [M + H]+ |
| 562* | Me-N(Me)-CH₂CH₂- | 3-OEt-phenyl-methyl | amorphous powder MS (APCI) 690 [M + H]+ |
| 563* | pyrrolidin-1-yl-ethyl | 3-OEt-phenyl-methyl | amorphous powder MS (APCI) 716 [M + H]+ |

*hydrochloride
Me: methyl group, Et: ethyl group, n-Pr: n-propyl group

TABLE 19

(No. 13)

| Ex. Nos. | R² | Physicochemical properties etc. |
|---|---|---|
| 564* | 6-methyl-2-n-Pr-pyridin-yl | amorphous powder MS (APCI) 545 [M + H]+ |
| 565* | 3-OEt-phenyl | amorphous powder MS (APCI) 546 [M + H]+ |

*hydrochloride
Me: methyl group, Et: ethyl group, n-Pr: n-propyl group

TABLE 19

(No. 14)

| Ex. Nos. | R' | Physicochemical properties etc. |
|---|---|---|
| 566 | morpholinylmethyl | amorphous powder MS (ESI) 548 [M + H]+ |
| 567 | piperidinylmethyl | amorphous powder MS (ESI) 546 [M + H]+ |

Et: ethyl group

EXAMPLES 568 TO 577

The corresponding materials are treated in the same manner as described in Example 381 to give the compounds as shown in the following Table 20.

TABLE 20 (No. 1)

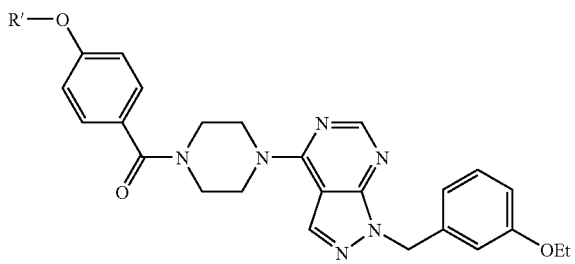

| Ex. Nos. | R' | Physicochemical properties etc. |
|---|---|---|
| 568* | Et-N(Et)-CH2-C(Me)(Me)-Et | amorphous powder MS (APCI) 600 [M + H]+ |
| 569* | Me-N(4-methylpiperidine) | amorphous powder MS (APCI) 556 [M + H]+ |
| 570* | Me-N(Me)-CH2-CH(Me)-Et | amorphous powder MS (APCI) 558 [M + H]+ |

*hydrochloride
Me: methyl group, Et: ethyl group

TABLE 20 (No. 2)

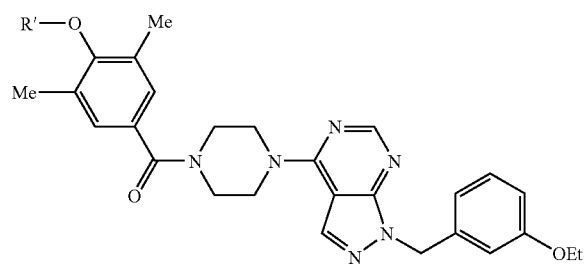

| Ex. Nos. | R' | Physicochemical properties etc. |
|---|---|---|
| 571* | Me-N(Me)-Pr | amorphous powder MS (APCI) 558 [M + H]+ |
| 572* | Me-N(Me)-Bu | amorphous powder MS (APCI) 572 [M + H]+ |
| 573* | pyrrolidinyl-propyl | amorphous powder MS (APCI) 584 [M + H]+ |
| 574* | Me-N(Me)-CH2-C(Me)(Me)-Et | amorphous powder MS (APCI) 600 [M + H]+ |

*: hydrochloride
Me: methyl group, Et: ethyl group

TABLE 20 (No. 3)

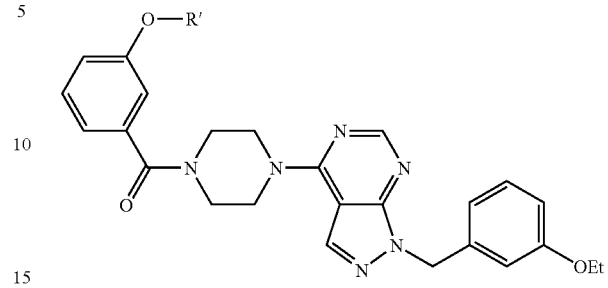

| Ex. Nos. | R' | Physicochemical properties etc. |
|---|---|---|
| 575* | Me-N(Me)-(CH2)3-Me | amorphous powder MS (APCI) 544 [M + H]+ |
| 576* | pyrrolidinyl-propyl | amorphous powder MS (APCI) 556 [M + H]+ |
| 577* | Me-N(Me)-CH2-C(Me)(Me)-Et | amorphous powder MS (APCI) 572 [M + H]+ |

*hydrochloride
Me: methyl group, Et: ethyl group

EXAMPLES 578 TO 616

The corresponding materials are treated in the same manner as described in Example 366 to give the compounds as shown in the following Table 21.

TABLE 21 (No. 1)

| Ex. Nos. | R | R² | Physicochemical properties etc. |
|---|---|---|---|
| 578 | Me | 4-methyl-2-n-propyl-thiazolyl | amorphous powder MS (APCI) 618 [M + H]+ |
| 579 | Me | 6-methyl-2-n-propyl-pyridinyl | amorphous powder MS (APCI) 612 [M + H]+ |

TABLE 21-continued (No. 1)

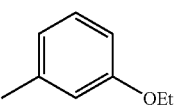

| Ex. Nos. | R | R² | Physicochemical properties etc. |
|---|---|---|---|
| 580* | Me | 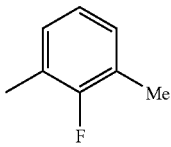 | amorphous powder MS (APCI) 613 [M + H]+ |
| 581* | Me |  | amorphous powder MS (APCI) 601 [M + H]+ |
| 582* | 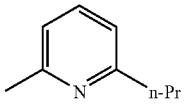 |  | amorphous powder MS (APCI) 638 [M + H]+ |
| 583* | 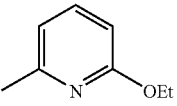 |  | amorphous powder MS (APCI) 640 [M + H]+ |
| 584* | 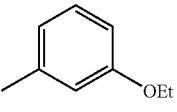 |  | amorphous powder MS (APCI) 639 [M + H]+ |
| 585* | 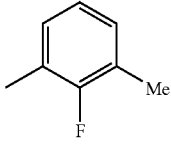 |  | amorphous powder MS (APCI) 627 [M + H]+ |
| 586* | 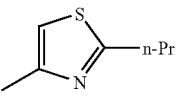 | 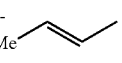 | amorphous powder MS (APCI) 644 [M + H]+ |

*hydrochloride
Me: methyl group, Et: ethyl group, n-Pr: n-propyl group

TABLE 21 (No. 2)

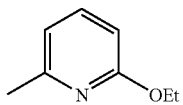

| Ex. Nos. | R | R² | Physicochemical properties etc. |
|---|---|---|---|
| 587* | (E)- 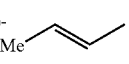 | 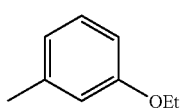 | amorphous powder MS (APCI) 640 [M + H]+ |
| 588* | (E)- 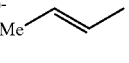 | 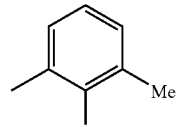 | amorphous powder MS (APCI) 639 [M + H]+ |
| 589* | (E)- 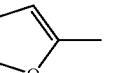 | 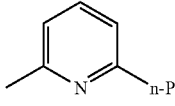 | amorphous powder MS (APCI) 627 [M + H]+ |
| 590 | 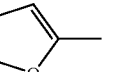 | 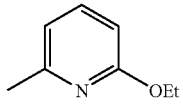 | amorphous powder MS (APCI) 664 [M + H]+ |
| 591* | 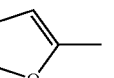 | 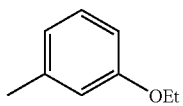 | amorphous powder MS (APCI) 666 [M + H]+ |
| 592 | 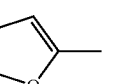 | 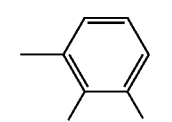 | amorphous powder MS (APCI) 665 [M + H]+ |
| 593 | 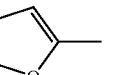 | 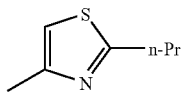 | amorphous powder MS (APCI) 653 [M + H]+ |
| 594* | 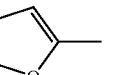 | 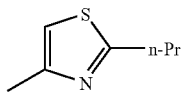 | amorphous powder MS (APCI) 670 [M + H]+ |

*hydrochloride
Me: methyl group, Et: ethyl group, n-Pr: n-propyl group

TABLE 21

(No. 3)

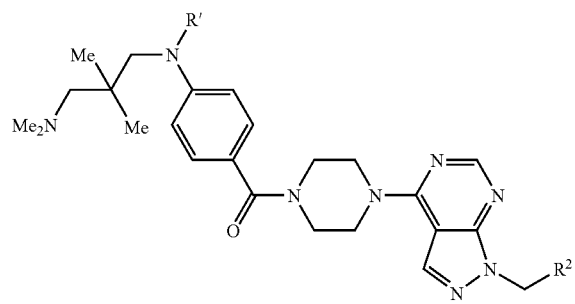

| Ex. Nos. | R' | R² | Physicochemical properties etc. |
|---|---|---|---|
| 595* | Et | 6-methyl-2-n-propyl-pyridin-3-yl | amorphous powder MS (APCI) 598 [M + H]+ |
| 596* | cyclopropylmethyl | 6-methyl-2-n-propyl-pyridin-3-yl | amorphous powder MS (APCI) 524 [M + H]+ |
| 597* | n-Pr | 3-methyl-5-ethoxyphenyl | amorphous powder MS (APCI) 613 [M + H]+ |
| 598* | Et | 3-methyl-5-ethoxyphenyl | amorphous powder MS (APCI) 599 [M + H]+ |
| 599* | cyclopropylmethyl | 3-methyl-5-ethoxyphenyl | amorphous powder MS (APCI) 625 [M + H]+ |
| 600* | i-Bu | 3-methyl-5-ethoxyphenyl | amorphous powder MS (APCI) 627 [M + H]+ |

*hydrochloride
Me: methyl group, Et: ethyl group, n-Pr: n-propyl group, i-Bu: isobutyl group

TABLE 21

(No. 4)

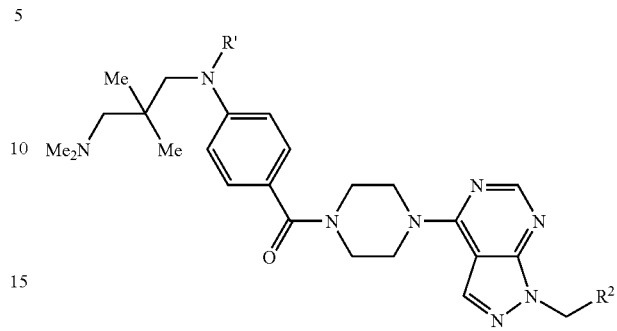

| Ex. Nos. | R' | R² | Physicochemical properties etc. |
|---|---|---|---|
| 601* | Et | 2-fluoro-3,5-dimethylphenyl | amorphous powder MS (APCI) 587 [M + H]+ |
| 602* | cyclopropylmethyl | 2-fluoro-3,5-dimethylphenyl | amorphous powder MS (APCI) 613 [M + H]+ |
| 603* | Et | 4-methyl-2-n-propyl-thiazol-5-yl | amorphous powder MS (APCI) 604 [M + H]+ |
| 604* | cyclopropylmethyl | 4-methyl-2-n-propyl-thiazol-5-yl | amorphous powder MS (APCI) 630 [M + H]+ |

*hydrochloride
Me: methyl group, Et: ethyl group, n-Pr: n-propyl group

TABLE 21

(No. 5)

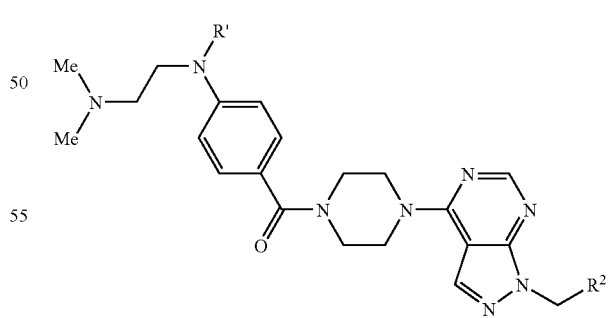

| Ex. Nos. | R' | R² | Physicochemical properties etc. |
|---|---|---|---|
| 605* | cyclopropylmethyl | 4-methyl-2-n-propyl-thiazol-5-yl | amorphous powder MS (APCI) 588 [M + H]+ |

TABLE 21-continued (No. 5)

| Ex. Nos. | R' | R² | Physicochemical properties etc. |
|---|---|---|---|
| 606* | cyclopropylmethyl | 6-methyl-2-n-propyl-pyridin-3-yl | amorphous powder MS (APCI) 582 [M + H]+ |
| 607* | Et | 6-methyl-2-n-propyl-pyridin-3-yl | amorphous powder MS (APCI) 556 [M + H]+ |
| 608* | Me | 6-methyl-2-n-propyl-pyridin-3-yl | amorphous powder MS (APCI) 542 [M + H]+ |
| 609* | cyclopropylmethyl | 3-ethoxyphenyl | amorphous powder MS (APCI) 583 [M + H]+ |
| 610* | Et | 3-ethoxyphenyl | amorphous powder MS (APCI) 557 [M + H]+ |
| 611* | Me | 3-ethoxyphenyl | amorphous powder MS (APCI) 543 [M + H]+ |
| 612* | cyclopropylmethyl | 3-methyl-2-fluoro-phenyl (with Me) | amorphous powder MS (APCI) 571 [M + H]+ |

*hydrochloride
Me: methyl group, Et: ethyl group, n-Pr: n-propyl group

TABLE 21

(No. 6)

| Ex. Nos. | R' | R² | Physicochemical properties etc. |
|---|---|---|---|
| 613* | Et | 2,6-dimethyl-fluorophenyl | amorphous powder MS (APCI) 545 [M + H]+ |
| 614* | Me | 2,6-dimethyl-fluorophenyl | amorphous powder MS (APCI) 531 [M + H]+ |
| 615* | Et | 4-methyl-2-n-propyl-thiazol-5-yl | amorphous powder MS (APCI) 562 [M + H]+ |
| 616* | Me | 4-methyl-2-n-propyl-thiazol-5-yl | amorphous powder MS (APCI) 548 [M + H]+ |

*hydrochloride
Me: methyl group, Et: ethyl group, n-Pr: n-propyl group

EXAMPLE 617

(1) Trans-4-[N-methyl-N-(tert-butoxycarbonyl)aminomethyl]cyclohexanecarboxylic acid (compound obtained in Reference Example 239) is treated in the same manner as described in Example 3 to give 1-(3-ethoxybenzyl)-4-[4-[[trans-4-[N-methyl-N-(tert-butoxycarbonyl)aminomethyl]cyclohexyl]carbonyl]piperazin-1-yl]-1H-pyrazolo[3,4-d]pyrimidine as an amorphous powder. MS (APCI) m/z; 592 [M+H]+

(2) The compound obtained in the above step (1) is treated in the same manner as described in Example 404(2) to give 1-(3-ethoxybenzyl)-4-[4-[[trans-4-(methyl-aminomethyl)cyclohexyl]carbonyl]piperazin-1-yl]-1H-pyrazolo[3,4-d]pyrimidine dihydrochloride as an amorphous powder. MS (APCI) m/z; 492 [M+H]+

EXAMPLE 618

(1) 4-[[2-(dimethylamino)ethyl]amino]-3-methylbenzoic acid hydrochloride (compound obtained in Reference Example 251) is treated in the same manner as described in Example 3 to give 1-(3-ethoxybenzyl)-4-[4-[3-methyl-4-[2-

(dimethylamino)ethylamino]benzoyl]piperazin-1-yl]-1H-pyrazolo[3,4-d]pyrimidine as an amorphous powder. MS (APCI) m/z; 543 [M+H]+

(2) To a solution of the compound obtained in the above step (1) (50 mg) in 1,2-dichloroethane (1 mL) is added successively acetaldehyde (10 μL), acetic acid (10 μL) and sodium triacetoxyborohydride (29 mg) under ice-cooling. The mixture is stirred at room temperature overnight. To the reaction mixture is further added successively acetaldehyde (10 μL), acetic acid (10 μL), and sodium triacetoxyborohydride (29 mg). The mixture is stirred at room temperature overnight. To the reaction mixture is added a saturated sodium hydrogencarbonate solution and the mixture is extracted with chloroform. The extract is concentrated and the residue is purified by HPLC (Solvent; 10 mM ammonium carbonate:methanol=80:20→5:95). The resultant product is treated in the same manner as described in Example 4(3) to give 1-(3-ethoxybenzyl)-4-[4-[3-methyl-4-[N-ethyl-N-[2-(dimethylamino)ethyl]amino]benzoyl]-piperazin-1-yl]-1H-pyrazolo[3,4-d]pyrimidine 2 hydrochloride (22 mg, yield; 37%) as an amorphous powder. MS (APCI) m/z; 571 [M+H]+

EXAMPLE 619 TO 629

The corresponding materials are treated in the same manner as described in Example 618 to give the compounds as shown in the following Table 22.

TABLE 22

(No. 1)

| Ex. Nos. | R' | R" | Physicochemical properties etc. |
|---|---|---|---|
| 619 | benzyl | H | amorphous powder MS (ESI) 568 [M + H]+ |
| 620 | i-Pr | H | amorphous powder MS (ESI) 520 [M + H]+ |
| 621 | cyclopentyl | H | amorphous powder MS (ESI) 546 [M + H]+ |
| 622 | cyclopropylmethyl | cyclopropylmethyl | amorphous powder MS (ESI) 586 [M + H]+ |
| 623 | i-Bu | H | amorphous powder MS (ESI) 534 [M + H]+ |

TABLE 22-continued (No. 1)

| Ex. Nos. | R' | R" | Physicochemical properties etc. |
|---|---|---|---|
| 624* | Et | H | amorphous powder MS (APCI) 506 [M + H]+ |

*hydrochloride,
Et: ethyl group, i-Pr: isopropyl group, i-Bu: isobutyl group

TABLE 22

(No. 2)

| Ex. Nos. | R' | R² | Physicochemical properties etc. |
|---|---|---|---|
| 625** | i-Bu | 3-ethoxybenzyl | amorphous powder MS (APCI) 599 [M + H]+ |
| 626** | cyclopropylmethyl | 3-ethoxybenzyl | amorphous powder MS (APCI) 597 [M + H]+ |
| 627** | Me | (6-n-Pr-pyridin-2-yl)methyl | amorphous powder MS (APCI) 556 [M + H]+ |
| 628** | Et | (6-n-Pr-pyridin-2-yl)methyl | amorphous powder MS (APCI) 570 [M + H]+ |

TABLE 22-continued (No. 2)

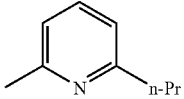

| Ex. Nos. | R' | R² | Physicochemical properties etc. |
|---|---|---|---|
| 629** | i-Bu | ![pyridine-n-Pr] | amorphous powder MS (APCI) 598 [M + H]+ |

**dihydrochloride
Me: methyl group, Et: ethyl group, n-Pr: n-propyl group, i-Bu: isobutyl group

EXAMPLE 630

(1) To a solution of 1-(3-ethoxybenzyl)-4-(1-piperadinyl)-1H-pyrazolo[3,4-d]pyrimidine dihydrochloride (60 mg) in methylene chloride (1.2 mL) is added N,N-diisopropylethylamine (85 μL) and 4-nitrophenyl chloroformate (49 mg) at 0° C., and the mixture is stirred at room temperature for 2.5 hours. The reaction mixture is diluted with chloroform (1 mL) and thereto is added a saturated sodium hydrogencarbonate solution (1.5 mL). After stirring, the organic layer is separated and the aqueous layer is extracted with chloroform. The organic layers are combined, dried over sodium sulfate, and filtered. The filtrate is concentrated and the residue is purified by column chromatography on silica gel (Solvent; n-hexane:ethyl acetate=9:1→0:10) to give 1-(3-ethoxybenzyl)-4-[4-[(4-nitrophenoxy)carbonyl]piperazin-1-yl]-1H-pyrazolo[3,4-d]pyrimidine (72 mg, yield; 100%) as an amorphous powder. MS (APCI) m/z; 504 [M+H]+

(2) To a solution of the compound obtained in the above step (1) (25 mg) in N,N-dimethylformamide (1.5 mL) is added N,N-diisopropylethylamine (51 μL) and 4-(1-pyrrolidinyl)piperidine (65 mg) at room temperature and the mixture is stirred at 70° C. for 4 hours. After cooling, the reaction mixture is diluted with chloroform (1 mL) and thereto is added a saturated sodium hydrogencarbonate solution (1.5 mL). After stirring, the organic layer is separated and the aqueous layer is extracted with chloroform. The organic layers are combined, dried over sodium sulfate, and filtered. The filtrate is concentrated and the residue is purified by column chromatography on silica gel (Solvent; chloroform:methanol=10:0→85:15) to give 1-(3-ethoxybenzyl)-4-[4-[[4-(1-pyrrolidinyl)piperidin-1-yl]carbonyl]piperazin-1-yl]-1H-pyrazolo-[3,4-d]pyrimidine (19 mg, yield; 73%) as an amorphous powder. MS (APCI) m/z; 519 [M+H]+

(3) The compound obtained in the above step (2) (19 mg) is treated in the same manner as described in Example 4(3) to give 1-(3-ethoxybenzyl)-4-[4-[[4-(1-pyrrolidin-yl)piperidin-1-yl]carbonyl]piperazin-1-yl]-1H-pyrazolo[3,4-d]pyrimidine 2 hydrochloride as an amorphous powder. MS (APCI) m/z; 519 [M+H]+

EXAMPLES 631 TO 632

The corresponding materials are treated in the same manner as described in Example 630 to give the compounds as shown in the following Table 23.

TABLE 23

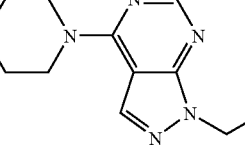

| Ex. Nos. | R¹ | Physicochemical properties etc. |
|---|---|---|
| 631** | ![piperidinyl-piperidinyl] | amorphous powder MS (APCI) 533 [M + H]+ |
| 632** | ![morpholinyl-piperidinyl] | amorphous powder MS (APCI) 535 [M + H]+ |

**dihydrochloride
Et: ethyl group

EXAMPLE 633

(1) Methyl 4-[[1-(tert-butoxycarbonylaminomethyl)-1-cyclopropyl]methoxy]-benzoate (compound obtained in Reference Example 235, 245 mg) is treated in the same manner as described in Example 1 to give 1-(3-ethoxybenzyl)-4-[4-[4-[[1-(tert-butoxycarbonylaminomethyl)-1-cyclopropyl]methoxy]benzoyl]piperazin-1-yl]-1H-pyrazolo[3,4-d]pyrimidine (380 mg, yield; 98%) as colorless liquid. MS (APCI) m/z; 642.5 [M+H]+

(2) The compound obtained in the above step (1) (100 mg) is treated in the same manner as described in Example 404(2) to give 1-(3-ethoxybenzyl)-4-[4-[4-[[1-(aminomethyl)-1-cyclopropyl]methoxy]benzoyl]piperazin-1-yl]-1H-pyrazolo[3,4-d]-pyrimidine dihydrochloride (crude product) and the product is treated in the same manner as described in Example 618(2) 1-(3-ethoxybenzyl)-4-[4-[4-[[1-(dimethylaminomethyl)-1-cyclopropyl]methoxy]benzoyl]piperazin-1-yl]-1H-pyrazolo[3,4-d]-pyrimidine hydrochloride (33 mg, yield; 34%) as an amorphous powder. MS (APCI) m/z; 570 [M+H]+

EXAMPLES 634 TO 636

The corresponding materials are treated in the same manner as described in Example 633 to give the compounds as shown in the following Table 24.

TABLE 24

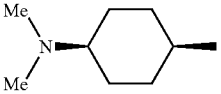

| Ex. Nos. | R' | Physicochemical properties etc. |
|---|---|---|
| 634* | 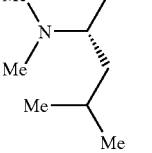 | amorphous powder MS (APCI) 584 [M + H]+ |
| 635* | 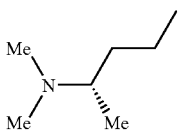 | amorphous powder MS (APCI) 586 [M + H]+ |
| 636* | 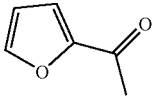 | amorphous powder MS (APCI) 558 [M + H]+ |

*hydrochloride
Me: methyl group, Et: ethyl group

EXAMPLE 637

1-(3-Ethoxybenzyl)-4-[4-[3-methyl-4-[2-(dimethylamino)ethylamino]benzoyl]-piperazin-1-yl]-1H-pyrazolo[3,4-d]pyrimidine (compound obtained in Example 618(1)) is treated in the same manner as described in Example 416 to give 1-(3-Ethoxybenzyl)-4-[4-[3-methyl-4-[N-acetyl-N-[2-(dimethylamino)ethyl]amino]benzoyl]piperazin-1-yl]-1H-pyrazolo[3,4-d]pyrimidine (26 mg, yield; 42%) as an amorphous powder. MS (APCI) m/z; 585 [M+H]$^+$

EXAMPLES 638 TO 650

The corresponding materials are treated in the same manner as described in Example 637 to give the compounds as shown in the following Table 25.

TABLE 25

(No. 1)

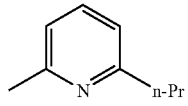

| Ex. Nos. | R' | R² | Physicochemical properties etc. |
|---|---|---|---|
| 638* | 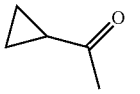 | 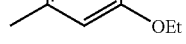 | amorphous powder MS (APCI) 636 [M + H]+ |
| 639* | 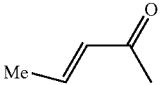 | 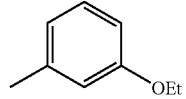 | amorphous powder MS (APCI) 611 [M + H]+ |
| 640* | 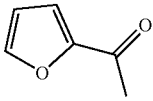 | 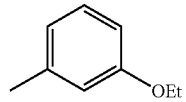 | E-isomer amorphous powder MS (APCI) 611 [M + H]+ |
| 641* | 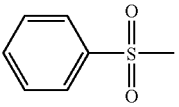 | 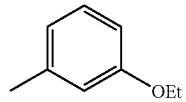 | amorphous powder MS (APCI) 637 [M + H]+ |
| 642* | 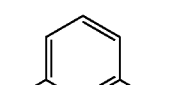 | 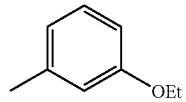 | amorphous powder MS (APCI) 683 [M + H]+ |
| 643* | MeCO— | 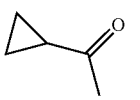 | amorphous powder MS (APCI) 584 [M + H]+ |
| 644* | 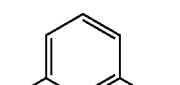 | 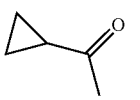 | amorphous powder MS (APCI) 610 [M + H]+ |

*hydrochloride
Me: methyl group, Et: ethyl group, n-Pr: n-propyl group

TABLE 25 (No. 2)

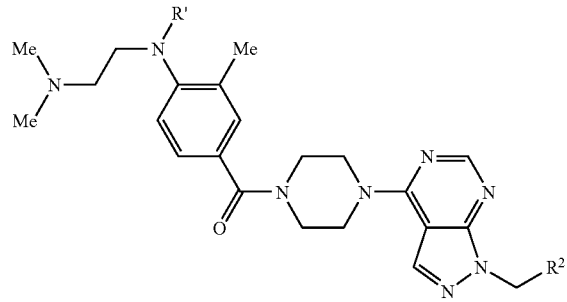

| Ex. Nos. | R' | R² | Physicochemical properties etc. |
|---|---|---|---|
| 645* | Me-CH=CH-C(O)- | 6-methyl-2-n-Pr-pyridin-3-yl | amorphous powder MS (APCI) 610 [M + H]+ |
| 646* | PhSO₂- | 6-methyl-2-n-Pr-pyridin-3-yl | amorphous powder MS (APCI) 682 [M + H]+ |
| 647* | MeCO— | 4-methyl-2-n-Pr-thiazol-5-yl | amorphous powder MS (APCI) 590 [M + H]+ |
| 648* | MeCO— | 6-methyl-2-OEt-pyridin-3-yl | amorphous powder MS (APCI) 586 [M + H]+ |

*hydrochloride
Me: methyl group, Et: ethyl group, n-Pr: n-propyl group

TABLE 25 (No. 3)

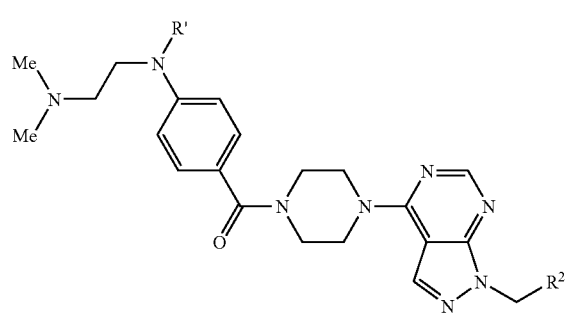

| Ex. Nos. | R' | R² | Physicochemical properties etc. |
|---|---|---|---|
| 649* | H₃C-SO₂- | 3-OEt-phenyl | amorphous powder MS (APCI) 607 [M + H]+ |
| 650* | PhSO₂- | 3-OEt-phenyl | amorphous powder MS (APCI) 669 [M + H]+ |

*hydrochloride
Me: methyl group, Et: ethyl group

EXAMPLE 651

(1) Ethyl trans-4-(methoxymethoxy)cyclohexanecarboxylate (compound obtained in Reference Example 237, 2.0 g) is treated in the same manner as described in Example 1 to give 1-(3-ethoxybenzyl)-4-[4-[[trans-4-(methoxymethoxy)cyclohexyl]-carbonyl]piperazin-1-yl]-1H-pyrazolo[3,4-d]pyrimidine (2.88 g, yield; 78%) as an amorphous powder. MS (APCI) m/z; 509 [M+H]⁺

(2) To a suspension of the compound obtained in the above step (1) (2.8 g) in ethanol (20 mL) is added conc. hydrochloric acid (2.0 mL) and water (0.2 mL), and the mixture is stirred at 80° C. for 1 hour. The reaction mixture is diluted with ether and the resultant crystals are collected by filtration to give 1-(3-ethoxybenzyl)-4-[4-[(trans-4-hydroxycyclohexyl)carbonyl]piperazin-1-yl]-1H-pyrazolo[3, 4-d]pyrimidine hydrochloride (2.81 g, yield; 99%) as colorless crystals. MS (APCI) m/z; 465 [M+H]⁺

(3) To a suspension of the compound obtained in the above step (2) (50 mg) in toluene (0.5 mL) is added 2-(dimethylamino)ethyl chloride hydrochloride (80 mg) and sodium hydride (60% dispersion in mineral oil, 50 mg), and the mixture is stirred at 100° C. for 2 days. To the reaction mixture is added water and the mixture is extracted with chloroform. The extract is concentrated in vacuo and the residue is purified by flash column chromatography on silica gel (Solvent; ethyl acetate) and then the resultant product is treated in the same manner as described in Example 4(3) to give 1-(3-ethoxybenzyl)-4-[4-[[trans-4-[2-(dimethylamino) ethoxy]cyclohexyl]carbonyl]-piperazin-1-yl]-1H-pyrazolo [3,4-d]pyrimidine hydrochloride (14 mg, yield; 24%) as an amorphous powder. MS (APCI) m/z; 536 [M+H]⁺

EXAMPLE 652

Methyl 4-[(2S)-2-(tert-butoxycarbonylamino)-4-methylpentyloxy]benzoate (compound obtained in Reference Example 285, 256 mg) is treated in the same manner as described in Example 1 to give 1-(3-ethoxybenzyl)-4-[4-[4-

[(2S)-2-(tert-butoxy-carbonylamino)-4-methylpentyloxy]benzoyl]piperazin-1-yl]-1H-pyrazolo[3,4-d]-pyrimidine (400 mg, yield; 99%) as a colorless oil. MS (APCI) m/z; 659 [M+H]$^+$ (2) To a solution of the compound obtained in the above step (1) (50 mg) in tetrahydrofuran (3 mL) is added sodium hydride (60% dispersion in mineral oil; 10 mg) under ice-cooling and the mixture is stirred for 0.5 hour. To the mixture is added dropwise methyl iodide (55 mg) and the mixture is stirred at room temperature for 3 hours. To the reaction mixture is added water and the mixture is extracted with ethyl acetate. The extract is concentrated and the residue is purified by flash column chromatography on NH-silica gel (Solvent; n-hexane:ethyl acetate=9:1→1:9) to give 1-(3-ethoxybenzyl)-4-[4-[4-[(2S)-2-[N-methyl-N-(tert-butoxycarbonyl)amino]-4-methylpentyloxy]benzoyl]piperazin-1-yl]-1H-pyrazolo[3,4-d]pyrimidine (35 mg, yield; 67%) as a colorless oil. MS (APCI) m/z; 672 [M+H]$^+$ (3) The compound obtained in the above step (2) is treated in the same manner as described in Example 404(2) to give 1-(3-ethoxybenzyl)-4-[4-[4-[(2S)-2-(methyl-amino)-4-methylpentyloxy]benzoyl]piperazin-1-yl]-1H-pyrazolo[3,4-d]pyrimidine (15 mg, yield; 46%) as an amorphous powder. MS (APCI) m/z; 572 [M+H]$^+$

EXAMPLE 653

The corresponding materials are treated in the same manner as described in Example 652 to give the compound as shown in the following Table 26.

TABLE 26

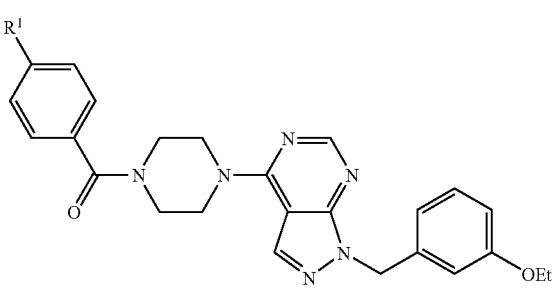

| Ex. Nos. | R' | Physicochemical properties etc. |
|---|---|---|
| 653** | Me-NH-CH2-C(Me)(Me)-CH2-O- | amorphous powder MS (APCI) 558 [M + H]+ |

**dihydrochloride
Me: methyl group, Et: ethyl group

EXAMPLE 654

(1) To a solution of oxalyl chloride (4.48 mL) in methylene chloride (50 mL) is added dropwise dimethylsulfoxide (4.55 g) in methylene chloride (5 mL) at −60° C. over a period of 15 minutes. To the mixture is added dropwise a solution of methyl trans-4-(hydroxymethyl)cyclohexanecarboxylate (compound obtained in Reference Example 238; 5.9 g) in methylene chloride (30 mL) over a period of 30 minutes. The mixture is stirred at the same temperature for 1 hour and thereto is added dropwise triethylamine (16.7 mL) at −60° C. The mixture is stirred at the same temperature for 30 minutes and at 0° C. for 1 hour. The reaction mixture is diluted with chloroform, and washed successively with water, 5% citric acid solution, water, and saturated brine. The organic layer is dried over anhydrous sodium sulfate and concentrated in vacuo to give methyl trans-4-formylcyclohexanecarboxylate (5.32 g, yield; 91%) as an oil.

(2) To a solution of the compound obtained in the above step (1) (500 mg) and 3-dimethylaminopropylamine (600 mg) in methylene chloride (10 mL) is added successively sodium triacetoxyborohydride (983 mg) and acetic acid (353 mg), and the mixture is stirred at room temperature for 5 days. The reaction mixture is neutralized carefully with a saturated sodium hydrogencarbonate solution and the mixture is extracted with chloroform (×2). The extract is concentrated in vacuo and the residue is purified by flash column chromatography on silica gel (Solvent; chloroform: methanol: 28% aqueous ammonia solution=9:1:0.1) to give methyl trans-4-[3-(dimethylamino)propylaminomethyl]cyclohexanecarboxylate (293 mg, yield; 32%) as oil. MS (APCI) m/z; 257 [M+H]$^+$ (3) To a solution of the compound obtained in the above step (2) (92 mg) in chloroform (0.5 mL) is added a solution of 2-furoyl chloride (68 μL) in chloroform (0.5 mL) and pyridine (67 μL) under ice-cooling, and the mixture is stirred at room temperature for one day. To the reaction mixture is added a saturated sodium hydrogencarbonate solution and the mixture is extracted with chloroform (×3). The organic layers are combined and concentrated in vacuo. The resultant crude product is purified by flash column chromatography on NH-silica gel (Solvent; n-hexane:ethyl acetate=9: 1→1:1) to give methyl trans-4-[[N-(2-furoyl)-N-[3-(dimethylamino)-propyl]amino]methylcyclohexanecarboxylate (102 mg, yield; 75%) as oil. MS (APCI) m/z; 373 [M+H]$^+$ (4) The compound obtained in the above step (3) is treated in the same manner as described in Example 1 to give 1-(3-ethoxybenzyl)-4-[4-[[trans-4-[N-(2-furoyl)-N-[3-(dimethylamino)propyl]aminomethyl]cyclohexyl]carbonyl]piperazin-1-yl]-1H-pyrazolo[3,4-d]pyrimidine hydrochloride as an amorphous powder. MS (APCI) m/z; 657 [M+H]$^+$

EXAMPLE 655 TO 670

The corresponding materials are treated in the same manner as described in Example 654 to the compounds as shown in the following Table 27.

TABLE 27

(No. 1)

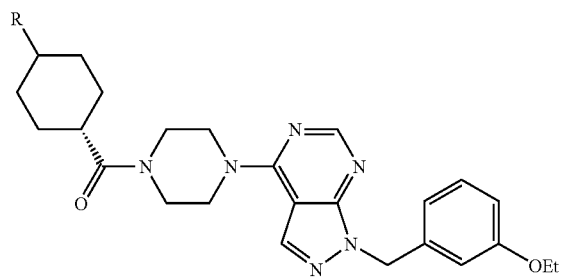

| Ex. Nos. | R | Physicochemical properties etc. |
|---|---|---|
| 655* | 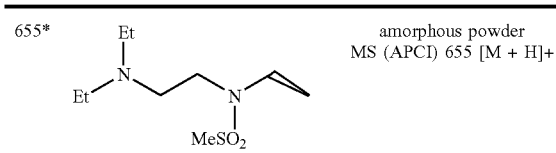 | amorphous powder MS (APCI) 655 [M + H]+ |
| 656 | 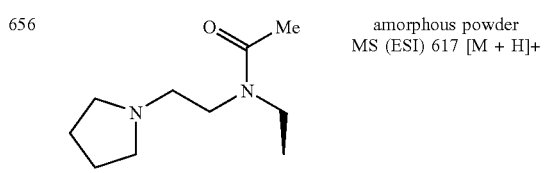 | amorphous powder MS (ESI) 617 [M + H]+ |
| 657 | 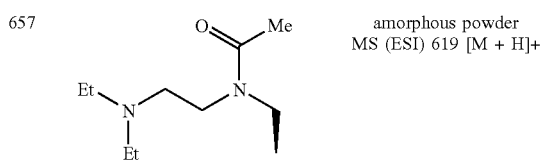 | amorphous powder MS (ESI) 619 [M + H]+ |
| 658 | 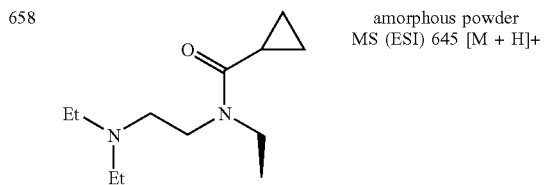 | amorphous powder MS (ESI) 645 [M + H]+ |
| 659 | 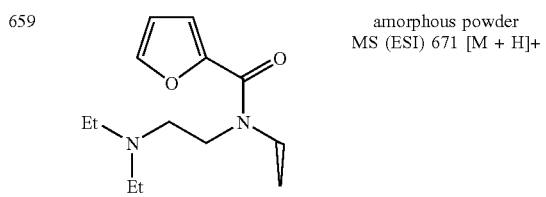 | amorphous powder MS (ESI) 671 [M + H]+ |
| 660 | 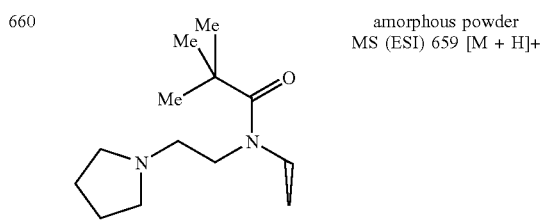 | amorphous powder MS (ESI) 659 [M + H]+ |

*hydrochloride
Me: methyl group, Et: ethyl group

TABLE 27

(No. 2)

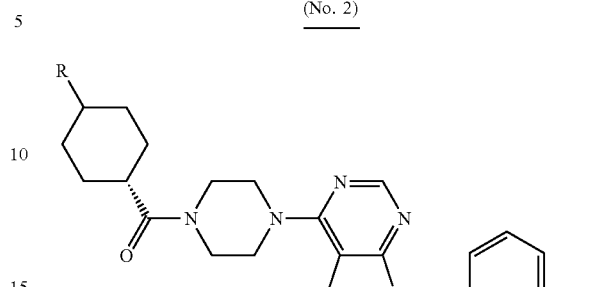

| Ex. Nos. | R | Physicochemical properties etc. |
|---|---|---|
| 661 | 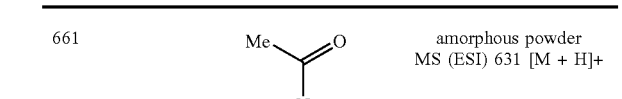 | amorphous powder MS (ESI) 631 [M + H]+ |
| 662* | 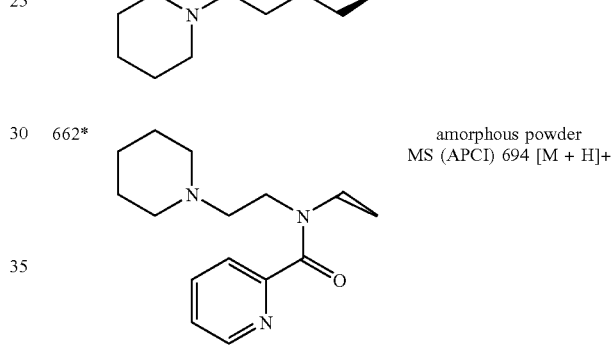 | amorphous powder MS (APCI) 694 [M + H]+ |
| 663* | 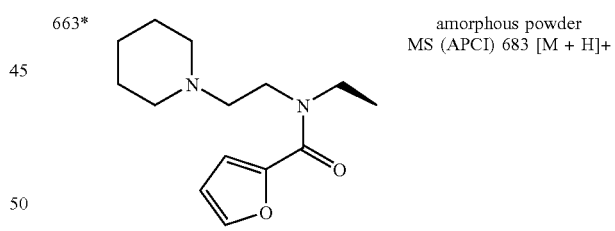 | amorphous powder MS (APCI) 683 [M + H]+ |
| 664* | 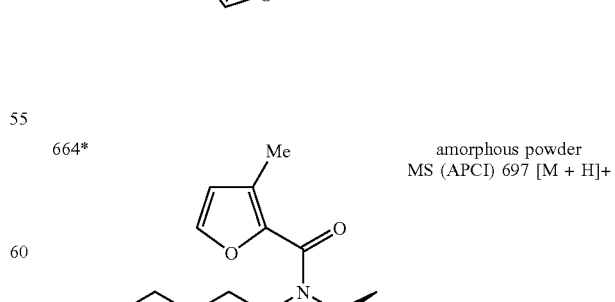 | amorphous powder MS (APCI) 697 [M + H]+ |

TABLE 27-continued (No. 2)

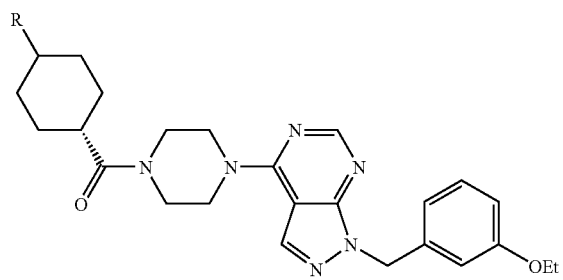

| Ex. Nos. | R | Physicochemical properties etc. |
|---|---|---|
| 665 | 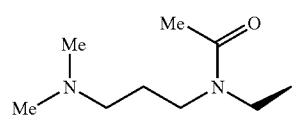 | amorphous powder MS (ESI) 605 [M + H]+ |
| 666* | 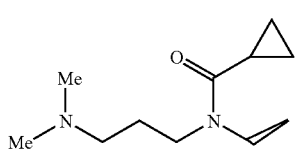 | amorphous powder MS (APCI) 631 [M + H]+ |

*hydrochloride
Me: methyl group, Et: ethyl group

TABLE 27

(No. 3)

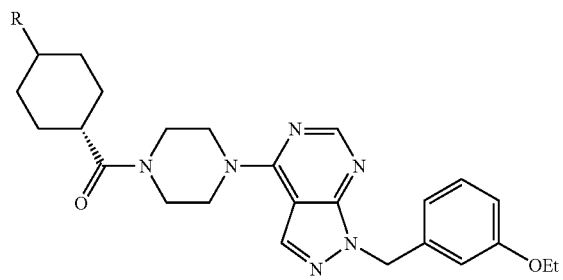

| Ex. Nos. | R | Physicochemical properties etc. |
|---|---|---|
| 667* | 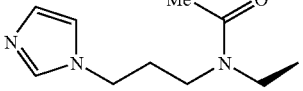 | amorphous powder MS (APCI) 628 [M + H]+ |
| 668* | 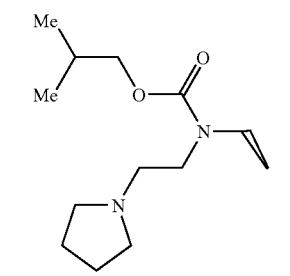 | amorphous powder MS (APCI) 675 [M + H]+ |

TABLE 27-continued (No. 3)

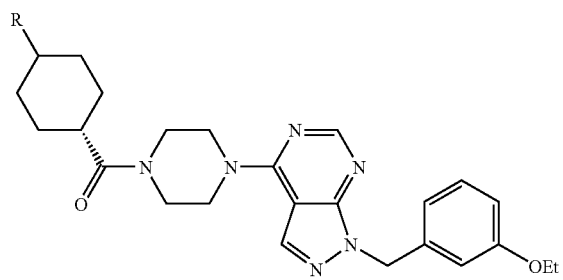

Ex. Nos.    R    Physicochemical properties etc.

*hydrochloride
Me: methyl group, Et: ethyl group

TABLE 27

(No. 4)

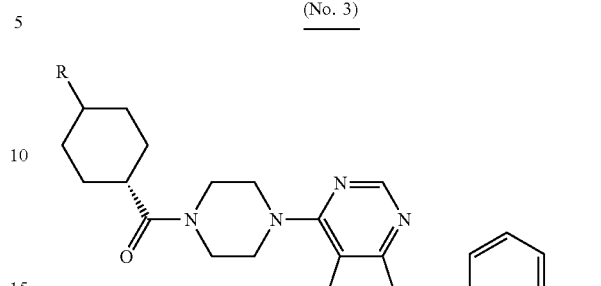

| Ex. Nos. | R | Physicochemical properties etc. |
|---|---|---|
| 669* | (pyrrolidinyl-ethyl-N(vinyl)-C(O)-NMe2) | amorphous powder MS (APCI) 646 [M + H]+ |
| 670* | (Me2N-propyl-N(vinyl)-C(O)-C6H4-F) | amorphous powder MS (APCI) 685 [M + H]+ |

*hydrochloride
Me: methyl group, Et: ethyl group

EXAMPLES 671 TO 703

The corresponding materials are treated in the same manner as described in either one of the aforementioned Example 404, 407, 617 and 652 to give the compounds as shown in the following Table 27.1.

TABLE 27.1

(No. 1)

| Ex. Nos. | R | R² | Physicochemical properties etc. |
|---|---|---|---|
| 671** | Me-NH-CH₂CH₂-O-Me | 3-OEt-phenyl | amorphous powder MS (APCI) 516 [M + H]+ |
| 672** | Me-NH-CH₂-C(cyclopropyl)-CH₂-O-Me | 3-OEt-phenyl | amorphous powder MS (APCI) 556 [M + H]+ |
| 673** | Me-NH-CH(Me)-CH₂-CH₂-O-Me | 3-OEt-phenyl | amorphous powder MS (APCI) 544 [M + H]+ |
| 674** | H₂N-CH₂CH₂-O-Me | 3-OEt-phenyl | amorphous powder MS (APCI) 502 [M + H]+ |
| 675** | H₂N-CH₂-C(Me)₂-CH₂-O-Me | 3-OEt-phenyl | amorphous powder MS (APCI) 544 [M + H]+ |
| 676** | Me-NH-CH₂-C≡C-Me | 6-n-Pr-pyridin-3-yl (2-Me) | amorphous powder MS (APCI) 509 [M + H]+ |
| 677** | (Z)-MeCH=CH-CH₂-NH-Me | 6-n-Pr-pyridin-3-yl (2-Me) | amorphous powder MS (APCI) 525 [M + H]+ |
| 678** | Me-NH-CH₂-C≡C-Me | 3-OEt-phenyl (with Me) | amorphous powder MS (APCI) 510 [M + H]+ |
| 679** | (Z)-MeCH=CH-CH₂-NH-Me | 3-OEt-phenyl (with Me) | amorphous powder MS (APCI) 526 [M + H]+ |
| 680** | Me-NH-CH₂-C≡C-Me | 2-n-Pr-4-Me-thiazol-5-yl | amorphous powder MS (APCI) 515 [M + H]+ |

**dihydrochloride
Me: methyl group, Et: ethyl group, n-Pr: n-propyl group

TABLE 27.1

(No. 2)

| Ex. Nos. | R | R² | Physicochemical properties etc. |
|---|---|---|---|
| 681** | (cis-CH₂-CH=CH-CH₂-NH-Et, Me shown) | 4-methyl-2-n-Pr-thiazol-5-yl | amorphous powder MS (APCI) 531 [M + H]+ |
| 682** | n-Bu-NH-Et | 6-methyl-2-n-Pr-pyridin-3-yl | amorphous powder MS (APCI) 527 [M + H]+ |
| 683** | n-Bu-NH-Et | 3-methyl-5-OEt-phenyl | amorphous powder MS (APCI) 528 [M + H]+ |
| 684** | n-Bu-NH-Et | 4-methyl-2-n-Pr-thiazol-5-yl | amorphous powder MS (APCI) 533 [M + H]+ |
| 685** | Me-NH-CH₂-C≡C-Me (Et on N) | 3-methyl-5-OEt-phenyl | amorphous powder MS (APCI) 524 [M + H]+ |
| 686** | cis-CH₂-CH=CH-CH₂-NH-Me | 3-methyl-5-OEt-phenyl | amorphous powder MS (APCI) 512 [M + H]+ |
| 687** | n-Bu-NH-Me | 3-methyl-5-OEt-phenyl | amorphous powder MS (APCI) 514 [M + H]+ |
| 688* | cyclopentyl-NH-Et | 2,6-dimethyl-3-F-phenyl | amorphous powder MS (APCI) 528 [M + H]+ |
| 689* | (Me)₂CH-NH-Et | 2,6-dimethyl-3-F-phenyl | amorphous powder MS (APCI) 502 [M + H]+ |
| 690* | cyclopentyl-NH-Et | 3-methyl-5-OEt-phenyl | amorphous powder MS (APCI) 540 [M + H]+ |

TABLE 27.1-continued (No. 2)

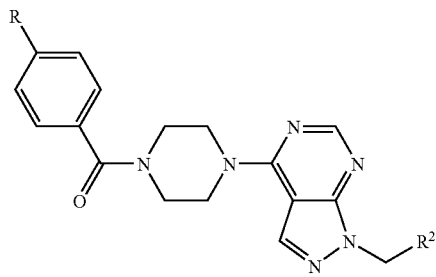

| Ex. Nos. | R | R² | Physicochemical properties etc. |
|---|---|---|---|

*hydrochloride,
**dihydrochloride
Me: methyl group, Et: ethyl group, n-Pr: n-propyl group

TABLE 27.1

(No. 3)

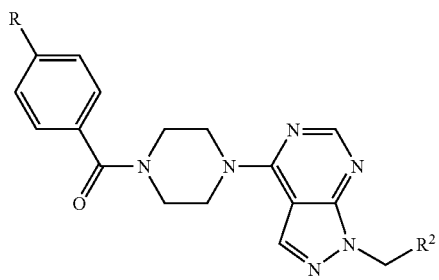

| Ex. Nos. | R | R² | Physicochemical properties etc. |
|---|---|---|---|
| 691* | Me-NH-CH₂- | 6-n-Pr-pyridin-2-yl | amorphous powder MS (APCI) 485 [M + H]+ |
| 692* | Me-CH₂-CH₂-NH-CH₂- | 6-n-Pr-pyridin-2-yl | amorphous powder MS (APCI) 513 [M + H]+ |
| 693* | Me-CH(Me)-NH-CH₂- | 6-n-Pr-pyridin-2-yl | amorphous powder MS (APCI) 513 [M + H]+ |
| 694* | cyclopentyl-NH-CH₂- | 6-n-Pr-pyridin-2-yl | amorphous powder MS (APCI) 539 [M + H]+ |
| 695* | Me-NH-CH₂- | 3-OEt-phenyl | amorphous powder MS (APCI) 486 [M + H]+ |
| 696 | Me-CH₂-CH₂-NH-CH₂- | 3-OEt-phenyl | amorphous powder MS (APCI) 514 [M + H]+ |

TABLE 27.1-continued (No. 3)

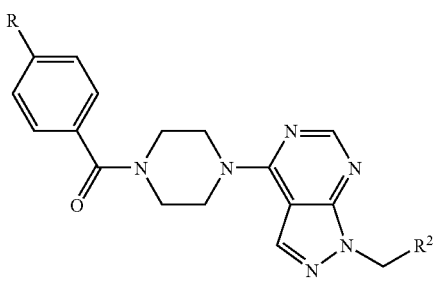

| Ex. Nos. | R | R² | Physicochemical properties etc. |
|---|---|---|---|
| 697* | Me-CH(Me)-NH-CH₂- | 3-OEt-phenyl | amorphous powder MS (APCI) 514 [M + H]+ |
| 698* | Me-NH-CH₂- | 2-F-3,6-diMe-phenyl | amorphous powder MS (APCI) 474 [M + H]+ |
| 699* | Me-NH-CH₂- | 2-n-Pr-thiazol-4-yl | amorphous powder MS (APCI) 491 [M + H]+ |
| 700* | Me-CH₂-CH₂-NH-CH₂- | 2-n-Pr-thiazol-4-yl | amorphous powder MS (APCI) 519 [M + H]+ |

*hydrochloride
Me: methyl group, Et: ethyl group, n-Pr: n-propyl group

TABLE 27.1

(No. 4)

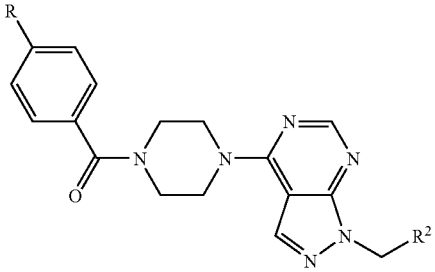

| Ex. Nos. | R | R² | Physicochemical properties etc. |
|---|---|---|---|
| 701* | 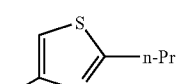 | 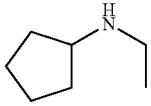 | amorphous powder MS (APCI) 519 [M + H]+ |
| 702 | 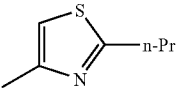 | 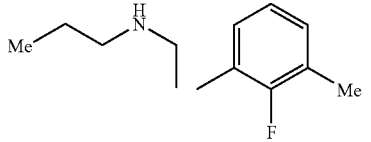 | amorphous powder MS (APCI) 545 [M + H]+ |
| 703 | 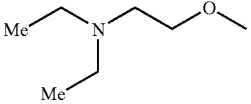 | 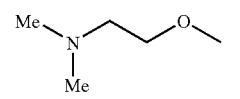 | amorphous powder MS (APCI) 502 [M + H]+ |

*hydrochloride

Me: methyl group, n-Pr: n-propyl group

EXAMPLES 704 TO 712

The corresponding materials are treated in the same manner as described in Example 1 to give the compounds as shown in the following Table 27.2.

TABLE 27.2

(No. 1)

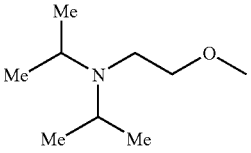

| Ex. Nos. | R | Physicochemical properties etc. |
|---|---|---|
| 704** | 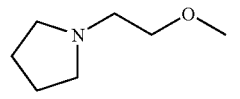 | amorphous powder MS (APCI) 687 [M + H]+ |
| 705** | 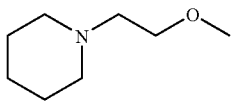 | amorphous powder MS (APCI) 659 [M + H]+ |
| 706** | 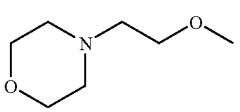 | amorphous powder MS (APCI) 715 [M + H]+ |
| 707** | 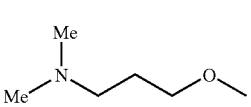 | amorphous powder MS (APCI) 685 [M + H]+ |
| 708** |  | amorphous powder MS (APCI) 699 [M + H]+ |
| 709** |  | amorphous powder MS (APCI) 701 [M + H]+ |
| 710** |  | amorphous powder MS (APCI) 673 [M + H]+ |

**dihydrochloride

Me: methyl group, Et: ethyl group

TABLE 27.2

(No. 2)

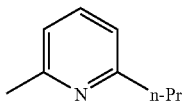

| Ex. Nos. | R² | Physicochemical properties etc. |
|---|---|---|
| 711** | 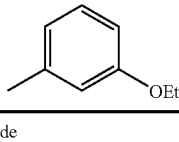 (2-n-Pr-6-Me-pyridyl-methyl) | amorphous powder MS (APCI) 616 [M + H]+ |
| 712** | (3-OEt-benzyl) | amorphous powder MS (APCI) 617 [M + H]+ |

**dihydrochloride
Me: methyl group, Et: ethyl group, n-Pr: n-propyl group

EXAMPLE 713

(1) The compound obtained in Example 630 (1) (730 mg) and 4-piperidone monohydrate hydrochloride (1.05 g) are treated in the same manner as described in Example 630 (2) to give 1-(3-ethoxybenzyl)-4-[4-[[4-oxopiperidin-1-yl)carbonyl]-piperidin-1-yl]-1H-pyrazolo[3,4-d]pyrimidine (654 mg, yield; 97%) as an amorphous powder. MS (APCI) m/z: 464 [M+H]+

(2) The compound obtained in the above step (1) (50 mg) is treated in the same manner as described in Example 6 to give 1-(3-ethoxybenzyl)-4-[4-[[4-(dimethylamino)piperidin-1-yl]carbonyl]piperazin-1-yl]-1H-pyrazolo[3,4-d]pyrimidine (15.6 mg, yield; 30%) as an amorphous powder. MS (APCI) m/z: 493 [M+H]+

(3) The compound obtained in the above step (2) (13.8 mg) is treated in the same manner as described in Example 4 (3) to give 1-(3-ethoxybenzyl)-4-[4-[[4-(dimethylamino)piperidin-1-yl]carbonyl]piperazin-1-yl]-1H-pyrazolo[3,4-d]pyrimidine dihydrochloride (15.9 mg, yield; 99.6%) as an amorphous powder. MS (APCI) m/z: 493 [M+H]+

EXAMPLE 714

The compound obtained in Example 441 (50 mg) is treated in the same manner as described in Example 6 to give 1-(3-ethoxybenzyl)-4-[4-[[trans-4-(N-ethyl-N-n-propylamino)cyclohexyl]carbonyl]piperazin-1-yl]-1H-pyrazolo[3,4-d]pyrimidine (59.3 mg; yield; 64%) as an amorphous powder. MS (APCI) m/z: 534 [M+H]+

EXAMPLE 715

(1) To a solution of 4-fluorobenzenesulfonyl chloride (2.1 g) in methylene chloride (20 mL) is added pyridine (6 mL) and 1-(3-ethoxybenzyl)-4-piperazin-1-yl-1H-pyrazolo[3,4-d]pyrimidine dihydrochloride (3 g) under ice-cooling and the mixture is stirred at room temperature for 16 hours. The reaction mixture is diluted with chloroform (20 mL). Thereto is added a saturated sodium hydrogencarbonate solution. After stirring, the organic layer is separated and the aqueous layer is extracted with chloroform. The organic layers are combined, dried over anhydrous sodium sulfate and filtered. The filtrate is concentrated and the residue is purified by chromatography on silica gel (solvent; n-hexane:ethyl acetate=1:1→1:3) to give 1-(3-ethoxy-benzyl)-4-[4-(4-fluorobenesulfonyl)piperazin-1-yl]-1H-pyrazolo[3,4-d]pyrimidine (3.2 g, yield; 88%) as an amorphous powder. MS (APCI) m/z: 497 [M+H]+

(2) The compound obtained in the above step (1) (100 mg) is treated in the same manner as described in Reference Example 1 (1) to give 1-(3-ethoxybenzyl)-4-[4-[4-[[2-(dimethylamino)ethyl]amino]benzenesulfonyl]piperazin-1-yl]-1H-pyrazolo[3,4-d]pyrimidine (91 mg, yield; 80%) as an amorphous powder. MS (APCI) m/z: 565 [M+H]+

EXAMPLE 716

The compound obtained in Example 715 (2) (57 mg) is treated in the same manner as described in Example 416 and Example 4 (3) to give 1-(3-ethoxybenzyl)-4-[4-[4-[N-acetyl-N-[2-(dimethylamino)ethyl]amino]benzenesulfonyl]piperazin-1-yl]-1H-pyrazolo[3,4-d]pyrimidine dihydrochloride (51 mg, yield; 75%) as an amorphous powder. MS (APCI) m/z: 607 [M+H]+

EXAMPLE 717

The compound obtained in Example 441 is treated in the same manner as described in Example 422 (2) and then the resultant product is treated in the same manner as described in Example 4 (3) to give 1-(3-ethoxybenzyl)-4-[4-[[trans-4-[N-(2-dimethylamino)ethyl-N-propyl]amino]cyclohexyl]carbonyl]piperazin-1-yl]-1H-pyrazolo[3,4-d]pyrimidine dihydrochloride (3.4 mg, yield; 6.5%) as an amorphous powder. MS (ESI) m/z: 577 [M+H]+

EXAMPLE 718

The corresponding materials are treated in the same manner as described in Example 713 to give 1-(3-ethoxybenzyl)-4-[4-[[4-[[2-(dimethylamino)ethyl]amino]-piperidin-1-yl]carbonyl]piperazin-1-yl]-1H-pyrazolo[3,4-d]pyrimidine. The product (53 mg) is treated in the same manner as described in Example 416 to give 1-(3-ethoxy-benzyl)-4-[4-[[4-[N-(cyclopropylcarbonyl)-N-[2-(dimethylamino)ethyl]amino]piperidin-1-yl]carbonyl]piperazin-1-yl]-1H-pyrazolo[3,4-d]pyrimidine dihydrochloride (23 mg, yield; 34%) as an amorphous powder. MS (APCI) m/z: 604 [M+H]+

EXAMPLE 719

(1) To a solution of 4-piperidinopiperidine (1.0 g) in methylene chloride (5 mL) and isopropanol (15 mL) is added diphenylcyanocarbonimide (1.56 g) and the mixture is stirred at room temperature for 24 hours. The reaction mixture is diluted with ethyl acetate (20 mL) and thereto is added a saturated sodium hydrogencarbonate solution (30 mL). After stirring, the organic layer is separated and the aqueous layer is extracted with chloroform. The organic layers are combined, washed with saturated brine, dried over anhydrous sodium sulfate and filtered. The filtrate is concentrated and the residue is purified by column chromatography on silica gel (solvent; chloroform:methanol=9:1→5:1) to give phenyl N-cyano-1,4-bipiperidine-1'-carboximidoate (2.5 g, yield; quantitative) as an amorphous powder. MS (APCI) m/z: 313 [M+H]+

(2) To the solution of the compound obtained in the above step (1) (70 mg) in tetrahydrofuran (3 mL) is added sodium hydride (14.4 mg) and 1-(2-fluoro-3-methyl-benzyl)-4-[4-(1-piperidyl)piperidin-1-yl]piperazin-1-yl]-1H-pyrazolo[3,4-d]pyrimidine (60 mg) and the mixture is stirred at 100° C. for 24 hours. The reaction mixture is diluted with chloroform (3 mL) and thereto is added a saturated sodium hydrogencarbonate solution (5 mL). After stirring, the organic layer is separated and the aqueous layer is extracted with chloroform. The organic layers are combined, dried over anhydrous sodium sulfate, filtered and concentrated. The residue is purified by column chromatography on silica gel (Purif 8, Hi-flash/M, solvent; chloroform:methanol=100:0→85:15) to give 1-(2-fluoro-3-methylbenzyl)-4-[4-[1,4'-bipiperidin-1'-yl(cyanoimino)methyl]-1H-pyrazolo[3,4-d]pyrimidine (77.4 mg, yield; 95%) as an amorphous powder. MS (APCI) m/z: 545 [M+H]+

EXAMPLE 720

(1) The compound obtained in Example 407 (282 mg) is treated in the same manner as described in Example 719 (1) to give 1-(3-ethoxybenzyl)-4-[4-[4-[N-[(cyanoimino)(phenoxy)methyl]-N-ethyl]amino]methyl]benzoyl]piperazin-1-yl]-1H-pyrazolo[3,4-d]pyrimidine (221 mg, yield; 69%) as an amorphous powder. MS (APCI) m/z: 644 [M+H]+

(2) To a solution of the compound obtained in the above step (1) (64 mg) in acetonitrile is added an aqueous dimethylamine solution (241 µL) and the mixture is stirred at 100° C. for 16 hours. After cooling, the reaction mixture is concentrated and the residue is purified by column chromatography on silica gel (Purif 8, Hi-flash/M, solvent; chloroform:methanol=100:0→90:10) to give 1-(3-ethoxybenzyl) 4-[4-[[N-[(cyanoimino)(dimethylamino)methyl]-N-ethyl]amino]methyl]benzoyl]piperazin-1-yl]-1H-pyrazolo[3,4-d]pyrimidine (51 mg, yield; 86%) as an amorphous powder. MS (APCI) m/z: 595 [M+H]+

(3) The compound obtained in the above step (2) (51 mg) is treated in the same manner as described in Example 4 (3) to give 1-(3-ethoxybenzyl)-4-[4-[4-[[N-[(cyanoimino)(dimethylamino)methyl]-N-ethyl]amino]methyl]benzoyl]piperazin-1-yl]-1H-pyrazolo[3,4-d]pyrimidine dihydrochloride (45.8 mg, yield; 80%) as an amorphous powder. MS (APCI) m/z: 595 [M+H]+

EXAMPLE 721

The corresponding materials are treated in the same manner as described in Example 366 to give 1-(3-ethoxybenzyl)-4-[4-[4-[2-(dimethylamino)ethylamino]-benzoyl]piperazin-1-yl]-1H-pyrazolo[3,4-d]pyrimidine. To a solution of the resultant product (50 mg) in methylene chloride/isopropanol (1:1, 1 mL) is added diphenyl cyanocarbonimidate (25 mg) and the mixture is stirred at 50° C. for 6 hours. The reaction mixture is diluted with chloroform (2 mL) and thereto is added a saturated sodium hydrogencarbonate solution (2 mL). After stirring, the organic layer is separated and the aqueous layer is extracted with chloroform. The organic layers are combined, dried over anhydrous sodium sulfate, filtered and concentrated. The residue is purified by column chromatography on silica gel (Purif 8, Hi-flash/M, solvent; chloroform:methanol=100:0→90:10) to give 1-(3-ethoxybenzyl)-4-[4-[4-[N-[2-(dimethylamino)ethyl]-N-[(2-propyloxy)(cyanoimino)methyl]amino]benzoyl]-piperazin-1-yl]-1H-pyrazolo[3,4-d]pyrimidine (44.3 mg, yield; 69%) as an amorphous powder. MS (APCI) m/z: 639 [M+H]+

EXAMPLE 722

(1) Cyclohexane-1,4-dicarboxylic acid monomethyl ester (1.0 g) is treated in the same manner as described in Example 3 to give 1-(3-ethoxybenzyl)-4-[4-[[trans-4-(methoxycarbonyl)cyclohexyl]carbonyl]piperazin-1-yl]-1H-pyrazolo[3,4-d]pyrimidine (1.83 g, yield; 81%) as an amorphous powder. MS (APCI) m/z: 507 [M+H]+

(2) The compound obtained in the above step (1) and N,N,N'-triethyl-1,2-ethylenediamine are treated in the same manner as described in Example 4 (2) and (3) to give 1-(3-ethoxybenzyl)-4-[4-[[trans-4-[N-ethyl-N-[2-(diethylamino)ethyl]carbamoyl]-cyclohexyl]carbonyl]piperazin-1-yl]-1H-pyrazolo[3,4-d]pyrimidine dihydrochloride as an amorphous powder. MS (ESI) m/z: 619 [M+H]+

EXAMPLE 723

Ethyl 4-(2-dimethylaminoethylamino)cyclohexanecarboxylate is treated in the same manner as described in Example 654 (3) and (4) to give 1-(6-propyl-2-pyridylmethyl)-4-[4-[[4-[N-naphthoyl-N-[2-(dimethylamino)ethyl]amino]cyclohexyl]-carbonyl]piperazin-1-yl]-1H-pyrazolo[3,4-d]pyrimidine as an amorphous powder. MS (ESI) m/z: 688 [M+H]+

EXAMPLE 724

(1) To a solution of ethyl 6-chloropyridazine-3-carboxylate (37 mg) in tetrahydrofuran (1.5 mL) is added N,N,N'-trimethylpropane-1,3-diamine (46 mg) and the mixture is stirred at room temperature overnight. The reaction mixture is diluted with tetrahydrofuran (1.5 mL) and thereto is added MP-Isocyanate (polystyrene methylisocyanate, 1.43 mmol/g, 400 mg). The mixture is shaken at room temperature overnight. The reaction mixture is filtered to remove the resin and the filtrate is extracted with chloroform/methanol. The organic layer is concentrated to give crude ethyl 6-[N-(3-dimethylaminopropyl)-methylamino]-3-pyridazinecarboxylate. MS (ESI) m/z: 267 [M+H]+

(2) The compound obtained in the above step (1) is treated in the same manner as described in Example 1 and Example 4 (3) to give 1-(3-ethoxybenzyl)-4-[4-[[6-[N-methyl-N-[3-(dimethylamino)propyl]amino]pyridazin-3-yl]carbonyl]piperazin-1-yl]-1H-pyrazolo[3,4-d]pyrimidine hydrochloride as an amorphous powder. MS (APCI) m/z: 559 [M+H]+

EXAMPLE 725

(1) To a solution of the compound obtained in Example 22 (500 mg) and N-benzyloxycarbonyl-β-alanine (291 mg) in methylene chloride (5 mL) is added diethyl cyanophosphonate (230 µL) and the mixture is stirred at room temperature overnight. To the reaction mixture is added a saturated sodium hydrogencarbonate solution and the mixture is extracted with chloroform. The organic layer is evaporated to remove solvent and the residue is purified by column chromatography on silica gel (solvent; chloroform/methanol=10:1) to 1-(3-ethoxybenzyl)-4-[4-[4-[N-[3-[N'-methyl-N'-(benzyloxycarbonyl)amino]propionyl]-N-[2-(dimethylamino)ethyl]amino]benzoyl]-piperazin-1-yl]-1H-pyrazolo[3,4-d]pyrimidine give (431 mg, yield; 61%) as an yellow liquid. MA (APCI) m/z: 748 [M+H]+

(2) A suspension of the compound obtained in the above step (1) (480 mg), ammonium formate (81 mg) and 10% palladium-carbon (100 mg) in methanol (5 mL) is refluxed under heating for 2 hours. The reaction mixture is filtered and the filtrate is concentrated in vacuo. The residue is purified by column chromatography on silica gel (solvent; chloroform/methanol=5:1), and then the resultant product is treated in the same manner as described in Example 4 (3) to give 1-(3-ethoxybenzyl)-4-[4-[4-[N-[3-(methylamino)propionyl]-N-[2-(dimethylamino)ethyl]amino]benzoyl]piperazin-1-yl]-1H-pyrazolo[3,4-d]pyrimidine hydrochloride (390 mg, yield; 99%) as a yellow liquid. MA (APCI) m/z: 614 [M+H]+

EXAMPLE 726

(1) Methyl 4-[trans-4-[(2-nitrophenyl)sulfonyl]piperazin-1-yl]cyclohexanecarboxylate (compound obtained in Reference Example 310, 1.29 g) treated in the same manner as described in Example 1 to give 1-(3-ethoxybenzyl)-4-[4-[[trans-4-[4-[(2-nitrophenyl)sulfonyl]piperazin-1-yl]cyclohexyl]carbonyl]piperazin-1-yl]-1H-pyrazolo-[3,4-d]pyrimidin (1.91 g, yield; 85%) as an yellow liquid. MS (APCI) m/z: 718 [M+H]+

(2) A suspension of the compound obtained in the above step (1) (1.71 g), potassium carbonate (658 mg) and thiophenol (270 μL) in N,N-dimethylformamide (10 mL) is stirred at room temperature for 4 hours. The reaction mixture is diluted with water/ethyl acetate and the mixture is treated with cation-exchange resin (SCX-2, IST Ltd., solvent; methanol/water=1:1→1N ammonia/methanol) to give 1-(3-ethoxy-benzyl)-4-[trans-4-[[4-(1-piperazinyl)cyclohexyl] carbonyl]piperazin-1-yl]-1H-pyrazolo-[3,4-d]pyrimidin (1.09 g, yield; 86%) as a colorless solid. MS (APCI) m/z: 533 [M+H]+

(3) To a solution of the compound obtained in the above step (2) (50 mg) in 1,2-dichloroethane (1 mL) is added successively formaldehyde solution (15 μL), acetic acid (11 μL) and sodium triacetoxyborohydride (30 mg) under ice-cooling and the mixture is stirred at room temperature overnight. To the reaction mixture is added a saturated sodium hydrogencarbonate solution and the mixture is extracted with chloroform. The organic layer is evaporated to remove solvent and the resultant crude product is purified by HPLC (solvent; 10 mM ammonium carbonate/methanol) to give 1-(3-ethoxybenzyl)-4-[4-[[trans-4-(4-methylpiperazin-1-yl)cyclohexyl]carbonyl]-piperazin-1-yl]-1H-pyrazolo[3,4-d]pyrimidin (47 mg, yield; 92%) as a colorless solid. MS (APCI) m/z: 547 [M+H]+

EXAMPLE 727

To a solution of the compound obtained in Example 725 (50 mg) in methylene chloride (3 mL) is added ethyl chloroformate (10 μL) and triethylamine (22 μL) and the mixture is stirred at room temperature overnight. The reaction mixture is diluted with a saturated sodium hydrogencarbonate solution and the mixture is extracted with chloroform. The organic layer is evaporated to remove solvent and the residue is purified by column chromatography on silica gel (solvent; chloroform/methanol=10:1), and the resultant product is treated in the same manner as described in Example 4 (3) to give 1-(3-ethoxybenzyl)-4-[4-[4-[N-[3-[N-methyl-N-(ethoxycarbonyl)amino]-propionyl)-N-[2-(dimethylamino)ethyl]amino]benzoyl]piperazin-1-yl]-1H-pyrazolo-[3,4-d]pyrimidine hydrochloride (17 mg, yield; 30%) as an amorphous powder. MS (APCI) m/z: 686 [M+H]+

EXAMPLES 728 TO 738

The corresponding materials are treated in the same manner as described in either one of Examples 416, 714, 715, 716 and 717 to give the compounds as shown in the following Table 27.3.

TABLE 27.3

(No. 1)

| Ex. Nos. | R¹ | Physicochemical properties etc. |
|---|---|---|
| 728 | Me, cyclopentyl-N-cyclohexyl | amorphous powder MS (APCI) 546 [M + H]+ |
| 729 | Me-CH2-N(cyclopentyl)-cyclohexyl | amorphous powder MS (APCI) 560 [M + H]+ |
| 730 | Me-CH2-N(CHMe2)-cyclohexyl | amorphous powder MS (APCI) 534 [M + H]+ |
| 731** | Me-CH2-N(CH2-Me)-cyclohexyl | amorphous powder MS (APCI) 520 [M + H]+ |
| 732** | Me2N-CH2CH2-N(CH2Me)=cyclohexylidene | amorphous powder MS (APCI) 563 [M + H]+ |

**dihydrochloride
Me: methyl group, Et: ethyl group, n-Pr: n-propyl group

TABLE 27.3

(No. 2)

[Structure: R-phenyl-SO2-piperazine-pyrazolopyrimidine-CH2-phenyl-OEt]

| Ex. Nos. | R | Physicochemical properties etc. |
|---|---|---|
| 733** | Me-C(=O)-N(Me)-CH2CH2-N(Et)(Et) with Me | amorphous powder MS (ESI) 635 [M + H]+ |
| 734 | Me2N-CH2CH2-N(Me)2 with Me | amorphous powder MS (APCI) 579 [M + H]+ |
| 735** | Me2N-CH2CH2CH2-N(Me)2 | amorphous powder MS (APCI) 593 [M + H]+ |
| 736** | Me(Et)N-CH2CH2-N(Me)2 | amorphous powder MS (APCI) 593 [M + H]+ |

TABLE 27.3-continued (No. 2)

[Structure: R-phenyl-SO2-piperazine-pyrazolopyrimidine-CH2-phenyl-OEt]

| Ex. Nos. | R | Physicochemical properties etc. |
|---|---|---|
| 737** | Et2N-CH2CH2-N(Me)(Et) with Me | amorphous powder MS (APCI) 621 [M + H]+ |
| 738** | cyclopropyl-C(=O)-N(Me)-CH2CH2-N(Me)2 | amorphous powder MS (APCI) 633 [M + H]+ |

**dihydrochloride
Me: methyl group, Et: ethyl group

EXAMPLES 739 TO 745

The corresponding materials are treated in the same manner as described in either one of Examples 1, 366 and 407 to give the compounds as shown in the following Table 27.4.

TABLE 27.4

(No. 1)

[Structure: R-phenyl-C(=O)-piperazine-pyrazolopyrimidine-CH2-R2]

| Ex. Nos. | R | R² | Physicochemical properties etc. |
|---|---|---|---|
| 739** | MeNH-CH2-C(Me)(Me)-CH2-N(Me)(Me) | 3-OEt-phenyl-Me | amorphous powder MS (APCI) 571 [M + H]+ |

TABLE 27.4-continued (No. 1)

| Ex. Nos. | R | R² | Physicochemical properties etc. |
|---|---|---|---|
| 740** | MeNH-CH2-C(Me)(Me)-CH2-N(Me)Me | 6-n-Pr-pyridin-2-yl | amorphous powder MS (APCI) 570 [M + H]+ |
| 741** | MeNH-CH2-C(Me)(Me)-CH2-N(Me)Me | 2-F-3-Me-phenyl (Me at other position) | amorphous powder MS (APCI) 559 [M + H]+ |
| 742** | MeNH-CH2-C(Me)(Me)-CH2-N(Me)Me | 4-Me-2-n-Pr-thiazol-5-yl | amorphous powder MS (APCI) 576 [M + H]+ |
| 743** | MeO-CH2-C(Me)(Me)-CH2-N(Me)Me | 2-OEt-3-Me-6-OH-phenyl | amorphous powder MS (APCI) 588 [M + H]+ |

**dihydrochloride
Me: methyl group, Et: ethyl group, n-Pr: n-propyl group

TABLE 27.4

(No. 2)

| Ex. Nos. | R | Physicochemical properties etc. |
|---|---|---|
| 744** | Me2N-CH2-C(Me)(Me)-SMe | amorphous powder MS (APCI) 574 [M + H]+ |
| 745** | Me2N-CH2-C(Me)(Me)-CH2-SMe | amorphous powder MS (APCI) 588 [M + H]+ |

TABLE 27.4-continued (No. 2)

| Ex. Nos. | R | Physicochemical properties etc. |
|---|---|---|

**dihydrochloride
Me: methyl group, Et: ethyl group

EXAMPLES 746 TO 749

The corresponding materials are treated in the same manner as described in either one of Examples 3, 407 and 434 to give the compounds as shown in the following Table 27.5.

TABLE 27.5

| Ex. Nos. | R¹ | R² | Physicochemical properties etc. |
|---|---|---|---|
| 746** | pyrrolidinyl-cyclohexyl | 3-methyl-2-ethoxy-phenol | amorphous powder MS (APCI) 534 [M + H]+ |
| 747** | pyrrolidinyl-cyclohexyl | 3-methylbenzyl-COOMe | amorphous powder MS (APCI) 532 [M + H]+ |
| 748 | 4-Me-piperidinyl-cyclohexyl | 3-methyl-OEt phenyl | amorphous powder MS (APCI) 546 [M + H]+ |
| 749 | azepanyl-cyclohexyl | 3-methyl-OEt phenyl | amorphous powder MS (APCI) 546 [M + H]+ |

**dihydrochloride
Me: methyl group, Et: ethyl group, n-Pr: n-propyl group

EXAMPLES 750 TO 770

The corresponding materials are treated in the same manner as described in either one of Examples 713 and 718 to give the compounds as shown in the following Table 27.6.

TABLE 27.6

(No. 1)

| Ex. Nos. | R | Physicochemical properties etc. |
|---|---|---|
| 750** | Me-CH=CH-C(O)-N(Me)-CH₂CH₂-N(Me)₂ | amorphous powder MS (APCI) 604 [M + H]+ |

TABLE 27.6-continued (No. 1)

| Ex. Nos. | R | Physicochemical properties etc. |
|---|---|---|
| 751** | furan-2-C(O)-N(Me)-CH₂CH₂-N(Me)Me | amorphous powder MS (APCI) 630 [M + H]+ |
| 752 | Me-C(O)-NH-(1-methylpyrrolidin-3-yl) | amorphous powder MS (ESI) 576 [M + H]+ |

TABLE 27.6-continued (No. 1)

Core structure: R-piperidine-C(O)-piperazine-pyrazolopyrimidine-CH2-C6H4-OEt

| Ex. Nos. | R | Physicochemical properties etc. |
|---|---|---|
| 753 | 4-methyl-thiomorpholinyl | amorphous powder MS (ESI) 551 [M + H]+ |
| 754** | MeHN-CH2CH2-N(Me)Me | amorphous powder MS (APCI) 536 [M + H]+ |
| 755* | t-Bu-piperidin-N-yl | amorphous powder MS (APCI) 589 [M + H]+ |
| 756* | n-Bu-N(piperazin)-N- | amorphous powder MS (APCI) 590 [M + H]+ |
| 757* | 2,5-dihydropyrrol-N-yl | amorphous powder MS (APCI) 517 [M + H]+ |

*hydrochloride,
**dihydrochloride
Me: methyl group, Et: ethyl group, t-Bu: tert-butyl group, n-Bu: n-butyl group

TABLE 27.6 (No. 2)

Core structure: R-piperidine-C(O)-piperazine-pyrazolopyrimidine-CH2-C6H4-OEt

| Ex. Nos. | R | Physicochemical properties etc. |
|---|---|---|
| 758* | (S)-1-methylpyrrolidine-2-carboxamide | amorphous powder MS (APCI) 562 [M + H]+ |
| 759* | 3,3-dimethyl-1-methylpiperidin-N-yl | amorphous powder MS (APCI) 561 [M + H]+ |
| 760* | 1-methylazepan-N-yl | amorphous powder MS (APCI) 547 [M + H]+ |
| 761* | Me-CH2-N(Me)-CH2-Me | amorphous powder MS (APCI) 507 [M + H]+ |
| 762* | Me2CH-CH2-N(Me)-CH2-Me | amorphous powder MS (APCI) 521 [M + H]+ |
| 763* | Me2N-CH2CH2-N(Me)-CH2-Me | amorphous powder MS (APCI) 564 [M + H]+ |
| 764* | Me2N-CH2CH2-N(Me)-CH2-Me (larger) | amorphous powder MS (APCI) 592 [M + H]+ |
| 765* | (S)-1-methyl-2-(methoxymethyl)pyrrolidine | amorphous powder MS (APCI) 563 [M + H]+ |
| 766* | Me2N-CH2CH2-N(Me)2 | amorphous powder MS (APCI) 550 [M + H]+ |
| 767* | 2,2,6,6-tetramethyl-4-methylmorpholine | amorphous powder MS (APCI) 563 [M + H]+ |

TABLE 27.6-continued (No. 2)

[Structure: R-piperidine-C(O)-piperazine-pyrazolopyrimidine-CH2-C6H4-OEt]

| Ex. Nos. | R | Physicochemical properties etc. |
|---|---|---|

*hydrochloride
Me: methyl group, Et: ethyl group

TABLE 27.6

(No. 3)

[Structure: R-piperidine-C(O)-piperazine-pyrazolopyrimidine-CH2-C6H4-OEt]

| Ex. Nos. | R | Physicochemical properties etc. |
|---|---|---|
| 768* | Me-C(O)-NH-(3-pyrrolidinyl)-N-Me | amorphous powder MS (APCI) 576 [M + H]+ |
| 769* | MeO-CH2CH2-N(Me)-N(Me)- | amorphous powder MS (APCI) 537 [M + H]+ |
| 770* | MeO-CH2CH2-N(Me)-N(Et)- | amorphous powder MS (APCI) 551 [M + H]+ |

*hydrochloride
Me: methyl group, Et: ethyl group

EXAMPLES 771 TO 798

The corresponding materials are treated in the same manner as described in either one of Examples 720 and 724 to give the compounds as shown in the following Table 27.7.

TABLE 27.7

(No. 1)

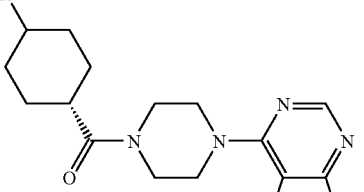

| Ex. Nos. | R | Physicochemical properties etc. |
|---|---|---|
| 771 | NC-N=C(N(Me)2)-N(Me)- (cyanoguanidine with Me groups) | amorphous powder MS (APCI) 573 [M + H]+ |

Me: methyl group, Et: ethyl group

TABLE 27.7

(No. 2)

[Structure: R'-pyrimidine(R")-C(O)-piperazine-pyrazolopyrimidine-CH2-pyridine-n-Pr]

| Ex. Nos. | R' | R" | Physicochemical properties etc. |
|---|---|---|---|
| 772* | Me2N-CH2CH2-N(Me)- with NH | CF3 | amorphous powder MS (APCI) 598 [M + H]+ |
| 773* | Me2N-CH2CH2-NH(Me)- | H | amorphous powder MS (APCI) 530 [M + H]+ |
| 774* | Me2N-CH2CH2-N(Me)-CH2-N(Me)- | CF3 | amorphous powder MS (APCI) 626 [M + H]+ |
| 775* | Me2N-CH2CH2-N(Me)-CH2-N(Et)- | H | amorphous powder MS (APCI) 558 [M + H]+ |

TABLE 27.7-continued (No. 2)

Structure: Pyrimidine (with R' at 2-position, R'' at 4-position)-C(=O)-piperazine-pyrazolopyrimidine-N-CH2-pyridine-n-Pr

| Ex. Nos. | R' | R'' | Physicochemical properties etc. |
|---|---|---|---|
| 776* | Me-N(Me)-CH2-CH2-N(Me)-CH2- (Me,Et-N-CH2CH2-N-Me,Me) | CF3 | amorphous powder MS (APCI) 640 [M + H]+ |
| 777* | Me-Et-N-CH2CH2-N-Me,Me | H | amorphous powder MS (APCI) 572 [M + H]+ |
| 778* | Me,Me-N-CH2CH2-N-Me,Me | H | amorphous powder MS (APCI) 544 [M + H]+ |
| 779* | Me,Me-N-CH2CH2CH2-N-Me,Me | CF3 | amorphous powder MS (APCI) 626 [M + H]+ |
| 780* | Me,Me-N-CH2CH2CH2-N-Me,Me | H | amorphous powder MS (APCI) 558 [M + H]+ |

*hydrochloride
Me: methyl group, n-Pr: n-propyl group

TABLE 27.7

(No. 3)

Structure: Pyrimidine (with R' at 2-position, R'' at 4-position)-C(=O)-piperazine-pyrazolopyrimidine-N-CH2-phenyl-OEt

| Ex. Nos. | R' | R'' | Physicochemical properties etc. |
|---|---|---|---|
| 781* | Me,Me-N-CH2CH2-NH-Me | CF3 | amorphous powder MS (APCI) 599 [M + H]+ |
| 782* | Me,Me-N-CH2CH2-NH-Me | H | amorphous powder MS (APCI) 531 [M + H]+ |
| 783* | Me,Me-N-CH2CH2-N-Me,Et | CF3 | amorphous powder MS (APCI) 627 [M + H]+ |
| 784* | Me,Me-N-CH2CH2-N-Me,Et | H | amorphous powder MS (APCI) 559 [M + H]+ |
| 785* | Me,Et-N-CH2CH2-N-Me,Me | CF3 | amorphous powder MS (APCI) 641 [M + H]+ |
| 786* | Me,Et-N-CH2CH2-N-Me,Me | H | amorphous powder MS (APCI) 573 [M + H]+ |
| 787* | Me,Me-N-CH2CH2-N-Me,Me | H | amorphous powder MS (APCI) 545 [M + H]+ |
| 788* | Me,Me-N-CH2CH2CH2-N-Me,Me | CF3 | amorphous powder MS (APCI) 627 [M + H]+ |

| 789* | 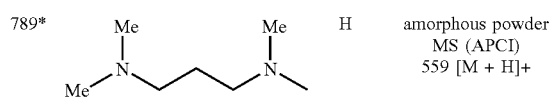 | H | amorphous powder MS (APCI) 559 [M + H]+ |

*hydrochloride
Me: methyl group, Et: ethyl group

TABLE 27.7

(No. 4)

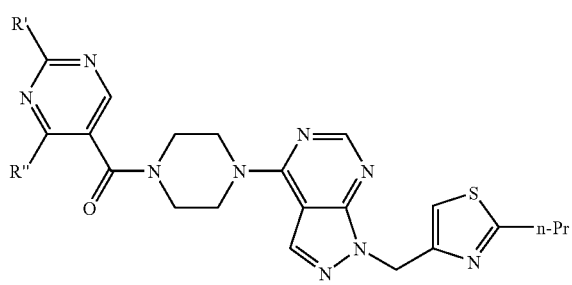

| Ex. Nos. | R' | R" | Physicochemical properties etc. |
|---|---|---|---|
| 790* |  | $CF_3$ | amorphous powder MS (APCI) 604 [M + H]+ |
| 791* | 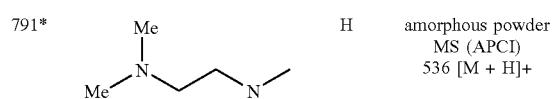 | H | amorphous powder MS (APCI) 536 [M + H]+ |
| 792* | 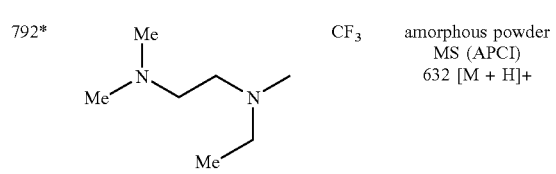 | $CF_3$ | amorphous powder MS (APCI) 632 [M + H]+ |
| 793* | 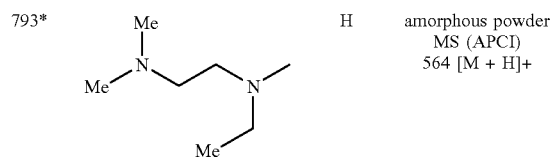 | H | amorphous powder MS (APCI) 564 [M + H]+ |
| 794* | 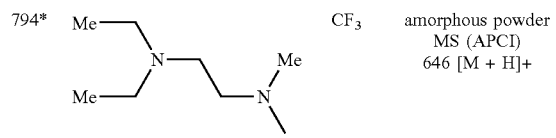 | $CF_3$ | amorphous powder MS (APCI) 646 [M + H]+ |
| 795* | 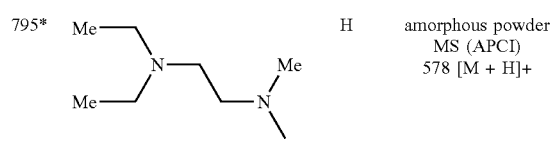 | H | amorphous powder MS (APCI) 578 [M + H]+ |
| 796* | 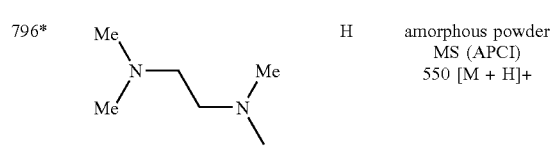 | H | amorphous powder MS (APCI) 550 [M + H]+ |

TABLE 27.7-continued (No. 4)

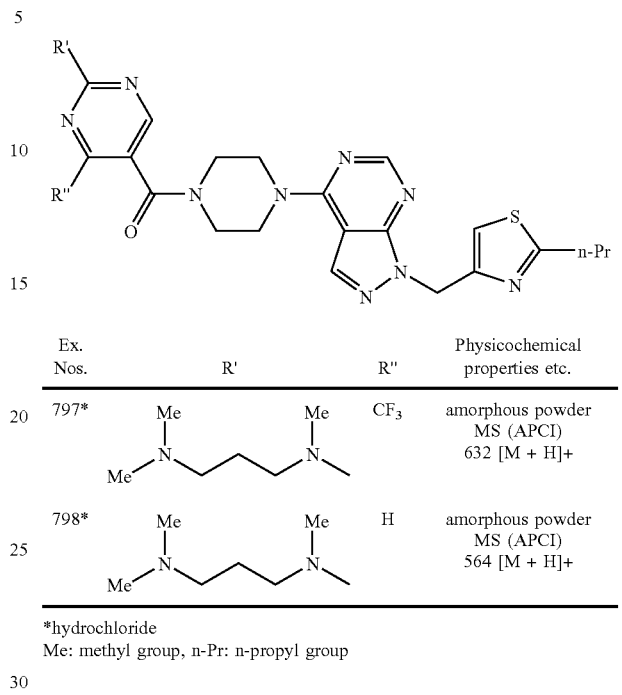

| Ex. Nos. | R' | R" | Physicochemical properties etc. |
|---|---|---|---|
| 797* | 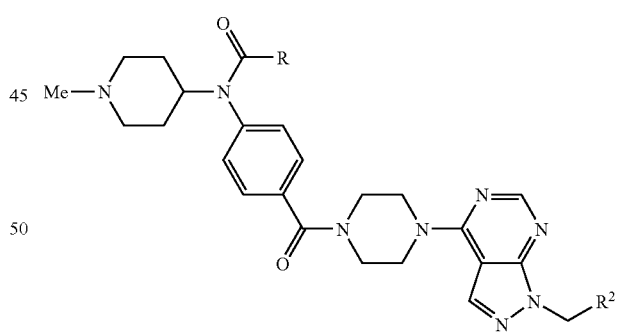 | $CF_3$ | amorphous powder MS (APCI) 632 [M + H]+ |
| 798* | 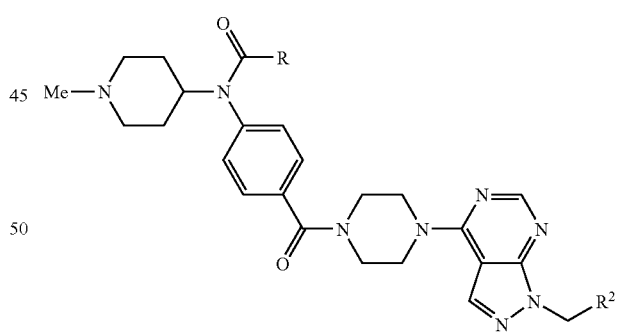 | H | amorphous powder MS (APCI) 564 [M + H]+ |

*hydrochloride
Me: methyl group, n-Pr: n-propyl group

EXAMPLES 799 TO 874

The corresponding materials are treated in the same manner as described in Example 1 to give the compounds as shown in the following Table 27.8.

TABLE 27.8

(No. 1)

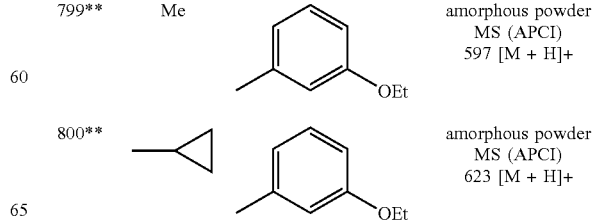

| Ex. Nos. | R | $R^2$ | Physicochemical properties etc. |
|---|---|---|---|
| 799** | Me | 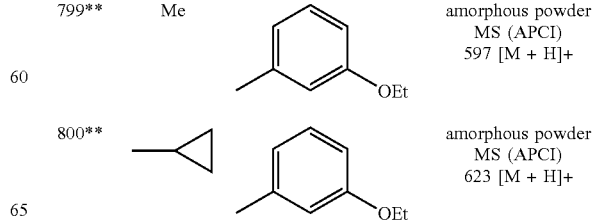 | amorphous powder MS (APCI) 597 [M + H]+ |
| 800** | 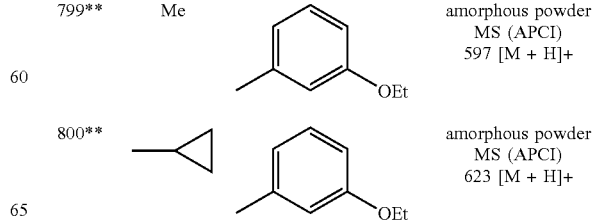 | 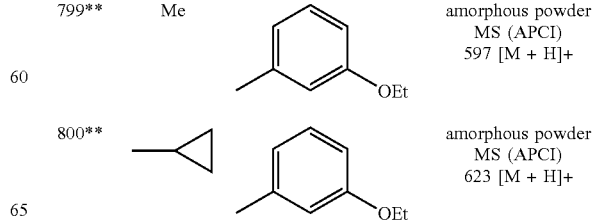 | amorphous powder MS (APCI) 623 [M + H]+ |

TABLE 27.8-continued
(No. 1)

| Ex. Nos. | R | R² | Physicochemical properties etc. |
|---|---|---|---|
| 801** | 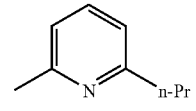 |  | amorphous powder MS (APCI) 622 [M + H]+ |
| 802** | 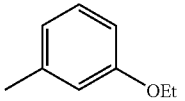 |  | amorphous powder MS (APCI) 649 [M + H]+ |
| 803** | 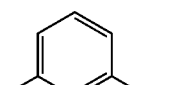 |  | amorphous powder MS (APCI) 648 [M + H]+ |
| 804** | 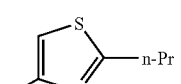 | 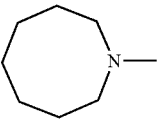 | amorphous powder MS (APCI) 654 [M + H]+ |

**dihydrochloride
Me: methyl group, Et: ethyl group, n-Pr: n-propyl group

TABLE 27.8
(No. 2)

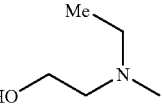

| Ex. Nos. | R | Physicochemical properties etc. |
|---|---|---|
| 805 | 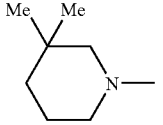 | amorphous powder MS (ESI) 549 [M + H]+ |
| 806 | 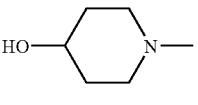 | amorphous powder MS (ESI) 573 [M + H]+ |
| 807 | 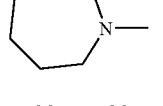 | amorphous powder MS (ESI) 573 [M + H]+ |
| 808 | 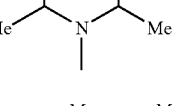 | amorphous powder MS (ESI) 561 [M + H]+ |
| 809 | 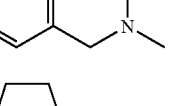 | amorphous powder MS (ESI) 559 [M + H]+ |
| 810 | 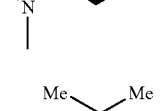 | amorphous powder MS (ESI) 561 [M + H]+ |
| 811 | 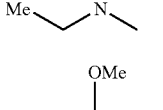 | amorphous powder MS (ESI) 609 [M + H]+ |
| 812 | 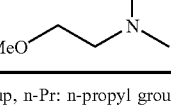 | amorphous powder MS (ESI) 575 [M + H]+ |
| 813 | Me, Me / Me, / Me | amorphous powder MS (ESI) 547 [M + H]+ |
| 814 | OMe / MeO | amorphous powder MS (ESI) 593 [M + H]+ |

Me: methyl group, n-Pr: n-propyl group

TABLE 27.8

(No. 3)

[Structure: R-CH2-cyclohexyl-C(=O)-piperazine-pyrazolopyrimidine-CH2-pyridine-n-Pr]

| Ex. Nos. | R | Physicochemical properties etc. |
|---|---|---|
| 815 | Me-CH(Me)-N(Me)-CH2CH2-OH | amorphous powder MS (ESI) 563 [M + H]+ |
| 816 | Me-N(Me)-C(Me)2-Me | amorphous powder MS (ESI) 547 [M + H]+ |
| 817 | Me-C(=O)-N-piperazine-N-Me | amorphous powder MS (ESI) 588 [M + H]+ |
| 818 | Et-N(Me)-C(Me)2-Me | amorphous powder MS (ESI) 561 [M + H]+ |
| 819 | 2,6-dimethyl-4-methylmorpholine | amorphous powder MS (ESI) 575 [M + H]+ |
| 820 | MeO-CH2CH2-N(Me)-C(Me)2-Me | amorphous powder MS (ESI) 591 [M + H]+ |
| 821 | Me-CH(Me)-N-piperazine-N-Me | amorphous powder MS (ESI) 588 [M + H]+ |
| 822 | N-methylisoindoline | amorphous powder MS (ESI) 579 [M + H]+ |
| 823 | EtO-CH2CH2-N-piperazine-N-Me | amorphous powder MS (ESI) 618 [M + H]+ |

TABLE 27.8-continued (No. 3)

| Ex. Nos. | R | Physicochemical properties etc. |
|---|---|---|
| 824 | Me-N(Me)-3-(1-methylpyrrolidinyl) | amorphous powder MS (ESI) 574 [M + H]+ |

Me: methyl group, Et: ethyl group, n-Pr: n-propyl group

TABLE 27.8

(No. 4)

[Structure: R-CH2-cyclohexyl-C(=O)-piperazine-pyrazolopyrimidine-CH2-pyridine-OEt]

| Ex. Nos. | R | Physicochemical properties etc. |
|---|---|---|
| 825 | Et-N(Me)-CH2CH2-OH | amorphous powder MS (ESI) 551 [M + H]+ |
| 826 | HO-4-(1-methylpiperidinyl) | amorphous powder MS (ESI) 563 [M + H]+ |
| 827 | Me-CH(Me)-N(Me)-CH(Me)-Me | amorphous powder MS (ESI) 563 [M + H]+ |
| 828 | PhCH2-N(Me)-CH(Me)-Me | amorphous powder MS (ESI) 611 [M + H]+ |
| 829 | (S)-1-methyl-2-(methoxymethyl)pyrrolidine | amorphous powder MS (ESI) 577 [M + H]+ |

TABLE 27.8-continued
(No. 4)

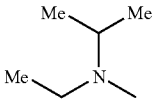

| Ex. Nos. | R | Physicochemical properties etc. |
|---|---|---|
| 830 | 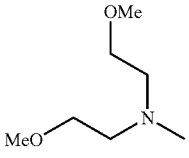 Me, Me, Me, N, Me | amorphous powder MS (ESI) 549 [M + H]+ |
| 831 | OMe, MeO, N, Me | amorphous powder MS (ESI) 595 [M + H]+ |
| 832 | Me, Me, HO, N, Me | amorphous powder MS (ESI) 565 [M + H]+ |
| 833 | Me, Me, Me, Me, N, Me | amorphous powder MS (ESI) 549 [M + H]+ |
| 834 | Me, Me, Me, MeO, N, Me | amorphous powder MS (ESI) 593 [M + H]+ |

Me: methyl group, Et: ethyl group

TABLE 27.8
(No. 5)

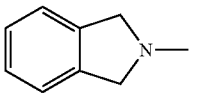

| Ex. Nos. | R | Physicochemical properties etc. |
|---|---|---|
| 835 | 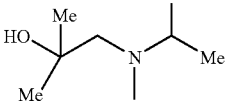 | amorphous powder MS (ESI) 581 [M + H]+ |
| 836 | Me, HO, Me, N, Me, Me | amorphous powder MS (ESI) 593 [M + H]+ |

Me: methyl group, Et: ethyl group

TABLE 27.8
(No. 6)

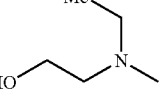

| Ex. Nos. | R | Physicochemical properties etc. |
|---|---|---|
| 837 | Me, HO, N, Me | amorphous powder MS (ESI) 550 [M + H]+ |
| 838 | 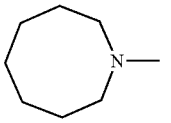 | amorphous powder MS (ESI) 574 [M + H]+ |
| 839 | Me, Me, N— | amorphous powder MS (ESI) 574 [M + H]+ |
| 840 | HO, N— | amorphous powder MS (ESI) 562 [M + H]+ |

TABLE 27.8-continued (No. 6)

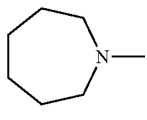

| Ex. Nos. | R | Physicochemical properties etc. |
|---|---|---|
| 841 | 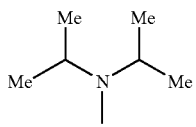 | amorphous powder MS (ESI) 560 [M + H]+ |
| 842 | 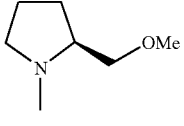 | amorphous powder MS (ESI) 562 [M + H]+ |
| 843 | 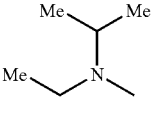 | amorphous powder MS (ESI) 576 [M + H]+ |
| 844 | 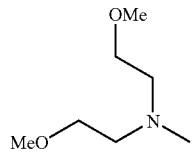 | amorphous powder MS (ESI) 548 [M + H]+ |
| 845 | 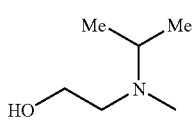 | amorphous powder MS (ESI) 594 [M + H]+ |
| 846 | 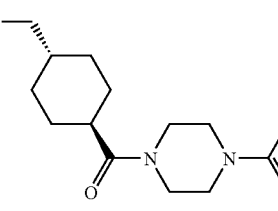 | amorphous powder MS (ESI) 564 [M + H]+ |

Me: methyl group, Et: ethyl group

TABLE 27.8

(No. 7)

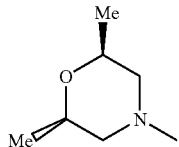

| Ex. Nos. | R | Physicochemical properties etc. |
|---|---|---|
| 847 | 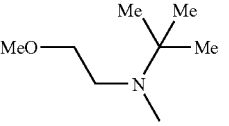 | amorphous powder MS (ESI) 589 [M + H]+ |
| 848 | 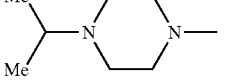 | amorphous powder MS (ESI) 576 [M + H]+ |
| 849 | 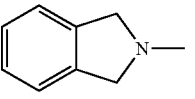 | amorphous powder MS (ESI) 592 [M + H]+ |
| 850 | 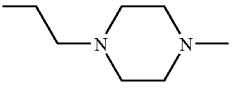 | amorphous powder MS (ESI) 589 [M + H]+ |
| 851 | 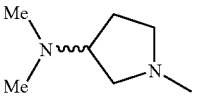 | amorphous powder MS (ESI) 580 [M + H]+ |
| 852 | 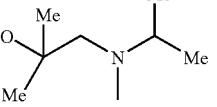 | amorphous powder MS (ESI) 619 [M + H]+ |
| 853 |  | amorphous powder MS (ESI) 575 [M + H]+ |
| 854 |  | amorphous powder MS (ESI) 592 [M + H]+ |

Me: methyl group, Et: ethyl group

TABLE 27.8

(No. 8)

| Ex. Nos. | R | Physicochemical properties etc. |
|---|---|---|
| 855 | N-methylazocane | amorphous powder MS (ESI) 579 [M + H]+ |
| 856 | 1,3,3-trimethylpiperidine | amorphous powder MS (ESI) 579 [M + H]+ |
| 857 | 4-hydroxy-1-methylpiperidine | amorphous powder MS (ESI) 567 [M + H]+ |
| 858 | 1-methylazepane | amorphous powder MS (ESI) 565 [M + H]+ |
| 859 | N-methyl-N,N-diisopropylamine | amorphous powder MS (ESI) 567 [M + H]+ |

TABLE 27.8-continued (No. 8)

| Ex. Nos. | R | Physicochemical properties etc. |
|---|---|---|
| 860 | N-benzyl-N-methyl-isopropylamine derivative | amorphous powder MS (ESI) 615 [M + H]+ |
| 861 | (S)-2-(methoxymethyl)-1-methylpyrrolidine | amorphous powder MS (ESI) 581 [M + H]+ |
| 862 | N-ethyl-N-methyl-isopropylamine | amorphous powder MS (ESI) 553 [M + H]+ |
| 863 | N-methyl-bis(2-methoxyethyl)amine | amorphous powder MS (ESI) 599 [M + H]+ |
| 864 | N,N-dimethyl-tert-butylamine derivative | amorphous powder MS (ESI) 553 [M + H]+ |

Me: methyl group, n-Pr: n-propyl group

TABLE 27.8

(No. 9)

| Ex. Nos. | R | R² | Physicochemical properties etc. |
|---|---|---|---|
| 865 | 2,6-dimethylmorpholin-4-ylmethyl (Me, Me on morpholine) | 4-methyl-2-n-propyl-thiazol-5-yl | amorphous powder MS (ESI) 581 [M + H]+ |
| 866 | MeOCH₂CH₂-N(Me)-C(Me)₂- | 4-methyl-2-n-propyl-thiazol-5-yl | amorphous powder MS (ESI) 597 [M + H]+ |
| 867 | HOC(Me)₂CH₂-N(Me)-CH(Me)₂ | 4-methyl-2-n-propyl-thiazol-5-yl | amorphous powder MS (ESI) 597 [M + H]+ |
| 868* | HOCH₂CH₂-N(Me)-C(Me)₂- | 3-ethoxyphenyl | amorphous powder MS (APCI) 578 [M + H]+ |
| 869* | PhCH₂-N(Me)-CH(Me)₂ | 3-ethoxyphenyl | amorphous powder MS (APCI) 610 [M + H]+ |
| 870* | Me-N(Me)-C(Me)₃ type | 3-ethoxyphenyl | amorphous powder MS (APCI) 548 [M + H]+ |
| 871* | EtCH₂-N(Me)-C(Me)₂- | 3-ethoxyphenyl | amorphous powder MS (APCI) 562 [M + H]+ |
| 872* | HOCH₂CH₂-N(Me)-CH₂Me | 4-methyl-2-n-propyl-thiazol-5-yl | amorphous powder MS (APCI) 555 [M + H]+ |
| 873* | HOCH₂CH₂-N(Me)-CH(Me)₂ | 4-methyl-2-n-propyl-thiazol-5-yl | amorphous powder MS (APCI) 569 [M + H]+ |

TABLE 27.8-continued (No. 9)

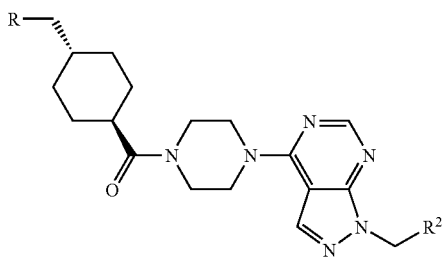

| Ex. Nos. | R | R² | Physicochemical properties etc. |
|---|---|---|---|
| 874* | isoindolin-2-yl-methylene | 4-methyl-2-n-propyl-thiazol-5-yl | amorphous powder MS (APCI) 585 [M + H]+ |

*hydrochloride
Me: methyl group, Et: ethyl group, n-Pr: n-propyl group

EXAMPLE 875

The corresponding materials are treated in the same manner as described in Example 3 to give the compound as shown in the following Table 27.9.

TABLE 27.9

| Ex. Nos. | R | Physicochemical properties etc. |
|---|---|---|
| 875 | 1-methyl-piperidin-4-yl | amorphous powder MS (APCI) 546 [M + H]+ |

Me: methyl group

EXAMPLES 876 TO 891

The corresponding materials are treated in the same manner as described in Example 723 to give the compounds as shown in the following Table 27.10.

TABLE 27.10

(No. 1)

| Ex. Nos. | R | Physicochemical properties etc. |
|---|---|---|
| 876 | phenyl | amorphous powder MS (ESI) 638 [M + H]+ |
| 877 | 2,6-dichloro-3-methyl-phenyl | amorphous powder MS (ESI) 706 [M + H]+ |
| 878** | isopropyl | amorphous powder MS (APCI) 604 [M + H]+ |
| 879** | Me | amorphous powder MS (APCI) 576 [M + H]+ |
| 880** | propenyl | amorphous powder MS (APCI) 602 [M + H]+ |
| 881** | cyclopropyl | amorphous powder MS (APCI) 602 [M + H]+ |

TABLE 27.10-continued (No. 1)

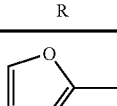

| Ex. Nos. | R | Physicochemical properties etc. |
|---|---|---|
| 882 | 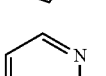 | amorphous powder MS (ESI) 628 [M + H]+ |
| 883 | 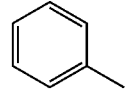 | amorphous powder MS (ESI) 639 [M + H]+ |

**dihydrochloride
Me: methyl group, n-Pr: n-propyl group

TABLE 27.10 (No. 2)

| Ex. Nos. | R | Physicochemical properties etc. |
|---|---|---|
| 884 | 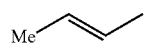 | amorphous powder MS (ESI) 639 [M + H]+ |
| 885** | Me–⟨Me⟩–Me (isopropyl) | amorphous powder MS (APCI) 605 [M + H]+ |
| 886 | Me | amorphous powder MS (ESI) 577 [M + H]+ |
| 887** | Me–CH=CH– | amorphous powder MS (APCI) 603 [M + H]+ |
| 888 | cyclopropyl | amorphous powder MS (ESI) 603 [M + H]+ |
| 889 |  | amorphous powder MS (ESI) 629 [M + H]+ |

TABLE 27.10-continued (No. 2)

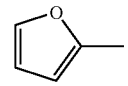

| Ex. Nos. | R | Physicochemical properties etc. |
|---|---|---|
| 890** | 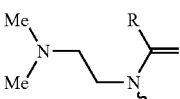 | amorphous powder MS (APCI) 689 [M + H]+ |
| 891 | 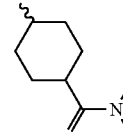 | amorphous powder MS (ESI) 640 [M + H]+ |

**dihydrochloride
Me: methyl group, Et: ethyl group

EXAMPLES 892 TO 900

The corresponding materials are treated in the same manner as described in Example 633 or 726 to give the compounds as shown in the following Table 27.11.

TABLE 27.11

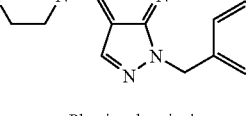

| Ex. Nos. | R | Physicochemical properties etc. |
|---|---|---|
| 892 | 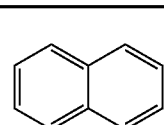 | amorphous powder MS (APCI) 575 [M + H]+ |
| 893 | 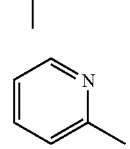 | amorphous powder MS (APCI) 561 [M + H]+ |
| 894* | Me–N⟨⟩N– | amorphous powder MS (APCI) 547 [M + H]+ |

TABLE 27.11-continued

[Structure: R-cyclohexyl-C(O)-piperazine-pyrazolopyrimidine-N-CH2-phenyl-OEt]

| Ex. Nos. | R | Physicochemical properties etc. |
|---|---|---|
| 895* | Me-N(Me)-CH2CH2-N(-)-cyclopentyl | amorphous powder MS (APCI) 603 [M + H]+ |
| 896 | Me-N(Me)-CH2CH2-N(-)-CH2-CH(Me)2 | amorphous powder MS (APCI) 591 [M + H]+ |
| 897 | Me-N(Me)-CH2CH2-N(-)-CH2-cyclopropyl | amorphous powder MS (APCI) 589 [M + H]+ |
| 898 | Me-N(Me)-CH2CH2-N(-)-CH2CH2-Me | amorphous powder MS (APCI) 577 [M + H]+ |
| 899 | Me-N(Me)-CH2CH2-N(-)-CH2-Me | amorphous powder MS (APCI) 563 [M + H]+ |
| 900 | Me-N(Me)-CH2CH2-N(-)-Me | amorphous powder MS (APCI) 549 [M + H]+ |

*hydrochloride
Me: methyl group, Et: ethyl group

TABLE 27.12

[Structure: piperidine-N-CH2CH2-N(C(O)R)-phenyl-C(O)-piperazine-pyrazolopyrimidine-N-CH2-R²]

| Ex. Nos. | R | R² | Physicochemical Properties etc. |
|---|---|---|---|
| 901** | t-Bu | 6-methyl-2-n-Pr-pyridin-3-yl | amorphous powder MS (ESI) 652 [M + H]+ |
| 902** | MeO-CH2CH2- | 6-methyl-2-n-Pr-pyridin-3-yl | amorphous powder MS (ESI) 640 [M + H]+ |
| 903** | 2-furyl | 6-methyl-2-n-Pr-pyridin-3-yl | amorphous powder MS (ESI) 662 [M + H]+ |
| 904** | Me | 3-OEt-phenyl | amorphous powder MS (ESI) 611 [M + H]+ |
| 905** | MeO-CH2CH2- | 3-OEt-phenyl | amorphous powder MS (ESI) 641 [M + H]+ |
| 906** | Me-CH=CH- | 3-OEt-phenyl | amorphous powder MS (ESI) 637 [M + H]+ |
| 907** | cyclopropyl | 3-OEt-phenyl | amorphous powder MS (ESI) 637 [M + H]+ |
| 908** | 2-furyl | 3-OEt-phenyl | amorphous powder MS (ESI) 663 [M + H]+ |

**dihydrochloride
Me: methyl group, Et: ethyl group, n-Pr: n-propyl group, t-Bu: tert-butyl group

EXAMPLES 901 TO 908

The corresponding materials are treated in the same manner as described in Example 366 to give the compounds as shown in the following Table 27.12.

EXAMPLES 909 TO 915

The corresponding materials are treated in the same manner as described in Example 719 to give the compounds as shown in the following Table 27.13.

TABLE 27.13

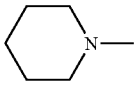

| Ex. Nos. | R | R² | Physicochemical properties etc. |
|---|---|---|---|
| 909 | piperidin-1-yl | 2-fluoro-3-methylphenyl (Me at 3, F at 2) | amorphous powder MS (APCI) 545 [M + H]+ |
| 910 | piperidin-1-yl | 4-methyl-2-n-propyl-thiazol-5-yl | amorphous powder MS (APCI) 562 [M + H]+ |
| 911 | pyrrolidin-1-yl | 3-ethoxy-5-methylphenyl | amorphous powder MS (APCI) 543 [M + H]+ |
| 912 | pyrrolidin-1-yl | 6-n-propyl-4-methyl-pyridin-2-yl | amorphous powder MS (APCI) 542 [M + H]+ |
| 913 | pyrrolidin-1-yl | 2-fluoro-3-methylphenyl | amorphous powder MS (APCI) 531 [M + H]+ |
| 914 | pyrrolidin-1-yl | 4-methyl-2-n-propyl-thiazol-5-yl | amorphous powder MS (APCI) 548 [M + H]+ |

TABLE 27.13-continued

| Ex. Nos. | R | R² | Physicochemical properties etc. |
|---|---|---|---|
| 915** | piperidin-1-yl | 3-ethoxyphenyl | amorphous powder MS (APCI) 557 [M + H]+ |

**dihydrochloride
Me: methyl group, Et: ethyl group, n-Pr: n-propyl group

EXAMPLE 916

The corresponding materials are treated in the same manner as described in Example 720 to give the compounds as shown in the following Table 27.14.

TABLE 27.14

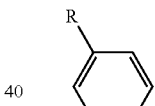

| Ex. Nos. | R | Physicochemical properties etc. |
|---|---|---|
| 916** | N,N-diethyl-N'-(2-(dimethylamino)ethyl)-N''-cyanoguanidino (Me, Et substituted guanidine) | amorphous powder MS (APCI) 638 [M + H]+ |

**dihydrochloride
Me: methyl group, Et: ethyl group

EXAMPLES 917 TO 927

The corresponding materials are treated in the same manner as described in Example 722 to give the compounds as shown in the following Table 27.15.

TABLE 27.15

(No. 1)

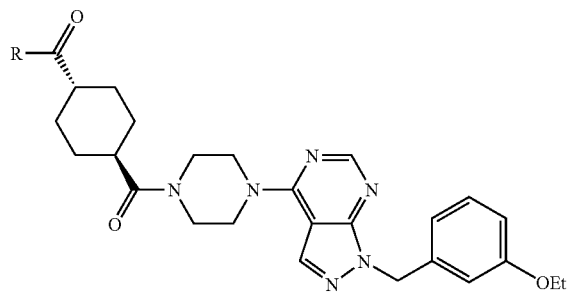

| Ex. Nos. | R | Physicochemical properties etc. |
|---|---|---|
| 917** | pyrrolidine-CH2CH2-NHMe | amorphous powder<br>MS (ESI) 589 [M + H]+ |
| 918** | Me2N-CH2CH2-NHMe | amorphous powder<br>MS (ESI) 563 [M + H]+ |
| 919** | Et2N-CH2CH2-NHMe | amorphous powder<br>MS (ESI) 591 [M + H]+ |
| 920** | Me2N-CH2CH2-N(Me)Me | amorphous powder<br>MS (ESI) 591 [M + H]+ |
| 921** | Et2N-CH2CH2-N(Me)Me | amorphous powder<br>MS (ESI) 605 [M + H]+ |
| 922** | pyrrolidine-CH2CH2CH2-NHMe | amorphous powder<br>MS (ESI) 603 [M + H]+ |
| 923** | Me2N-CH2CH2-N(Me)Me | amorphous powder<br>MS (ESI) 577 [M + H]+ |
| 924** | Me2N-CH2CH2CH2-N(Me)Me | amorphous powder<br>MS (ESI) 591 [M + H]+ |

**dihydrochloride
Me: methyl group, Et: ethyl group

TABLE 27.15

(No. 2)

[Structure: R-C(=O)-cyclohexyl-C(=O)-piperazine-pyrazolopyrimidine-N-CH2-phenyl-OEt]

| Ex. Nos. | R | Physicochemical properties etc. |
|---|---|---|
| 925** | Me2CH-N(CH2CH2NHMe)-CHMe2 | amorphous powder MS (ESI) 619 [M + H]+ |
| 926** | piperidinyl-CH2CH2CH2-NHMe | amorphous powder MS (ESI) 617 [M + H]+ |
| 927** | 1-ethyl-2-(methylaminomethyl)pyrrolidine (Me substituent) | amorphous powder MS (ESI) 603 [M + H]+ |

**dihydrochloride
Me: methyl group, Et: ethyl group

EXAMPLES 928 TO 939

The corresponding materials are treated in the same manner as described in Example 723 to give the compounds as shown in the following Table 27.16.

TABLE 27.16

(No. 1)

[Structure: R-C(=O)-N(CH2CH2NMe2)-thiophene-C(=O)-piperazine-pyrazolopyrimidine-N-CH2-R2]

| Ex. Nos. | R | R² | Physicochemical properties etc. |
|---|---|---|---|
| 928** | t-Bu | 6-methyl-2-n-propyl-pyridin-yl | amorphous powder MS (ESI) 618 [M + H]+ |
| 929** | Me | 6-methyl-2-n-propyl-pyridin-yl | amorphous powder MS (ESI) 576 [M + H]+ |
| 930** | cyclopropyl | 6-methyl-2-n-propyl-pyridin-yl | amorphous powder MS (ESI) 602 [M + H]+ |
| 931** | t-Bu | 6-methyl-2-OEt-pyridin-yl | amorphous powder MS (ESI) 620 [M + H]+ |
| 932** | Me | 6-methyl-2-OEt-pyridin-yl | amorphous powder MS (ESI) 578 [M + H]+ |
| 933** | cyclopropyl | 6-methyl-2-OEt-pyridin-yl | amorphous powder MS (ESI) 604 [M + H]+ |
| 934** | t-Bu | 3-methyl-5-OEt-phenyl | amorphous powder MS (ESI) 619 [M + H]+ |
| 935** | Me | 3-methyl-5-OEt-phenyl | amorphous powder MS (ESI) 577 [M + H]+ |
| 936** | cyclopropyl | 3-methyl-5-OEt-phenyl | amorphous powder MS (ESI) 603 [M + H]+ |

**dihydrochloride
Me: methyl group, Et: ethyl group, n-Pr: n-propyl group, t-Bu: tert-butyl group

TABLE 27.16 (No. 2)

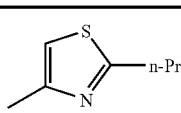

| Ex. Nos. | R | R² | Physicochemical properties etc. |
|---|---|---|---|
| 937** | t-Bu | 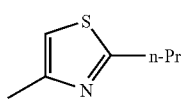 4-Me, 2-n-Pr thiazole | amorphous powder MS (ESI) 624 [M + H]+ |
| 938** | Me |  4-Me, 2-n-Pr thiazole | amorphous powder MS (ESI) 582 [M + H]+ |
| 939** | cyclopropyl-CH₂ | 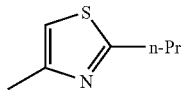 4-Me, 2-n-Pr thiazole | amorphous powder MS (ESI) 608 [M + H]+ |

**dihydrochloride
Me: methyl group, n-Pr: n-propyl group, t-Bu: tert-butyl group

EXAMPLES 940 TO 941

The corresponding materials are treated in the same manner as described in Example 727 to give the compounds as shown in the following Table 27.17.

TABLE 27.17

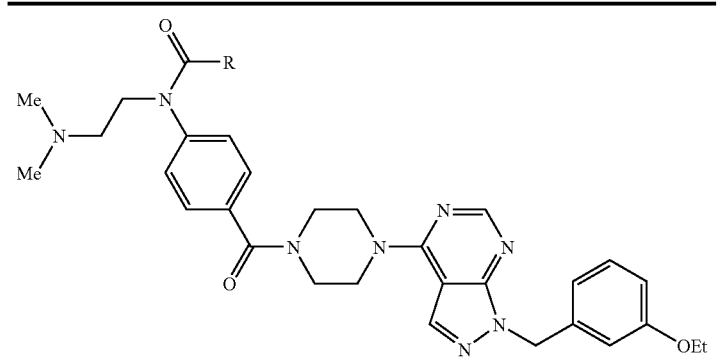

| Ex. Nos. | R | Physicochemical properties etc. |
|---|---|---|
| 940* | 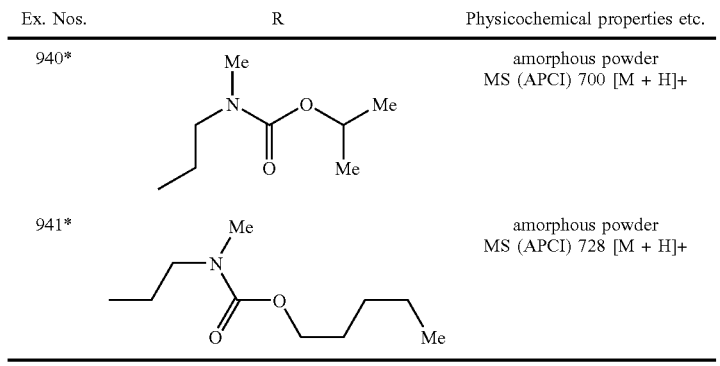 N(Me)(n-Pr)C(O)O-CH(Me)₂ | amorphous powder MS (APCI) 700 [M + H]+ |
| 941* | N(Me)(n-Pr)C(O)O-n-Bu | amorphous powder MS (APCI) 728 [M + H]+ |

TABLE 27.17-continued

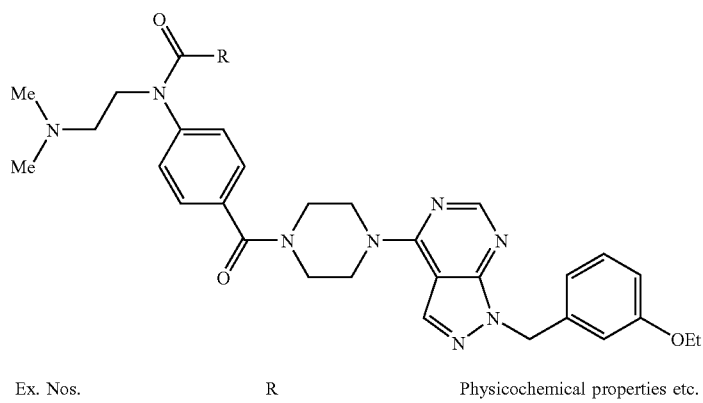

| Ex. Nos. | R | Physicochemical properties etc. |

*hydrochloride
Me: methyl group, Et: ethyl group

EXAMPLES 942 TO 947

The corresponding materials are treated in the same manner as described in Example 630 to give the compounds as shown in the following Table 27.18.

TABLE 27.18

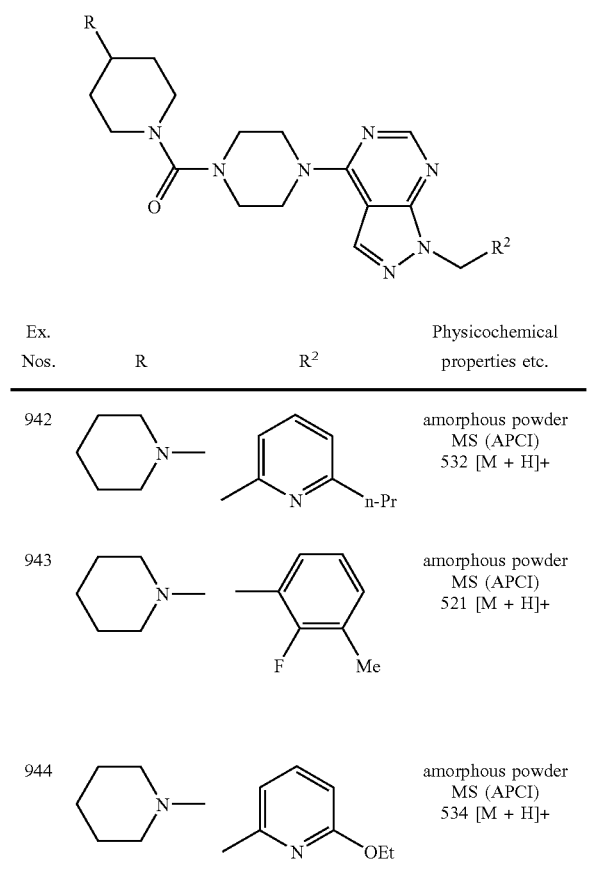

| Ex. Nos. | R | R² | Physicochemical properties etc. |
|---|---|---|---|
| 942 | piperidine-N— | 2-methyl-6-(n-Pr)-pyridin-3-yl | amorphous powder MS (APCI) 532 [M + H]+ |
| 943 | piperidine-N— | 3-F-2-Me-phenyl | amorphous powder MS (APCI) 521 [M + H]+ |
| 944 | piperidine-N— | 6-OEt-2-Me-pyridin-3-yl | amorphous powder MS (APCI) 534 [M + H]+ |

TABLE 27.18-continued

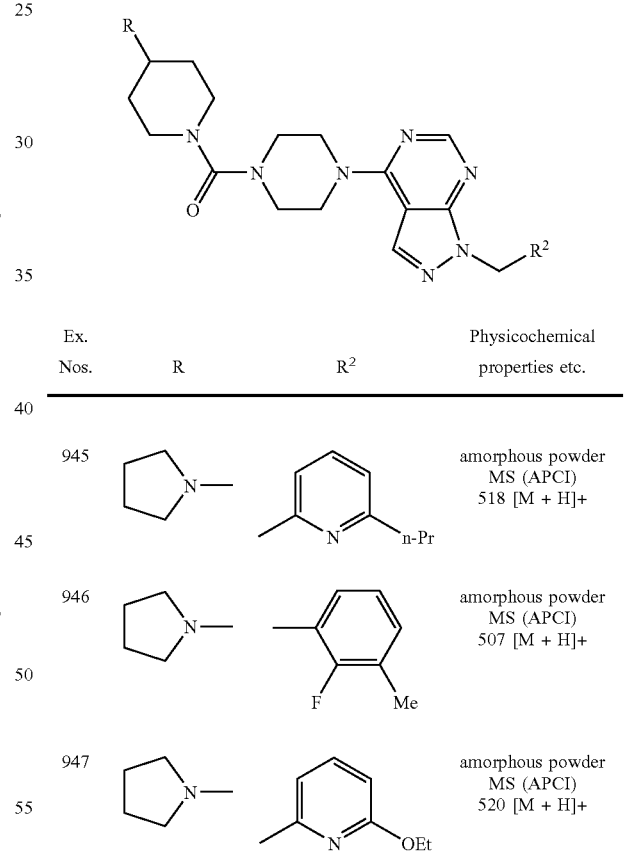

| Ex. Nos. | R | R² | Physicochemical properties etc. |
|---|---|---|---|
| 945 | pyrrolidine-N— | 2-methyl-6-(n-Pr)-pyridin-3-yl | amorphous powder MS (APCI) 518 [M + H]+ |
| 946 | pyrrolidine-N— | 3-F-2-Me-phenyl | amorphous powder MS (APCI) 507 [M + H]+ |
| 947 | pyrrolidine-N— | 6-OEt-2-Me-pyridin-3-yl | amorphous powder MS (APCI) 520 [M + H]+ |

Me: methyl group, Et: ethyl group, n-Pr: n-propyl group

EXAMPLES 948 TO 967

The corresponding materials are treated in the same manner as described in Example 723 or 725 to give the compounds as shown in the following Table 27.19.

TABLE 27.19

(No. 1)

| Ex. Nos. | R | R² | Physicochemical properties etc. |
|---|---|---|---|
| 948* | phenyl-C(O)-CH2- | 6-n-Pr-pyridin-2-yl | amorphous powder MS (APCI) 638 [M + H]+ |
| 949* | phenyl-C(O)-CH2- | 6-OEt-pyridin-2-yl | amorphous powder MS (APCI) 640 [M + H]+ |
| 950* | phenyl-C(O)-CH2- | 2-n-Pr-thiazol-4-yl | amorphous powder MS (APCI) 644 [M + H]+ |
| 951* | (Me)2CH-C(O)-CH2- | 6-n-Pr-pyridin-2-yl | amorphous powder MS (APCI) 604 [M + H]+ |
| 952* | (Me)2CH-C(O)-CH2- | 6-OEt-pyridin-2-yl | amorphous powder MS (APCI) 606 [M + H]+ |
| 953* | (Me)2CH-C(O)-CH2- | 2-n-Pr-thiazol-4-yl | amorphous powder MS (APCI) 610 [M + H]+ |
| 954* | Me-C(O)-CH2- | 6-n-Pr-pyridin-2-yl | amorphous powder MS (APCI) 576 [M + H]+ |
| 955* | Me-C(O)-CH2- | 6-OEt-pyridin-2-yl | amorphous powder MS (APCI) 578 [M + H]+ |
| 956* | Me-C(O)-CH2- | 2-n-Pr-thiazol-4-yl | amorphous powder MS (APCI) 582 [M + H]+ |
| 957* | Me-CH=CH-C(O)-CH2- | 6-n-Pr-pyridin-2-yl | amorphous powder MS (APCI) 602 [M + H]+ |
| 958* | Me-CH=CH-C(O)-CH2- | 6-OEt-pyridin-2-yl | amorphous powder MS (APCI) 604 [M + H]+ |
| 959* | Me-CH=CH-C(O)-CH2- | 2-n-Pr-thiazol-4-yl | amorphous powder MS (APCI) 608 [M + H]+ |
| 960* | cyclopropyl-C(O)-CH2- | 6-n-Pr-pyridin-2-yl | amorphous powder MS (APCI) 602 [M + H]+ |
| 961* | cyclopropyl-C(O)-CH2- | 2-n-Pr-thiazol-4-yl | amorphous powder MS (APCI) 608 [M + H]+ |
| 962* | furan-2-yl-C(O)-CH2- | 6-n-Pr-pyridin-2-yl | amorphous powder MS (APCI) 628 [M + H]+ |

*hydrochloride
Me: methyl group, Et: ethyl group, n-Pr: n-propyl group

TABLE 27.19-continued (No. 2)

| Ex. Nos. | R | R² | Physicochemical properties etc. |
|---|---|---|---|
| 963* | 2-furyl-C(=O)- | 4-methyl-2-(n-Pr)-thiazol-5-yl | amorphous powder MS (APCI) 634 [M + H]+ |
| 964* | Me-S(=O)₂- | 6-(n-Pr)-pyridin-2-yl | amorphous powder MS (APCI) 612 [M + H]+ |
| 965* | pyridin-2-yl-C(=O)- | 6-(n-Pr)-pyridin-2-yl | amorphous powder MS (APCI) 639 [M + H]+ |
| 966* | pyridin-2-yl-C(=O)- | 6-OEt-pyridin-2-yl | amorphous powder MS (APCI) 641 [M + H]+ |

TABLE 27.19-continued (No. 2)

| Ex. Nos. | R | R² | Physicochemical properties etc. |
|---|---|---|---|
| 967* | pyridin-2-yl-C(=O)- | 4-methyl-2-(n-Pr)-thiazol-5-yl | amorphous powder MS (APCI) 645 [M + H]+ |

*hydrochloride

Me: methyl group, Et: ethyl group, n-Pr: n-propyl group

EXAMPLES 968 TO 969

The corresponding materials are treated in the same manner as described in Example 720 or 727 to give the compounds as shown in the following Table 27.20.

TABLE 27.20

| Ex. Nos. | R | Physicochemical properties etc. |
|---|---|---|
| 968 | Me₂N-CH₂CH₂-N(Me)-C(=O)-CH₂CH₂-N(Me)-C(=O)-O-CH₂-(4-methyl-1,3-dioxol-2-on-5-yl) | amorphous powder MS (APCI) 770 [M + H]+ |

TABLE 27.20-continued

| Ex. Nos. | R | Physicochemical properties etc. |
|---|---|---|
| 969** | Me, ethyl, N-C(=N-CN)NH2 group | amorphous powder MS (APCI) 567 [M + H]+ |

**dihydrochloride
Me: methyl group, Et: ethyl group

EXAMPLES 970 TO 989

The corresponding materials are treated in the same manner as described in Example 723 or 724 to give the compounds as shown in the following Table 27.21.

TABLE 27.21

(No. 1)

| Ex. Nos. | R | R² | Physicochemical properties etc. |
|---|---|---|---|
| 970* | Me2N-CH2CH2-NH-Me | 6-n-Pr-pyridin-3-yl (2-methyl) | amorphous powder MS (APCI) 529 [M + H]+ |
| 971* | Me2N-CH2CH2-N(Me)-C(O)-cyclopropyl | 6-n-Pr-pyridin-3-yl (2-methyl) | amorphous powder MS (APCI) 597 [M + H]+ |
| 972* | Me2N-CH2CH2-NH-Me | 3-OEt-phenyl (methyl) | amorphous powder MS (APCI) 530 [M + H]+ |

TABLE 27.21-continued (No. 1)

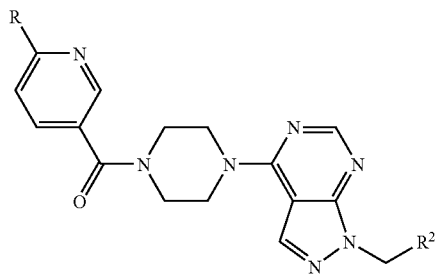

| Ex. Nos. | R | $R^2$ | Physicochemical properties etc. |
|---|---|---|---|
| 973* | Me-N(Me)-CH2CH2-N(Me)-C(O)-CH=CH-Me | 3-OEt-phenyl | amorphous powder MS (APCI) 598 [M + H]+ |
| 974* | Me-N(Me)-CH2CH2-N(Me)-C(O)-cyclopropyl | 3-OEt-phenyl | amorphous powder MS (APCI) 598 [M + H]+ |
| 975* | Me2N-CH2CH2-NH-Me | 4-Me-2-n-Pr-thiazol-5-yl | amorphous powder MS (APCI) 535 [M + H]+ |
| 976* | Me-N(Me)-CH2CH2-N(Me)-C(O)-cyclopropyl | 4-Me-2-n-Pr-thiazol-5-yl | amorphous powder MS (APCI) 603 [M + H]+ |
| 977* | Me-N(Me)-CH2CH2-N(Me)-C(O)-CH(Me)-Me | 6-n-Pr-pyridin-2-yl-Me | amorphous powder MS (APCI) 599 [M + H]+ |

*hydrochloride

Me: methyl group, Et: ethyl group, n-Pr: n-propyl group

TABLE 27.21
(No. 2)
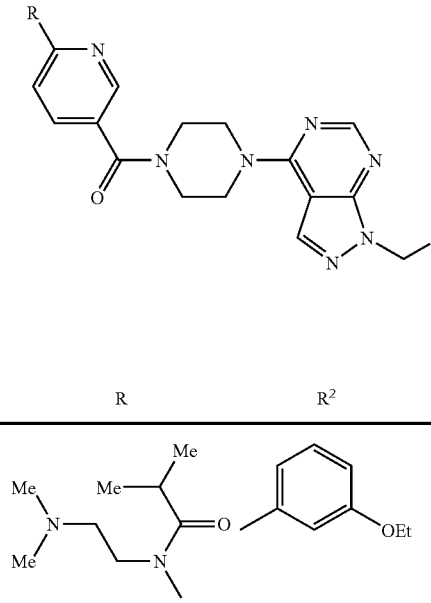
| Ex. Nos. | R | R² | Physico-chemical properties etc. |
|---|---|---|---|
| 978* |  | 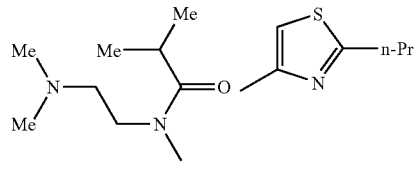 | amorphous powder MS (APCI) 600 [M + H]+ |
| 979* |  | 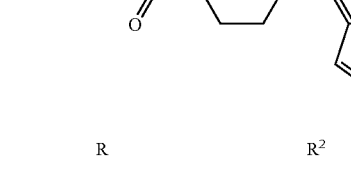 | amorphous powder MS (APCI) 605 [M + H]+ |
*hydrochloride
Me: methyl group, Et: ethyl group, n-Pr: n-propyl group
TABLE 27.21
(No. 3)
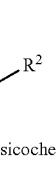
| Ex. Nos. | R | R² | Physicochemical properties etc. |
|---|---|---|---|
| 980* | Me\N/Me, Me/N\Me (ethylene linker) | 6-n-Pr-pyridin-2-yl-methyl | amorphous powder MS (APCI) 558 [M + H]+ |

TABLE 27.21-continued (No. 3)

| Ex. Nos. | R | R² | Physicochemical properties etc. |
|---|---|---|---|
| 981* | Me-N(Me)-CH₂CH₂-N(Me)-Me (Et on one N) | 6-n-Pr-pyridin-2-yl | amorphous powder MS (APCI) 572 [M + H]+ |
| 982* | Me₂N-CH₂CH₂-N(Me)- | 6-n-Pr-pyridin-2-yl | amorphous powder MS (APCI) 544 [M + H]+ |
| 983* | Me₂N-CH₂CH₂CH₂-N(Me)-Me | 6-n-Pr-pyridin-2-yl | amorphous powder MS (APCI) 558 [M + H]+ |
| 984* | Me-N(Me)-CH₂CH₂-N(Me)-Et | 3-OEt-phenyl | amorphous powder MS (APCI) 559 [M + H]+ |
| 985* | Me₂N-CH₂CH₂-NH- | 4-Me-2-n-Pr-thiazol-5-yl | amorphous powder MS (APCI) 536 [M + H]+ |
| 986* | Me-N(Me)-CH₂CH₂-N(Me)-Et | 4-Me-2-n-Pr-thiazol-5-yl | amorphous powder MS (APCI) 564 [M + H]+ |

*hydrochloride
Me: methyl group, Et: ethyl group, n-Pr: n-propyl group

TABLE 27.21

(No. 4)

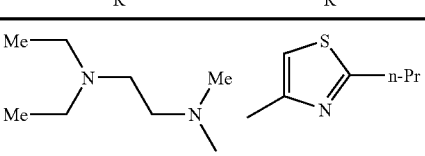

| Ex. Nos. | R | R² | Physicochemical properties etc. |
|---|---|---|---|
| 987* | 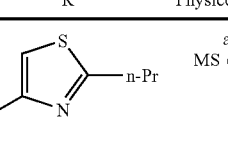 | 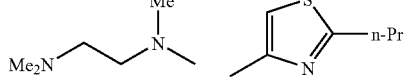 | amorphous powder<br>MS (APCI) 578 [M + H]+ |
| 988* | 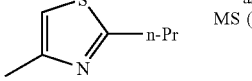 | 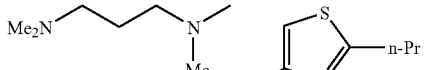 | amorphous powder<br>MS (APCI) 550 [M + H]+ |
| 989* | 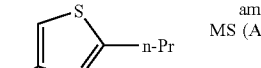 | 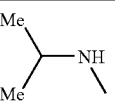 | amorphous powder<br>MS (APCI) 564 [M + H]+ |

*hydrochloride
Me: methyl group, n-Pr: n-propyl group

EXAMPLES 990 TO 994

The corresponding materials are treated in the same manner as described in Example 713 to give the compounds as shown in the following Table 27.22.

TABLE 27.22

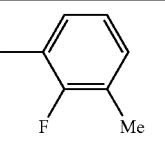

| Ex. Nos. | R | R² | Physicochemical properties etc. |
|---|---|---|---|
| 990* | 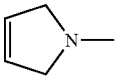 |  | amorphous powder<br>MS (APCI) 495 [M + H]+ |
| 991* | (pyrroline-N—) | (3-F-2-Me-phenyl) | amorphous powder<br>MS (APCI) 505 [M + H]+ |

TABLE 27.22-continued

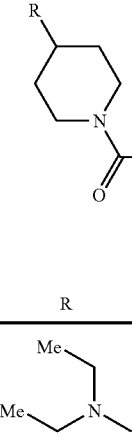

| Ex. Nos. | R | R² | Physicochemical properties etc. |
|---|---|---|---|
| 992* | Me-N(Me)-CH₂- | 2-F-3,6-Me₂-phenyl | amorphous powder MS (APCI) 509 [M + H]+ |
| 993* | 4-(C(Me)₃)-piperidinyl | 2-F-3,6-Me₂-phenyl | amorphous powder MS (APCI) 577 [M + H]+ |
| 994* | Me-CH(Me)-NH-Me | 6-OEt-pyridin-2-yl-Me | amorphous powder MS (APCI) 508 [M + H]+ |

*hydrochloride
Me: methyl group, Et: ethyl group

EXAMPLES 995 TO 1018

The corresponding materials are treated in the same manner as described in Example 713 to give the compounds as shown in the following Table 27.23.

TABLE 27.23

(No. 1)

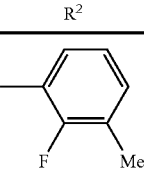

| Ex. Nos. | R | R² | Physicochemical properties etc. |
|---|---|---|---|
| 995* | 4-t-Bu-piperidinyl | 6-OEt-pyridin-2-yl-Me | amorphous powder MS (APCI) 590 [M + H]+ |

TABLE 27.23-continued (No. 1)

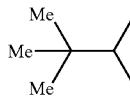

| Ex. Nos. | R | R² | Physicochemical properties etc. |
|---|---|---|---|
| 996* | (S)-2-(OMe-CH₂)-1-Me-pyrrolidinyl | 6-n-Pr-pyridin-2-yl-Me | amorphous powder MS (APCI) 562 [M + H]+ |
| 997* | azepan-1-yl | 6-n-Pr-pyridin-2-yl-Me | amorphous powder MS (APCI) 546 [M + H]+ |

TABLE 27.23-continued
(No. 1)
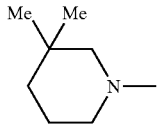
| Ex. Nos. | R | R² | Physico-chemical properties etc. |
|---|---|---|---|
| 998* | 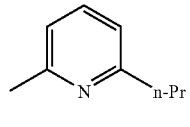 | 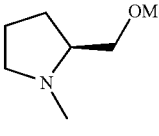 | amorphous powder MS (APCI) 560[M + H]+ |
| 999* | 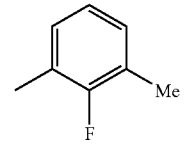 | 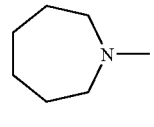 | amorphous powder MS (APCI) 551 [M + H]+ |
| 1000* | 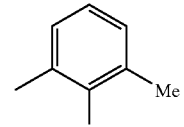 | 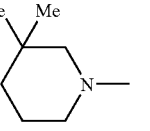 | amorphous powder MS (APCI) 535 [M + H]+ |
| 1001* | 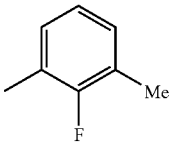 | 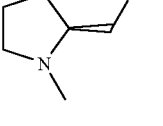 | amorphous powder MS (APCI) 549 [M + H]+ |
| 1002* | 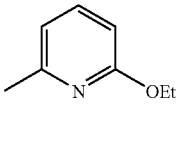 | 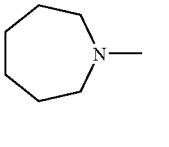 | amorphous powder MS (APCI) 564 [M + H]+ |
| 1003* | 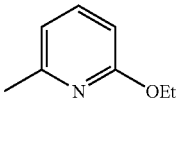 | 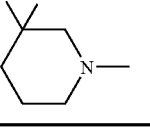 | amorphous powder MS (APCI) 548 [M + H]+ |
| 1004* | 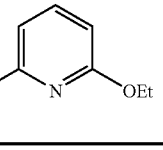 | | amorphous powder MS (APCI) 562 [M + H]+ |
*hydrochloride,
Me: methyl group, Et: ethyl group, n-Pr: n-propyl group, t-Bu: tert-butyl group

TABLE 27.23

(No. 2)

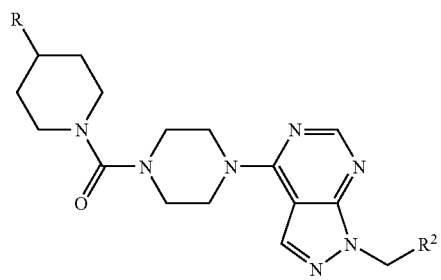

| Ex. Nos. | R | R² | Physicochemical properties etc. |
|---|---|---|---|
| 1005* | azepan-1-ylmethyl (7-membered ring N-CH₂-) | 4-methyl-2-n-Pr-thiazol-5-yl | amorphous powder<br>MS (APCI) 552 [M + H]+ |
| 1006* | 3,3-dimethylpiperidin-1-yl | 4-methyl-2-n-Pr-thiazol-5-yl | amorphous powder<br>MS (APCI) 566 [M + H]+ |
| 1007* | Me₂N-CH₂CH₂-N(Me)-CH₂- | 6-OEt-pyridin-2-yl-methyl | amorphous powder<br>MS (APCI) 551 [M + H]+ |
| 1008* | MeO-CH₂CH₂-N(Me)-CH₂- | 6-n-Pr-pyridin-2-yl-methyl | amorphous powder<br>MS (APCI) 550 [M + H]+ |
| 1009* | Me₂N-CH₂CH₂-N(Me)-CH₂- | 6-n-Pr-pyridin-2-yl-methyl | amorphous powder<br>MS (APCI) 563 [M + H]+ |
| 1010* | MeO-CH₂CH₂-N(Me)-CH₂- | 2-F-3-Me-phenyl | amorphous powder<br>MS (APCI) 539 [M + H]+ |
| 1011* | Me₂N-CH₂CH₂-N(Me)-CH₂- | 2-F-3-Me-phenyl | amorphous powder<br>MS (APCI) 552 [M + H]+ |
| 1012* | MeO-CH₂CH₂-N(Me)-CH₂- | 6-OEt-pyridin-2-yl-methyl | amorphous powder<br>MS (APCI) 552 [M + H]+ |

*hydrochloride,
Me: methyl group, Et: ethyl group, n-Pr: n-propyl group, t-Bu: tert-butyl group

TABLE 27.23

(No. 3)

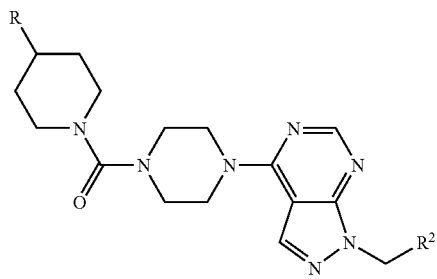

| Ex. Nos. | R | R² | Physicochemical properties etc. |
|---|---|---|---|
| 1013* | Me-N(Me)-CH₂CH₂-N(Me)-CH₂- | 6-OEt-pyridin-2-yl-CH₂- | amorphous powder MS (APCI) 565 [M + H]+ |
| 1014* | Me-N(Me)-CH₂CH₂-N(Me)-CH₂- | 2-n-Pr-thiazol-4-yl-CH₂- | amorphous powder MS (APCI) 569 [M + H]+ |
| 1015* | Me-N(Me)-CH₂- | 6-OEt-pyridin-2-yl-CH₂- | amorphous powder MS (APCI) 522 [M + H]+ |
| 1016* | Et₂N-CH₂CH₂-NH-CH₂- | 3-OEt-phenyl-CH₂- | amorphous powder MS (APCI) 564 [M + H]+ |
| 1017* | (i-Pr)₂N-CH₂CH₂-NH-CH₂- | 3-OEt-phenyl-CH₂- | amorphous powder MS (APCI) 592 [M + H]+ |
| 1018* | piperidin-1-yl-CH₂CH₂-NH-CH₂- | 3-OEt-phenyl-CH₂- | amorphous powder MS (APCI) 576 [M + H]+ |

*hydrochloride,
Me: methyl group, Et: ethyl group, n-Pr: n-propyl group

EXAMPLES 1019 TO 1040

The corresponding materials are treated in the same manner as described in Example 718 to give the compounds as shown in the following Table 27.24.

TABLE 27.24

(No. 1)

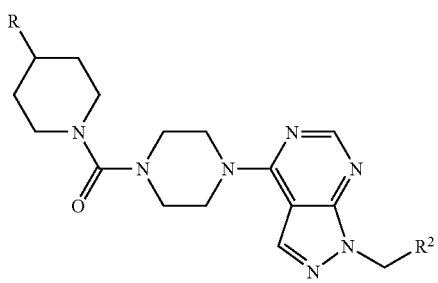

| Ex. Nos. | R | R² | Physicochemical properties etc. |
|---|---|---|---|
| 1019* | Me-CH=CH-C(O)-N(Me)-CH₂CH₂-N(Me)Me | 6-methyl-2-n-Pr-pyridin-3-yl | amorphous powder MS (APCI) 603 [M + H]+ |
| 1020* | cyclopropyl-C(O)-N(Me)-CH₂CH₂-N(Me)Me | 6-methyl-2-n-Pr-pyridin-3-yl | amorphous powder MS (APCI) 603 [M + H]+ |
| 1021* | Me-CH=CH-C(O)-N(Me)-CH₂CH₂-N(Me)Me | 2-F-3,6-diMe-phenyl | amorphous powder MS (APCI) 592 [M + H]+ |
| 1022* | cyclopropyl-C(O)-N(Me)-CH₂CH₂-N(Me)Me | 2-F-3,6-diMe-phenyl | amorphous powder MS (APCI) 592 [M + H]+ |
| 1023* | Me-CH=CH-C(O)-N(Me)-CH₂CH₂-N(Me)Me | 6-methyl-2-OEt-pyridin-3-yl | amorphous powder MS (APCI) 605 [M + H]+ |

*hydrochloride,
Me: methyl group, Et: ethyl group, n-Pr: n-propyl group

TABLE 27.24 (No. 2)

Structure: R''-C(=O)-N(R')-[piperidine]-C(=O)-[piperazine]-[pyrazolo[3,4-d]pyrimidine]-CH2-[3-ethoxyphenyl]

| Ex. Nos. | R' | R'' | Physicochemical properties etc. |
|---|---|---|---|
| 1024* | Me2N-CH2CH2CH2- | Et | amorphous powder MS (APCI) 592 [M + H]+ |
| 1025* | Me2N-CH2CH2CH2- | iPr (Me2CH-) | amorphous powder MS (APCI) 606 [M + H]+ |
| 1026* | Me2N-CH2CH2CH2- | n-Pr | amorphous powder MS (APCI) 606 [M + H]+ |
| 1027* | Et2N-CH2CH2CH2- | Me | amorphous powder MS (APCI) 606 [M + H]+ |
| 1028* | Et2N-CH2CH2CH2- | cyclopropyl | amorphous powder MS (APCI) 632 [M + H]+ |
| 1029* | Et2N-CH2CH2CH2- | CH=CH-Me | amorphous powder MS (APCI) 632 [M + H]+ |
| 1030* | Et2N-CH2CH2CH2- | 3-furyl | amorphous powder MS (APCI) 658 [M + H]+ |
| 1031* | (iPr)2N-CH2CH2CH2- | Me | amorphous powder MS (APCI) 634 [M + H]+ |

TABLE 27.24 (No. 3)

Structure: R''-C(=O)-N(R')-[piperidine]-C(=O)-[piperazine]-[pyrazolo[3,4-d]pyrimidine]-CH2-[3-ethoxyphenyl]

| Ex. Nos. | R' | R'' | Physicochemical properties etc. |
|---|---|---|---|
| 1032* | (iPr)2N-CH2CH2CH2- | cyclopropyl | amorphous powder MS (APCI) 660 [M + H]+ |
| 1033* | (iPr)2N-CH2CH2CH2- | CH=CH-Me | amorphous powder MS (APCI) 660 [M + H]+ |
| 1034* | (iPr)2N-CH2CH2CH2- | 3-furyl | amorphous powder MS (APCI) 686 [M + H]+ |
| 1035* | piperidino-CH2CH2CH2- | Me | amorphous powder MS (APCI) 618 [M + H]+ |
| 1036* | piperidino-CH2CH2CH2- | cyclopropyl | amorphous powder MS (APCI) 644 [M + H]+ |
| 1037* | piperidino-CH2CH2CH2- | CH=CH-Me | amorphous powder MS (APCI) 644 [M + H]+ |
| 1038* | piperidino-CH2CH2CH2- | 3-furyl | amorphous powder MS (APCI) 670 [M + H]+ |
| 1039 | Me2N-CH2CH2CH2CH2- | cyclopropyl | amorphous powder MS (APCI) 618 [M + H]+ |

*hydrochloride,
Me: methyl group, Et: ethyl group, n-Pr: n-propyl group

TABLE 27.24-continued (No. 3)

| Ex. Nos. | R' | R" | Physicochemical properties etc. |
|---|---|---|---|
| 1040 | Me₂N~~~ | (3-methylfuran) | amorphous powder MS (APCI) 644 [M + H]+ |

*hydrochloride,
Me: methyl group, Et: ethyl group

EXAMPLES 1041 TO 1048

The corresponding materials are treated in the same manner as described in Example 1 to give the compounds as shown in the following Table 27.25.

TABLE 27.25

| Ex. Nos. | R | R² | Physicochemical properties etc. |
|---|---|---|---|
| 1041 | 1,4-oxazepan-4-yl | 3-ethoxyphenyl | amorphous powder MS (APCI) 562 [M + H]+ |
| 1042 | 1,4-oxazepan-4-yl | 6-n-propylpyridin-2-yl | amorphous powder MS (APCI) 561 [M + H]+ |
| 1043 | 1,4-oxazepan-4-yl | 6-ethoxy-2-methylpyridin-3-yl | amorphous powder MS (APCI) 563 [M + H]+ |
| 1044 | (3R,5S)-3,5-dimethylmorpholin-4-yl | 3-ethoxyphenyl | amorphous powder MS (APCI) 576 [M + H]+ |

TABLE 27.25-continued

| Ex. Nos. | R | R² | Physicochemical properties etc. |
|---|---|---|---|
| 1045 | (3,5-dimethylmorpholin-4-yl)methyl | 6-n-propylpyridin-2-yl | amorphous powder<br>MS (APCI) 575 [M + H]+ |
| 1046 | (3,5-dimethylmorpholin-4-yl)methyl | 3-ethoxyphenyl | amorphous powder<br>MS (APCI) 576 [M + H]+ |
| 1047 | (3,5-dimethylmorpholin-4-yl)methyl | 6-n-propylpyridin-2-yl | amorphous powder<br>MS (APCI) 575 [M + H]+ |
| 1048 | (3,5-dimethylmorpholin-4-yl)methyl | 6-ethoxypyridin-2-yl | amorphous powder<br>MS (APCI) 577 [M + H]+ |

Me: methyl group, Et: ethyl group, n-Pr n-propyl group

EXAMPLES 1049 TO 1071

The corresponding materials are treated in the same manner as described in Example 654 to give the compounds as shown in the following Table 27.26.

TABLE 27.26

(No. 1)

| Ex. Nos. | R | R² | Physicochemical properties etc. |
|---|---|---|---|
| 1049* | t-Bu | 6-methyl-2-(n-Pr)-pyridin-yl | amorphous powder MS (APCI) 632 [M + H]+ |
| 1050* | Me | 6-methyl-2-(n-Pr)-pyridin-yl | amorphous powder MS (APCI) 590 [M + H]+ |
| 1051* | MeOCH₂CH₂- | 6-methyl-2-(n-Pr)-pyridin-yl | amorphous powder MS (APCI) 620 [M + H]+ |
| 1052* | Me-CH=CH- | 6-methyl-2-(n-Pr)-pyridin-yl | amorphous powder MS (APCI) 616 [M + H]+ |
| 1053* | 2-furyl | 6-methyl-2-(n-Pr)-pyridin-yl | amorphous powder MS (APCI) 642 [M + H]+ |
| 1054* | t-Bu | 3-methyl-5-OEt-phenyl | amorphous powder MS (APCI) 633 [M + H]+ |
| 1055* | Me | 3-methyl-5-OEt-phenyl | amorphous powder MS (APCI) 591 [M + H]+ |
| 1056* | MeOCH₂CH₂- | 3-methyl-5-OEt-phenyl | amorphous powder MS (APCI) 621 [M + H]+ |
| 1057* | Me-CH=CH- | 3-methyl-5-OEt-phenyl | amorphous powder MS (APCI) 617 [M + H]+ |
| 1058* | 2-furyl | 3-methyl-5-OEt-phenyl | amorphous powder MS (APCI) 643 [M + H]+ |

*hydrochloride,
Me: methyl group, Et: ethyl group, n-Pr: n-propyl group, t-Bu: tert-butyl group

TABLE 27.26
(No. 2)

| Ex. Nos. | R | R² | Physicochemical properties etc. |
|---|---|---|---|
| 1059* | cyclopropyl | 6-methyl-2-(n-Pr)-pyridin-yl | amorphous powder MS (APCI) 616 [M + H]+ |
| 1060* | cyclopropyl | 3-methyl-5-OEt-phenyl | amorphous powder MS (APCI) 617 [M + H]+ |

*hydrochloride,
Me: methyl group, Et: ethyl group, n-Pr: n-propyl group, t-Bu: tert-butyl group

TABLE 27.26

(No. 3)

[Structure: R-CH2-cyclohexyl-C(=O)-piperazine-pyrazolopyrimidine-N-CH2-phenyl-OEt]

| Ex. Nos. | R | Physicochemical properties etc. |
|---|---|---|
| 1061* | Me-N(Me)-CH2CH2-N(Me)-C(=O)-CH2- | amorphous powder MS (APCI) 633 [M + H]+ |
| 1062* | Me-N(Me)-CH2CH2-N(Me)-C(=O)-C(Me)2- | amorphous powder MS (APCI) 661 [M + H]+ |
| 1063* | Me-N(Me)-CH2CH2-N(Me)-C(=O)-CH=CH- (with Me) | amorphous powder MS (APCI) 645 [M + H]+ |
| 1064* | MeO-C6H4-C(=O)-N(Me)-CH2CH2CH2-N(Me)- | amorphous powder MS (APCI) 697 [M + H]+ |
| 1065* | Me-N(Me)-CH2CH2CH2-N(Me)-C(=O)-CH=CH- | amorphous powder MS (APCI) 631 [M + H]+ |

TABLE 27.26-continued (No. 3)

| Ex. Nos. | R | Physicochemical properties etc. |
|---|---|---|
| 1066* | t-Bu-O-C(=O)-N(Me)-CH2CH2CH2-NMe2 | amorphous powder MS (APCI) 647 [M + H]+ |

*hydrochloride,
Me: methyl group, Et: ethyl group, t-Bu: tert-butyl group (dimethylamino)ethyl]amino]benzoate (4.2 g, yield; 84%) as a pale yellow crystals. MS (APCI) m/z: 394 [M+H]+

REFERENCE EXAMPLE 68

(1) To a solution of methyl 4-bromomethylbenzoate (22.8 g) in N,N-dimethylformamide (450 ml) is added dropwise 50% aqueous dimethylamine solution (27 mL) and the mixture is stirred at room temperature for 3 hours. The reaction mixture is poured into water with ice and extracted with ethyl acetate. The extract is washed successively with water and saturated brine, dried over anhydrous sodium sulfate, and concentrated in vacuo. The resultant crude product is purified by flash column chromatography on silica gel (Solvent; chloroform:methanol=10:1) to give methyl 4-[(dimethylamino) methyl]benzoate (27.5 g, yield; 99%) as brown oil. MS (APCI) m/z: 194 [M+H]+

(2) To the compound obtained in the above step (1) (19.2 g) is added conc. hydrochloric acid (66 mL) and water (167 mL) and the mixture is refluxed overnight. The reaction mixture is concentrated in vacuo. The resultant crude crystals are washed with ether to give 4-[(dimethylamino)methyl]benzoic acid hydrochloride (19.0 g, yield; 88%) as a colorless powder. MS (APCI) m/z: 179 [M+H]+

REFERENCE EXAMPLE 69

(1) To a solution of methyl 6-methylnicotinate (6.3 g) in carbon tetrachloride (100 mL) is added successively N-bromosuccinimide (8.9 g) and 2,2'-azobisisobutyronitrile (342 mg), and the mixture is refluxed under heating for 6 hours. After cooling to room temperature, to the reaction mixture is added n-hexane (300 mL) and the insoluble materials are removed by filtration. The filtrate is concentrated in vacuo and the resultant crude product is purified by column chromatography on silica gel (Solvent; n-hexane:ethyl acetate=10:1) and stirred in n-hexane to give methyl 6-(bromomethyl)nicotinate (3.4 g, yield; 35%) as colorless crystals.

(2) To a solution of the compound obtained in the above step (1) (350 mg) in tetrahydrofuran (5 mL) is added 50% aqueous dimethylamine solution (3 mL) and the mixture is stirred at room temperature for 10 minutes. To the reaction mixture is added ethyl acetate. The mixture is washed successively with water and saturated brine, dried over anhydrous sodium sulfate and purified by column chromatography on silica gel (Solvent; chloroform:methanol=100:1) to give methyl 6-(dimethylamino-methyl)nicotinate (276 mg, yield; 93%) as a colorless oil. MS (APCI) m/z: 195 [M+H]+

EXAMPLES 1072 TO 1074

The corresponding materials are treated in the same manner as described in Example 416 to give the compounds as shown in the following Table 27.27.

TABLE 27.26

(No. 4)

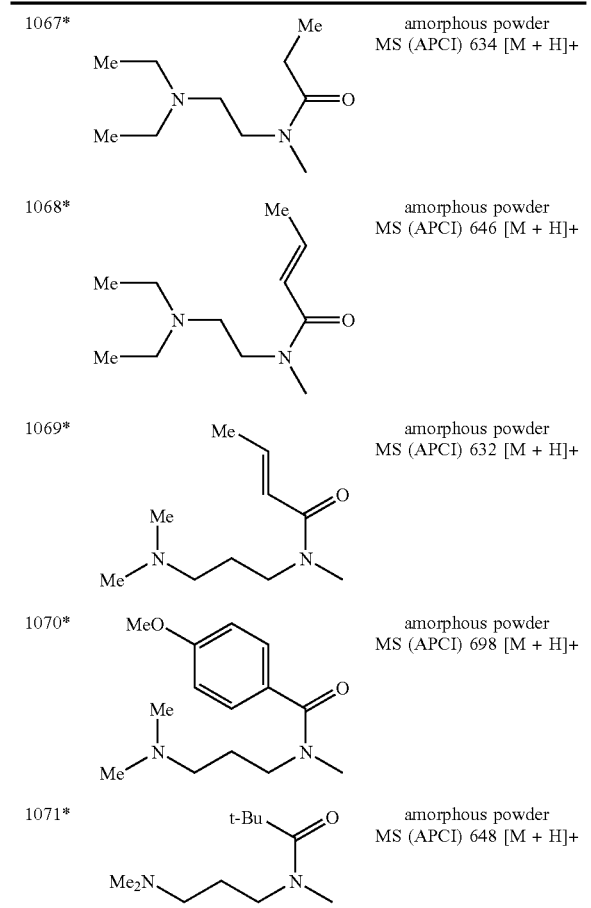

| Ex. Nos. | R | Physicochemical properties etc. |
|---|---|---|
| 1067* | Me-N(Me)-CH2CH2-N(Me)-C(O)-CH2- | amorphous powder MS (APCI) 634 [M + H]+ |
| 1068* | Me-N(Me)-CH2CH2-N(Me)-C(O)-CH=C(Me)- | amorphous powder MS (APCI) 646 [M + H]+ |
| 1069* | Me-N(Me)-CH2CH2CH2-N(Me)-C(O)-CH=C(Me)- | amorphous powder MS (APCI) 632 [M + H]+ |
| 1070* | MeO-C6H4-C(O)-N(Me)-CH2CH2CH2-N(Me)- | amorphous powder MS (APCI) 698 [M + H]+ |
| 1071* | Me2N-CH2CH2CH2-N(Me)-C(O)-t-Bu | amorphous powder MS (APCI) 648 [M + H]+ |

*hydrochloride,
Me: methyl group, Et: ethyl group, t-Bu: tert-butyl group

TABLE 27.27

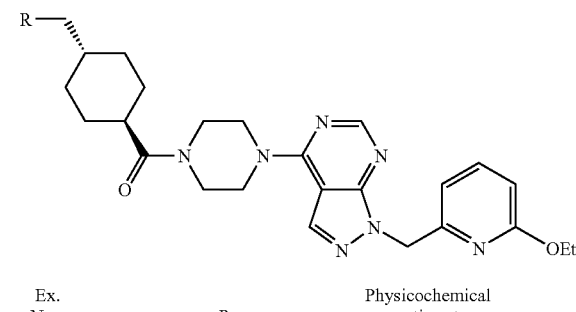

| Ex. Nos. | R | Physicochemical properties etc. |
|---|---|---|
| 1072* | Me-CH2CH2- | amorphous powder MS (APCI) 591 [M + H]+ |
| 1073* | Me-CH2CH2CH2- | amorphous powder MS (APCI) 605 [M + H]+ |
| 1074* | cyclopentyl | amorphous powder MS (APCI) 631 [M + H]+ |

*hydrochloride,
Me: methyl group, Et: ethyl group

EXAMPLE 1075

The compound obtained in Example 726(2) (45 mg) is treated in the same manner as described in Example 416 to give 1-(3-ethoxybenzyl)-4-[trans-4-[[4-(4-acetyl-piperazin-1-yl)cyclohexyl]carbonyl]piperazin-1-yl]-1H-pyrazolo[3,4-d]pyrimidine as an yellow oil. Subsequently, the compound is treated in the same manner as described in Example 4(3) to give 1-(3-ethoxybenzyl)-4-[trans-4-[[4-(4-acetyl-piperazin-1-yl)cyclohexyl]carbonyl]piperazin-1-yl]-1H-pyrazolo[3,4-d]pyrimidine hydrochloride (39.8 mg, yield: 78%) as an amorphous powder.

MS (APCI) 575 [M+H]+

EXAMPLE 1076

The corresponding materials are treated in the same manner as described in Example 1075 to give the compounds as shown in the following Table 27.28.

TABLE 27.28

| Ex. Nos. | R | Physicochemical properties etc. |
|---|---|---|
| 1076* | (Me-C(O)-N-piperazine-N-CH2-) | amorphous powder MS (APCI) 589 [M + H]+ |

*hydrochloride,
Me: methyl group, Et: ethyl group

EXAMPLES 1077 TO 1078

The corresponding materials are treated in the same manner as described in Example 637 to give the compounds as shown in the following Table 27.29.

TABLE 27.29

| Ex. Nos. | R² | Physicochemical properties etc. |
|---|---|---|
| 1077* | (3-methoxyphenyl) | amorphous powder MS (APCI) 557 [M + H]+ |
| 1078* | (2-fluoro-3-ethoxy-methylphenyl) | amorphous powder MS (APCI) 589 [M + H]+ |

*hydrochloride,
Me: methyl group, Et: ethyl group

EXAMPLES 1079 TO 1081

The corresponding materials are treated in the same manner as described in Example 407 to give the compounds as shown in the following Table 27.30.

TABLE 27.30

| Ex. Nos. | R² | Physicochemical properties etc. |
|---|---|---|
| 1079* | (3-methoxy-methylphenyl) | amorphous powder MS (APCI) 486 [M + H]+ |
| 1080* | (2-fluoro-3-ethoxy-methylphenyl) | amorphous powder MS (APCI) 518 [M + H]+ |
| 1081* | (3-methyl-ethylketone-phenyl) | amorphous powder MS (APCI) 512 [M + H]+ |

*hydrochloride,
Me: methyl group, Et: ethyl group

EXAMPLES 1082 TO 1087

The corresponding materials are treated in the same manner as described in Example 1 or 3 to give the compounds as shown in the following Table 27.31.

TABLE 27.31

| Ex. Nos. | R | R² | Physicochemical properties etc. |
|---|---|---|---|
| 1082 | (piperidinyl) | (3-methoxy-methylphenyl) | amorphous powder MS (APCI) 518 [M + H]+ |

TABLE 27.31-continued

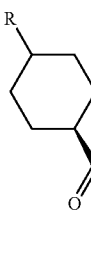

| Ex. Nos. | R | R² | Physico-chemical properties etc. |
|---|---|---|---|
| 1083* | 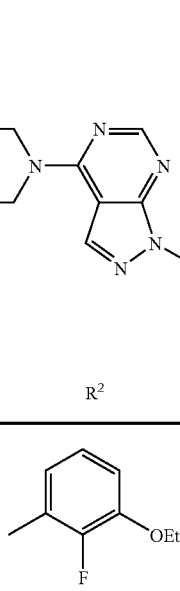 | 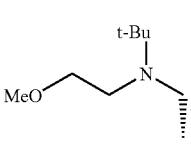 | amorphous powder MS (APCI) 550 [M + H]+ |
| 1085* | 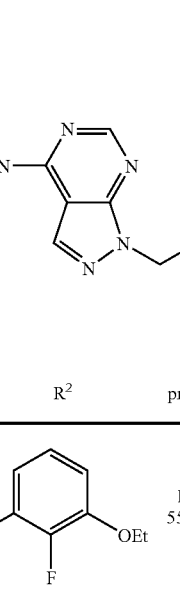 | 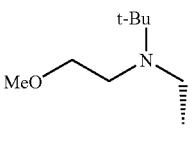 | amorphous powder MS (APCI) 578 [M + H]+ |
| 1086* | 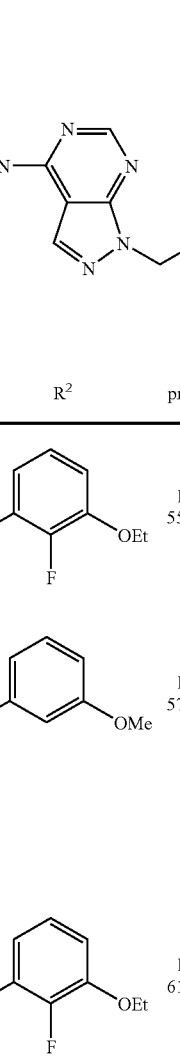 | 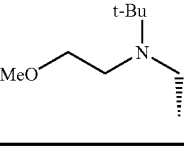 | amorphous powder MS (APCI) 610 [M + H]+ |
| 1087* | 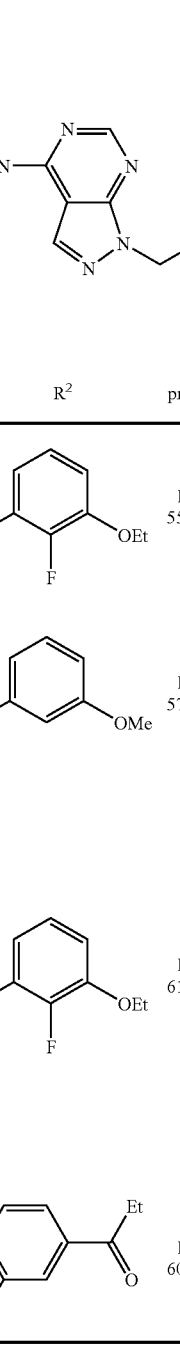 | 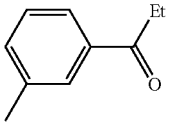 | amorphous powder MS (APCI) 604 [M + H]+ |

*hydrochloride,
Me: methyl group, Et: ethyl group, t-Bu: tert-butyl group

EXAMPLES 1088 TO 1092

The corresponding materials are treated in the same manner as described in Example 637 to give the compounds as shown in the following Table. 27.32.

TABLE 27.32

| Ex. Nos. | R | R² | Physicochemical properties etc. |
|---|---|---|---|
| 1088* | Me | 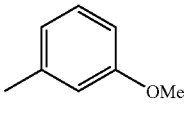 | amorphous powder MS (APCI) 583 [M + H]+ |
| 1089* |  | 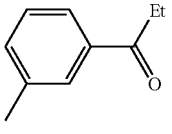 | amorphous powder MS (APCI) 583 [M + H]+ |
| 1090* | 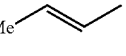 | 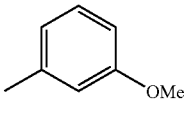 | amorphous powder MS (APCI) 609 [M + H]+ |
| 1091* | 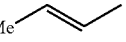 | 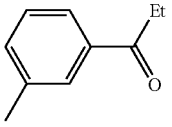 | amorphous powder MS (APCI) 583 [M + H]+ |
| 1092* |  |  | amorphous powder MS (APCI) 609 [M + H]+ |

*hydrochloride,
Me: methyl group, Et: ethyl group

EXAMPLES 1093 TO 1094

The corresponding materials are treated in the same manner as described in Example 1 to give the compounds as shown in the following Table 27.33.

TABLE 27.33

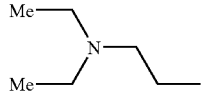

| Ex. Nos. | R | Physicochemical properties etc. |
|---|---|---|
| 1093** | Me—\\N—/—Me (propyl dimethylamine) | amorphous powder MS (APCI) 645 [M + H]+ |

TABLE 27.33-continued

| Ex. Nos. | R | Physicochemical properties etc. |
|---|---|---|
| 1094** | Me-CH(Me)-N(propyl)-CH(Me)Me | amorphous powder MS (APCI) 673 [M + H]+ |

**dihydrochloride,
Me: methyl group, Et: ethyl group

EXAMPLES 1095 TO 1102

The corresponding materials are treated in the same manner as described in Example 1 to give the compounds as shown in the following Table. 27.34.

TABLE 27.34

(No. 1)

| Ex. Nos. | R | R² | Physicochemical properties etc. |
|---|---|---|---|
| 1095* | Me-N(Me)-CH2CH2-N(Me)-CH2- | 3-OEt-phenyl | amorphous powder MS (APCI) 605 [M + H]+ |
| 1096* | Me-N(Me)-CH2CH2-N(Me)-CH(Me)- | 3-OEt-phenyl | amorphous powder MS (APCI) 619 [M + H]+ |

TABLE 27.34-continued (No. 1)

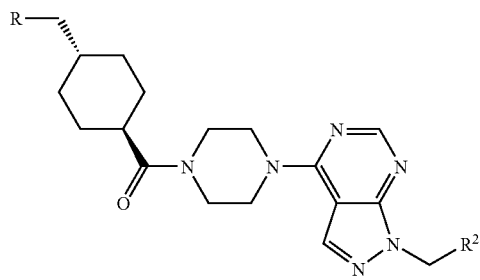

| Ex. Nos. | R | R² | Physicochemical properties etc. |
|---|---|---|---|
| 1097* | Me-N(Me)-CH2CH2-N(Me)-CH2-Me | 6-methyl-2-ethoxypyridin-3-yl | amorphous powder MS (APCI) 606 [M + H]+ |
| 1098* | Me-N(Me)-CH2CH2-N(Me)-CH(Me)Me | 6-methyl-2-ethoxypyridin-3-yl | amorphous powder MS (APCI) 620 [M + H]+ |

*hydrochloride,
Me: methyl group, Et: ethyl group

TABLE 27.34

(No. 2)

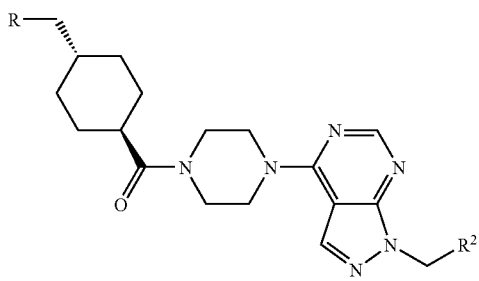

| Ex. Nos. | R | R² | Physicochemical properties etc. |
|---|---|---|---|
| 1099** | Me-N(Me)-CH2CH2CH2-N(Me)-Me | 3-methyl-5-ethoxyphenyl | amorphous powder MS (APCI) 591 [M + H]+ |
| 1100** | Me-N(Me)-CH2CH2CH2-N(Me)-C(Me)2 | 3-ethoxyphenyl | amorphous powder MS (APCI) 605 [M + H]+ |
| 1101** | Me-N(Me)-CH2CH2CH2-N(Me)-Me | 6-methyl-2-ethoxypyridin-3-yl | amorphous powder MS (APCI) 592 [M + H]+ |

TABLE 27.34-continued (No. 2)

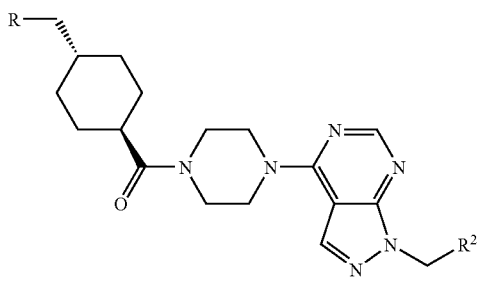

| Ex. Nos. | R | R² | Physicochemical properties etc. |
|---|---|---|---|
| 1102** | Me₂N-CH₂CH₂CH₂-N(Me)-CH(Me)- | 6-ethoxypyridin-2-yl (via CH(Me)) | amorphous powder MS (APCI) 606 [M + H]+ |

**dihydrochloride,
Me: methyl group, Et: ethyl group

EXAMPLES 1103 TO 1123

The corresponding materials are treated in the same manner as described in Example 1 or 637 to give the compounds as shown in the following Table. 27.35.

TABLE 27.35

(No. 1)

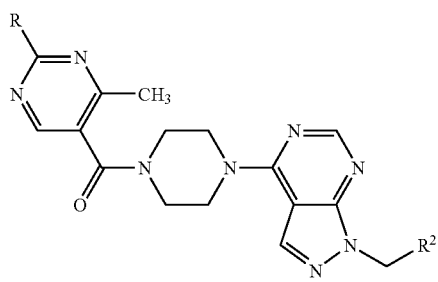

| Ex. Nos. | R | R² | Physicochemical properties etc. |
|---|---|---|---|
| 1103* | Me₂N-CH₂CH₂-NH-Me | 3-ethoxyphenyl | amorphous powder MS (APCI) 545 [M + H]+ |
| 1104* | Me₂N-CH₂CH₂-N(Me)-Me | 3-ethoxyphenyl | amorphous powder MS (APCI) 559 [M + H]+ |
| 1105* | (iPr)₂N-NH-Me | 3-ethoxyphenyl | amorphous powder MS (APCI) 601 [M + H]+ |
| 1106 | Me₂N-CH₂CH₂-N(Me)-C(O)Me | 3-ethoxyphenyl | oil MS (APCI) 587 [M + H]+ |

TABLE 27.35-continued (No. 1)

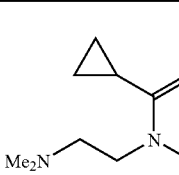

| Ex. Nos. | R | $R^2$ | Physicochemical properties etc. |
|---|---|---|---|
| 1107 | 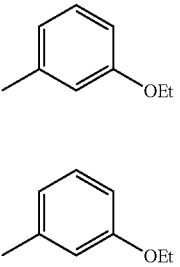 | 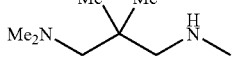 | oil MS (APCI) 613 [M + H]+ |
| 1108* | 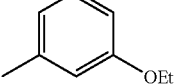 | 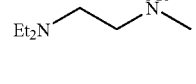 | amorphous powder MS (APCI) 587 [M + H]+ |
| 1109* | 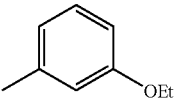 | 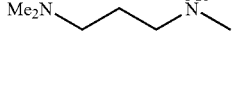 | amorphous powder MS (APCI) 587 [M + H]+ |
| 1110* | 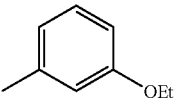 | 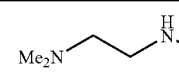 | amorphous powder MS (APCI) 573 [M + H]+ |

*hydrochloride,
Me: methyl group, Et: ethyl group, n-Pr: n-propyl group

TABLE 27.35

(No. 2)

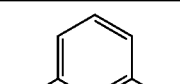

| Ex. Nos. | R | $R^2$ | Physicochemical properties etc. |
|---|---|---|---|
| 1111* | 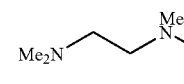 | 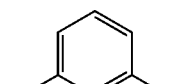 | amorphous powder MS (APCI) 546 [M + H]+ |
| 1112* | (structure) | (structure) | amorphous powder MS (APCI) 560 [M + H]+ |

TABLE 27.35-continued (No. 2)

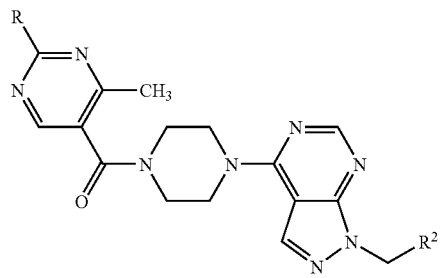

| Ex. Nos. | R | R² | Physicochemical properties etc. |
|---|---|---|---|
| 1113* | Me₂CH-N(CHMe₂)-CH₂CH₂-NH- | 6-ethoxypyridin-2-yl | amorphous powder MS (APCI) 602 [M + H]+ |
| 1114* | Me₂N-CH₂-C(Me)₂-CH₂-NH- | 6-ethoxypyridin-2-yl | amorphous powder MS (APCI) 588 [M + H]+ |
| 1115* | Et₂N-CH₂CH₂-N(Me)- | 6-ethoxypyridin-2-yl | amorphous powder MS (APCI) 588 [M + H]+ |
| 1116* | Me₂N-CH₂CH₂-NH- | 2-n-propylthiazol-4-yl | amorphous powder MS (APCI) 550 [M + H]+ |
| 1117* | Me₂N-CH₂CH₂-N(Me)- | 2-n-propylthiazol-4-yl | amorphous powder MS (APCI) 564 [M + H]+ |
| 1118* | Me₂CH-N(CHMe₂)-CH₂CH₂-NH- | 2-n-propylthiazol-4-yl | amorphous powder MS (APCI) 606 [M + H]+ |
| 1119* | Me₂N-CH₂-C(Me)₂-CH₂-NH- | 2-n-propylthiazol-4-yl | amorphous powder MS (APCI) 592 [M + H]+ |

*hydrochloride,
Me: methyl group, Et: ethyl group, n-Pr: n-propyl group

TABLE 27.35

(No. 3)

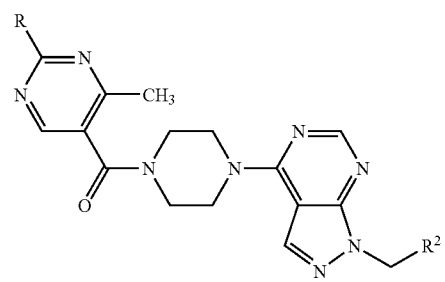

| Ex. Nos. | R | R² | Physicochemical properties etc. |
|---|---|---|---|
| 1120* | Me₂N–CH₂CH₂–N(H)–Me | 6-methyl-2-n-Pr-pyridin-3-yl | amorphous powder<br>MS (APCI) 544 [M + H]+ |
| 1121* | Me₂N–CH₂CH₂–N(Me)–Me | 6-methyl-2-n-Pr-pyridin-3-yl | amorphous powder<br>MS (APCI) 558 [M + H]+ |
| 1122* | (iPr)₂N–CH₂CH₂–N(H)–CH₂– | 6-methyl-2-n-Pr-pyridin-3-yl | amorphous powder<br>MS (APCI) 600 [M + H]+ |
| 1123* | Me₂N–CH₂–C(Me)₂–CH₂–N(H)–Me | 6-methyl-2-n-Pr-pyridin-3-yl | amorphous powder<br>MS (APCI) 586 [M + H]+ |

*hydrochloride,
Me: methyl group, Et: ethyl group, n-Pr: n-propyl group

EXAMPLES 1124 TO 1125

The corresponding materials are treated in the same manner as described in Example 723 to give the compounds as shown in the following Table. 27.36.

Table 27.36

| Ex. Nos. | R | R² | Physicochemical properties etc. |
|---|---|---|---|
| 1124* | MeSO₂— | (6-ethoxypyridin-2-yl)methyl | amorphous powder MS (APCI) 614 [M + H]+ |
| 1125* | MeSO₂— | (4-methyl-2-n-propylthiazol-5-yl)methyl | amorphous powder MS (APCI) 618 [M + H]+ |

*hydrochloride,
Me: methyl group, Et: ethyl group, n-Pr: n-propyl group

REFERENCE EXAMPLE 1

(1) A solution of ethyl 4-fluorobenzoate (20 g), N,N-dimethylethylenediamine (20 g) and potassium carbonate (32.9 g) in dimethylsulfoxide (200 mL) is stirred at 80° C. for 3 days. After cooling to room temperature, to the reaction mixture is added ethyl acetate and water, and the mixture is stirred and extracted with ethyl acetate (×2). The organic layer is treated with 10% HCl to transfer basic materials to the aqueous layer. The aqueous layer is washed with ethyl acetate, neutralized with 10% sodium hydroxide solution and extracted with ethyl acetate (×3). The combined extract is dried over anhydrous sodium sulfate and concentrated in vacuo. The resultant crude product is purified by flash column chromatography on NH-silica gel (Solvent; n-hexane:ethyl acetate=8:1→4:1) to give ethyl 4-[[2-(dimethylamino)ethyl]amino]-benzoate (12.45 g, yield; 44%) as an oil. MS (APCI) m/z: 237 [M+H]⁺

(2) To a solution of the compound obtained in the above step (1) (5 g) and pyridine (10 mL) in methylene chloride (20 mL) is added dropwise acryloyl chloride (2.55 mL) under ice-cooling and the mixture is stirred at room temperature for 3 hours. To the reaction mixture is added successively water and a saturated sodium hydrogencarbonate solution, and the mixture is stirred and extracted with chloroform. The extract is washed with a saturated brine, dried over anhydrous sodium sulfate, and concentrated in vacuo. The resultant crude product is purified by flash column chromatography on silica gel (Solvent; Chloroform:methanol=1:0→50:1) to give ethyl 4-[N-acryloyl-N-[2-(dimethylamino)ethyl]amino]benzoate (1.62 g, yield; 26%) as a red oil.

(3) A mixture of the compound obtained in the above step (2) (1.62 g) and a 50% aqueous dimethylamine solution (5 mL) in acetonitrile (20 mL) is stirred at room temperature for 1.5 hours and the reaction mixture is concentrated in vacuo. The resultant crude product is purified by flash column chromatography on silica gel (Solvent; chloroform: methanol=1:0→50:1→chloroform:methanol:aqueous ammonia=25:1:0.1) to give ethyl 4-[N-[3-(dimethylamino)propionyl]-N-[2-(dimethylamino)ethyl]amino]benzoate (1.78 g, yield; 95%) as a red oil. MS (APCI) m/z; 336 [M+H]⁺

REFERENCE EXAMPLES 2 TO 10

The corresponding materials are treated in the same manner as described in Reference Example 1 to give the compounds as shown in the following Table 28.

TABLE 28

| Ref. Ex. Nos. | R' | R" | Physicochemical properties etc. |
|---|---|---|---|
| 2 | Me₂N-CH₂CH₂- | NEt₂ | oil MS (APCI) 364 [M + H]+ |
| 3 | EtO-CH₂CH₂CH₂- | NMe₂ | oil MS (APCI) 337 [M + H]+ |
| 4 | EtO-CH₂CH₂CH₂- | NEt₂ | oil MS (APCI) 365 [M + H]+ |
| 5 | Ph-CH₂CH₂- | NMe₂ | oil MS (APCI) 355 [M + H]+ |
| 6 | Ph-CH₂CH₂- | NEt₂ | oil MS (APCI) 383 [M + H]+ |
| 7 | Ph-CH₂CH₂- | pyrrolidin-1-yl | oil MS (APCI) 381 [M + H]+ |
| 8 | nPr | NMe₂ | oil MS (APCI) 307 [M + H]+ |
| 9 | nPr | NEt₂ | oil MS (APCI) 335 [M + H]+ |
| 10 | nPr | pyrrolidin-1-yl | oil MS (APCI) 333 [M + H]+ |

Me: methyl group, Et: ethyl group, nPr: n-propyl group, Ph: phenyl group

REFERENCE EXAMPLE 11

To a solution of the compound obtained in Reference Example 1(1) (200 mg) and cyclopropanecarbonyl chloride (115 μL) in methylene chloride (4 mL) is added dropwise pyridine (137 μL) under ice-cooling and the mixture is stirred at room temperature for 23 hours. To the reaction mixture is added successively water and a saturated sodium hydrogencarbonate solution, and the mixture is stirred. The mixture is extracted with chloroform and the extract is concentrated. The resultant crude product is purified by flash column chromatography on NH-silica gel (Hi-Flash column; Yamazen, Solvent; chloroform:methanol=1:0→89:11) to give ethyl 4-[N-(cyclo-propylcarbonyl)-N-[2-(dimethylamino)ethyl]amino]benzoate (209 mg, yield; 81%) as a yellow oil. MS (APCI) m/z: 305 [M+H]$^+$

REFERENCE EXAMPLES 12 TO 26

The corresponding materials are treated in the same manner as described in Reference Example 11 to give the compounds as shown in the following Table 29.

TABLE 29

(No. 1)

| Ref. Ex. Nos. | R | Physicochemical properties etc. |
|---|---|---|
| 12 | ∕∖Me | oil MS (APCI) 293 [M + H]+ |
| 13 | ∕∖∕∖Me | oil MS (APCI) 321 [M + H]+ |
| 14 | ∕∖OMe | oil MS (APCI) 309 [M + H]+ |
| 15 | MeO∕∖∕OMe | oil MS (APCI) 339 [M + H]+ |
| 16 | —Me | oil MS (APCI) 279 [M + H]+ |
| 17 | ∕∖∕Me | oil MS (APCI) 307 [M + H]+ |
| 18 | (Me)(Me)CH— | oil MS (APCI) 307 [M + H]+ |
| 19 | t-Bu— | oil MS (APCI) 321 [M + H]+ |

Me: methyl group, Et: ethyl group, t-Bu: tert-butyl group

TABLE 29

(No. 2)

| Ref. Ex. Nos. | R | Physicochemical properties etc. |
|---|---|---|
| 20 | ∕═\Me | oil MS (APCI) 305 [M + H]+ |
| 21 | ∕O∕C(O)∕Me | oil MS (APCI) 337 [M + H]+ |
| 22 | C(Me)=CHMe | oil MS (APCI) 319 [M + H]+ |
| 23 | 2-thienyl-CH2— | oil MS (APCI) 347 [M + H]+ |
| 24 | 2-furyl-CH2— | amorphous powder MS (APCI) 331 [M + H]+ |
| 25 | ∕∖tBu | oil MS (APCI) 335 [M + H]+ |
| 26 | cyclopentyl-CH2— | oil MS (APCI) 333 [M + H]+ |

Me: methyl group, Et: ethyl group, tBu: tert-butyl group

REFERENCE EXAMPLE 27

A solution of the compound obtained in Reference Example 1(1) (200 mg) and n-butyl isocyanate (143 µL) in methylene chloride (4 mL) is stirred at room temperature for 23 hours. To the reaction mixture is further added n-butyl isocyanate (143 µL) and the mixture is stirred at 50° C. for 17 hours. The reaction mixture is concentrated and the resultant crude product is purified by gel-permeation chromatography (JAI Gel-H column, Solvent; chloroform) to give ethyl 4-[N-(butylcarbamoyl)-N-[2-(dimethylamino)ethyl]amino]benzoate (179 mg, yield; 63%) as a yellow resin. MS (APCI) m/z: 336 [M+H]$^+$

REFERENCE EXAMPLES 28 TO 30

The corresponding materials are treated in the same manner as described in Reference Example 27 to give the compounds as shown in the following Table 30.

TABLE 30

[Structure: Me₂N-CH₂CH₂-N(R)-C₆H₄-CO₂Et]

| Ref. Ex. Nos. | —R | Physicochemical properties etc. |
|---|---|---|
| 28 | C(=S)-NH-Me | oil MS (APCI) 310 [M + H]+ |
| 29 | C(=S)-NH-CH₂CH₂CH₂-Me | oil MS (APCI) 352 [M + H]+ |
| 30 | C(=S)-NH-CH₂-CH(Me)-Me | oil MS (APCI) 352 [M + H]+ |

Me: methyl group, Et: ethyl group

REFERENCE EXAMPLE 31

To a solution of ethyl 4-benzylaminobenzoate (1.5 g) in methylene chloride (15 mL) is added dropwise successively chloroacetyl chloride (0.56 mL) and N,N-diisopropylethylamine (1.54 mL) under ice-cooling, and the mixture is stirred for 1 hour. To the reaction mixture is added diethylamine (3 mL) at the same temperature and the mixture is stirred at room temperature for 12 hours. To the reaction mixture is added water (10 mL) and the organic layer is separated. The aqueous layer is extracted with chloroform (5 mL). The organic layers are combined and concentrated. The resultant crude product is purified by flash column chromatography on NH-silica gel (Solvent; n-hexane:ethyl acetate=6:1→3:1) to give ethyl 4-[N-(N',N'-diethyl-glycyl)-N-benzylamino]benzoate (2.0 g, yield; 92%) as a brown oil. MS (APCI) m/z; 369 [M+H]⁺

REFERENCE EXAMPLES 32 TO 35

The corresponding materials are treated in the same manner as described in Reference Example 31 to give the compounds as shown in the following Table 31.

TABLE 31

[Structure: R''-CH₂-C(=O)-N(R')-C₆H₄-CO₂Et]

| Ref. Ex. Nos. | R' | R'' | Physicochemical properties etc. |
|---|---|---|---|
| 32 | EtO-CH₂CH₂CH₂- | NMe₂ | oil MS (APCI) 323 [M + H]+ |

TABLE 31-continued

[Structure: R''-CH₂-C(=O)-N(R')-C₆H₄-CO₂Et]

| Ref. Ex. Nos. | R' | R'' | Physicochemical properties etc. |
|---|---|---|---|
| 33 | EtO-CH₂CH₂CH₂- | NEt₂ | oil MS (APCI) 351 [M + H]+ |
| 34 | Ph-CH₂CH₂- | NMe₂ | oil MS (APCI) 341 [M + H]+ |
| 35 | Ph-CH₂CH₂- | pyrrolidin-1-yl | oil MS (APCI) 367 [M + H]+ |

Me: methyl group, Et: ethyl group, Ph: phenyl group

REFERENCE EXAMPLE 36

(1) To a solution of methyl 4-formylbenzoate (25 g) in methylene chloride (250 mL) is added successively N,N-dimethylethylenediamine (67 g), acetic acid (87 mL), and sodium triacetoxyborohydride (50.6 g). The mixture is stirred at room temperature overnight. The reaction mixture is concentrated in vacuo and to the residue is added a saturated potassium carbonate solution. The mixture is extracted with ethyl acetate, and the organic layer is dried over anhydrous sodium sulfate and concentrated in vacuo to give methyl 4-[[[2-(dimethylamino)ethyl]amino]methyl]-benzoate (31.9 g, yield; 89%) as a colorless oil. MS (APCI) m/z: 237 [M+H]⁺

(2) To a solution of p-nitrophenyl chloroformate (18.1 g) in methylene chloride (300 mL) is added dropwise 3-(dimethylamino)propanol (14.2 mL) and the mixture is stirred at room temperature for 4 hours. To the mixture is added successively methyl 4-[[[2-(dimethylamino)ethyl]amino]methyl]benzoate (13.7 g) and triethylamine (25 mL) and the mixture is stirred at room temperature for one day. The reaction mixture is washed with a saturated potassium carbonate solution, dried over anhydrous sodium sulfate and concentrated in vacuo. The resultant crude product is purified by flash column chromatography on NH-silica gel (Chromatorex NH silica gel, Solvent; ethyl acetate:n-hexane=1:1) to give methyl 4-[[N-[2-(dimethylamino)ethyl]-N-[[3-(dimethylamino)propoxy]carbonyl]amino]methyl]benzoate (7.97 g, yield; 38%) as a colorless oil. MS (APCI) m/z: 366 [M+H]$^+$

REFERENCE EXAMPLE 37

To a solution of the compound obtained in Reference Example 36(1) (200 mg) in methylene chloride (4 mL) is added propionyl chloride (110 µL) and thereto is added dropwise pyridine (137 µL) under ice-cooling. The mixture is stirred at room temperature for 4 hours. The reaction mixture is diluted with chloroform (5 mL) and thereto is added a saturated sodium hydrogencarbonate solution (10 mL). After stirring, the organic layer is separated and concentrated. The resultant crude product is purified by column chromatography on silica gel (Solvent; chloroform:methanol=100:0→90:10) to give methyl 4-[[N-propionyl-N-[2-(dimethylamino)ethyl]amino]-methyl]benzoate (191 mg, yield; 78%) as an amorphous powder. MS (APCI) m/z: 293 [M+H]$^+$

REFERENCE EXAMPLES 38 TO 42

The corresponding materials are treated in the same manner as described in Reference Example 37 to give the compounds as shown in the following Table 32.

TABLE 32

| Ref. Ex. Nos. | R | Physicochemical properties etc. |
|---|---|---|
| 38 | cyclopropyl | oil<br>MS (APCI) 305 [M + H]+ |
| 39 | propyl (Me) | oil<br>MS (APCI) 321 [M + H]+ |
| 40 | CH2OMe | oil<br>MS (APCI) 309 [M + H]+ |
| 41 | —NMe$_2$ | oil<br>MS (APCI) 308 [M + H]+ |
| 42 | CH2OCH2CH2OMe | oil<br>MS (APCI) 339 [M + H]+ |

Me: methyl group

REFERENCE EXAMPLE 43

To a solution of methyl 4-[[[2-(dimethylamino)ethyl]amino]methyl]benzoate (compound obtained in Reference Example 36(1), 200 mg) in methylene chloride (4 mL) is added n-butyl isocyanate (143 µL) and the mixture is stirred at room temperature for 4 hours. The reaction mixture is diluted with chloroform (5 mL) and thereto is added a saturated sodium hydrogencarbonate solution (10 mL). After stirring, the organic layer is separated and concentrated. The resultant crude product is purified by column chromatography on silica gel (Solvent; chloroform:methanol=100:0→90:10) to give methyl 4-[[N-(butylcarbamoyl)-N-[2-(dimethylamino)ethyl]amino]methyl]-benzoate (261 mg, yield; 92%) as a pale yellow oil. MS (APCI) m/z: 336 [M+H]$^+$

REFERENCE EXAMPLE 44

To a solution of methyl 4-formylbenzoate (300 mg) in 1,2-dichloroethane (6 mL) is added diethylamine (113 µL), and thereto is added sodium triacetoxyborohydride (581 mg) and acetic acid (261 µL) under ice-cooling. The mixture is stirred at room temperature for 18 hours. The reaction mixture is diluted with chloroform (5 mL) and thereto is added a saturated sodium hydrogencarbonate solution (10 mL). After stirring, the organic layer is separated and concentrated. The resultant crude product is purified by column chromatography on NH-silica gel (Solvent; n-hexane:ethyl acetate=70:30→40:60) to give methyl 4-(diethylaminomethyl)benzoate (144 mg, yield; 60%) as an oil. MS (APCI) m/z: 222 [M+H]$^+$

REFERENCE EXAMPLES 45 TO 59

The corresponding materials are treated in the same manner as described in Reference Example 44 to give the compounds as shown in the following Table 33.

TABLE 33

(No. 1)

| Ref. Ex. Nos. | —NRR' | Physicochemical properties etc. |
|---|---|---|
| 45 | Me-N(-CH2CH2CH2-Me) | oil<br>MS (APCI) 236 [M + H]+ |
| 46 | Et-N(-CH2CH2CH2-Me) | oil<br>MS (APCI) 250 [M + H]+ |
| 47 | Me2CH-N(-CH2CH2OMe) | oil<br>MS (APCI) 266 [M + H]+ |

TABLE 33-continued (No. 1)

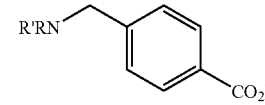

| Ref. Ex. Nos. | —NRR' | Physicochemical properties etc. |
|---|---|---|
| 48 | 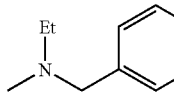 | oil<br>MS (APCI) 284 [M + H]+ |
| 49 | 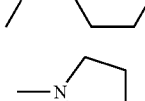 | oil<br>MS (APCI) 262 [M + H]+ |
| 50 | 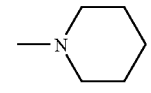 | oil<br>MS (APCI) 220 [M + H]+ |
| 51 | 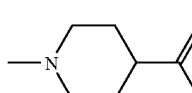 | oil<br>MS (APCI) 234 [M + H]+ |
| 52 | 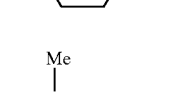 | oil<br>MS (APCI) 277 [M + H]+ |
| 53 |  | oil<br>MS (APCI) 238 [M + H]+ |

Me: methyl group, Et: ethyl group

TABLE 33

(No. 2)

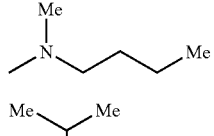

| Ref. Ex. Nos. | —NRR' | Physicochemical properties etc. |
|---|---|---|
| 54 | —NMe$_2$ | oil<br>MS (APCI) 194 [M + H]+ |
| 55 | 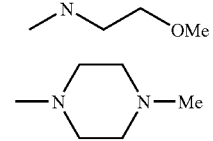 | oil<br>MS (APCI) 236 [M + H]+ |
| 56 | 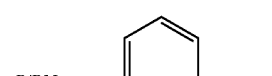 | oil<br>MS (APCI) 266 [M + H]+ |
| 57 | 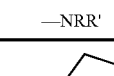 | oil<br>MS (APCI) 249 [M + H]+ |

TABLE 33-continued (No. 2)

| Ref. Ex. Nos. | —NRR' | Physicochemical properties etc. |
|---|---|---|
| 58 | 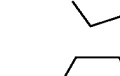 | oil<br>MS (APCI) 220 [M + H]+ |
| 59 | 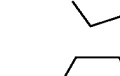 | oil<br>MS (APCI) 234 [M + H]+ |

Me: methyl group

REFERENCE EXAMPLE 60

To a solution of ethyl 4-[[2-(dimethylamino)ethyl]amino]benzoate (compound obtained in Reference example 1(1), 200 mg) in 1,2-dichloroethane (4 mL) is added isobutylaldehyde (384 μL) and thereto is added sodium triacetoxyborohydride (448 mg) and acetic acid (145 μL) under ice-cooling. The mixture is stirred at room temperature for 24 hours. The reaction mixture is diluted with chloroform (5 mL) and thereto is added a saturated sodium hydrogencarbonate solution (10 mL). After stirring, the organic layer is separated and concentrated. The resultant crude product is purified by column chromatography on NH-silica gel (Solvent; n-hexane:ethyl acetate=80:20→50:50) to give ethyl 4-[N-[2-(dimethylamino)ethyl]-N-isobutylamino]benzoate (239 mg, yield; 97%) as a pale yellow oil. MS (APCI) m/z: 293 [M+H]$^+$

REFERENCE EXAMPLES 61 TO 66

The corresponding materials are treated in the same manner as described in Reference Example 60 to give the compounds as shown in the following Table 34.

TABLE 34

| Ref. Ex. Nos. | R' | R'' | Physicochemical properties etc. |
|---|---|---|---|
| 61 | Me$_2$N—CH$_2$CH$_2$—N(Me)—CH$_2$CH$_2$—Me | Et | oil<br>MS (APCI) 279 [M + H]+ |
| 62 | Me$_2$N—CH$_2$CH$_2$—N(Me)—CH$_2$-cyclohexyl | Et | oil<br>MS (APCI) 333 [M + H]+ |

TABLE 34-continued

R'—[benzene ring]—CO₂R''

| Ref. Ex. Nos. | R' | R'' | Physicochemical properties etc. |
|---|---|---|---|
| 63 | Me₂N—CH₂CH₂—N(Et)—CH₂—N(Me)— | Me | oil<br>MS (APCI) 251 [M + H]+ |
| 64 | Me₂N—CH₂CH₂—N(Et)—CH₂CH₂—N(Me)— | Me | oil<br>MS (APCI) 279 [M + H]+ |
| 65 | Me₂N—CH₂CH₂—N(Et)—CH₂CH(Me)—N(Me)— | Me | oil<br>MS (APCI) 293 [M + H]+ |
| 66 | Me₂N—CH₂CH₂—N(Et)—CH₂—(cyclohexyl)—N(Me)— | Me | oil<br>MS (APCI) 333 [M + H]+ |

Me: methyl group, Et: ethyl group

REFERENCE EXAMPLE 67

To a solution of ethyl 4-[[2-(dimethylamino)ethyl]amino] benzoate (compound obtained in Reference Example 1(1), 3.0 g) in methylene chloride (30 mL) is added N-(tert-butoxycarbonyl)glycine (2.89 g) and thereto is added diethyl cyanophosphonate (2.89 mL) under ice-cooling. The mixture is stirred at room temperature for 24 hours. The reaction mixture is diluted with chloroform (20 mL) and thereto is added a saturated sodium hydrogencarbonate solution (50 mL). After, stirring, the organic layer is separated, washed with a saturated brine, dried over anhydrous sodium sulfate and concentrated in vacuo. The resultant crude product is purified successively by column chromatography on silica gel (Solvent; chloroform:methanol:28% aqueous ammonia=100:10:1) and gel-permeation chromatography (Nippon Bunseki Kogyo, Solvent; chloroform) to give ethyl 4-[N-[N'-(tert-butoxycarbonyl)glycyl]-N-[2

REFERENCE EXAMPLE 70 TO 77

The corresponding materials are treated in the same manner as described in Reference Example 69 to give the compounds as shown in the following Table 35.

TABLE 35

R'RN—CH₂—[pyridine]—CO₂Me

| Ref. Ex. Nos. | —NRR' | Physicochemical properties etc. |
|---|---|---|
| 70 | —N(Me)(Et) | oil<br>MS (APCI) 209 [M + H]+ |
| 71 | —NEt₂ | amorphous powder<br>MS (APCI) 223 [M + H]+ |
| 72 | pyrrolidin-1-yl | oil<br>MS (APCI) 221 [M + H]+ |
| 73 | piperidin-1-yl | amorphous powder<br>MS (APCI) 235 [M + H]+ |
| 74 | 4-methylpiperazin-1-yl | amorphous powder<br>MS (APCI) 250 [M + H]+ |
| 75 | Me₂CH—N(Me)—CH₂CH₂—OMe | oil<br>MS (APCI) 267 [M + H]+ |
| 76 | Me₂CH—N(Me)— (N,N-dimethyl isopropyl) | amorphous powder<br>MS (APCI) 223 [M + H]+ |
| 77 | isoindolin-2-yl | amorphous powder<br>MS (APCI) 269 [M + H]+ |

Me: methyl group, Et: ethyl group

REFERENCE EXAMPLE 78

(1) To a solution of ethyl 4-hydroxybenzoate (15.3 g) in N,N-dimethylformamide (150 mL) is added successively 2-dimethylaminoethyl chloride hydrochloride (15.9 g) and potassium carbonate (43.2 g) and the mixture is stirred at 110° C. overnight. To the reaction mixture is added water and the mixture is extracted with ethyl acetate. The organic layer is washed successively with a saturated sodium hydrogencarbonate solution and water, dried over anhydrous sodium sulfate, and concentrated in vacuo. The resultant crude product is purified by flash column chromatography on silica gel (Solvent; chloroform:methanol=10:1) to give ethyl 4-[2-(dimethylamino)ethoxy]benzoate (14.1 g, yield; 65%) as a brown oil. MS (APCI) m/z: 238 [M+H]⁺

(2) To the compound obtained in the above step (1) (14.1 g) is added conc. hydrochloric acid (40 mL) and water (100 mL) and the mixture is refluxed overnight. The reaction mixture is concentrated in vacuo and the resultant crystals is washed with methanol/ether to give 4-[2-(dimethylamino)

ethoxy]benzoic acid hydrochloride (14.1 g, yield; 56%) as a brown powder. MS (APCI) m/z: 210 [M+H]$^+$

REFERENCE EXAMPLE 79

The corresponding materials are treated in the same manner as described in Reference Example 78 to give the compounds as shown in the following Table 36.

TABLE 36

RO—⟨phenyl⟩—CO$_2$H

| Ref. Ex. Nos. | R | Physicochemical properties etc. |
|---|---|---|
| 79 | piperidine-N-CH$_2$CH$_2$- | pale yellow amorphous powder MS (APCI) 250 [M + H] |

Me: methyl group

REFERENCE EXAMPLE 80

(1) Thionyl chloride (1.33 mL) is added dropwise to methanol (30 mL) under ice-cooling and the solution is stirred for 10 minutes. To the solution is added 4-hydroxycinnamic acid (3.0 g) and the mixture is stirred at room temperature for 4 days. The reaction mixture is concentrated and the residue is diluted with ethyl acetate (50 mL), washed successively with a saturated sodium hydrogencarbonate solution and saturated brine, dried over anhydrous sodium sulfate, and concentrated in vacuo. The residue is re-crystallized from ethyl acetate/n-hexane to methyl 4-hydroxycinnamate (2.86 g, yield; 88%) as pale yellow crystals.

M.p. 136.5-137° C.

(2) To a solution of the compound obtained in the above step (1) (1.53 g) in N,N-dimethylformamide (25 mL) is added successively 3-chloropropyldimethylamine hydrochloride (1.69 g), potassium carbonate (3.12 g), and tetrabutylammonium iodide (105 mg). The mixture is stirred at 80° C. for 17 hours. After cooling, to the reaction mixture is added water (100 mL) and the mixture is extracted with ethyl acetate (150 mL×2). The organic layer is separated, washed successively with water (150 mL, ×2) and saturated brine, dried over anhydrous sodium sulfate, and concentrated in vacuo to give methyl trans-3-[4-[3-(dimethylamino)propyloxy]phenyl]acrylate (2.07 g, yield; 92%) as a pale yellow oil. MS (APCI) m/z: 264 [M+H]$^+$ (3) To a solution of the compound obtained in the above step (2) (2.07 g) in methanol (15 mL) is added 1N sodium hydroxide solution (15 mL) and the mixture is stirred at room temperature for 15 hours. The reaction mixture is concentrated and the residue is neutralized (pH 7) with 1N HCl and thereto is added methanol. The mixture is stirred and the precipitated crystals are collected to give trans-3-[4-[3-(dimethylamino)propyloxy]phenyl]acrylic acid (1.93 g, yield; 98%) as colorless crystals. M.p. 191-193° C.

REFERENCE EXAMPLE 81

(1) To a solution of methyl 4-(aminomethyl)benzoate (5.08 g) in methylene chloride (30 mL) is added di-tert-butyl dicarbonate (6.4 g) under ice-cooling and the mixture is stirred at room temperature for 24 hours. The reaction mixture is diluted with methylene chloride (20 mL) and thereto is added water (40 mL). After stirring, the organic layer is separated and concentrated to give methyl 4-[N-(tert-butoxy-carbonyl)aminomethyl]benzoate.

(2) To a solution of the compound obtained in the above step (1) (1.5 g) in tetrahydrofuran (15 mL) and thereto is added sodium hydride (60% dispersion in mineral oil, 407 mg) under ice-cooling. The mixture is stirred at room temperature for 30 minutes. To the reaction mixture is added dropwise ethyl iodide (2.26 mL) under ice-cooling and the mixture is stirred at 60° C. for 1 hour. After cooling to room temperature, the reaction mixture is diluted with ethyl acetate (10 mL) and thereto is added water. After standing, the organic layer is separated and concentrated. The resultant product is purified by flash column chromatography on NH-silica gel (Solvent; n-hexane:ethyl acetate=20:1) to give methyl 4-[[N-ethyl-N-(tert-butoxycarbonyl)]-aminomethyl]benzoate (929 mg, yield; 56%) as an amorphous powder. MS (APCI) m/z: 294 [M+H]$^+$

REFERENCE EXAMPLE 82

(1) To a solution of 4-hydroxybenzaldehyde (610 mg) in N,N-dimethylformamide (20 mL) is added successively 2-dimethylaminoethyl chloride hydrochloride (1.08 g) and potassium carbonate (2.0 g), and the mixture is stirred at room temperature for 18 hours. To the reaction mixture is added ethyl acetate, and the mixture is washed with water and saturated brine and dried over anhydrous sodium sulfate. The resultant crude product is purified by column chromatography in silica gel (Solvent; chloroform:methanol=20:1→10:1) to give 4-[2-(dimethylamino)-ethoxy]benzaldehyde (640 mg, yield; 66%) as a pale yellow oil. MS (APCI) m/z: 194 [M+H]$^+$ (2) To a solution of tert-butyl dimethylphosphonoacetate (807 mg) in tetrahydrofuran (20 mL) is added sodium hydride (60% dispersion in mineral oil, 144 mg) under ice-cooling and the mixture is stirred for 30 minutes. To the reaction mixture is added a solution of the compound obtained in the above step (1) (580 mg) in tetrahydrofuran (10 mL) and the mixture is stirred at room temperature for 1 hour. To the reaction mixture is added ice-water. The mixture is extracted with ethyl acetate and the organic layer is washed with saturated brine and dried over anhydrous sodium sulfate. The resultant crude product is purified by column chromatography on silica gel (Solvent; chloroform:methanol=20:1) to give tert-butyl trans-3-[4-[2-(dimethylamino)ethoxy]phenyl]acrylate (920 mg, yield; quantitative) as colorless crystals. MS (APCI) m/z: 292 [M+H]$^+$ (3) A solution of the compound obtained in the above step (2) (880 mg) in 4N HCl-dioxane (10 mL) is stirred at room temperature for 6 hours. The reaction mixture is diluted with diethylether, and the precipitated crystals are collected by filtration and washed with diethylether to give trans-3-[4-[2-(dimethylamino)ethoxy]phenyl]acrylic acid hydrochloride (750 mg, yield; 91%) as colorless crystals. MS (APCI) m/z: 236 [M+H]$^+$

REFERENCE EXAMPLE 83

(1) Thionyl chloride (8.7 mL) is added dropwise to methanol (90 mL) at −30° C. under argon gas atmosphere over a period of 15 minutes and a mixture is stirred at −20° C. for 30 minutes. To the mixture is added 3-amino-4-methoxybenzoic acid (5.0 g) and the solution is stirred at the same temperature for 15 minutes and at room temperature for 3 days. The reaction mixture is concentrated in vacuo and the resultant crystals are washed with methanol/ether to give methyl 3-amino-4-methoxybenzoate hydrochloride (6.25 g, yield; 96%) as colorless crystals. M.p. 213-215° C., MS (APCI) m/z: 182 [M+H]+

(2) To a suspension of the compound obtained in the above step (1) (1.08 g) in tetrahydrofuran (10 mL) is added pyridine (2.4 mL) and methanesulfonyl chloride (0.56 mL) and the mixture is stirred at room temperature for 30 minutes. To the reaction mixture is added water and the mixture is stirred. The mixture is extracted with ethyl acetate. The extract is treated by column chromatography on diatomite and concentrated in vacuo. The resultant residue is recrystallized from ether/hexane to give methyl 3-methanesulfonylamino-4-methoxybenzoate (1.08 g, yield; 69%) as crystals. MS (APCI) m/z: 258 [M+H]+

(3) A solution of the compound obtained in the above step (2) (260 mg), potassium carbonate (222 mg), and 2-chloroethyldiethylamine hydrochloride (414 mg) in dimethylsulfoxide (2 mL) is vigorously stirred. To the reaction mixture is added water. After stirring, the mixture is extracted with ethyl acetate. The extract is washed with saturated brine, filtered through NH-silica gel column and concentrated in vacuo. The resultant residue is purified by flash column chromatography on NH-silica gel (HI-flash column, Solvent; chloroform:methanol=1:0→95:5) and treated with HCl/ethyl acetate to 3-[N-[2-(diethylamino)ethyl]-N-(methanesulfonyl)amino]-4-methoxybenzoate hydrochloride (228 mg, yield; 93%) as colorless resin. MS (APCI) m/z: 359 [M+H]+

REFERENCE EXAMPLE 84

(1) To a solution of vanilin (76.1 g) in N,N-dimethylformamide (500 mL) is added successively 4-(2-chloroethyl) morpholine hydrochloride (130 g), sodium iodide (7.5 g), and potassium carbonate (207 g). The mixture is stirred at 80° C. for 15 hours. The reaction mixture is concentrated in vacuo. The residue is diluted with ethyl acetate, washed with saturated brine, dried over anhydrous sodium sulfate, and concentrated in vacuo. To the residue is added diisopropyl ether and the resultant crystals are collected by filtration to give 3-methoxy-4-(2-morpholinoethoxy)-benzaldehyde (112.6 g, yield; 85%) as orange crystals. MS (APCI) m/z: 266 [M+H]+

(2) To a solution of triethyl phosphonoacetate (37.0 g) in tetrahydrofuran (150 mL) is added sodium hydride (60% dispersion in mineral oil, 6.4 g) with ice cooling and the mixture is stirred for 0.5 hour. To the mixture is added dropwise a solution of the compound obtained in the above step (1) (40.0 g) in tetrahydrofuan (140 mL) under ice-cooling and the mixture stirred at the same temperature for 2 hours. The reaction mixture is diluted with ethyl acetate (500 mL), washed with saturated brine, dried over anhydrous sodium sulfate, and concentrated in vacuo. To the precipitated product is added diisopropyl ether and the resultant crystals are collected by filtration to give ethyl trans-3-[3-methoxy-4-(2-morpholinoethoxy)phenyl]acrylate (46.2 g, yield; 91%) as orange crystals. MS (APCI) m/z: 336 [M+H]+

(3) To a solution of the compound obtained in the above step (2) (43.3 g) in methanol (250 mL) is added 2N sodium hydroxide solution (100 mL) and the mixture is stirred at room temperature overnight. The reaction mixture is concentrated in vacuo and neutralized. The precipitated crystals are collected by filtration and dissolved in ethanol. The insoluble materials are removed by filtration and the resultant crystals are recrystallized to give trans-3-[3-methoxy-4-(2-morpholinoethoxy)phenyl]acrylic acid (34.8 g, yield; 88%) as yellow crystals. MS (APCI) m/z: 308 [M+H]+

REFERENCE EXAMPLE 85

(1) To methanol (1500 mL) is added dropwise thionyl chloride (254 mL) at −30° C. over a period of one hour and the mixture is stirred at room temperature for 0.5 hour. To the mixture is added trans-cyclohexane-1,4-dicarboxylic acid (500.0 g) and the mixture is stirred at room temperature for 17 hours. The reaction mixture is concentrated in vacuo and the residue is diluted with chloroform, washed with a saturated sodium hydrogencarbonate solution and saturated brine, dried over anhydrous sodium sulfate and concentrated in vacuo. The residue is crystallized from n-hexane, collected by filtration, and dried to give dimethyl trans-cyclohexane-1,4-dicarboxylate (545.0 g). MS (APCI) m/z: 201 [M+H]+

(2) To a solution of the compound obtained in the above step (1) (150.0 g) in tetrahydrofuran (1500 mL) is added dropwise a mixture of a solution of 28% sodium methoxide-methanol (149 g) and water (13.2 g) under ice-cooling. The mixture is stirred at room temperature for 3.5 hours and thereto is added n-hexane (150 mL). The resultant precipitate is collected by filtration and added to a mixture of conc hydrochloric acid (50 mL), water (450 mL) and chloroform (1000 mL). The mixture is stirred at room temperature for 20 minutes. The chloroform layer is separated and the aqueous layer is extracted with chloroform. The organic layers are combined, dried over anhydrous sodium sulfate, and concentrated in vacuo. The residue is crystallized from n-hexane, collected by filtration, and dried to give mono-methyl trans-cyclohexane-1,4-dicarboxylate (106.0 g). MS (ESI) m/z: 185 [M−H]−

(3) To a solution of the compound obtained in the above step (2) (100.0 g) in tert-butanol (1000 mL) is added diphenylphosphoryl azide (155 g) and triethylamine (78.6 mL). The mixture is stirred at 60° C. for 1 hour and refluxed under heating for 17 hours. After cooling, ice-cooled water is poured into the reaction mixture and the mixture is extracted with ethyl acetate. The organic layer is washed with a saturated sodium hydrogencarbonate solution and saturated brine, dried over anhydrous sodium sulfate, and concentrated in vacuo. The residue is dissolved in methanol (250 mL) and thereto is added water (750 mL). The mixture is stirred for 0.5 hour under ice-cooling. The resultant precipitate is collected by filtration, washed with water/methanol (3:1, 1000 mL) and n-hexane, and dried over anhydrous sodium sulfate to give methyl trans-4-(tert-butoxycarbonylamino)cyclohexanecarboxylate (117.0 g). MS (APCI) m/z: 275 [M+NH$_4$]+

REFERENCE EXAMPLE 86

(1) To a solution of the compound obtained in Reference Example 85 (234.0 g) in dioxane (500 mL) is added 4N HCl-dioxane (500 mL) and the mixture is stirred at room temperature for 19 hours. The reaction mixture is concentrated in vacuo and the residue is suspended in diethyl ether. The precipitate is collected by filtration to give methyl trans-4-aminocyclohexanecarboxylate hydrochloride (121.9 g). MS (APCI) m/z: 158 [M+H]+

(2) To a solution of the compound obtained in the above step (1) (93.0 g) in methanol (1000 mL) is added 35% formaldehyde solution (95.4 mL), sodium acetate (39.4 g) and 10% palladium-carbon (10 g) and the mixture is stirred at room temperature under atmospheric pressure of hydrogen for 3.5 hours. The insoluble materials are removed through Celite and the filtrate is concentrated in vacuo. To the residue is added 20% potassium carbonate solution (500 mL) and the mixture is extracted with chloroform. The organic layer is dried over anhydrous sodium sulfate and potassium carbonate, and concentrated in vacuo. The residue is purified by column chromatography on NH-silica gel (Solvent; n-hexane:ethyl acetate=2:1) to give methyl trans-4-(dimethylamino)cyclohexanecarboxylate (87.3 g). MS (APCI) m/z: 186 [M+H]$^+$ (3) To a solution of the compound obtained in the above step (2) (27.6 g) in dioxane (300 mL) and water (100 mL) is added 6N HCl (50 mL) and the mixture is refluxed under heating for 4 hours. To the reaction mixture is added 6N HCl (50 mL) and the mixture is further refluxed for 1 hour. The reaction mixture is concentrated in vacuo and the residue is subjected to azeotropic distillation with toluene. The residue is suspended in diisopropyl ether and the resultant precipitate is collected by filtration, washed with diisopropyl ether, and dried to give trans-4-(dimethylamino)cyclohexanecarboxylic acid (27.5 g). MS (APCI) m/z: 172 [M+H]$^+$

REFERENCE EXAMPLE 87

(1) A suspension of the compound obtained in Reference Example 86(1) (10 g), 1,4-diiodobuthane (19.2 g), and sodium carbonate (16.4 g) in tetrahydrofuran (300 mL) and N,N-dimethylacetamide (60 mL) is stirred at 70° C. for 20 hours. The reaction mixture is concentrated in vacuo and the residue is dissolved in ethyl acetate/water. The organic layer is separated, washed with water and saturated brine, dried over anhydrous sodium sulfate, and concentrated in vacuo. The residue is purified by column chromatography on NH-silica gel (Solvent; ethyl acetate:n-hexane=1:5) to give methyl trans-4-(1-pyrrolidinyl)cyclohexanecarboxylate (10.9 g). MS (APCI) m/z: 212 [M+H]$^+$ (2) To a solution of the compound obtained in the above step (1) (10.9 g) in dioxane (150 mL) is added 2N aqueous HCl (80 mL) and the mixture is stirred at 110° C. for 3 hours while evaporating to remove methanol. The reaction mixture is concentrated in vacuo. The residue is triturated with diethyl ether and collected by filtration to give trans-4-(1-pyrrolidinyl)cyclohexanecarboxylic acid hydrochloride (11.1 g). MS (APCI) m/z: 198 [M+H]$^+$

REFERENCE EXAMPLE 88

(1) A suspension of the compound obtained in Reference Example 86(1) (47.5 g), bis(2-chloroethyl) ether (34.5 mL), sodium carbonate (77.9 g), and sodium iodide (88 g) in tetrahydrofuran (1400 mL) and N,N-dimethylacetamide (280 mL) is refluxed for 18 hours. To the reaction mixture is added bis(2-chloroethyl)ether (23 mL) and sodium iodide (22 g) and the mixture is refluxed for 6 hours. The reaction mixture is concentrated in vacuo and the residue is dissolved in ethyl acetate/water. The organic layer is separated, washed with water and saturated brine, dried over anhydrous sodium sulfate, and concentrated in vacuo. The residue is purified by column chromatography on NH-silica gel (Solvent; ethyl acetate:n-hexane=1:30→1:5→1:3) to give methyl trans-4-morpholinocyclohexanecarboxylate (53.9 g). MS (APCI) m/z: 228 [M+H]$^+$ (2) To a solution of the compound obtained in the above step (1) (53.8 g) in dioxane (750 mL) is added 2N aqueous HCl (400 mL) and the mixture is stirred at 110° C. for 4 hours while evaporating to remove methanol. The reaction mixture is concentrated in vacuo. The residue is suspended in diethyl ether and collected by filtration to give trans-4-morpholinocyclohexanecarboxylic acid hydrochloride (54.8 g). MS (APCI) m/z: 214 [M+H]$^+$

REFERENCE EXAMPLE 89

(1) To a suspension of trans-4-(aminomethyl)cyclohexanecarboxylic acid (6.29 g) in methanol (32 mL) is added dropwise thionyl chloride (6 mL) under ice-cooling and the mixture is stirred at room temperature overnight. The reaction mixture is concentrated in vacuo to give methyl trans-4-(aminomethyl)cyclohexanecarboxylate hydrochloride (8.69 g). MS (APCI) m/z: 172 [M+H]$^+$ (2) To a suspension of the compound obtained in the above step (1) (8.69 g) in dichloromethane (400 mL) is added triethylamine (11.2 mL). After stirring at room temperature for a few minutes, to the reaction mixture is added 35% formaldehyde solution (15.9 mL) and sodium triacetoxyborohydride (25.43 g), and then the mixture is stirred at room temperature for 2 hours. To the reaction mixture is added a saturated sodium hydrogencarbonate solution and the mixture is extracted with chloroform. The organic layer is washed with water and saturated brine, dried over anhydrous sodium sulfate, and concentrated in vacuo to give methyl trans-4-(dimethylaminomethyl)-cyclohexanecarboxylate (7.42 g). MS (APCI) m/z: 200 [M+H]$^+$ (3) To a solution of the compound obtained in the above step (2) (7.41 g) in dioxane (140 mL) is added 2N aqueous HCl (70 mL), and the mixture is refluxed under heating for 3 hours. After cooling, the reaction mixture is concentrated in vacuo. The residue is subjected to azeotropic distillation with toluene and dried to give trans-4-(dimethylaminomethyl)cyclohexanecarboxylic acid hydrochloride (8.45 g) as an amorphous powder. MS (APCI) m/z: 186 [M+H]$^+$

REFERENCE EXAMPLE 90

(1) To a suspension of sodium hydride (60% dispersion in mineral oil, 33.6 g) in tetrahydrofuran (600 mL) is added dropwise a solution of triethyl phosphonoacetate (188.4 g) in tetrahydrofuran (100 mL) under ice-cooling. The mixture is stirred at the same temperature for 0.5 hour and thereto is added dropwise a solution of pyridine 4-carboxaldehyde (75.00 g) in tetrahydrofuran (100 mL). The mixture is stirred for 1 hour. To the reaction mixture is added ice water (1000 mL) and the mixture is extracted with ethyl acetate. The organic layer is washed with water, a saturated sodium hydrogencarbonate solution and saturated brine, dried over anhydrous sodium sulfate and concentrated in vacuo. The residue is suspended in a small amount of diisopropyl ether under ice-cooling. The resultant precipitates are collected by filtration, washed with diisopropylether, and n-hexane and dried to give ethyl 3-(4-pyridyl)acrylate (77.53 g). MS (APCI) m/z: 178 [M+H]$^+$ (2) To a solution of the compound obtained in the above step (1) (28.00 g) in acetic acid (280 mL) is added platinum oxide (1.80 g), and the mixture is stirred at room temperature under hydrogen gas atmosphere for 24 hours. The reaction mixture is filtered to remove insoluble materials and the filtrate is concentrated in vacuo. The resultant residue is dissolved in dioxane (200 mL) and thereto is added 4N HCl-dioxane (200 mL). The mixture is concentrated in vacuo and the residue is suspended in diethyl ether/diisopropylether. The resultant precipitates are collected by filtration, washed with diisopropylether, and dried to give ethyl 3-(4-piperidyl)propionate hydrochloride (33.50 g). MS (APCI) m/z: 186 [M+H]$^+$

REFERENCE EXAMPLE 91

To a solution of ethyl (4-pyridyl)acetate (50.00 g) in acetic acid (500 mL) is added platinum oxide (3.44 g), and the mixture is shaken at room temperature under hydrogen gas atmosphere for 20 hours. The reaction mixture is filtered to remove insoluble materials and the filtrate is concentrated in vacuo. The resultant residue is dissolved in dioxane (200 mL) and thereto is added 4N HCl-dioxane (400 mL). The mixture is concentrated in vacuo and the residue is suspended in diethyl ether/diisopropylether. The resultant precipitate is collected by filtration, washed with diisopropylether and dried to give ethyl (4-piperidyl)acetate hydrochloride (61.80 g). MS (APCI) m/z: 172 [M+H]$^+$

REFERENCE EXAMPLE 92

(1) To a solution of the compound obtained in Reference Example 90 (70.83 g) in ethanol (700 mL) is added 2-iodopropane (38.2 mL) and potassium carbonate (132.3 g), and the mixture is refluxed under heating for 6 hours. The reaction mixture is filtered to remove insoluble materials and the filtrate is concentrated in vacuo. The residue is diluted with ethyl acetate (800 mL), washed with water and saturated brine, dried over anhydrous sodium sulfate, and concentrated in vacuo. The residue is purified by column chromatography on NH-silica gel (Solvent; n-hexane:ethyl acetate=20:1→9:1) to give ethyl 3-(1-isopropylpiperidin-4-yl)propionate (57.13 g). MS (APCI) m/z: 228 [M+H]$^+$ (2) To a solution of the compound obtained in the above step (1) (57.12 g) in dioxane (1200 mL) is added 2N HCl (600 mL) and the mixture is refluxed under heating for 3 hours. The reaction mixture is concentrated in vacuo and subjected to azeotropic distillation with dioxane. The resultant residue is triturated with diethyl ether/diisopropylether (1:1, 500 mL). The precipitates are collected by filtration, washed with diisopropylether and dried to give 3-(isopropylpiperidin-4-yl)propionic acid hydrochloride (55.36 g). MS (APCI) m/z: 200 [M+H]$^+$

REFERENCE EXAMPLES 93 TO 94

The corresponding materials are treated in the same manner as described in Reference Example 92(1) and (2) to give the compounds as shown in the following Table 37.

TABLE 37

| Ref. Ex. Nos. | —Y—COO—R' | Physicochemical properties etc. |
|---|---|---|
| 93 | | |
| (1) | —CH$_2$COOC$_2$H$_5$ | MS (APCI) 214 [M + H]+ |
| (2) | —CH$_2$COOH | hydrochloride MS (APCI) 200 [M + H]+ |
| 94 | | |
| (1) | —COOC$_2$H$_5$ | MS (APCI) 186 [M + H]+ |
| (2) | —COOH | hydrochloride MS (APCI) 172 [M + H]+ |

REFERENCE EXAMPLE 95

(1) A suspension of the compound obtained in Reference Example 91 (5.00 g), 4-chloropyridine hydrochloride (3.62 g), and triethylamine (10.01 mL) in xylene (130 mL) is refluxed under heating for 20 hours. After cooling, the reaction mixture is filtered to remove insoluble materials and the filtrate is concentrated in vacuo. The residue is diluted with chloroform, washed with water, dried over anhydrous sodium sulfate, and concentrated in vacuo. The residue is purified by column chromatography on NH-silica gel (Solvent; chloroform:ethyl acetate=4:1) to give ethyl [1-(4-pyridyl)piperidin-4-yl]acetate (4.15 g). MS (APCI) m/z: 249 [M+H]$^+$ (2) To a solution of the compound obtained in the above step (1) (4.15 g) in dioxane (200 mL) is added 1N aqueous HCl (70 mL), and the mixture is refluxed under heating for 4 hours. The reaction mixture is concentrated in vacuo and the residue is lyophilized to give [1-(4-pyridyl)piperidin-4-yl]acetic acid hydrochloride (3.90 g). MS (APCI) m/z: 221 [M+H]$^+$

REFERENCE EXAMPLE 96

(1) A mixture of ethyl isonipecotate (1.57 g), propionaldehyde (1.0 g), and 10% palladium-carbon (500 mg) in methanol (20 mL) is vigorously stirred at room temperature under hydrogen gas atmosphere for 2 hours. After substituting the argon gas for hydrogen, the palladium-carbon is collected by filtration and washed with methanol (100 mL). The washing and the filtrate are combined and concentrated in vacuo. The residue is dissolved in ethanol (20 mL) and thereto is added 4N HCl-dioxane (20 mL). The mixture is concentrated in vacuo and the residue is crystallized from ethanol/ether to give ethyl 1-propylpiperidin-4-carboxylate hydrochloride (1.81 g, yield; 77%) as colorless crystals. M.p. 114-117° C.

(2) A mixture of the compound obtained in the above step (1) (1.79 g) and conc. hydrochloric acid (20 mL) is refluxed under heating for 2 hours. After cooling, the reaction mixture is concentrated in vacuo and ether is added to the residue. The mixture is stirred and the supernatant is separated. The ether layer of the supernatant is removed and the residue is crystallized from ethanol/ether to give 1-propylpiperidin-4-carboxylic acid hydrochloride (1.11 g, yield; 70%) as colorless crystals. M.p. 222-224° C.

REFERENCE EXAMPLE 97

To a solution of 4-[[2-(dimethylamino)ethyl]amino]benzaldehyde (300 mg) in methylene chloride (4 mL) is added 2-methoxyethyl chloroformate (234 μL) and thereto is added dropwise pyridine (252 μL) under ice-cooling. The mixture is stirred at 50° C. for 2 days. The reaction mixture is diluted with chloroform (5 mL) and thereto is added a saturated sodium hydrogencarbonate solution (10 mL). After stirring, the organic layer is separated and concentrated. The residue is purified by column chromatography on silica gel (Solvent; chloroform:methanol=100:0→90:10) to give 4-[N-[(2-methoxyethoxy)carbonyl]-N-[2-(dimethylamino)ethyl]amino]benzaldehyde (290 mg, yield; 63%) as an amorphous powder. MS (APCI) m/z: 294 [M+H]$^+$

REFERENCE EXAMPLE 98

A solution of mono-methyl terephthaloyl chloride (500 mg), N,N-dimethylethylenediamine (178 mg) and diisoprpylethylamine (650 mg) in methylene chloride (5.0 mL) is stirred at room temperature overnight. The reaction mixture is diluted with ethyl acetate and thereto is added a saturated sodium hydrogencarbonate solution. After stirring, the organic layer is separated and concentrated in vacuo. The residue is purified by flash column chromatography on NH-silica gel (Solvent; n-hexane:ethyl acetate=9:1) to give methyl 4-[[[2-(dimethylamino)-ethyl]amino]carbonyl]benzoate (355 mg, yield; 70%) as yellow crystals. MS (APCI) m/z: 251 [M+H]$^+$

REFERENCE EXAMPLE 99

Under argon gas atmosphere, lithium aluminum hydride (1.19 g) is suspended in tetrahydrofuran (50 mL) and thereto is added dropwise a solution of ethyl (1-isopropylpiperidin-4-yl)acetate (compound obtained in Reference Example 93(1), 6.43 g) in tetrahydrofuran (50 mL) over a period of 15 minutes under ice-cooling. The mixture is stirred at room temperature for 1.5 hours. To the reaction mixture is added successively water (1.2 mL), 2N sodium hydroxide solution (2.4 mL), and water (2.4 mL) under ice-cooling. The mixture is stirred at room temperature for 2 hours. After addition of magnesium sulfate, the reaction mixture is stirred for 10 minutes and filtered. The filtrate is concentrated in vacuo and the residue is purified by flash column chromatography on NH-silica gel (Solvent; n-hexane:ethyl acetate=1:1) to give 2-(1-isopropylpiperidin-4-yl)ethanol (5.09 g, yield; 99%) as a colorless oil. MS (APCI) m/z: 172 [M+H]$^+$

REFERENCE EXAMPLE 100

Under argon gas atmosphere, lithium aluminum hydride (3.29 g) is suspended in tetrahydrofuran (160 mL) and thereto is added ethyl 1-isopropylpiperidin-4-carboxylate (compound obtained in Reference Example 94(1), 5.00 g) under ice-cooling. The mixture is stirred at room temperature for 14 hours. To the reaction mixture is added successively water (3.3 mL), 2N sodium hydroxide solution (6.6 mL) and water (6.6 mL) under ice-cooling. The mixture is stirred at room temperature for 1 hour. After addition of magnesium sulfate, the reaction mixture is stirred for 10 minutes and filtered. The filtrate is concentrated in vacuo and the residue is purified by flash column chromatography on NH-silica gel (Solvent; n-hexane:ethyl acetate=1:1) to give (1-isopropylpiperidin-4-yl)methanol (3.75 g, yield; 99%) as a colorless oil. MS (APCI) m/z: 158 [M+H]$^+$

REFERENCE EXAMPLE 101

To a solution of 1-methyl-2-imidazolecarboxaldehyde (10 g) in a mixture of ethanol (80 mL) and tatrahydrofuran (80 mL) is added sodium borohydride (4.2 g) under ice-cooling and the mixture is stirred at room temperature for 2 hours. The reaction mixture is concentrated in vacuo and the residue is dissolved in chloroform, washed with a saturated sodium hydrogencarbonate solution, dried over anhydrous sodium sulfate, and concentrated in vacuo. To the residue is added diisopropylether and the resultant crystals are collected by filtration to give (1-methyl-1H-imidazole-2-yl) methanol (9.9 g, yield; 98%) as colorless crystals. MS (APCI) m/z: 113 [M+H]$^+$

REFERENCE EXAMPLE 102

(1) To a solution of methyl 4-[[(tert-butoxycarbonyl) amino]methyl]benzoate (compound obtained in Reference Example 81(1), 2.0 g) in tetrahydrofuran (20 mL) is added sodium hydride (60% dispersion in mineral oil, 0.9 g) under ice-cooling. The mixture is stirred at room temperature for 30 minutes and then to the reaction mixture is added dropwise methyl iodide (2.3 mL). The mixture is stirred at room temperature for 3 hours. The reaction mixture is diluted with ethyl acetate, washed with water, and concentrated in vacuo to give methyl 4-[[N-methyl-N-(tert-butoxycarbonyl)amino]-methyl]benzoate (1.9 g, yield; 94%) as a yellow oil. MS (APCI) m/z: 280 [M+H]$^+$ (2) To a solution of the compound obtained in the above step (1) (1.5 g) in methanol (5.0 mL) is added 4N HCl-dioxane (10.0 mL) and the mixture is stirred at room temperature for 1 hour. The reaction mixture is diluted with ether and the precipitated crystals are collected by filtration to give methyl 4-[(methylamino)-methyl]benzoate (0.89 g, yield; 78%) as colorless crystals. MS (APCI) m/z: 180 [M+H]$^+$ (3) A suspension of the compound obtained in the above step (2) (100 mg), 2-(diethylamino)ethyl chloride hydrochloride (160 mg), and potassium carbonate (260 mg) in N,N-dimethylformamide (3.0 mL) is stirred at 80° C. for 3 hours. The reaction mixture is diluted with water and extracted with ethyl acetate. The extract is concentrated in vacuo and the residue is purified by column chromatography on silica gel (Solvent; chloroform:methanol=10:1) to give methyl 4-[[N-methyl-N-[[2-(diethylamino)ethoxy]carbonyl]amino]methyl]benzoate (94 mg, yield; 64%) as a yellow oil. MS (APCI) m/z: 323 [M+H]$^+$

REFERENCE EXAMPLE 103

(1) To a solution of methyl 5-aminofuran-2-carboxylate (1.0 g) and pyridine (1.2 mL) in methylene chloride (6.0 mL) is added dropwise cyclopropanecarbonyl chloride (0.78 mL) under ice-cooling and the mixture is stirred at room temperature for 2 hours. To the reaction mixture is added a saturated sodium hydrogencarbonate solution and the mixture is extracted with chloroform. The extract is dried over anhydrous sodium sulfate and concentrated in vacuo. The residue is purified by column chromatography on silica gel (Solvent; n-hexane:ethyl acetate=3:1) to give methyl 5-[(cyclopropylcarbonyl)amino]furan-2-carboxylate (0.82 g, yield; 56%) as colorless crystals. MS (APCI) m/z: 210 [M+H]$^+$ (2) A suspension of the compound obtained in the above step (1) (200 mg), 2-(dimethylamino)ethyl chloride hydrochloride (275 mg) and potassium carbonate (530 mg) in N,N-dimethylformamide (3.0 mL) is stirred at 80° C. for 3 hours. The reaction mixture is diluted with water and extracted with ethyl acetate. The extract is concentrated in vacuo and the residue is purified by column chromatography on silica gel (Solvent; chloroform:methanol=10:1) to give methyl 5-[N-(cyclopropyl-carbonyl)-N-[2-(dimethylamino) ethyl]amino]furan-2-carboxylate (196 mg, yield; 73%) as a colorless oil. MS (APCI) m/z: 281 [M+H]$^+$

REFERENCE EXAMPLE 104

(1) To a solution of 2-nitorthiophen-4-carboxylic acid (10 g) in ethanol (50 mL) is added thionyl chloride (5.0 mL) under ice-cooling and the mixture is stirred at room temperature overnight. The reaction mixture is concentrated in vacuo and to the residue is added a saturated sodium hydrogencarbonate solution. The mixture is extracted with ethyl acetate and the extract is dried over anhydrous sodium sulfate and concentrated in vacuo. To the residue is added iron powder (16 g), ammonium chloride (16 g), ethanol (100 mL) and water (100 mL) and the mixture is refluxed under heating for 2 hours. The reaction mixture is diluted with ethyl acetate and filtered to remove insoluble materials. The filtrate is washed with a saturated sodium hydrogencarbonate solution and saturated brine, dried over anhydrous sodium sulfate and concentrated in vacuo to give ethyl 5-aminothiophen-3-carboxylate (6.34 g, yield; 65%) as a brown oil. MS (APCI) m/z: 172 [M+H]$^+$ (2) A solution of the compound obtained in the above step (1) (5.62 g), di-tert-butyl dicarbonate (15.8 g), pyridine (6.4 mL), and 4-(dimethylamino)pyridine (0.4 g) in methylene chloride (50 mL) is stirred at room temperature for 3 hours. The reaction mixture is washed with water, dried over anhydrous sodium sulfate, and concentrated in vacuo. To the residue is added cesium carbonate (22 g) and ethanol (50 mL), and the mixture is stirred at 80° C. overnight. The reaction mixture is filtered to remove insoluble materials and the filtrate is diluted with water. The resultant crystals are collected by filtration to give ethyl 5-[(tert-butoxycarbonyl)amino]thiophen-3-carboxylate (6.07 g, yield; 68%) as brown crystals. MS (APCI) m/z: 272 [M+H]$^+$ (3) A suspension of the compound obtained in the above step (2) (1.5 g), 2-(dimethylamino)ethyl chloride hydrochloride (1.5 g), and potassium carbonate (3.0 g) in N,N-dimethylfromamide (15 mL) is stirred at 80° C. for 3 hours. The reaction mixture is diluted with water and extracted with ethyl acetate. The extract is concentrated in vacuo and the residue is purified by column chromatography on silica gel (Solvent; chloroform:methanol=50:1) to give ethyl 5-[N-(tert-butoxycarbonyl)-N-[2-(dimethylamino)ethyl]amino]thiophen-3-carboxylate (1.53 g, yield; 81%) as a brown oil. MS (APCI) m/z: 343 [M+H]$^+$ (4) To the compound obtained in the above step (3) is added methanol (5.0 mL) and 4N HCl-dioxane (10.0 mL), and the mixture is stirred at room temperature for 3 hours. The reaction mixture is concentrated in vacuo, neutralized with a saturated sodium hydrogencarbonate solution, and extracted with chloroform. The extract is dried over anhydrous sodium sulfate and concentrated in vacuo. The residue is purified by column chromatography on silica gel (Solvent; chloroform:methanol=10:1) to give ethyl 5-[[2-(dimethylamino)ethyl]amino]thiophen-3-carboxylate (0.75 g, yield; 56%) as a brown oil. MS (APCI) m/z: 243 [M+H]$^+$ (5) To a solution of the compound obtained in the above step (4) (50 mg) and pyridine (33 mg) in methylene chloride is added dropwise acetyl chloride (24 mg) under ice-cooling and the mixture is stirred at room temperature overnight. To the reaction mixture is added a saturated sodium hydrogencarbonate solution and the mixture is extracted with chloroform. The extract is dried over anhydrous sodium sulfate and concentrated in vacuo. The residue is purified by column chromatography on silica gel (Solvent; n-hexane:ethyl acetate=1:1) to give ethyl 5-[N-acetyl-N-[2-(dimethylamino)ethyl]amino]thiophen-3-carboxylate (46 mg, yield; 79%) as a yellow oil. MS (APCI) m/z: 285 [M+H]$^+$

REFERENCE EXAMPLE 105

A solution of the compound obtained in Reference Example 104(4) (50 mg) and n-butyl isocyanate (31 mg) in chloroform (3 mL) is stirred at 60° C. overnight. To the reaction mixture is added a saturated sodium hydrogencarbonate solution and extracted with chloroform. The extract is dried over anhydrous sodium sulfate and concentrated in vacuo. The residue is purified by column chromatography on silica gel (Solvent; n-hexane:ethyl acetate=1:1) to give ethyl 5-[N-(butylcarbamoyl)-N-[2-(dimethylamino)ethyl]amino]thiophen-3-carboxylate (58 mg, yield; 82%) as a yellow oil. MS (APCI) m/z: 342 [M+H]$^+$

REFERENCE EXAMPLE 106

To 5-(ethoxycarbonyl)thiophen-2-carboxylic acid (250 mg) is added successively methylene chloride (3.0 mL), N,N-dimethylethylenediamine (100 mg), 1-hydroxybenzotriazole (205 mg), triethylamine (610 mg), and 1-ethyl-3-(3-dimethylaminopropyl)carbodiimide hydrochloride (290 mg). The mixture is stirred at room temperature overnight. The reaction mixture is diluted with chloroform and thereto is added a saturated sodium hydrogencarbonate solution. After stirring, the organic layer is separated and concentrated in vacuo. The residue is purified by flash column chromatography on NH-silica gel (Solvent; ethyl acetate) to give ethyl 5-[[[2-(dimethylamino)ethyl]amino]carbonyl]thiophen-2-carboxylate (160 mg, yield; 53%) as brown crystals. MS (APCI) m/z: 271 [M+H]$^+$

REFERENCE EXAMPLE 107

(1) A mixture of tert-butyl 4-fluorobenzoate (2.14 g) and 1-(2-aminoethyl)pyrrolidine (1 mL) is stirred at 120° C. for one day. After cooling, to the reaction mixture is added water and the mixture is extracted with ethyl acetate (×2). The extract is concentrated by centrifugal concentrator and the residue is purified by flash column chromatography on NH-silica gel (Solvent; n-hexane:ethyl acetate=8:1→4:1) to give tert-butyl 4-[[2-(1-pyrrolidinyl)ethyl]amino]benzoate (1.62 g, yield; 51%) as an oil. MS (APCI) m/z: 291 [M+H]$^+$ (2) To a solution of the compound obtained in the above step (1) (96 mg) and pyridine (67 μL) in chloroform (1 mL) is added acetyl chloride (47 μL) under ice-cooling and the mixture is stirred at room temperature for one day. The reaction mixture is diluted with chloroform and washed with a saturated sodium hydrogencarbonate solution. The washing is extracted with chloroform (×2), and the extracts are combined and concentrated by centrifugation. The residue is purified by flash column chromatography on NH-silica gel (Solvent; n-hexane:ethyl acetate=4:1→2:3) to give tert-butyl 4-[N-acetyl-N-[2-(1-pyrrolidinyl)ethyl]amino]benzoate (37 mg, yield; 33%) as a colorless oil. MS (APCI) m/z: 333 [M+H]$^+$

REFERENCE EXAMPLE 108

(1) To a solution of oxalyl chloride (2.0 mL) in dichloromethane (120 mL) is added dropwise a solution of dimethylsulfoxide (3.3 mL) in dichloromethane (15 mL) under cooling with dry ice-acetone bath and the mixture is stirred at the same temperature for 10 minutes. To the reaction mixture is added dropwise a solution of the compound obtained in Reference Example 100 ((1-isopropylpiperidin-4-yl)methanol) (3.00 g) in dichloromethane (30 mL) over a period of 15 minutes. The mixture is stirred at the same temperature for 2 hours and thereto is added dropwise triethylamine (13.3 mL) over a period of 10 minutes. The mixture is stirred at room temperature for 1 hour, poured into a saturated sodium hydrogencarbonate solution and extracted with dichloromethane. The extract is concentrated in vacuo and the aqueous layer is extracted with ethyl acetate. The extract and the dichloromethane layer are combined, washed with water and saturated brine, dried over anhydrous sodium sulfate, and concentrated in vacuo to give crude 1-isopropylpiperidin-4-carboxaldehyde (1.96 g). MS (APCI) m/z: 156 [M+H]$^+$ (2) To a solution of triethyl phosphonoacetate (7.96 g) in tetrahydrofuran (50 mL) is added portionwise sodium hydride (60% dispersion in mineral oil, 1.45 g) under ice-cooling and the mixture is stirred at the same temperature for 20 minutes. To the mixture is added a solution of the compound obtained in the above step (1) (5.03 g) in tetrahydrofuran (25 mL). The mixture is stirred at the same temperature for 3 hours and diluted with diethyl ether. After addition of water, the reaction mixture is extracted with ethyl acetate. The organic layer is washed with water and saturated brine, dried over anhydrous sodium sulfate, and concentrated in vacuo. The residue is purified by flash column chromatography on NH-silica gel (Solvent; n-hexane:ethyl acetate=9:1) to give ethyl 3-(1-isopropylpiperidin-4-yl)acrylate (6.87 g). MS (APCI) m/z: 226 $[M+H]^+$ (3) To a solution of the compound obtained in the above step (2) (1.01 g) in ethanol (20 mL) is added 2N sodium hydroxide solution (4.5 mL) and the mixture is stirred at room temperature for 24 hours. To the reaction mixture is added 2N HCl (9 mL) and the mixture is concentrated in vacuo. The residue is lyophilized to give 3-(1-isopropylpiperidin-4-yl)acrylic acid hydrochloride (1.43 g). MS (APCI) m/z: 198 $[M+H]^+$

REFERENCE EXAMPLE 109

A mixture of ethyl p-aminobenzoate (25.2 g), triethyl orthoformate (80 g) and trifluoroacetic acid (0.2 mL) is refluxed under heating for 3 hours. After cooling, the reaction mixture is concentrated in vacuo and the residue is subjected to azeotropic distillation with ethanol. The residue is suspended in ethanol (400 mL) and thereto is added sodium borohydride (23 g), and the mixture is refluxed under heating for 3 hours. After cooling, to the reaction mixture is added ethyl acetate and water. The mixture is stirred at room temperature for 1 day. The organic layer is separated, dried over anhydrous sodium sulfate, and concentrated in vacuo. The residue is purified by flash column chromatography on silica gel (Solvent; n-hexane:ethyl acetate=4:1) to give ethyl 4-(methylamino)benzoate (12.7 g, yield; 46%) as a pale yellow amorphous powder. MS (APCI) m/z: 180 $[M+H]^+$

REFERENCE EXAMPLE 110

To a suspension of trans-4-(aminomethyl)cyclohexanecarboxylic acid (8.35 g) in dioxane (100 mL) is added water (50 mL) and 1N sodium hydroxide solution (50 mL), and then added dropwise di-tert-butyl dicarbonate (12.7 g) under ice-cooling. The mixture is stirred at room temperature for 4 hours. The reaction mixture is concentrated in vacuo and the residue is diluted with ethyl acetate and thereto is added an aqueous citric acid solution to acidify the solution (pH 3-4). The mixture is extracted with ethyl acetate, and the organic layer is washed with water and saturated brine, dried over anhydrous sodium sulfate, and concentrated in vacuo. The residue is triturated with n-hexane, collected by filtration, and dried to give trans-4-(tert-butoxycarbonylaminomethyl)cyclohexanecarboxylic acid (13.30 g, yield; 97%) as crystals. MS (APCI) m/z: 256 $[M-H]^-$

REFERENCE EXAMPLE 111

(1) To a solution of the compound obtained in Reference Example 85 (30.0 g) in N,N-dimethylformamide (150 mL) is added sodium hydride (60% dispersion in mineral oil, 5.60 g) under ice-cooling. The mixture is stirred at the same temperature for 0.5 hour and thereto is added successively methyl iodide (14.5 mL) and methanol (0.15 mL). The mixture is stirred at room temperature for 4 hours. To the reaction mixture is added a saturated ammonium chloride solution and ice water, and the mixture is extracted with ethyl acetate. The organic layer is washed with water and saturated brine, dried over anhydrous sodium sulfate and concentrated in vacuo. The residue is purified by column chromatography on silica gel (Solvent; n-hexane:ethyl acetate=10:1→7:1) to give methyl trans-4-[N-methyl-N-(tert-butoxycarbonyl)amino]cyclohexanecarboxylate (26.3 g, yield; 83%) as an amorphous powder. MS (APCI) m/z: 272 $[M+H]^+$ (2) To a solution of the compound obtained in the above step (1) (44.78 g) in methanol (300 mL) is added 2N sodium hydroxide solution (100 mL), and the mixture is stirred at room temperature for 6 hours. The reaction mixture is concentrated in vacuo and to the residue is added ice water, ethyl acetate, and 10% HCl. The mixture is extracted with ethyl acetate and the organic layer is washed with water and saturated brine, dried over anhydrous sodium sulfate and concentrated in vacuo. The residue is suspended in a small amount of ethyl acetate and thereto is added n-hexane. The precipitated crystals are collected by filtration, washed with n-hexane-diisopropylether in several times and dried to give trans-4-[n-methyl-N-(tert-butoxycarbonyl)amino]-cyclohexanecarboxylic acid (39.20 g, yield; 92%) as crystals. MS (APCI) m/z: 256 $[M-H]^-$

REFERENCE EXAMPLE 112

(1) 3-Methoxy-4-methylbenzoic acid (1 g) is treated in the same manner as described in Reference Example 69 to give methyl 3-methoxy-4-[(dimethylamino)-methyl]benzoate (792 mg, yield; 64%) as an oil. MS (APCI) m/z: 224 $[M+H]^+$ (2) To a solution of the compound obtained in the above step (1) (792 mg) in ethanol (10 mL) is added 2N sodium hydroxide solution (2.1 mL) and the mixture is stirred at 60° C. for 2 hours. After cooling, to the reaction mixture is added 2N HCl (4.3 mL). The mixture is concentrated in vacuo and to the residue is added methanol. The mixture is filtered to remove insoluble materials and the filtrate is concentrated in vacuo to give 3-methoxy-4-[(dimethylamino)methyl]benzoate hydrochloride (890 mg, yield; quantitative) as an amorphous powder. MS (APCI) m/z: 210 $M+H]^+$

REFERENCE EXAMPLE 113

To a solution of the compound obtained in Reference Example 156 (200 mg) in dimethylformamide (2 mL) is added successively methylboronic acid (132 mg), [1,1-bis(diphenylphophino)ferrocene]dichloropalladium(II) complex with dichloromethane (60 mg) and potassium carbonate (305 mg). The mixture is stirred at 115° C. under argon gas atmosphere for 3 hours. The reaction mixture is diluted with ethyl acetate (10 mL) and thereto is added a saturated sodium hydrogencarbonate solution. After stirring, the organic layer is separated and concentrated by centrifugal concentrater. The residue is purified by column chromatography on silica gel (Solvent; chloroform:methanol=100:0→90:10) to give methyl 3-methyl-4-[(dimethylamino)methyl]-benzoate (65 mg, yield; 43%) as an amorphous powder. MS (APCI) m/z: 208 $[M+H]^+$

REFERENCE EXAMPLE 114

To a suspension of cesium hydroxide (24.5 g) in dimethylformamide (500 mL) is added successively Molecular sieve 4A (44.5 g) and the compound obtained in Reference Example 86(1) (7.7 g), and the mixture is stirred at room temperature for 30 minutes. To the reaction mixture is added dimethylaminoethyl chloride hydrochloride (11 g), and the mixture is stirred for 22 hours. The reaction mixture is filtered to remove insoluble materials through Celite and washed with ethyl acetate. The filtrate and washing are combined and concentrated in vacuo. The residue is dissolved in chloroform (100 mL). To the solution is added a solution of di-tert-butyl dicarbonate (16 g) in chloroform (10 mL) under ice-cooling and the mixture is stirred at room temperature for 1.5 hours. The reaction mixture is washed with a saturated sodium hydrogencarbonate solution, dried over anhydrous sodium sulfate, and concentrated in vacuo. The residue is purified by column chromatography on silica gel (Solvent; chloroform:methanol=100:0→50:1) to give methyl trans-4-[N-(tert-butoxy-carbonyl)-N-[2-(dimethylamino)ethyl]amino]cyclohexanecarboxylate (1.7 g, yield; 11%) as an amorphous powder. MS (APCI) m/z: 329 [M+H]$^+$

REFERENCE EXAMPLE 115

To a suspension of the compound obtained in Reference Example 90 (500 mg) in dichloromethane (10 mL) is added diethylketone (388 μL), triethylamine (471 μL) and sodium triacetoxyborohydride (956 mg) under ice-cooling, and the mixture is stirred at room temperature overnight. The reaction mixture is diluted with chloroform and thereto is added a saturated sodium hydrogencarbonate solution. After stirring, the organic layer is separated and concentrated in vacuo. The residue is purified by column chromatography on silica gel (Solvent; chloroform:methanol=100:0→90:10) to give ethyl 3-[1-(3-pentyl)piperidin-4-yl]propionate (130 mg). MS (APCI) m/z: 256 [M+H]$^+$

REFERENCE EXAMPLES 116 TO 234

The corresponding materials are treated in the same manner as described in either one of the aforementioned Reference Examples 1 to 115 to give the compounds as shown in the following Table 38.

TABLE 38

(No. 1)

| Ref. Ex. Nos. | R$^a$ | R$^b$ | Physicochemical properties etc. |
|---|---|---|---|
| 116 | cyclohexylethyl | NMe$_2$ | oil MS (APCI) 361 [M + H]+ |
| 117 | cyclohexylethyl | pyrrolidinyl | oil MS (APCI) 387 [M + H]+ |
| 118 | cyclohexylethyl | NEt$_2$ | oil MS (APCI) 389 [M + H]+ |
| 119 | Me | NMe$_2$ | oil MS (APCI) 279 [M + H]+ |
| 120 | Me | pyrrolidinyl | oil MS (APCI) 305 [M + H]+ |
| 121 | Me | NEt$_2$ | oil MS (APCI) 307 [M + H]+ |

Me: methyl group, Et: ethyl group

TABLE 38

(No. 2)

| Ref. Ex. Nos. | R$^a$ | R$^b$ | Physicochemical properties etc. |
|---|---|---|---|
| 122 | cyclohexylethyl | pyrrolidinyl | oil MS (APCI) 373 [M + H]+ |
| 123 | Me | NMe$_2$ | oil MS (APCI) 265 [M + H]+ |
| 124 | Me | pyrrolidinyl | oil MS (APCI) 291 [M + H]+ |
| 125 | cyclohexylethyl | NMe$_2$ | oil MS (APCI) 347 [M + H]+ |

TABLE 38-continued (No. 2)

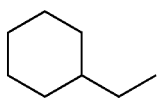

| Ref. Ex. Nos. | $R^a$ | $R^b$ | Physicochemical properties etc. |
|---|---|---|---|
| 126 | cyclohexylethyl | NEt$_2$ | oil MS (APCI) 375 [M + H]+ |

Me: methyl group, Et: ethyl group

TABLE 38

(No. 3)

| Ref. Ex. Nos. | $R^a$ | $R^b$ | Physicochemical properties etc. |
|---|---|---|---|
| 127 | Me$_2$N(CH$_2$)$_3$— | 2-furyl | oil MS (APCI) 373 [M + H]+ |
| 128 | pyrrolidinyl-propyl | CH$_2$OMe | oil MS (APCI) 363 [M + H]+ |
| 129 | pyrrolidinyl-propyl | n-Bu | oil MS (APCI) 375 [M + H]+ |
| 130 | pyrrolidinyl-propyl | c-Pr | oil MS (APCI) 359 [M + H]+ |
| 131 | Et$_2$N(CH$_2$)$_3$— | CH$_2$OMe | oil MS (APCI) 365 [M + H]+ |
| 132 | Et$_2$N(CH$_2$)$_3$— | Me | oil MS (APCI) 335 [M + H]+ |
| 133 | pyrrolidinyl-propyl | 2-furyl | oil MS (APCI) 385 [M + H]+ |
| 134 | Me$_2$N(CH$_2$)$_4$— | Me | oil MS (APCI) 321 [M + H]+ |
| 135 | Me$_2$N(CH$_2$)$_4$— | n-Bu | oil MS (APCI) 363 [M + H]+ |

TABLE 38-continued (No. 3)

| Ref. Ex. Nos. | $R^a$ | $R^b$ | Physicochemical properties etc. |
|---|---|---|---|
| 136 | Me$_2$N(CH$_2$)$_4$— | c-Pr | oil MS (APCI) 347 [M + H]+ |
| 137 | Me$_2$N(CH$_2$)$_4$— | CH$_2$OMe | oil MS (APCI) 351 [M + H]+ |
| 138 | Et$_2$N(CH$_2$)$_3$— | n-Bu | oil MS (APCI) 377 [M + H]+ |
| 139 | Et$_2$N(CH$_2$)$_3$— | c-Pr | oil MS (APCI) 361 [M + H]+ |
| 140 | Et$_2$N(CH$_2$)$_3$— | 2-furyl | oil MS (APCI) 387 [M + H]+ |

Me: methyl group, Et: ethyl group, n-Pr: n-propyl group
c-Pr: cyclopropyl group, n-Bu: n-butyl group

TABLE 38

(No. 4)

| Ref. Ex. Nos. | —$R^c$ | Physicochemical properties etc. |
|---|---|---|
| 141 | 1,2,5-trimethylpyrrolidin-2-yl | oil MS (APCI) 248 [M + H]+ |
| 142 | (1-methylpyrrolidin-2-yl)methanol | oil MS (APCI) 250 [M + H]+ |
| 143 | 2-(methoxymethylene)-1-methylpyrrolidine | oil MS (APCI) 264 [M + H]+ |
| 144 | 1-methylpiperidin-4-ol | oil MS (APCI) 250 [M + H]+ |
| 145 | 1,4-dimethylpiperazine | oil MS (APCI) 249 [M + H]+ |

TABLE 38-continued (No. 4)

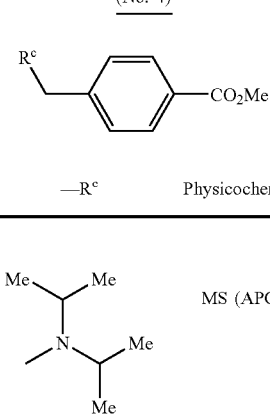

| Ref. Ex. Nos. | —$R^c$ | Physicochemical properties etc. |
|---|---|---|
| 146 | (structure) | oil<br>MS (APCI) 249 [M + H]+ |

Me: methyl group

TABLE 38

(No. 5)

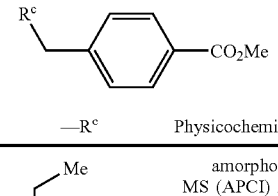

| Ref. Ex. Nos. | —$R^c$ | Physicochemical properties etc. |
|---|---|---|
| 147 | (structure) | amorphous powder<br>MS (APCI) 236 [M + H]+ |
| 148 | (structure) | amorphous powder<br>MS (APCI) 234 [M + H]+ |
| 149 | (structure) | amorphous powder<br>MS (APCI) 248 [M + H]+ |
| 150 | (structure) | amorphous powder<br>MS (APCI) 236 [M + H]+ |

Me: methyl group

TABLE 38

(No. 6)

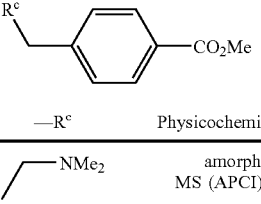

| Ref. Ex. Nos. | —$R^c$ | Physicochemical properties etc. |
|---|---|---|
| 151 | —$NMe_2$ | amorphous powder<br>MS (APCI) 208 [M + H]+ |

TABLE 38-continued (No. 6)

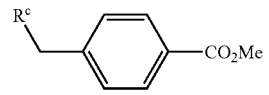

| Ref. Ex. Nos. | —$R^c$ | Physicochemical properties etc. |
|---|---|---|
| 152 | (structure) | amorphous powder<br>MS (APCI) 222 [M + H]+ |
| 153 | (structure) | amorphous powder<br>MS (APCI) 236 [M + H]+ |
| 154 | (structure) | amorphous powder<br>MS (APCI) 234 [M + H]+ |
| 155 | (structure) | amorphous powder<br>MS (APCI) 248 [M + H]+ |

Me: methyl group

TABLE 38

(No. 7)

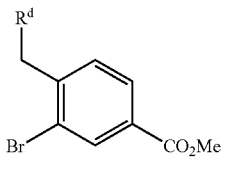

| Ref. Ex. Nos. | —$R^d$ | Physicochemical properties etc. |
|---|---|---|
| 156 | (structure) | amorphous powder<br>MS (APCI) 272/274 [M + H]+ |
| 157 | (structure) | amorphous powder<br>MS (APCI) 300/302 [M + H]+ |
| 158 | (structure) | amorphous powder<br>MS (APCI) 298/300 [M + H]+ |

Me: methyl group

TABLE 38

(No. 8)

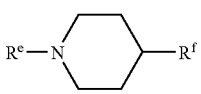

| Ref. Ex. Nos. | —Rᵉ | —Rᶠ | Physicochemical properties etc. |
|---|---|---|---|
| 159 | —Me | 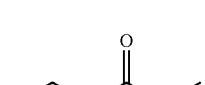 | oil MS (APCI) 200 [M + H]+ |
| 160 | —Me | 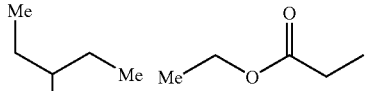 | oil MS (APCI) 186 [M + H]+ |
| 161 |  | 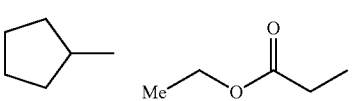 | oil MS (APCI) 241 [M + H]+ |
| 162 |  | 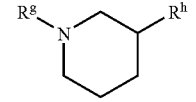 | oil MS (APCI) 254 [M + H]+ |
| 163 | 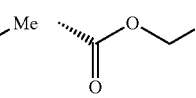 | 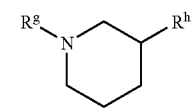 | oil MS (APCI) 240 [M + H]+ |
| 164 | 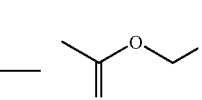 | 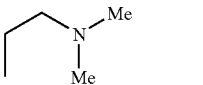 | oil MS (APCI) 226 [M + H]+ |

Me: methyl group, Ph: phenyl group

TABLE 38

(No. 9)

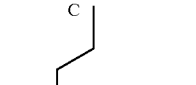

| Ref. Ex. Nos. | —Rᵍ | —Rʰ | Physicochemical properties etc. |
|---|---|---|---|
| 165 | 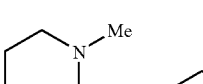 | 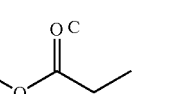 | oil MS (APCI) 228 [M + H]+ |
| 166 | 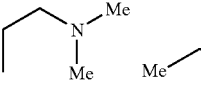 | 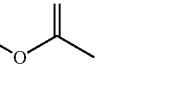 | oil MS (APCI) 200 [M + H]+ |

TABLE 38-continued (No. 9)

| Ref. Ex. Nos. | —Rᵍ | —Rʰ | Physicochemical properties etc. |
|---|---|---|---|
| 167 | 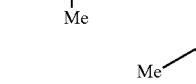 | 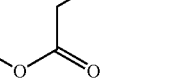 | oil MS (APCI) 228 [M + H]+ |
| 168 |  | 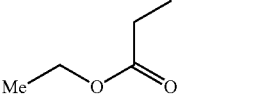 | oil MS (APCI) 226 [M + H]+ |

Me: methyl group

TABLE 38

(No. 10)

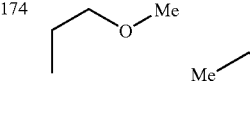

| Ref. Ex. Nos. | —Rᵏ | —Rᵐ | X | Physicochemical properties etc. |
|---|---|---|---|---|
| 169 | 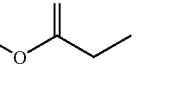 | | C | oil MS (APCI) 257 [M + H]+ |
| 170 | | | C | oil MS (APCI) 243 [M + H]+ |
| 171 | | | C | oil MS (APCI) 229 [M + H]+ |
| 172 | | | N | oil MS (APCI) 244 [M + H]+ |
| 173 | | | C | oil MS (APCI) 244 [M + H]+ |
| 174 | | | C | oil MS (APCI) 230 [M + H]+ |

TABLE 38-continued

(No. 10)

R$^k$—N⟨piperidine ring⟩X—R$^m$

| Ref. Ex. Nos. | —R$^k$ | —R$^m$ | X | Physicochemical properties etc. |
|---|---|---|---|---|
| 175 | CH₃CH₂CH(OMe)– | –C(=O)OCH₂Me | N | oil MS (APCI) 231 [M + H]+ |

Me: methyl group

TABLE 38

(No. 11)

R$^k$—N⟨ring⟩X—R$^m$

| Ref. Ex. Nos. | —R$^k$ | —R$^m$ | X | Physicochemical properties etc. |
|---|---|---|---|---|
| 176 | CH₃CH₂CH(OMe)– | –CH₂OC(=O)Me | C | oil MS (APCI) 216 [M + H]+ |
| 177 | —n-Bu | –CH₂CH₂C(=O)OCH₂Me | C | oil MS (APCI) 242 [M + H]+ |
| 178 | —n-Bu | –CH₂C(=O)OCH₂Me | C | oil MS (APCI) 228 [M + H]+ |
| 179 | —n-Bu | –CH₂C(=O)OCH₂Me | N | oil MS (APCI) 229 [M + H]+ |
| 180 | —n-Pr | –CH₂CH₂C(=O)OCH₂Me | C | oil MS (APCI) 228 [M + H]+ |

Me: methyl group

TABLE 38

(No. 12)

R$^k$—N⟨ring⟩X—R$^m$

| Ref. Ex. Nos. | —R$^k$ | —R$^m$ | X | Physicochemical properties etc. |
|---|---|---|---|---|
| 181 | -n-Pr | –C(=O)OCH₂Me | C | oil MS (APCI) 214 [M + H]+ |
| 182 | —Et | –CH₂CH₂C(=O)OCH₂Me | C | oil MS (APCI) 214 [M + H]+ |
| 183 | Me₂CHCH₂– | –CH₂CH₂C(=O)OCH₂Me | N | oil MS (APCI) 243 [M + H]+ |
| 184 | cyclopentyl-CH₂– | — | 2 N | oil MS (APCI) 241 [M + H]+ |
| 185 | -i-Pr | –CH₂CH₂C(=O)OCH₂Me | N | oil MS (APCI) 215 [M + H]+ |

Et: ethyl group, i-Pr: isopropyl group, n-Pr: n-propyl group, n-Bu: n-butyl group

TABLE 38

(No. 13)

R$^n$—N⟨piperidine⟩—R$^p$

| Ref. Ex. Nos. | —R$^n$ | —R$^p$ | Physicochemical properties etc. |
|---|---|---|---|
| 186 | n-Pr-N(Me)-CH(Me)– | –OCH₂Me (C=O) | oil MS (APCI) 229 [M + H]+ |
| 187 | n-Pr-N(Me)-CH(Me)– | –CH₂OC(=O)Me | oil MS (APCI) 229 [M + H]+ |

TABLE 38-continued (No. 13)

[Structure: piperidine with $R^n$ on N and $R^p$ at position 3]

| Ref. Ex. Nos. | —$R^n$ | —$R^p$ | Physicochemical properties etc. |
|---|---|---|---|
| 188 | [CH2CH2CH2-O-Me] | [OCH2CH3 ester, wedge] | oil MS (APCI) 216 [M + H]+ |
| 189 | [CH2CH2CH2-O-Me] | [OCH2CH3 ester] | oil MS (APCI) 216 [M + H]+ |
| 190 | n-Bu | [OCH2CH3 ester] | oil MS (APCI) 214 [M + H]+ |

Me: methyl group, n-Bu: n-butyl group

TABLE 38

(No. 14)

[Structure: $R^q$-C(=O)-phenyl-$CO_2Me$]

| Ref. Ex. Nos. | $R^q$ | Physicochemical properties etc. |
|---|---|---|
| 191 | [MeN(Me)-CH2CH2-NMe2] | amorphous powder MS (APCI) 265 [M + H]+ |
| 192 | [HN(Me)-CH2CH2CH2-NMe2] | oil MS (APCI) 265 [M + H]+ |
| 193 | [HN(Me)-CH2CH2CH2-imidazolyl] | oil MS (APCI) 288 [M + H]+ |

Me: methyl group

TABLE 38

(No. 15)

[Structure: Me-N($R^s$)-CH2-phenyl-$CO_2Me$]

| Ref. Ex. Nos. | —$R^s$ | Physicochemical properties etc. |
|---|---|---|
| 194 | [CH3-C(=O)-O-CH2CH2-pyrrolidinyl] | oil MS (APCI) 321 [M + H]+ |
| 195 | [CH2CH2CH2-O-tetrahydropyranyl] | oil MS (APCI) 308 [M + H]+ |

Me: methyl group

TABLE 38

(No. 16)

[Structure: $Me_2N$-CH2CH2-N(C(=O)$R^t$)-thiophene-$CO_2Et$]

| Ref. Ex. Nos. | —$R^t$ | Physicochemical properties etc. |
|---|---|---|
| 196 | cyclopropyl | oil MS (APCI) 311 [M + H]+ |
| 197 | CH=CH-Me | oil MS (APCI) 311 [M + H]+ |

Me: methyl group, Et: ethyl group

TABLE 38

(No. 17)

[Structure: $Me_2N$-CH2CH2-N($R^u$)-thiophene-$CO_2Et$]

| Ref. Ex. Nos. | —$R^u$ | Physicochemical properties etc. |
|---|---|---|
| 198 | [CH3-C(=S)-N(Me)-] | oil MS (APCI) 316 [M + H]+ |

Me: methyl group, Et: ethyl group

TABLE 38

(No. 18)

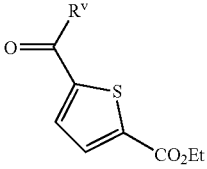

| Ref. Ex. Nos. | R^v | Physicochemical properties etc. |
|---|---|---|
| 199 | 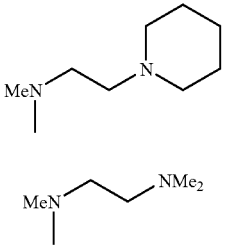 | oil<br>MS (APCI) 325 [M + H]+ |
| 200 | 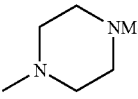 | oil<br>MS (APCI) 286 [M + H]+ |
| 201 | 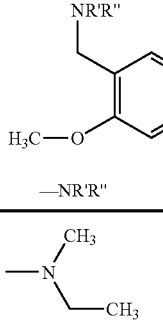 | oil<br>MS (APCI) 288 [M + H]+ |

Me: methyl group, Et: ethyl group

TABLE 38

(No. 19)

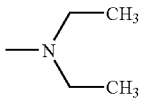

| Ref. Ex. Nos. | —NR'R" | Physicochemical properties etc. |
|---|---|---|
| 202 | 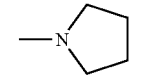 | amorphous powder<br>MS (ESI) 242 [M − H]− |
| 203 | 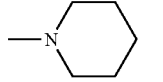 | amorphous powder<br>MS (ESI) 228 [M − H]− |
| 204 | 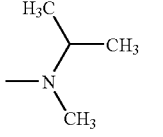 | amorphous powder<br>MS (ESI) 242 [M − H]− |
| 205 | 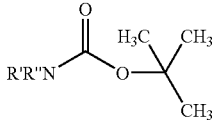 | amorphous powder<br>MS (ESI) 256 [M − H]− |

TABLE 38

(No. 20)

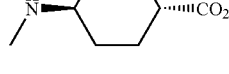

| Ref. Ex. Nos. | —NR'R" | Physicochemical properties etc. |
|---|---|---|
| 206 | 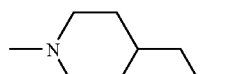 | amorphous powder<br>MS (APCI) 224 [M + H]+ |
| 207 | 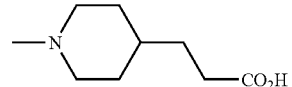 | amorphous powder<br>MS (APCI) 238 [M + H]+ |
| 208 | 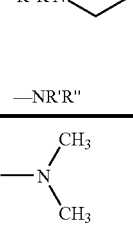 | amorphous powder<br>MS (APCI) 236 [M + H]+ |
| 209 | 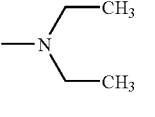 | amorphous powder<br>MS (APCI) 250 [M + H]+ |
| 210 |  | amorphous powder<br>MS (APCI) 238 [M + H]+ |

TABLE 38

(No. 21)

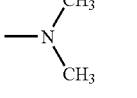

| Ref. Ex. Nos. | —NR'R" | X | Physicochemical properties etc. |
|---|---|---|---|
| 211 |  | S | amorphous powder<br>MS (APCI) 186 [M + H]+ |
| 212 |  | S | amorphous powder<br>MS (APCI) 214 [M + H]+ |
| 213 |  | S | amorphous powder<br>MS (APCI) 212 [M + H]+ |
| 214 |  | O | amorphous powder<br>MS (APCI) 170 [M + H]+ |

TABLE 38-continued (No. 21)

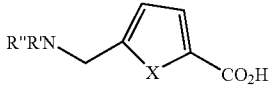

| Ref. Ex. Nos. | —NR'R" | X | Physicochemical properties etc. |
|---|---|---|---|
| 215 |  | O | amorphous powder MS (APCI) 198 [M + H]+ |
| 216 | 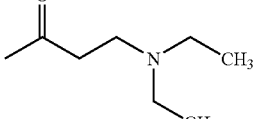 | O | amorphous powder MS (APCI) 196 [M + H]+ |

TABLE 38

(No. 22)

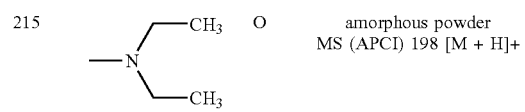

| Ref. Ex. Nos. | —NR'R" | Physicochemical properties etc. |
|---|---|---|
| 217 | 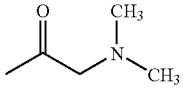 | amorphous powder MS (APCI) 236 [M + H]+ |
| 218 | 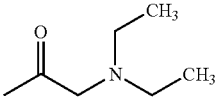 | amorphous powder MS (APCI) 234 [M + H]+ |

TABLE 38

(No. 23)

| Ref. Ex. Nos. | $R^w$ | n | Physicochemical properties etc. |
|---|---|---|---|
| 219 | 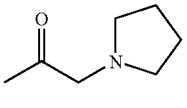 | 0 | oil MS (APCI) 243 [M + H]+ |

TABLE 38-continued (No. 23)

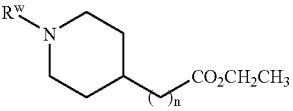

| Ref. Ex. Nos. | $R^w$ | n | Physicochemical properties etc. |
|---|---|---|---|
| 220 | 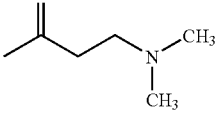 | 0 | oil MS (APCI) 257 [M + H]+ |
| 221 | 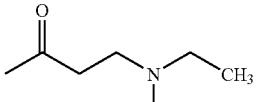 | 0 | oil MS (APCI) 285 [M + H]+ |
| 222 |  | 1 | oil MS (APCI) 257 [M + H]+ |
| 223 | 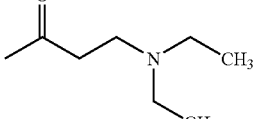 | 1 | oil MS (APCI) 285 [M + H]+ |
| 224 | 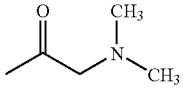 | 1 | oil MS (APCI) 283 [M + H]+ |
| 225 | 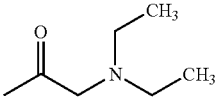 | 1 | oil MS (AFCI) 271 [M + H]+ |
| 226 | 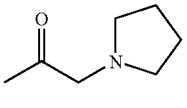 | 1 | oil MS (APCI) 299 [M + H]+ |

TABLE 38

(No. 24)

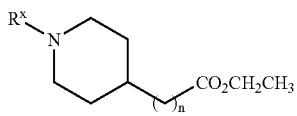

| Ref. Ex. Nos. | $R^x$ | n | Physicochemical properties etc. |
|---|---|---|---|
| 227 | -CH2-N(CH3)-) | 2 | oil<br>MS (APCI) 271 [M + H]+ |
| 228 | -CH2-C(O)-) | 2 | oil<br>MS (APCI) 299 [M + H]+ |
| 229 | -) | 2 | oil<br>MS (APCI) 297 [M + H]+ |
| 230 | -) | 2 | oil<br>MS (APCI) 311 [M + H]+ |

TABLE 38

(No. 25)

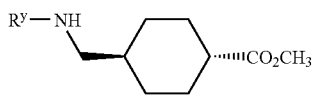

| Ref. Ex. Nos. | $-R^y$ | Physicochemical properties etc. |
|---|---|---|
| 231 | -CH2-N(CH3)-CH3) | amorphous powder<br>MS (APCI) 257 [M + H]+ |
| 232 | -CH2-C(O)-) | amorphous powder<br>MS (APCI) 285 [M + H]+ |
| 233 | -) | amorphous powder<br>MS (APCI) 283 [M + H]+ |
| 234 | -CH2CH2-C(O)-) | oil<br>MS (APCI) 271 [M + H]+ |

REFERENCE EXAMPLE 235

(1) To a solution of 1-(carbamoyl)-1-cyclopropanecarboxylic acid (500 mg) in tetrahydrofuran (2.0 mL) is added dropwise 2M boran-dimethylsulfide complex solution in tetrahydrofuran (7.5 mL) and the mixture is refluxed under heating for 4 hours. To the reaction mixture is added 10% HCl and the mixture is refluxed under heating for 30 minutes. After cooling, the reaction mixture is neutralized with a saturated sodium hydrogencarbonate solution, and thereto is added dioxane (10 mL) and di-tert-butyl dicarbonate (1.3 g). The mixture is stirred at room temperature for 3 hours. The reaction mixture is extracted with ethyl acetate and the extract is concentrated in vacuo. The residue is purified by flash column chromatography on silica gel (Solvent; n-hexane:ethyl acetate=3:1) to give 1-hydroxymethyl-1-(tert-butoxycarbonylamiomethyl)cyclopropane (337 mg, yield; 45%) as a yellow oil. MS (APCI) m/z; 202 [M+H]$^+$ (2) To a solution of the compound obtained in the above step (1) (337 mg), methyl 4-hidroxybenzoate (280 mg), and triphenylphosphine (650 mg) in tetrahydrofuran (3.0 mL) is added dropwise diisopropyl azodicarboxylate (510 mg) under ice-cooling and the mixture is stirred at room temperature overnight. The reaction mixture is concentrated in vacuo and the residue is purified by flash column chromatography on NH-silica gel (Solvent; n-hexane:ethyl acetate=3:2) to give methy 4-[[1-(tert-butoxycarbonylamiomethyl)cyclopropyl]methoxy]benzoate (515 mg, yield; 92%) as a yellow oil. MS (APCI) m/z; 353 [M+H]$^+$

REFERENCE EXAMPLE 236

A suspension of tert-butyl 4-fluorobenzoate (300 mg), 2-(dimethylamino)-ethanethiol hydrochloride (420 mg), and potassium carbonate (620 mg) in dimethylsulfoxide (3.0 mL) is stirred at 80° C. for 4 hours. The reaction mixture is diluted with water and extracted with ethyl acetate. The extract is concentrated in vacuo and to the residue is added 4N HCl-dioxane (1.5 mL). The mixture is stirred at room temperature overnight. The reaction mixture is diluted with ether and the precipitated crystals are collected by filtration to give 4-[2-(dimethylamino)ethylthio]-benzoic acid (380 mg, yield; 99%) as colorless crystals. MS (APCI) m/z; 226 [M+H]$^+$

REFERENCE EXAMPLE 237

To a solution of ethyl 4-cyclohexanonecarboxylate (24 g) in methanol (200 mL) is added sodium borohydride (2.67 g) at −78° C. and the mixture is stirred at the same temperature for 1 hour. To the reaction mixture is added water, and the mixture is evaporated to remove methanol and extracted with ethyl acetate. The organic layer is washed with saturated brine, dried over anhydrous sodium sulfate, and concentrated in vacuo. To a solution of the residue (20 g) in methylene chloride (200 mL) is added dropwise diisopropylethylamine (50 mL) and chloromethylmethylether (16 mL) under ice-cooling and the mixture is stirred at room temperature overnight. To the reaction mixture is added water and the mixture is extracted with ethyl acetate. The extract is concentrated and the residue is purified by flash column chromatography on silica gel (Solvent; n-hexane: ethyl acetate=15:1) to give ethyl trans-4-(methoxymethoxy)-cyclohexanecarboxylate (12.3 g, yield; 40%) as a colorless oil. MS (APCI) m/z; 234 [M+H]$^+$

REFERENCE EXAMPLE 238

The compound obtained in Reference Example 85(2) (mono-methyl trans-cyclohexane-1,4-dicarboxylate, 14.3 g) is dissolved in tetrahydrofuran (78 mL) and 1.0M borantetrahydrofuran complex solution in tetrahydrofuran (100 mL) is added dropwise thereto at −50° C. under argon gas atmosphere over a period of 1 hour. The mixture is stirred at −10° C. for 1 hour. To the reaction mixture is added water (160 mL) and a saturated sodium hydrogencarbonate solution (160 mL) under ice-cooling and the mixture is extracted with ethyl acetate (×4). The extract is washed with saturated brine, dried over anhydrous sodium sulfate and concentrated in vacuo. The residue is purified by flash column chromatography on silica gel (Solvent; chloroform:methanol=20:1) to give methyl trans-4-(hydroxymethyl)cyclohexanecarboxylate (13.25 g, yield; quantitative) as an oil. MS (APCI) m/z; 173 [M+H]$^+$

REFERENCE EXAMPLE 239

(1) To a solution of methyl trans-4-(aminomethyl)cyclohexanecarboxylate hydrochloride (5.86 g) and triethylamine (12 mL) in chloroform (100 mL) is added dropwise acetyl chloride (2.69 g) under ice-cooling and the mixture is stirred at room temperature for 2 hours. The reaction mixture is poured into water and the mixture is extracted with chloroform (×2). The combined extracts are washed successively with 10% HCl, saturated brine, a saturated sodium hydrogencarbonate solution, and saturated brine, dried over anhydrous sodium sulfate, and concentrated in vacuo. The residue is purified by flash column chromatography on silica gel (Solvent; n-hexane:ethyl acetate=1:1→0:1) to give methyl trans-4-(acetylaminomethyl)cyclohexanecarboxylate (5.92 g, yield; 98%) as an amorphous powder. MS (APCI) m/z; 214 [M+H]$^+$ (2) To a solution of the compound obtained in the above step (1) (4.32 g) in dimethylformamide (50 mL) is added successively sodium hydride (60% dispersion in mineral oil, 1.0 g), methyl iodide (5.91 g) and methanol (5 drops) under ice-cooling and the mixture is stirred at room temperature for 8 hours. After addition of sodium hydride (60% dispersion in mineral oil, 430 mg), methyl iodide (1.5 mL), and methanol (2 drops). The mixture is stirred for 2 hours. The reaction mixture is poured into water and extracted with ethyl acetate (×3). The extract is washed with water (×2), dried over anhydrous sodium sulfate and concentrated in vacuo. The residue is purified by flash column chromatography on silica gel (Solvent; n-hexane:ethyl acetate=1:2→0:1) to give methyl trans-4-(N-methyl-N-acetylaminomethyl) cyclohexanecarboxylate (3.04 g, yield; 66%) as an oil. MS (APCI) m/z; 228 [M+H]$^+$ (3) The compound obtained in the above step (2) (3.03 g) is hydrolyzed by 2N sodium hydroxide solution (14 mL) in methanol/tetrahydrofuran and the reaction mixture is concentrated in vacuo and nuetralized with diluted aqueous HCl. The mixture is extracted with chloroform and the extract is dried over anhydrous sodium sulfate and concentrated in vacuo to give a crude carboxylic acid compound (2.67 g, 94%). The compound (500 mg) is refluxed under heating in 5N HCl for 2 days and the reaction mixture is concentrated to give a crude amino acid compound. To the compound is added a mixture of 1N sodium hydroxide solution (6 mL) and dioxane (4 mL) and di-tert-butyl dicarbonate (1.0 g). The mixture is stirred at room temperature for 12 hours. The reaction mixture is diluted with water and washed with ether. After neutralizing the aqueous layer with 10% citric acid solution, the mixture is extracted with ethyl acetate. The extract is washed successively with water and saturated brine, dried over anhydrous sodium sulfate, and concentrated in vacuo to give trans-4-[N-methyl-N-(tert-butoxycarbonyl)aminomethyl]cyclohexanecarboxylic acid (680 mg, yield; 90%) as an oil. MS (ESI) m/z; 270 [M−H]$^−$

REFERENCE EXAMPLE 240

The compound obtained in Reference Example 238 (500 mg) and isopropyl-(2-methoxyethyl)amine (689 mg) are treated in the same manner as described in Example 654(1) and (2) to give methyl trans-4-[N-isopropyl-N-(2-methoxyethyl)aminomethyl]-cyclohexanecarboxylate (445 mg, yield; 56%) as oil. MS (APCI) m/z; 272 [M+H]$^+$

REFERENCE EXAMPLE 241

(1) To a solution of ethyl 4-benzylaminobenzoate (6.0 g) in methylene chloride (60 mL) is added dropwise chlorobutyryl chloride (3.95 mL) and N,N-diisopropylethylamine (6.14 mL) under ice-cooling, and the mixture is stirred for 12 hours. The reaction mixture is diluted with chloroform and thereto is added 10% HCl. The organic layer is separated, washed successively with water, a saturated sodium hydrogencarbonate solution, water, and saturated brine, dried over anhydrous sodium sulfate, and concentrated in vacuo. The residue is purified by flash column chromatography on silica gel (Solvent; n-hexane:ethyl acetate=4:1) to give ethyl 4-[N-benzyl-N-(4-chlorobutyryl)amino]benzoate (8.27 g, yield; quantitative) as an oil. MS (APCI) m/z; 360/362 [M+H]$^+$ (2) A solution of the compound obtained in the above step (1) (1.0 g), diethylamine (287 μL), and sodium iodide (417 mg) in dimethylsulfoxide (2.5 mL) is stirred at 100° C. under argon gas atmosphere for 1 day. After cooling, to the reaction mixture is added a saturated sodium hydrogencarbonate solution and the mixture is extracted with chloroform (×2). The extract is concentrated in vacuo and the residue is purified by flash column chromatography on NH-silica gel (Solvent; n-hexane:ethyl acetate=4:1) to give ethyl 4-[N-benzyl-N-[4-(diethylamino)butyryl]amino]benzoate (280 mg, yield; 25%) as an oil. MS (APCI) m/z; 397 [M+H]$^+$

REFERENCE EXAMPLE 242

To a solution of ethyl 3,4-dihydroxybenzoate (500 mg), N,N-dimethylethanol-amine (565 μL), and triphenylphosphine (1.51 g) in methylene chloride (20 mL) is added dropwise diisopropyl azodicarboxylate (1.37 mL) under argon gas atmosphere and ice-cooling. The mixture is stirred at room temperature for 1 day. The reaction mixture is diluted with ethyl acetate, washed with water and treated with 10% HCl to transfer basic materials in ethyl acetate layer to the aqueous layer. The aqueous layer is neutralized with saturated aqueous sodium hydrogencarbonate and extracted with chloroform/methanol/tetrahydrofuran (4:1:1, ×2). The extract is dried over anhydrous sodium sulfate and concentrated in vacuo. The residue is purified by flash column chromatography on NH-silica gel (Solvent; n-hexane:ethyl acetate=1:1→chloroform:methanol=19:1) to give ethyl 4-[2-(dimethylamino)ethoxy]-3-hydroxy-benzoate (240 mg, yield; 35%) as oil. MS (APCI) m/z; 254 [M+H]$^+$

REFERENCE EXAMPLE 243

To a solution of ethyl 4-aminobenzoate (10 g) and 4-(dimethylamino)benzaldehyde (9.0 g) in methylene chloride (200 mL) is added sodium triacetoxyborohydride (18.9 g) and acetic acid (3.47 mL) under ice-cooling, and the mixture is stirred at room temperature for 2 days. To the reaction mixture is added a saturated sodium hydrogencarbonate solution and extracted with chloroform (×2). The extract is concentrated in vacuo and the residue is triturated in n-hexane/ethyl acetate to give ethyl 4-[4-(dimethylamino)benzylamino]benzoate (11.6 g, yield; 64%) as powder. MS (APCI) m/z; 299 [M+H]$^+$

REFERENCE EXAMPLE 244

(1) A solution of 4-(bromomethyl)benzaldehyde (15.9 g) and (1-ethoxy-carbonylethylidene)triphenylphosphorane (29 g) in chloroform (290 mL) is refluxed under heating for 12 hours. After cooling, the reaction mixture is concentrated and the residue is purified by column chromatography on silica gel (Solvent; chloroform) to give ethyl 3-[4-(bromomethyl)phenyl]-2-methylacrylate (18 mg, yield; 79%) as an oil.

(2) To a solution of pyrrolidine (0.89 g) and potassium carbonate (1.38 g) in water (10 mL) is added dropwise a solution of the compound obtained in the above step (1) (2.83 g) in tetrahydrofuran (5 mL) and the mixture is stirred at room temperature overnight. The reaction mixture is diluted with ethyl acetate, washed with water, dried over anhydrous sodium sulfate, and concentrated in vacuo. The residue is dissolved in ether and filtered to remove insoluble materials. To the filtrate is added oxalic acid (0.9 g) and the resultant precipitate is collected by filtration to give ethyl 2-methyl-3-[4-[(1-pyrrolidinyl)methyl]phenyl]acrylate hemioxalate (2.67 g, yield; 83%) as an amorphous powder.

(3) The compound obtained in the above step (2) (2.2 g) is treated with ethyl acetate/10% potassium carbonate solution and the ethyl acetate layer is concentrated in vacuo. The residue (2-methyl-3-[4-pyrrolidin-1-yl)methylphenyl] acrylic acid) is dissolved in methanol (10 mL) and thereto is added potassium hydroxide (1.38 g). The mixture is stirred at 50° C. for 5 hours. After cooling, to the reaction mixture is added ethanol (5 mL) and the resultant crystals are collected by filtration to give potassium 2-methyl-3-[4-[(1-pyrrolidinyl)methyl]phenyl]acrylate (1.65 g, yield; 83%) as a powder.

M.p. 268° C. (dec.)

REFERENCE EXAMPLE 245

(1) To a solution of methyl 4-(bromomethyl)benzoate (500 mg) in tetrahydro-furan (5 mL) is added cyclopentylamine (929 mg) and the mixture is stirred at room temperature for 3 hours. The reaction mixture is diluted with chloroform (5 mL) and thereto is added a saturated sodium hydrogencarbonate solution. After stirring, the organic layer is separated, dried over anhydrous sodium sulfate, and filtered. The filtrate is concentrated and the residue is purified by column chromatography on silica gel (Solvent; n-hexane:ethyl acetate=9:1→5:5) to give methyl 4-(cyclopentyl-aminomethyl)benzoate (469 mg, yield; 92%) as a colorless oil. MS (APCI) m/z; 234 [M+H]$^+$ (2) The compound obtained in the above step (1) (480 mg) is treated in the same manner as described in Reference Example 89(2) to give methyl 4-[(N-cyclo-pentyl-N-methylamino)methyl]benzoate (420 mg, yield; 83%) as a colorless oil. MS (APCI) m/z; 248 [M+H]$^+$

REFERENCE EXAMPLE 246

(1) The corresponding materials are treated in the same manner as described in Reference Example 107(1) to give tert-butyl 4-[[3-(dimethylamino)-2,2-dimethyl-propyl]amino]benzoate.

(2) The compound obtained in the above step (1) (500 mg) is treated in the same manner as described in Reference Example 89(2) to give tert-butyl 4-[N-[3-(dimethylamino)-2,2-dimethylpropyl]-N-ethylamino]benzoate (468 mg, yield; 85%) as a colorless oil. MS (APCI) m/z; 335 [M+H]$^+$

REFERENCE EXAMPLE 247

The compound obtained in Reference Example 86(1) (1.00 g) is treated in the same manner as described in Reference Example 89(2) and the resultant product is treated in the same manner as described in Reference Example 81(1) to give methyl trans-4-[N-(tert-butoxycarbonyl)-N-ethylamino]cyclohexanecarboxylate (258.4 mg, yield; 14%) as a colorless oil. MS (APCI) m/z; 303 [M+NH$_4$]$^+$

REFERENCE EXAMPLE 248

(1) To a solution of malononitrile (28.2 g) in methanol (30 mL) is added a suspension of acetoin (25 g) in methanol (30 mL) and thereto is added dropwise diethylamine (11 mL) under ice-cooling (internal temp.: 10° C.). The mixture is stirred at room temperature for 3 hours. The reaction mixture is poured into ice water (300 mL) and the precipitated crystals are collected by filtration to give 2-amino-4,5-dimethyl-3-furonitrile (28.91 g, yield; 75%) as colorless crystals.

(2) To a solution of the compound obtained in the above step (1) (13.6 g) in methylene chloride (200 mL) is added piperidine (18.9 g) and thereto is added dropwise a solution of ethyl chlorooxoacetate (16.3 g) in methylene chlorode (200 mL) under ice-cooling. The mixture is stirred at 0° C. for 1.5 hours. The reaction mixture is diluted with chloroform (100 mL) and thereto is added water (300 mL). After stirring, the organic layer is separated and the aqueous layer is extracted with chloroform. The organic layers are combined and washed with saturated brine, dried over anhydrous sodium sulfate, and filtered. The filtrate is concentrated and the residue is purified by column chromatography on silica gel (Solvent; chloroform:ethyl acetate=9:1) to give ethyl [(3-cyano-4,5-dimethylfuran-2-yl)amino](oxo)acetate (17 g, yield; 72%) as a colorless powder. A mixture of formic acid (30 mL) and acetic anhydride (30 mL) is stirred at 60° C. under argon gas atmosphere for 2 hours and thereto is added ethyl [(3-cyano-4,5-dimethylfuran-2-yl)amino](oxo)acetate (7.07 g). The mixture is refluxed for 14 hours. The reaction mixture is concentrated and the residue is purified by column chromatography on silica gel (Solvent; chloroform:ethyl acetate=9:1→chloroform:methanol=19:1) to give ethyl 5,6-dimethyl-4-oxo-3,4-dihydrofuro[2,3-d]pyrimidine-2-carboxylate (4.30 g, yield; 61%) as a colorless powder. M.p. 180-182° C.

(3) The compound obtained in the above step (2) (2.36 g) is dissolved in N,N-dimethylformamide (60 mL) and thereto is added dimethyaminoethyl chloride hydrochloride (2.16 g) and potassium carbonate (4.14 g). The mixture is stirred at 60° C. for 14 hours. The reaction mixture is diluted with chloroform (50 mL) and thereto is added water (70 mL).

After stirring, the organic layer is separated and the aqueous layer is extracted with chloroform. The organic layers are combined and washed with saturated brine, dried over anhydrous sodium sulfate, and filtered. The filtrate is concentrated and the residue is purified by column chromatography on silica gel (Solvent; chloroform:ethyl acetate:methanol=6:2:1). The resultant product is treated in the same manner as described in Example 5(2) to give ethyl 4-[2-(dimethylamino)ethoxy]-5,6-dimethylfuro[2,3-d]pyrimidine-2-carboxylate fumarate (780 mg, yield; 18%) as a colorless powder. M.p. 173-174° C.

(4) The compound obtained in the above step (3) (1.44 g) is dissolved in ethanol (20 mL) and thereto is added 2N sodium hydroxide solution (2.34 mL). The mixture is stirred at room temperature for 2 hours. The reaction mixture is concentrated and to the residue is added diethyl ether. The resultant crystals are collected by filtration and purified by reverse phase column chromatography (HP-20 column, Solvent; water:methanol=1:0→1:1) to give 4-[2-(dimethylamino)-ethoxy]-5,6-dimethylfuro[2,3-d]pyrimidine-2-carboxylic acid (970 mg, yield; 74%) as a colorless powder. M.p. 179-180° C.

REFERENCE EXAMPLE 249

(1) To a solution of 5-hydroxy-2-(hydroxymethyl)-4H-pyranone (1 g) in N,N-dimethylformamide (20 mL) is added potassium carbonate (1.95 g) and tert-butyl bromoacetate (1.37 g) and the mixture is stirred at room temperature for 16 hours. The reaction mixture is diluted with tetrahydrofuran (10 mL), and thereto is added water and saturated brine. After stirring, the organic layer is separated and the aqueous layer is extracted with tetrahydrofuran. The organic layers are combined and washed with saturated brine, dried over anhydrous sodium sulfate, and filtered. The filtrate is concentrated and the residue is washed with diethyl ether and collected by filtration to give tert-butyl [[6-(hydroxymethyl)-4-oxo-4H-pyran-3-yl]oxy]acetate (1.49 g, yield; 88%) as a colorless powder. MS (ESI) m/z; 257 [M+H]$^+$, M.p. 90-92° C.

(2) To a solution of the compound obtained in the above step (1) (50 g) in methylene chloride (600 mL) is added Dess-Martin periodinate (1,1,1-tris(acetyloxy)-1,1-dihydro-1,2-benziodoxol-3(1H)-one, 91.04 g) and the mixture is stirred at room temperature for 5 days. The reaction mixture is filtered through Celite, and the filtrate is extracted with ethyl acetate and concentrated. The residue is washed with diethyl ether and collected by filtration to give tert-butyl [(6-formyl-4-oxo-4H-pyran-3-yl)-oxy]acetate (17.1 g, 34.5%) as a brown powder.

(3) The compound (2.0 g) obtained in the above step (2) is treated in the same manner as described in Example 6 to give tert-butyl [[4-oxo-6-[(1-pyrrolidinyl)methyl]-4H-pyran-3-yl]oxy]acetate (1.06 g, yield; 44%) as a yellow powder. MS (ESI) m/z; 310 [M+H]$^+$, M.p. 93-94° C.

(4) To a solution of the compound obtained in the above step (3) (700 mg) in methylene chloride (5 mL) is added trifluoroacetic acid (2.5 mL) at 0° C. and the mixture is stirred at room temperature for 24 hours. The reaction mixture is concentrated and thereto is added ethyl acetate and water. After stirring, the aqueous layer is separated and washed with ethyl acetate again. The aqueous layer is lyophilized to give [[4-oxo-6-[(1-pyrrolidinyl)methyl]-4H-pyran-3-yl]oxy]acetic acid (820 mg, yield; 99%) as a colorless powder. MS (ESI) m/z; 254 [M+H]$^+$

REFERENCE EXAMPLE 250

(1) To a solution of tert-butyl [[4-oxo-6-[(1-pyrrolidinyl)methyl]-4H-pyran-3-yl]oxy]acetate (compound obtained in Reference Example 249(2), 12 g) in toluene is added (1-methoxycarbonylmethylidene)triphenylphosphoran (17.36 g) and the mixture is stirred at 60° C. for 3 hours. The reaction mixture is concentrated and the residue is purified by flash column chromatography on silica gel (Solvent; n-hexane:ethyl acetate=1:1) to give tert-butyl [2-[(1E)-2-(methoxycarbonyl)vinyl]-4-oxo-4H-pyran-3-yl]-oxyacetate (10.99 g, yield; 75%) as colorless crystals. MS (ESI) m/z; 311 [M+H]$^+$, M.p. 115-116° C.

(2) To a solution of the compound obtained in the above step (1) (8.83 g) in tetrahydrofuran (100 mL) is added water (100 mL) and 2N sodium hydroxide solution (20.1 mL) and the mixture is stirred at room temperature for 4 hours. After addition of HCl (23 mL), the reaction mixture is concentrated and the residue (1.0 g) is dissolved in N,N-dimethylformamide (7 mL). To the solution is added N-methylmorpholine (3 mL) and polyphosphoric acid (3.9 mL) and the mixture is stirred at room temperature for 4 days. The reaction mixture is diluted with ethyl acetate and thereto is added a saturated sodium hydrogencarbonate solution and saturated brine. After stirring, the organic layer is separated and the aqueous layer is extracted with ethyl acetate. The organic layers are combined, washed with saturated brine, dried over anhydrous magnesium sulfate and filtered. The filtrate is concentrated and the residue is purified by flash column chromatography on silica gel (Solvent; chloroform:methanol=19:1) to give tert-butyl [2-[(1E)-2-[(4-methylpiperazin-1-yl)carbonyl]vinyl]-4-oxo-4H-pyran-3-yl]oxyacetate (450 mg, yield; 35%) as a yellow crystals. MS (ESI) m/z; 379 [M+H]$^+$, M.p. 124-125° C.

(3) To a solution of the compound obtained in the above step (2) (390 mg) in methylene chloride (5 mL) is added trifluoroacetic acid (2 mL) at 0° C. and the mixture is stirred at room temperature for 5 hours. The reaction mixture is concentrated and thereto is added water. The solution is lyophilized to give [2-[(1E)-2-[(4-methylpiperazin-1-yl)carbonyl]vinyl]-4-oxo-4H-pyran-3-yl]oxyacetic acid (330 mg, yield; 73%) as a colorless powder. MS (ESI) m/z; 323 [M+H]$^+$

REFERENCE EXAMPLE 251

(1) Tert butyl 4-fluoro-3-methylbenzoate (4 g) is treated in the same manner as described in Reference Example 1(1) to give tert-butyl 4-[[2-(dimethylamino)ethyl]-amino]-3-methylbenzoate (1.3 g, yield; 24%) as an oil. MS (APCI) m/z; 279 [M+H]$^+$ (2) To a solution of the compound obtained in the above step (1) (1.3 g) in dioxane (5 mL) is added 4N HCl-dioxane (5 mL) and 5N HCl (3 mL) and the mixture is stirred at 60° C. for 10 minutes. After cooling, the reaction mixture is concentrated in vacuo, and the residue is dissolved in water and lyophilized to give 4-[[2-(dimethylamino)ethyl]amino]-3-methylbenzoate dihydrochloride (1.35 g, yield; 98%) as an amorphous powder. MS (APCI) m/z; 223 [M+H]$^+$

REFERENCE EXAMPLE 252

(1) A mixture of ethyl 4,4,4-trifluoroacetoacetate (23.1 g), urea (7.54 g) and ethyl orthoformate (18.6 g) is stirred at 130° C. under argon gas atmosphere for 1.5 hours. To the reaction mixture is added xylene (100 mL) and the mixture is stirred at 140° C. for 17 hours. The reaction mixture is evaporated to remove solvent and the residue is diluted with methanol. The solution is treated with an activated carbon powder, concentrated in vacuo, and triturated in diisopropylether to give ethyl 2-hydroxy-4-trifluoromethyl-5-pyrimidinecarboxylate (20.3 g, yield; 69%) as crystals. MS (ESI) m/z; 235 [M–H]$^-$ (2) A solution of the compound obtained in the above step (1) (5.0 g) in phosphorus oxychloride (30 mL) is refluxed under heating for 2 hours. The reaction mixture is poured into water with ice and extracted with chloroform. The extract is washed with saturated brine, dried over anhydrous sodium sulfate and concentrated in vacuo. The residue is purified by column chromatography on silica gel (Solvent; n-hexane:ethyl acetate=5:1) to give ethyl 2-chloro-4-trifluoromethyl-5-pyrimidinecarboxylate (4.3 g, yield; 80%) as an oil. MS (GC-EI) m/z; 254 [M$^+$]

(3) To a solution of the compound obtained in the above step (2) (500 mg) in tetrahydrofuran (3 mL) is added a solution of N,N,N'-trimethylethylenediamine (421 mg) in tetrahydrofuran (2 mL) under argon gas atmosphere and the mixture is stirred at room temperature for 1 hour. The reaction mixture is diluted with ethyl acetate, washed successively with a saturated sodium hydrogencarbonate solution, water, and saturated brine. The organic layer is dried over anhydrous sodium sulfate and concentrated in vacuo. The residue is purified by column chromatography on silica gel (Solvent; chloroform:methanol=100:0→50:1) to give ethyl 2-[N-methyl-N-[2-(dimethylamino)ethyl]amino]-4-trifluoromethyl-5-pyrimidinecarboxylate (540 mg, yield; 77%) as an oil. MS (APCI) m/z; 321 [M+H]$^+$

REFERENCE EXAMPLE 253

To a solution of the compound obtained in Reference Example 86(1) (500 mg) in 1,2-dichloroethane (10 mL) is added triethylamine (665 μL), propionaldehyde (688 μL), sodium triacetoxyborohydride (1.68 g), and acetic acid (546 μL) under ice-cooling. The mixture is stirred at room temperature for 3 days. The reaction mixture is diluted with chloroform and thereto is added a saturated sodium hydrogencarbonate solution. The mixture is extracted with chloroform and the extract is concentrated in vacuo. The residue is dissolved in chloroform (6 mL) and thereto is added a solution of di-tert-butyl dicarbonate (690 mg) in chloroform (2 mL) under ice-cooling, and the mixture is stirred at room temperature for 2 hours. The reaction mixture is concentrated in vacuo and the residue is purified by column chromatography on silica gel (Solvent; chloroform:methanol=100:0→90:10) to give methyl trans-4-(dipropylamino) cyclohexanecarboxylate (600 mg, yield; 78%) as an oil. MS (APCI) m/z; 242 [M+H]$^+$

REFERENCE EXAMPLE 254

(1) To a solution of methyl 4-(3-hydroxy-1-propinyl) benzoate (2 g) in methanol (32 mL) is added Lindlar catalyst (238 mg) and the mixture is stirred under hydrogen gas atmosphere at room temperature for 18 hours. To the reaction mixture is added Lindlar catalyst (90 mg) and the mixture is stirred for 1 hour. The reaction mixture is filtered to remove insoluble materials through Celite. The filtrate is concentrated in vacuo and the residue is purified by column chromatography on silica gel (Solvent; n-hexane:ethyl acetate=100:0→50:50) to give methyl 4-(3-hydroxy-1-propenyl)-benzoate (1.5 g, yield; 75%) as an amorphous powder. MS (APCI) m/z; 175 [M+H–H$_2$O]$^+$ (2) To a solution of the compound obtained in the above step (1) (200 mg) in tetrahydrofuran (4 mL) is added triethylamine (218 μL) and methanesulfonyl chloride (105 μL) under ice-cooling and the mixture is stirred for 30 minutes. The reaction mixture is diluted with ethyl acetate and thereto is added 10% citric acid solution. The mixture is extracted with ethyl acetate and the extract is washed successively with water and saturated brine, dried over anhydrous sodium sulfate, and concentrated in vacuo. To the residue is dissolved in dimethylformamide (2 mL) and thereto is added 2M dimethylamine/tetrahydrofuran (2 mL). The mixture is stirred at room temperature for 2 days. The reaction mixture is diluted with ethyl acetate, washed with a saturated sodium hydrogencarbonate solution, and concentrated in vacuo. The residue purified by column chromatography on silica gel (Solvent; chloroform:methanol=100:0→90:10) to give methyl 4-[3-(dimethylamino)-1-propenyl]-benzoate (198 mg, yield; 87%) as an oil. MS (APCI) m/z; 220 [M+H]$^+$

REFERENCE EXAMPLE 255

To a solution of methyl 4-(3-tosyloxypropyl)benzoate (500 mg) in dimethylformamide (3 mL) is added 2M dimethylamine solution in tetrahydrofuran (2.2 mL) and the mixture is stirred at 50° C. for 15 hours. The reaction mixture is diluted with ethyl acetate, washed with a saturated sodium hydrogencarbonate solution and concentrated in vacuo. The residue is purified by column chromatography on silica gel (Solvent; chloroform:methanol=100:0→90:10) to give methyl 4-[3-(dimethylamino)-propyl]benzoate (357 mg, yield; quantitative) as an oil. MS (APCI) m/z; 222 [M+H]$^+$

REFERENCE EXAMPLE 256

Methyl 4-(3-hydroxy-1-propynyl)benzoate is treated in the same manner as described in Reference Example 254(2) to give methyl 4-[3-(1-pyrrolidinyl)-1-propynyl]benzoate (463 mg, yield; 91%) as an oil. MS (APCI) m/z; 244 [M+H]$^+$

REFERENCE EXAMPLE 257

Tert-butyl 4-fluorobenzoate is treated in the same manner as described in Reference Example 251 to give 4-[2-(dimethylamino)ethyl]aminobenzoic acid dihydrochloride as an amorphous powder. MS (APCI) m/z; 209 [M+H]$^+$

REFERENCE EXAMPLES 258 TO 303

The corresponding materials are treated in the same manner as described in either one of the aforementioned Reference Examples to give the compounds as shown in the following Table 39.

TABLE 39 (No. 1)

Structure: R'-cyclohexyl-COOR (trans)

| Ref. Ex. Nos. | R' | R | Physicochemical properties etc. |
|---|---|---|---|
| 258* | pyrrolidin-1-yl | H | amorphous powder MS (APCI) 198 [M + H]+ |
| 259 | 4-methylpiperazin-1-yl | Me | oil MS (APCI) 255 [M + H]+ |
| 260 | N(Me)-CH(Me)2 (N-methyl-N-isopropylamino) | Me | oil MS (APCI) 228 [M + H]+ |
| 261 | pyrrolidin-1-yl | Me | oil MS (APCI) 226 [M + H]+ |
| 262 | Et2N-CH2- | Me | oil MS (APCI) 228 [M + H]+ |
| 263 | MeO-CH2CH2-N(Me)-Et | Me | oil MS (APCI) 244 [M + H]+ |
| 264 | Boc-N(cyclopentyl)- | Me | amorphous powder MS (APCI) 326 [M + H]+ |
| 265 | Boc-N(CH(Me)2)- | Me | amorphous powder MS (APCI) 300 [M + H]+ |
| 266 | Boc-N(n-Pr)- | Me | amorphous powder MS (APCI) 300 [M + H]+ |

*hydrochloride

Me: methyl group, Et: ethyl group, n-Pr: n-propyl group, Boc: tert-butoxycarbonyl group

TABLE 39 (No. 2)

Structure: R'-cyclohexyl-COOR'' (trans)

| Ref. Ex. Nos. | R' | Physicochemical properties etc. |
|---|---|---|
| 267 | 4-methyl-1,4-diazepan-1-yl | oil MS (APCI) 269 [M + H]+ |
| 268 | 2-(piperidin-1-yl)ethyl-N(Me)- | oil MS (APCI) 297 [M + H]+ |
| 269 | Me2N-CH2CH2-N(Me)- | oil MS (APCI) 257 [M + H]+ |
| 270 | 2-(pyridin-2-yl)ethyl-N(Me)- | oil MS (APCI) 291 [M + H]+ |
| 271 | 4-carbamoylpiperidin-1-yl | amorphous powder MS (APCI) 283 [M + H]+ |
| 272 | piperidin-1-yl | amorphous powder MS (APCI) 226 [M + H]+ |
| 273 | morpholin-4-yl | oil MS (APCl) 242 [M + H]+ |
| 274 | piperidin-1-yl | oil MS (APCI) 240 [M + H]+ |

Me: methyl group

TABLE 39

(No. 3)

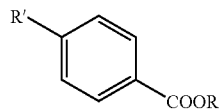

| Ref. Ex. Nos. | R' | R | Physicochemical properties etc. |
|---|---|---|---|
| 275 | Et₂N(Et)Boc [Et-N(Boc)-CH₂-] | Me | amorphous powder MS (APCI) 331 [M + H]+ |
| 276 | Me₂N-CH₂-C(Me)₂-CH₂-N(Me)-C(O)Me | t-Bu | amorphous powder MS (APCI) 349 [M + H]+ |
| 277 | Me₂N-CH₂-C(Me)₂-CH₂-N(Me)-C(O)-cyclopropyl | t-Bu | amorphous powder MS (APCI) 375 [M + H]+ |

*: hydrochloride
Me: methyl group, Et: ethyl group, t-Bu: tert-butyl group

TABLE 39

(No. 4)

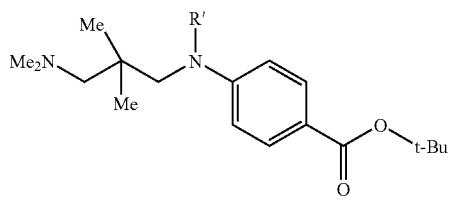

| Ref. Ex. Nos. | R' | Physicochemical properties etc. |
|---|---|---|
| 278 | (E)-Me-CH=CH-C(O)-Me | amorphous powder MS (APCI) 375 [M + H]+ |
| 279 | 2-furyl-C(O)- | amorphous powder MS (APCI) 401 [M + H]+ |
| 280 | cyclopropyl-CH₂-CH₂- | amorphous powder MS (APCI) 361 [M + H]+ |
| 281 | n-Pr | amorphous powder MS (APCI) 349 [M + H]+ |
| 282 | i-Bu | amorphous powder MS (APCI) 363 [M + H]+ |

Me: methyl group, n-Pr: n-propyl group, i-Bu: isobutyl group, t-Bu: tert-butyl group

TABLE 39

(No. 5)

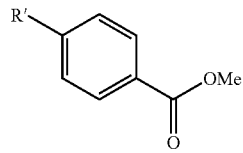

| Ref. Ex. Nos. | R' | Physicochemical properties etc. |
|---|---|---|
| 283 | Boc-HN-(cyclohexyl)-OMe | brown oil MS (APCI) 367 [M + NH₄]+ |
| 284 | Me₂CH-CH₂-CH(NHBoc)-CH₂-OMe | brown oil MS (APCI) 369 [M + NH₄]+ |
| 285 | (Z)-Et₂N-CH₂-CH=CH-CH₃ | amorphous powder MS (APCI) 248 [M + H]+ |
| 286 | (Z)-pyrrolidinyl-CH₂-CH=CH-CH₃ | amorphous powder MS (APCI) 246 [M + H]+ |
| 287 | Et₂N-CH₂CH₂CH₂CH₃ | amorphous powder MS (APCI) 249 [M + H]+ |
| 288 | pyrrolidinyl-CH₂CH₂CH₂CH₃ | amorphous powder MS (APCI) 248 [M + H]+ |
| 289 | Et-N(Me)-Et | amorphous powder MS (APCI) 208 [M + H]+ |

Me: methyl group, Et: ethyl group, Bzl: benzyl group, Boc: tert-butoxycarbonyl group

TABLE 39

(No. 6)

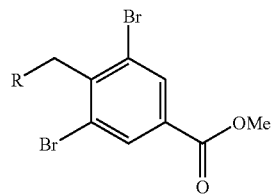

| Ref. Ex. Nos. | R | Physicochemical properties etc. |
|---|---|---|
| 290 | Me₂N— | amorphous powder (APCI) 350/352 [M + H]+ |

TABLE 39-continued

(No. 6)

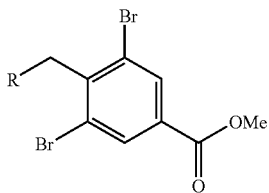

| Ref. Ex. Nos. | R | Physicochemical properties etc. |
|---|---|---|
| 291 | Et$_2$N— | amorphous powder (APCI) 378/380 [M + H]+ |
| 292 | pyrrolidin-1-yl | amorphous powder (APCI) 376/378 [M + H]+ |

Me: methyl group, Et: ethyl group

TABLE 39

(No. 7)

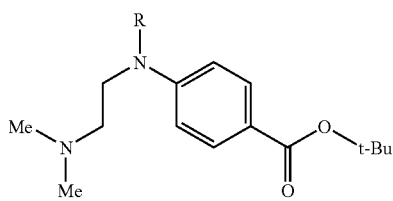

| Ref. Ex. Nos. | R | Physicochemical properties etc. |
|---|---|---|
| 293 | cyclopropylmethyl-CH$_2$- | amorphous powder MS (APCI) 319 [M+H]+ |
| 294 | Me | amorphous powder MS (APCI) 279 [M+H]+ |
| 295 | Et | amorphous powder MS (APCI) 293 [M+H]+ |

Me: methyl group, Et: ethyl group

TABLE 39

(No. 8)

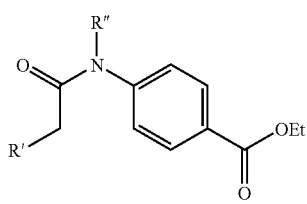

| Ref. Ex. Nos. | R' | R'' | Physicochemical properties etc. |
|---|---|---|---|
| 296 | Et$_2$N— | Me | amorphous powder MS (APCI) 293 [M+H]+ |

TABLE 39-continued

(No. 8)

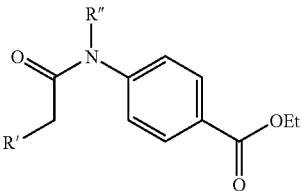

| Ref. Ex. Nos. | R' | R'' | Physicochemical properties etc. |
|---|---|---|---|
| 297 | Me$_2$N-CH$_2$CH$_2$CH$_2$- | benzyl | amorphous powder MS (APCI) 369 [M+H]+ |
| 298 | pyrrolidin-1-yl-propyl | benzyl | amorphous powder MS (APCI) 395 [M+H]+ |
| 299 | piperidin-1-yl-propyl | benzyl | oil MS (APCI) 409 [M+H]+ |

Me: methyl group, Et: ethyl group

TABLE 39

(No. 9)

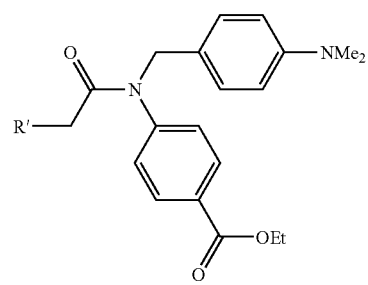

| Ref. Ex. Nos. | R' | Physicochemical properties etc. |
|---|---|---|
| 300 | pyrrolidin-1-yl | oil MS (APCI) 410 [M+H]+ |
| 301 | morpholin-4-yl | oil MS (APCI) 426 [M+H]+ |
| 302 | Me(Et)(Me)N— | oil MS (APCI) 398 [M+H]+ |
| 303 | N-ethyl-pyrrolidin-2-yl | oil MS (APCI) 424 [M+H]+ |

Me: methyl group, Et: ethyl group

REFERENCE EXAMPLE 304

(1) To a solution of 6-oxo-1,4,5,6-tetrahydropyridazine-3-carboxylic acid (20 g) in acetic acid (50 mL) is added 25% hydrobromic acid/acetic acid (200 mL) and thereto is added dropwise dimethylsulfoxide (22.0 g) at room temperature. The mixture is stirred at room temperature for 3 days. The resultant precipitates are collected by filtration, washed successively with acetic acid and water and dried at 40° C. overnight to give 6-oxo-1,6-dihydropyridazine-3-carboxylic acid (10.55 g, yield; 54%) as colorless crystals. MS (ESI) m/z: 139 [M−H]−

(2) To a solution of the compound obtained in the above step (1) (1.0 g) in toluene (5 mL) is added thionyl chloride (3 mL) and two drops of dimethylformamide under ice-cooling, and the mixture is stirred at 80° C. for 3 hours. After cooling, the reaction mixture is concentrated and to the residue is added ether. The resultant crystals are collected by filtration, washed with ether and dried to give ethyl 6-chloro-1,6-dihydropyridazine-3-carboxylate (813 mg, yield; 61%) as a colorless powder. MS (APCI) m/z: 187/189 [M+H]+

REFERENCE EXAMPLE 305

To a solution of ethyl 4-cyclohexanonecarboxylate (5 g), N,N-dimethyl-ethylene-1,2-diamine (6.45 mL) and acetic acid (3.36 mL) in chloroform (50 mL) is added sodium triacetoxyborohydride (9.8 g) under ice-cooling and the mixture is stirred at room temperature overnight. To the reaction mixture is added a saturated sodium hydrogencarbonate solution. After stirring, the mixture is basified with potassium carbonate and extracted with chloroform (×2). The extract is dried and concentrated in vacuo. The resultant crude product is purified by flash column chromatography on silica gel (Biotage, Flash 75M, solvent; chloroform/methano-1/aqueous ammonia=19:1:0.3) to give ethyl 4-(2-dimethylaminoethylamino)cyclohexanecarboxylate (a mixture of cis- and trans-isomer, 6.63 g, yield; 94%) as an oil. MS (APCI) m/z: 243 [M+H]+

REFERENCE EXAMPLE 306

The corresponding compounds are treated in the same manner as described in Reference Example 242 to give ethyl 4-(3-dimethylamino-2,2-dimethylpropoxy)-3-hydroxybenzoate (MS (APCI) m/z: 296 [M+H]+). To a solution of the compound (80 mg) in dimethylformamide (1.5 mL) is added sodium hydride (60% dispersion in mineral oil, 22.7 mg) and the mixture is stirred for 20 minutes. To the mixture is added 4-(2-chloroethyl)morpholine hydrochloride (55.4 mg) and the mixture is stirred at room temperature for one day. The reaction mixture is diluted with water and extracted with chloroform (×3). The extract is concentrated in vacuo and the resultant product is purified by flash column chromatography on NH-silica gel (solvent; ethyl acetate/n-hexane=5:95→25:75) to give ethyl 4-(3-dimethylamino-2,2-dimethyl-propoxy)-3-(2-morpholin-4-iyethoxy)benzoate (53 mg, yield; 70%) as an oil. MS (APCI) m/z: 409 [M+H]+

REFERENCE EXAMPLE 307

To a solution of methyl 6-chloronicotinate (10 g) in N,N-dimethylsulfoxide (15 mL) is added N,N-dimethylethylenediamine (10 mL) and the mixture is stirred at 75° C. overnight. The reaction mixture is diluted with water and extracted with ethyl acetate. The extract is concentrated in vacuo and the resultant product is purified by flash column chromatography on NH-silica gel (solvent; n-hexane/ethyl acetate=1:1) to give methyl 6-[(2-dimethlamino)ethyl]aminonicotinate (4.09 g, yield; 31%) as a yellow liquid. MS (APCI) m/z: 224 [M+H]+

REFERENCE EXAMPLE 308

(1) To a suspension of 1-amino-2-methyl-2-propanethiol hydrochloride (75 mg) in N,N-dimethylformamide (2 mL) is added sodium hydride (60% dispersion in mineral oil, 50 mg) and the mixture is stirred at room temperature for 30 minutes. To the mixture is added tert-butyl 4-fluorobenzoate (50 mg) and the mixture is stirred at 70° C. for 4 hours. The reaction mixture is diluted with water and extracted with ethyl acetate. The extract is concentrated in vacuo and the resultant product is purified by flash column chromatography on NH-silica gel (solvent; ethyl acetate) to give tert-butyl 4-[(2-amino-1,1-dimethylethyl)thio]benzoate (54 mg, yield; 75%) as a colorless oil. MS (APCI) m/z: 282 [M+H]+

(2) The compound obtained in the above step (1) (59 mg) is treated in the same manner as described in Example 618 (1) to give tert-butyl 4-[(2-dimethylamino-1,1-dimethylethyl)thio]benzoate (40 mg, yield; 62%) as a yellow oil. MS (APCI) m/z: 310 [M+H]+

REFERENCE EXAMPLE 309

(1) To a solution of 4-mercaptobenzoic acid (1.5 g) in methanol (20 mL) is added conc. sulfuric acid (0.5 mL) and the mixture is refluxed under heating overnight. The reaction mixture is evaporated to remove solvent and the residue is neutralized with a saturated sodium hydrogencarbonate solution. The mixture is extracted with ethyl acetate and the extract is concentrated in vacuo to give methyl 4-mercaptobenzoate (1.6 g, yield; 99%) as a colorless oil. MS (APCI) m/z: 167 [M−H]−

(2) The compound obtained in the above step (1) (50 mg) is treated in the same manner as described in Example 381 to give methyl 4-[(3-dimethylamino-2,2-dimethylpropyl)thio]benzoate (58 mg, yield; 69%) as a brown oil. MS (APCI) m/z: 282 [M+H]+

REFERENCE EXAMPLE 310

(1) To a solution of diethanolamine (5.0 g) and sodium carbonate (5.5 g) in water (25 mL) is added portionwise 2-nitrobenezenesulfonyl chloride (10.5 g) at 65° C. and the mixture is stirred at 90° C. for 3 hours. The reaction mixture is diluted with water and extracted with ethyl acetate. The extract is concentrated in vacuo and to the residue is added thionyl chloride (10 mL). The mixture is stirred at 90° C. for 2 hours. The reaction mixture is poured into water and the mixture is extracted with chloroform. The extract is concentrated in vacuo and the residue is purified by flash column chromatography on silica gel (solvent; n-hexane/ethyl acetate=4:1) to give N,N-di-(2-chloroethyl)-2-nitrobenzenesulfonamide (7.1 g, yield; 46%) as a yellow liquid. MS (APCI) m/z: 327/329 [M+H]+

(2) The compound obtained in the above step (1) (2.0 g) and methyl trans-4-aminocyclohexanecarboxylate (1.0 g) are treated in the same manner as described in Example 434 (1) to give methyl trans-4-[4-(2-nitrobenzenesulfonyl)piperazin-1-yl]-cyclohexanecarboxylate (1.29 g, yield; 61%) as a yellow oil. MS (APCI) m/z: 412 [M+H]+

REFERENCE EXAMPLE 311

Methyl trans-4-[N-(tert-butoxycarbonyl)-N-[2-(dimethylamino)ethyl]amino]-cyclohexanecarboxylate (compound obtained in Reference Example 114, 2.0 g) is treated in the same manner as described in Example 404 (2) to give methyl trans-4-[N-[2-(dimethylamino)ethyl]amino]cyclohexanecarboxylate (1.5 g, yield; 82%) as colorless crystals. MS (APCI) m/z: 229 [M+H]+

REFERENCE EXAMPLE 312

The corresponding compounds are treated in the same manner as described in Reference Example 256 to give methyl 4-[3-(methylamino)-1-propynyl]benzoate. To a solution of the compound (227 mg) in chloroform (4 mL) is added di-tert-butyl dicarbonate under ice-cooling and the mixture is stirred at room temperature overnight. The reaction mixture is concentrated in vacuo and the resultant product is purified by column chromatography on silica gel (solvent; n-hexane/ethyl acetate=8:1) to give methyl 4-[3-(N-methy-N-tert-butoxycarbonylamino)-1-propynyl]benzoate (225 mg, yield; 86%) as colorless crystals. MS (APCI) m/z: 321 [M+NH$_4$]+

REFERENCE EXAMPLE 313

The corresponding compounds are treated in the same manner as described in Reference Example 254 to give methyl 4-[3-(methylamino)-cis-1-propenyl]benzoate and then the compound (135 mg) is treated in the same manner as described in Reference Example 312 to give methyl 4-[3-(N-methy-N-tert-butoxycarbonylamino)-1-propenyl]benzoate (135 mg, yield; 86%) as colorless crystals. MS (APCI) m/z: 323 [M+NH$_4$]+

REFERENCE EXAMPLE 314

The corresponding compounds are treated in the same manner as described in Reference Example 255 to give methyl 4-[3-(methylamino)propyl]benzoate and then the compound (117 mg) is treated in the same manner as described in Reference Example 312 to give methyl 4-[3-(N-methy-N-tert-butoxycarbonylamino)propyl]-benzoate (123 mg, yield; 90%) as colorless crystals. MS (APCI) m/z: 325 [M+NH$_4$]+

REFERENCE EXAMPLES 315 TO 355

The corresponding materials are treated in the same manner as described in either one of the aforementioned Reference Examples to give the compounds as shown in the following Table 40.

TABLE 40

(No. 1)

R—⟨C$_6$H$_4$⟩—COOMe

| Ref. Ex. Nos. | R | Physicochemical properties etc. |
|---|---|---|
| 315 | CH$_2$=CH-CH$_2$-N(Boc)-CH$_2$-Me | colorless crystals MS (APCI) 337 [M+NH$_4$]+ |
| 316 | CH$_3$-CH$_2$-CH$_2$-N(Boc)-CH$_2$-Me | colorless crystals MS (APCI) 339 [M+NH$_4$]+ |
| 317 | Me-CH$_2$-N(Boc)-CH$_2$-C≡CH | colorless crystals MS (APCI) 335 [M+NH$_4$]+ |

Me: methyl group, Boc: tert-butoxycarbonyl group

TABLE 40

(No. 2)

Me$_2$N-CH$_2$-C(Me)$_2$-CH$_2$-O—⟨C$_6$H$_3$(R)⟩—C(=O)OEt

| Ref. Ex. Nos. | R | Physicochemical properties etc. |
|---|---|---|
| 318 | Me-CH$_2$-N(Me)-CH$_2$-CH$_2$-O-Me | oil MS (APCI) 395 [M+H]+ |
| 319 | Me-N(Me)-CH$_2$-CH$_2$-O-Me | oil MS (APCI) 367 [M+H]+ |
| 320 | (Me)$_2$CH-N(CH(Me)$_2$)-CH$_2$-CH$_2$-O-Me | oil MS (APCI) 423 [M+H]+ |
| 321 | pyrrolidinyl-CH$_2$-CH$_2$-O-Me | oil MS (APCI) 393 [M+H]+ |

TABLE 40-continued

(No. 2)

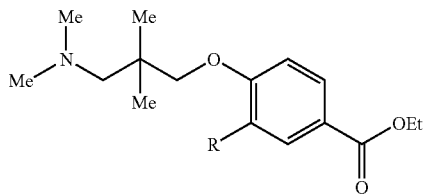

| Ref. Ex. Nos. | R | Physicochemical properties etc. |
|---|---|---|
| 322 | ![piperidine-ethyl-OMe] | oil MS (APCI) 407 [M+H]+ |
| 323 | Me$_2$N-CH$_2$CH$_2$CH$_2$-OMe | oil MS (APCI) 381 [M+H]+ |

Me: methyl group

TABLE 40

(No. 3)

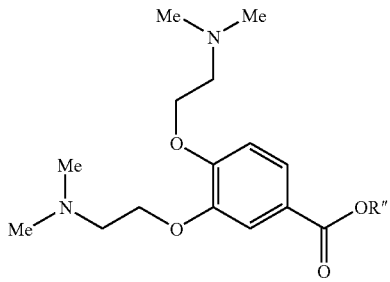

| Ref. Ex. Nos. | R″ | Physicochemical properties etc. |
|---|---|---|
| 324 | Et | oil MS (APCI) 325 [M+H]+ |

Me: methyl group, Et: ethyl group

TABLE 40

(No. 4)

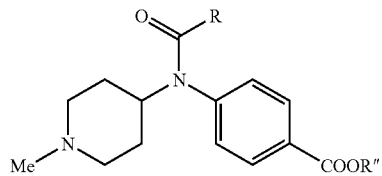

| Ref. Ex. Nos. | R | R″ | Physicochemical properties etc. |
|---|---|---|---|
| 325 | Me | Et | amorphous powder MS (APCI) 305 [M+H]+ |
| 326 | cyclopropyl | Et | oil MS (APCI) 331 [M+H]+ |

TABLE 40-continued

(No. 4)

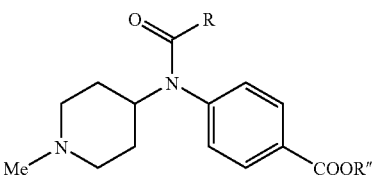

| Ref. Ex. Nos. | R | R″ | Physicochemical properties etc. |
|---|---|---|---|
| 327 | 5-methylfuran-2-yl | Et | amorphous powder MS (APCI) 357 [M+H]+ |

Me: methyl group, Et: ethyl group

TABLE 40

(No. 5)

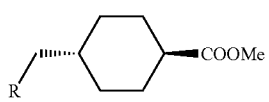

| Ref. Ex. Nos. | R | Physicochemical properties etc. |
|---|---|---|
| 328 | N(Me)(CH$_2$CH$_2$OH)(CH$_2$-) | oil MS (ESI) 244 [M+H]+ |
| 329 | N-methylazocan-1-yl | oil MS (ESI) 268 [M+H]+ |
| 330 | 1,3,3-trimethylpiperidinyl | oil MS (ESI) 268 [M+H]+ |
| 331 | 4-hydroxy-1-piperidinyl | oil MS (ESI) 256 [M+H]+ |
| 332 | 1-methylazepan-1-yl | oil MS (ESI) 254 [M+H]+ |
| 333 | N-methyl-N,N-diisopropylamino | oil MS (ESI) 256 [M+H]+ |
| 334 | N-methyl-N-(1-phenylethyl)amino derivative | oil MS (ESI) 304 [M+H]+ |

TABLE 40-continued (No. 5)

Structure: R-CH2-cyclohexyl-COOMe (trans)

| Ref. Ex. Nos. | R | Physicochemical properties etc. |
|---|---|---|
| 335 | N-methylpyrrolidin-2-yl-CH2-OMe | oil MS (ESI) 270 [M+H]+ |
| 336 | (Me)(Me)CH-N(Me)-CH2-Me (N,N-methyl-ethyl-isopropylamine) | oil MS (ESI) 242 [M+H]+ |
| 337 | (MeO-CH2-CH2)2-N-Me | oil MS (ESI) 288 [M+H]+ |
| 338 | (Me)2CH-N(Me)-CH2-CH2-OH | oil MS (ESI) 258 [M+H]+ |

Me: methyl group

TABLE 40

(No. 6)

Structure: R-CH2-cyclohexyl-COOMe (trans)

| Ref. Ex. Nos. | R | Physicochemical properties etc. |
|---|---|---|
| 339 | Me2N-C(Me)3 (N,N-dimethyl-tert-butylamine) | oil MS (ESI) 242 [M+H]+ |
| 340 | 1-acetyl-4-methylpiperazine | oil MS (ESI) 283 [M+H]+ |
| 341 | Me-N(CH2-C(Me)3) | oil MS (ESI) 256 [M+H]+ |

TABLE 40-continued (No. 6)

Structure: R-CH2-cyclohexyl-COOMe (trans)

| Ref. Ex. Nos. | R | Physicochemical properties etc. |
|---|---|---|
| 342 | 2,6-dimethyl-4-methylmorpholine | oil MS (ESI) 270 [M+H]+ |
| 343 | MeO-CH2-CH2-N(Me)-C(Me)3 | oil MS (ESI) 286 [M+H]+ |
| 344 | 1-(1-methylethyl)-4-methylpiperazine | oil MS (ESI) 283 [M+H]+ |
| 345 | 2-methylisoindoline | oil MS (ESI) 274 [M+H]+ |
| 346 | EtO-CH2-CH2-(4-methylpiperazin-1-yl) | oil MS (ESI) 313 [M+H]+ |
| 347 | 3-(dimethylamino)-1-methylpyrrolidine | oil MS (ESI) 269 [M+H]+ |
| 348 | HO-C(Me)2-CH2-N(Me)-CH(Me)2 | oil MS (ESI) 286 [M+H]+ |
| 349 | HO-CH2-CH2-N(Me)-C(Me)3 | oil MS (ESI) 272 [M+H]+ |

Me: methyl group, Et: ethyl group

TABLE 40

(No. 7)

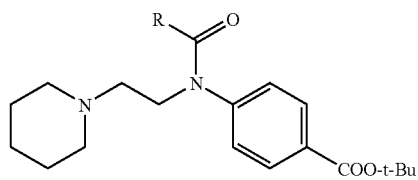

| Ref. Ex. Nos. | R | Physicochemical properties etc. |
|---|---|---|
| 350 | t-Bu | oil<br>MS (ESI) 389 [M+H]+ |
| 351 | MeO~ | oil<br>MS (ESI) 377 [M+H]+ |
| 352 | 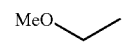 | oil<br>MS (ESI) 399 [M+H]+ |
| 353 | Me | oil<br>MS (ESI) 347 [M+H]+ |
| 354 | Me~ | oil<br>MS (ESI) 373 [M+H]+ |
| 355 | 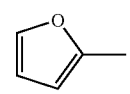 | oil<br>MS (ESI) 373 [M+H]+ |

Me: methyl group, t-Bu: tert-butyl group

REFERENCE EXAMPLES 356 TO 357

The corresponding materials are treated in the same manner as described in either one of the aforementioned Reference Examples to give the compounds as shown in the following Table 41.

TABLE 41

R¹COOR"

| Ref. Ex. Nos. | R¹ | R" | Physicochemical properties etc. |
|---|---|---|---|
| 356 | 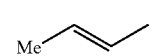 | t-Bu | oil<br>MS (APCI)<br>305<br>[M + H]+ |
| 357 |  | Et | oil<br>MS (APCI)<br>263<br>[M + H]+ |

Me: methyl group, Et: ethyl group, t-Bu: tert-butyl group

The invention claimed is:

1. A compound of the formula [I]:

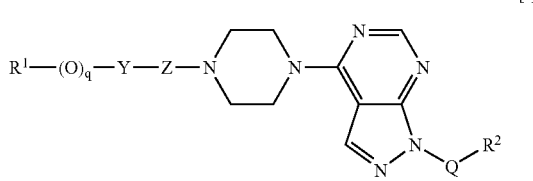

wherein R¹ is
(A) 6- to 10-membered, mono- or bicyclic aryl group substituted by one to three groups selected from the group consisting of (i) a hydroxyl group; (ii) a halogen atom; (iii) a $C_{1-6}$ alkyl group; (iv) an amino group optionally substituted by one or two groups selected from a $C_{1-6}$ alkyl group optionally substituted by a hydroxyl group, a $C_{1-6}$ alkoxy-$C_{1-6}$ alkyl group, an amino-$C_{2-7}$ alkanoyl group optionally substituted by a group selected from a $C_{1-6}$ alkyl group, a $C_{2-7}$ alkoxycarbonyl group and a group of the formula:

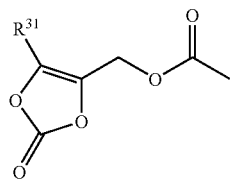

in which $R^{31}$ is a $C_{1-6}$ alkyl group at the amino moiety, a (mono- or di-$C_{1-6}$ alkyl)amino-$C_{2-7}$ alkyl group, a (mono- or di-$C_{1-6}$ alkyl)carbamoyl group, a $C_{2-7}$ alkanoyl group optionally substituted by a hydroxyl group, a $C_{3-8}$ cycloalkyl-carbonyl group, a $C_{1-6}$ alkoxy-$C_{2-7}$ alkanoyl group, a $C_{1-6}$ alkoxy-$C_{2-7}$ alkoxycarbonyl group, a $C_{3-8}$ cycloalkyl-$C_{1-6}$ alkyl group, a $C_{1-6}$ alkylsulfonyl group, a phenyl alkyl group optionally substituted by a (mono- or di-$C_{1-6}$ alkyl)amino group, a $C_{2-8}$ alkenoyl group, a thiocarbamoyl group optionally substituted by a $C_{1-6}$ alkyl group, a 5- to 14-membered, mono- or bicyclic heteroaryl-carbonyl group having at least one heteroatom selected from nitrogen atom, sulfur atom and oxygen atom, a 4- to 8-membered nitrogen-containing aliphatic heteromonocyclic group-substituted $C_{1-6}$ alkyl group, a 4- to 8-membered nitrogen-containing aliphatic heteromonocyclic group-substituted $C_{2-7}$ alkanoyl group, a phenylsulfonyl group optionally substituted by a (mono- or di-$C_{1-6}$ alkyl) amino group at the phenyl moiety; a group of the formula:

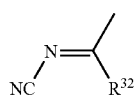

in which $R^{32}$ is a $C_{1-6}$ alkoxy group and a 4- to 8-membered nitrogen-containing aliphatic heteromonocyclic group optionally substituted by a $C_{1-6}$ alkyl group, (v) a $C_{1-6}$ alkoxy group optionally substituted by a group selected from an amino group (said amino group being optionally substituted by a group(s) selected from a $C_{1-6}$ alkyl group, and a phenyl $C_{1-6}$ alkyl group), a 5- to 14-membered, mono- or bicyclic heteroaryl group having at least one heteroatom selected from nitrogen atom, sulfur atom and oxygen atom and optionally substituted by a $C_{1-6}$ alkyl group and a 4- to 8-membered nitrogen-containing aliphatic heteromonocyclic group optionally substituted by a $C_{1-6}$ alkyl group; (vi) an amino-$C_{1-6}$ alkyl group optionally substituted by a group selected from a $C_{1-6}$ alkyl group optionally substituted by a hydroxyl group, a $C_{2-7}$ alkanoyl group, a (mono- or di-$C_{1-6}$ alkyl)amino-$C_{1-6}$ alkyl group, a (mono- or di-$C_{1-6}$ alkyl)amino-$C_{2-7}$ alkoxycarbonyl group, a $C_{1-6}$ alkoxy-$C_{2-7}$ alkanoyl group, a (mono- or di-$C_{1-6}$ alkyl)carbamoyl group, a $C_{1-6}$ alkoxy-$C_{2-7}$ alkoxycarbonyl group, a $C_{1-6}$ alkoxy-$C_{1-6}$ alkyl group, a $C_{3-8}$ cycloalkylcarbonyl group, a phenyl-$C_{1-6}$ alkyl group, a $C_{3-8}$ cycloalkyl group, a $C_{3-8}$ cycloalkyl-$C_{1-6}$ alkyl group, a 4- to 8-membered nitrogen-containing aliphatic heteromonocyclic group-substituted alkoxycarbonyl group and a group of the formula:

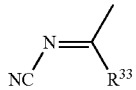

in which $R^{33}$ is an amino group, a (mono- or di-$C_{1-6}$ alkyl)amino group or a (mono- or di-$C_{1-6}$ alkyl)amino-$C_{1-6}$ alkylamino group; (vii) a 4- to 8-membered nitrogen-containing aliphatic heteromonocyclic group-substituted $C_{1-6}$ alkyl group optionally substituted by a group selected from a hydroxyl group, a $C_{1-6}$ alkyl group optionally substituted by a hydroxyl group, a $C_{1-6}$ alkoxy-$C_{1-6}$ alkyl group and a carbamoyl group; (viii) a carbamoyl group optionally substituted by a group selected from a $C_{1-6}$ alkyl group, a (mono- or di-$C_{1-6}$ alkyl)amino-$C_{1-6}$ alkyl group, a $C_{1-6}$ alkyl group substituted by a 5- to 14-membered, mono- or bicyclic heteroaryl group having at least one heteroatom selected from nitrogen atom, sulfur atom and oxygen atom and a 4- to 8-membered nitrogen-containing aliphatic heteromonocyclic group-substituted $C_{1-6}$ alkyl group; (ix) a 4- to 8-membered nitrogen-containing aliphatic heteromonocyclic group optionally substituted by a $C_{1-6}$ alkyl group (said nitrogen-containing aliphatic heteromonocyclic group may bond to the aryl moiety via an oxygen atom); (x) a nitro group; (xi) a $C_{3-8}$ cycloalkyl-oxy group optionally substituted by a (mono- or di-$C_{1-6}$ alkyl)amino group; (xii) a $C_{2-7}$ alkenyl group optionally substituted by a group selected from a (mono- or di-$C_{1-6}$ alkyl)amino group and a 4- to 8-membered nitrogen-containing aliphatic heteromonocyclic group; (xiii) a $C_{2-7}$ alkynyl group optionally substituted by a group(s) selected from a (mono- or di-$C_{1-6}$ alkyl)amino group and a 4- to 8-membered nitrogen-containing aliphatic heteromonocyclic group; (xiv) a $C_{1-6}$ alkylthio group optionally substituted by a (mono- or di-$C_{1-6}$ alkyl)amino group; and (xv) a $C_{3-8}$ cycloalkyl-$C_{1-6}$ alkoxy group optionally substituted by a (mono- or di-$C_{1-6}$ alkyl)amino group at the cycloalkyl moiety, (B) a 4- to 8-membered nitrogen-containing aliphatic heteromonocyclic group optionally substituted by a group selected from a $C_{1-6}$ alkyl group, a 4- to 8-membered nitrogen-containing aliphatic heteromonocyclic group-substituted $C_{2-7}$ alkanoyl group, a (mono- or di-$C_{1-6}$ alkyl)amino-$C_{2-7}$ alkanoyl group, a $C_{1-6}$ alkoxy-$C_{1-6}$ alkyl group, a (mono- or di-$C_{1-6}$ alkyl)amino-$C_{1-6}$ alkyl group, a $C_{3-8}$ cycloalkyl group, a 5- to 14-membered, mono- or bicyclic heteroaryl group having at least one heteroatom selected from nitrogen atom, sulfur atom and oxygen atom, a 4- to 8-membered nitrogen-containing aliphatic heteromonocyclic group optionally containing one or more double bond in the ring moiety and optionally substituted by a group(s) selected from a $C_{1-6}$ alkyl group, a $C_{1-6}$ alkoxy-$C_{1-6}$ alkyl group, a carbamoyl group and a $C_{2-7}$ alkanoylamino group and an amino group optionally substituted by a group(s) selected from a $C_{1-6}$ alkyl group, a (mono- or di-$C_{1-6}$ alkyl)amino group, a $C_{3-8}$ cycloalkylcarbonyl group, a $C_{2-8}$ alkenoyl group, a 5- to 14-membered, mono- or bicyclic heteroaryl-carbonyl group having at least one heteroatom selected from nitrogen atom, sulfur atom and oxygen atom, a $C_{1-6}$ alkoxy-$C_{1-6}$ alkyl group, a $C_{2-7}$ alkanoyl group and a 4- to 8-membered nitrogen-containing aliphatic heteromonocyclic group, (C) a $C_{3-8}$ cycloalkyl group substituted by a group selected from a group consisting of (i) an amino group optionally substituted by a group selected from a $C_{1-6}$ alkyl group, a (mono- or di-$C_{1-6}$ alkyl)amino-$C_{2-7}$ alkanoyl group, a 4- to 8-membered nitrogen-containing aliphatic heteromonocyclic group-substituted $C_{2-7}$ alkanoyl group, a mono- or di-$C_{1-6}$ alkyl)amino-$C_{1-6}$ alkyl group, a $C_{2-7}$ alkanoyl group, a $C_{3-8}$ cycloalkylcarbonyl group, a $C_{2-8}$ alkenoyl group, a 5- to 14-membered, mono- or bicyclic heteroaryl-carbonyl group having at least one heteroatom selected from nitrogen atom, sulfur atom and oxygen atom, a phenylcarbonyl group optionally substituted by a halogen atom(s), a $C_{1-6}$ alkyl-thiocarbamoyl group, an alkoxycarbonyl group, a cycloalkyl group, a group of the formula:

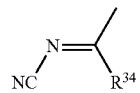

in which $R^{34}$ is a (mono- or di-$C_{1-6}$ alkyl)amino group, a $C_{3-8}$ cycloalkyl-$C_{1-6}$ alkyl group and a $C_{1-6}$ alkylsulfonyl group; (ii) an amino-$C_{1-6}$ alkyl group optionally substituted by a group selected from a $C_{1-6}$ alkyl group optionally substituted by a hydroxyl group, a (mono- or di-$C_{1-6}$ alkyl)amino-$C_{2-7}$ alkanoyl group, a 4- to 8-membered nitrogen-containing aliphatic heteromonocyclic group-substituted $C_{2-7}$ alkanoyl group, a 4- to 8-membered nitrogen-containing aliphatic heteromonocyclic group-substituted $C_{1-6}$ alkyl group, a (mono- or di-$C_{1-6}$ alkyl)amino-$C_{1-6}$ alkyl group, a $C_{1-6}$ alkyl group substituted by a 5- to 14-membered, mono- or bicyclic heteroaryl group having at least one heteroatom selected from nitrogen atom, sulfur atom and oxygen atom, a $C_{1-6}$ alkoxy-$C_{1-6}$ alkyl group, a $C_{2-7}$ alkanoyl group, a 5- to 14-membered, mono- or bicyclic heteroaryl-carbonyl group having at least one heteroatom selected from nitrogen atom, sulfur atom and oxygen atom (the heteroaryl moiety of said group is optionally substituted by a $C_{1-6}$ alkyl group), a $C_{3-8}$ cycloalkyl-carbonyl group, a phenyl-$C_{1-6}$ alkyl group, a $C_{3-8}$ cycloalkyl group, a $C_{1-6}$ cycloalkyl-$C_{1-6}$ alkyl group, a $C_{1-6}$ alkylsulfonyl group, a $C_{2-7}$ alkoxycarbonyl group, a mono- or di-$C_{1-6}$ alkylcarbamoyl group and an phenylcarbonyl group optionally substituted by a group(s) selected from a halogen atom and a $C_{1-6}$ alkoxy group, a $C_{1-6}$ alkoxy-$C_{2-7}$ alkanoyl group and a $C_{2-7}$ alkanoyl group; (iii) a 4- to 8-membered nitrogen-containing aliphatic heteromonocyclic group optionally substituted by a group(s) selected from a hydroxyl group, a $C_{1-6}$ alkyl group, a $C_{2-7}$ alkanoyl group and a $C_{1-6}$ alkoxy-$C_{1-6}$ alkyl group; (iv) a 4- to 8-membered nitrogen-containing aliphatic heteromonocyclic group-substituted $C_{1-6}$ alkyl group (said nitrogen-containing aliphatic heteromonocyclic group is optionally fused to a benzene ring and optionally substituted by a group selected from a $C_{1-6}$ alkyl group, a carbamoyl (or thiocarbamoyl) group, a hydroxyl group, a $C_{1-6}$ alkoxy-$C_{1-6}$ alkyl group, a $C_{2-7}$ alkanoyl group and a (mono- or di-$C_{1-6}$ alkyl)amino group); (v) a mono- or di-$C_{1-6}$ alkylamino-$C_{1-6}$ alkoxy group; and (vi) a carbamoyl group optionally substituted by a group(s) selected from a 4- to 8-membered nitrogen-containing aliphatic heteromonocyclic group-substituted $C_{1-6}$ alkyl group optionally substituted by a $C_{1-6}$ alkyl group, a (mono- or di-$C_{1-6}$ alkyl)amino group and a $C_{1-6}$ alkyl group, (D) an amino group optionally substituted by a $C_{1-6}$ alkyl group, or (E) a 5- to 14-membered, mono- or bicyclic heteroaryl group having least one heteroatom selected from nitrogen atom, sulfur atom and oxygen atom, optionally substituted by a group selected from (i) an amino-$C_{1-6}$ alkyl group optionally substituted by a group(s) selected from a $C_{1-6}$ alkyl group and a $C_{1-6}$ alkoxy-$C_{1-6}$ alkyl group; (ii) an amino group optionally substituted by a group selected from a $C_{3-8}$ cycloalkyl-carbonyl group, a (mono- or di-$C_{1-6}$ alkyl)amino-$C_{1-6}$ alkyl group, a $C_{2-7}$ alkanoyl group, a $C_{2-8}$ alkenoyl group, a (mono- or di-$C_{1-6}$ alkyl)thiocarbamoyl group, a (mono- or di-$C_{1-6}$ alkyl)carbamoyl group and a $C_{1-6}$ alkyl group; (iii) a carbamoyl group optionally substituted by a group selected from a $C_{1-6}$ alkyl group, a 4- to 8-membered nitrogen-containing aliphatic heteromonocyclic group-substituted $C_{1-6}$ alkyl group and a (mono- or di-$C_{1-6}$ alkyl)amino-$C_{1-6}$ alkyl group; (iv) a $C_{1-6}$ alkyl group optionally substituted by a halogen atom(s); (v) a (mono- or di-$C_{1-6}$ alkyl)amino-$C_{1-6}$ alkoxy group; (vi) an oxo group; and (vii) a group of the following formula:

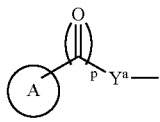

wherein ring A is a 4- to 8-membered nitrogen-containing aliphatic heteromonocyclic group optionally substituted by a $C_{1-6}$ alkyl group and optionally fused to a benzene ring, $Y^a$ is a single bond, a $C_{1-6}$ alkylene group or a $C_{2-7}$ alkenylene group and p is an integer of 0 or 1, $R^2$ is (a) a 5- to 14-membered, mono- or bycyclic heteroaryl group having at least one heteroatom selected from nitrogen atom, sulfur atom and oxygen atom, optionally substituted by the same or different one to three groups selected from a $C_{1-6}$ alkyl group, a $C_{1-6}$ alkoxy group and a (mono- or di-$C_{1-6}$ alkyl)amino group or (b) a 6- to 10-membered, mono- or bycyclic aryl group optionally substituted by the same or different one to three groups selected from a $C_{1-6}$ alkyl group, a halogen atom, a halogeno-$C_{1-6}$ alkoxy group, a (mono- or di-$C_{1-6}$ alkyl)amino group, a $C_{1-6}$ alkoxy group, a nitro group, a $C_{1-6}$ alkoxy-$C_{1-6}$ alkyl group, a hydroxyl group, a $C_{2-7}$ alkanoyl group and a $C_{2-7}$ alkoxycarbonyl group, Y is a single bond, a $C_{1-6}$ alkylene group or a $C_{2-8}$ alkenylene group, Z is a group of the formula: —CO—, —CH$_2$—, —SO$_2$— or

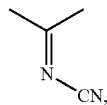

Q is a $C_{1-6}$ alkylene group, and q is an integer of 0 or 1 or a pharmaceutically acceptable salt thereof.

2. The compound according to claim 1 in which the aryl group in $R^1$ and $R^2$ is phenyl group or naphthyl group.

3. The compound according to claim 1 in which the 4- to 8-membered nitrogen-containing aliphatic heteromonocyclic group is an azetidinyl group, a pyrrolidinyl group, an imidazolidinyl group, a pyrazolidinyl group, a piperidyl group, a piperazinyl group, an azepinyl group, a diazepinyl group, an azeocinyl group, a diazeocinyl group, a 3-pyrrolinyl group or a morpholinyl group.

4. The compound according to claim 1 in which the heteroaryl group in $R^1$ and $R^2$ is a 5- to 10-membered mono- or bicyclic heteroaryl group.

5. The compound according to claim 4 in which the heteroaryl group is a nitrogen-containing heteroaryl group selected from a pyrrolyl group, an imidazolyl group, a pyrazolyl group, an oxazolyl group, a thiazolyl group, an isothiazolyl group, an isoxazolyl group, a pyridyl group, a dihydropyridyl group, a pyrazinyl group, a pyrimidinyl group, a tetrahydropyrimidinyl group, a furopyrimidinyl group, a pyridazinyl group, an imidazolidinyl group, an indolyl group, a quinolyl group, an isoquinolyl group, a purinyl group, a 1H-indazolyl group, a quinazolinyl group, a cinnolinyl group, a quinoxalinyl group, a phthalazinyl group and a pteridinyl group or an oxygen- or sulfur-containing heteroaryl group selected from a furyl group, a pyranyl group, a thienyl group, a benzofuryl group and a benzothienyl group.

6. The compound according to claim 5 in which Y is a single bond, a $C_{1-6}$ alkylene group or a $C_{2-7}$ alkenylene group, Z is —CO—, $R^2$ is a phenyl group substituted by a group selected from a $C_{1-6}$ alkoxy group, a $C_{1-6}$ alkyl group and a halogen atom, a $C_{1-6}$ alkoxy group-substituted 5- to 10-membered, mono- or bycyclic heteroaryl group having least one heteroatom selected from nitrogen atom, sulfur atom and oxygen atom or a $C_{1-6}$ alkyl group-substituted 5- to 10-membered, mono- or bycyclic heteroaryl group having at least one heteroatom selected from nitrogen atom, sulfur atom and oxygen atom and q is an integer of 0.

7. The compound according to claim 5 in which Y is a single bond, Z is —CH$_2$—, $R^2$ is a $C_{1-6}$ alkoxyphenyl group and q is an integer of 0.

8. The compound according to claim 6 in which $R^1$ is
(a) a phenyl group substituted by a group selected from (i) a $C_{1-6}$ alkoxy group substituted by a group selected from a (mono- or di-$C_{1-6}$ alkyl)amino group and a 4- to 8-membered nitrogen-containing aliphatic heteromonocyclic group, (ii) a $C_{1-6}$ alkyl group substituted by a group selected from a (mono- or di-$C_{1-6}$ alkyl)amino group and a 4- to 8-membered nitrogen-containing aliphatic heteromonocyclic group, and (iii) an amino group substituted by a group selected from a $C_{1-6}$ alkyl group, a $C_{3-8}$ cycloalkyl-carbonyl group, a (mono- or di-$C_{1-6}$ alkyl)amino-$C_{1-6}$ alkyl group, a $C_{1-6}$ alkoxy-$C_{2-7}$ alkoxycarbonyl group, a 4- to 8-membered nitrogen-containing aliphatic heteromonocyclic group-substituted $C_{1-6}$ alkyl group, a $C_{2-7}$ alkanoyl group and a $C_{1-6}$ alkenoyl group, (b) a $C_{3-8}$ cycloalkyl group substituted by a group selected from (i) an amino-$C_{1-6}$ alkyl group optionally substituted by a group(s) selected from a $C_{1-6}$ alkyl group, a hydroxy-$C_{1-6}$ alkyl group, a (mono- or di-$C_{1-6}$ alkyl)amino-$C_{1-6}$ alkyl) group, a $C_{12-7}$ alkanoyl group, a $C_{3-8}$ cycloalkyl-carbonyl group and a $C_{1-6}$ alkoxy-$C_{1-6}$ alkyl group; (ii) a 4- to 8-membered nitrogen-containing aliphatic heteromonocyclic group optionally substituted by a hydroxyl group; and (iii) an amino group substituted by a group selected from a $C_{1-6}$ alkyl group, a (mono- or di-$C_{1-6}$ alkyl)amino-$C_{1-6}$ alkyl group, a $C_{2-7}$ alkanoyl group, a 5- to 10-membered, a mono- or bicyclic heteroaryl-carbonyl group having at least one heteroatom selected from nitrogen atom, sulfur atom and oxygen atom, a $C_{1-6}$ alkylsulfonyl group and a $C_{1-6}$ alkyl-thiocarbamoyl group, or (c) a 4- to 8-membered nitrogen-containing aliphatic heteromonocyclic group substituted by a group selected from (i) a $C_{1-6}$ alkyl group, (ii) an amino group optionally substituted by a group selected from a $C_{1-6}$ alkyl group, a (mono- or di-$C_{1-6}$ alkyl)amino-$C_{1-6}$ alkyl group and a $C_{3-8}$ cycloalkyl-carbonyl group and (iii) a 4- to 8-membered nitrogen-containing aliphatic heteromonocyclic group substituted by a $C_{1-6}$ alkyl group, $R^2$ is a phenyl group substituted by a group selected from a halogen atom and a $C_{1-6}$ alkoxy group, a $C_{1-6}$ alkyl-substituted 5- to 10-membered heteroaryl group having at least one heteroatom selected from nitrogen atom, sulfur atom and oxygen atom or a $C_{1-6}$ alkoxy-substituted 5- to 10-membered heteroaryl group having at least one heteroatom selected from nitrogen atom, sulfur atom and oxygen atom and Q is methylene group.

9. The compound according to claim 6 in which the group of the formula: $R^1$—$(O)_q$—Y-Z- is a 4-(mono- or di-$C_{1-6}$ alkylamino-$C_{1-6}$ alkyl)benzoyl group; a 4-(pyrrolidino-$C_{1-6}$ alkyl)benzoyl group; a 4-(di-$C_{1-6}$ alkylamino-$C_{1-6}$ alkoxy)benzoyl group; a 3-(di-$C_{1-6}$ alkylamino-$C_{1-6}$ alkoxy)-4-(di-$C_{1-6}$ alkylamino-$C_{1-6}$ alkoxy)benzoyl group; a 4-(piperidino-$C_{1-6}$ alkoxy)benzoyl group; a 4-[N-$C_{1-6}$ alkyl-N-(di-$C_{1-6}$ alkylamino-$C_{1-6}$ alkyl)amino]benzoyl group; a 4-[N-$C_{2-7}$ alkanoyl-N-(di-$C_{1-6}$ alkylamino-$C_{1-6}$ alkyl)amino]benzoyl group; a 4-[N-$C_{2-8}$ alkenoyl-N-(di-$C_{1-6}$ alkylamino-$C_{1-6}$ alkyl)amino]benzoyl group; a 4-[N-($C_{3-8}$ cycloalkylcarbonyl)-N-(di-$C_{1-6}$ alkylamino-$C_{1-6}$ alkyl)amino]benzoyl group; a 4-[N-($C_{1-6}$ alkoxy-$C_{2-7}$ alkoxycarbonyl)-N-(di-$C_{1-6}$ alkylamino-$C_{1-6}$ alkyl)amino]benzoyl group; a 4-[N-$C_{2-7}$ alkanoyl-N-(pyrrolidino-$C_{1-6}$ alkyl)amino]benzoyl group; a [1-($C_{1-6}$ alkyl)piperidin-4-yl]carbonyl group; a 4-[N-$C_{1-6}$ alkyl-N-(di-$C_{1-6}$ alkylamino-$C_{1-6}$ alkyl)amino]piperidinocarbonyl group; a 4-[N-($C_{3-8}$ cycloalkylcarbonyl)-N-(di-$C_{1-6}$ alkylamino-$C_{1-6}$ alkyl)amino]-piperidinocarbonyl group; a 4-[4-(di-$C_{1-6}$ alkyl)piperidino]piperidinocarbonyl group; a [1-($C_{1-6}$ alkyl)piperidin-4-yl]-$C_{2-7}$ alkanoyl group; a [1-($C_{1-6}$ alkyl)piperidin-4-yl]-$C_{2-8}$ alkenoyl group; a 4-(di-$C_{1-6}$ alkylamino-$C_{1-6}$ alkyl)cyclohexylcarbonyl group; a 4-(mono- or di-$C_{1-6}$ alkylamino)cyclohexylcarbonyl group; a 4-[N-$C_{2-7}$ alkanoyl-N-(di-$C_{1-6}$ alkylamino-$C_{1-6}$ alkyl)amino]cyclohexylcarbonyl group; a 4-[N-$C_{2-8}$ alkenoyl-N-(di-$C_{1-6}$ alkylamino-$C_{1-6}$ alkyl)amino]cyclohexylcarbonyl group; a 4-[N-unsubstituted 5- to 10-membered, mono- or bycyclic heteroaryl)-carbonyl-N-(di-$C_{1-6}$ alkylamino-$C_{1-6}$ alkyl)amino]cyclohexylcarbonyl group; a 4-[N-$C_{1-6}$ alkylthiocarbamoyl-N-(di-$C_{1-6}$ alkylamino-$C_{1-6}$ alkyl)amino]-cyclohexylcarbonyl group; a 4-[N-(di-$C_{1-6}$ alkylamino-$C_{1-6}$ alkyl)-N-($C_{1-6}$ alkylsulfonyl)-amino]cyclohexylcarbonyl group; a 4-[[N-$C_{1-6}$ alkyl-N-(hydroxy-$C_{1-6}$ alkyl)amino]$C_{1-6}$ alkyl]cyclohexylcarbonyl group; a 4-[[N-$C_{1-6}$ alkyl-N-($C_{1-6}$ alkoxy-$C_{1-6}$ alkyl)amino]-$C_{1-6}$ alkyl]cyclohexylcarbonyl group; a 4-[[N-$C_{2-7}$ alkanoyl-N-(di-$C_{1-6}$ alkylamino-$C_{1-6}$ alkyl)amino]$C_{1-6}$ alkyl]cyclohexylcarbonyl group; a 4-[[N-($C_{3-8}$ cycloalkyl-carbonyl)-N-(di-$C_{1-6}$ alkylamino-$C_{1-6}$ alkyl)amino]$C_{1-6}$ alkyl]cyclohexylcarbonyl group; a 4-(pyrrolidino)cyclohexylcarbonyl group; a 4-(hydroxypyrrolidino)cyclohexylcarbonyl group; or a 4-(piperidino)cyclohexylcarbonyl group, and $R^2$ is a phenyl group substituted by one or two groups selected from an ethoxy group and a fluorine atom, an ethoxypyridyl group, a propylpyridyl group or a propylthiazolyl group.

10. The compound according to claim 8 in which $R^2$ is 3-ethoxyphenyl group, 6-propylpyridin-2-yl group, 6-ethoxypyridin-2-yl group, 2-propyl-1,3-thiazol-4-yl group or 3-ethoxy-2-fluorophenyl group.

11. The compound according to claim 1 which is
1-(3-ethoxybenzyl)-4-[4-[4-[2-(dimethylamino)ethoxy] benzoyl]piperazin-1-yl]-1H-pyrazolo[3,4-d]pyrimidine;

1-(3-ethoxybenzyl)-4-[4-[4-[2-(1-piperidyl)ethoxy]benzoyl]piperazin-1-yl]-1H-pyrazolo-[3,4-d]pyrimidine;

1-(3-ethoxybenzyl)-4-[4-[4-(dimethylaminomethyl)benzoyl]piperazin-1-yl]-1H-pyrazolo[3,4-d]pyrimidine;

1-(3-ethoxybenzyl)-4-[4-[4-(diethylaminomethyl)benzoyl]piperazin-1-yl]-1H-pyrazolo[3,4-d]pyrimidine;

1-(3-ethoxybenzyl)-4-[4-[4-(1-pyrrolidinylmethyl)benzoyl]piperazin-1-yl]-1H-pyrazolo[3,4-d]pyrimidine;

1-(3-ethoxybenzyl)-4-[4-[4-[N-(cyclopropylcarbonyl)-N-[2-(dimethylamino)ethyl]-amino]benzoyl]piperazin-1-yl]-1H-pyrazolo[3,4-d]pyrimidine;

1-(3-ethoxybenzyl)-4-[4-[4-[N-[(2-methoxyethoxy)carbonyl]-N-[2-(dimethylamino)-ethyl]amino]benzoyl] piperazin-1-yl]-1H-pyrazolo[3,4-d]pyrimidine;

1-(3-ethoxybenzyl)-4-[4-[4-[N-isobutyl-N-[2-(dimethylamino)ethyl]amino]benzoyl]-piperazin-1-yl]-1H-pyrazolo[3,4-d]pyrimidine;

1-(3-ethoxybenzyl)-4-[4-[(1-propylpiperidin-4-yl)carbonyl]piperazin-1-yl]-1H-pyrazolo[3,4-d]pyrimidine;

1-(3-ethoxybenzyl)-4-[4-[3-(1-isopropylpiperidin-4-yl) propionyl]piperazin-1-yl]-1H-pyrazolo[3,4-d]pyrimidine;

1-(3-ethoxybenzyl)-4-[4-[[trans-4-(dimethylaminomethyl)cyclohexyl]carbonyl]-piperazin-1-yl]-1H-pyrazolo[3,4-d]pyrimidine;

1-(3-ethoxybenzyl)-4-[4-[[trans-4-(1-pyrrolidinyl)cyclohexyl]carbonyl]piperazin-1-yl]-1H-pyrazolo[3,4-d]pyrimidine;

1-(3-ethoxybenzyl)-4-[4-[(E)-3-(1-isopropylpiperidin-4-yl)acryloyl]piperazin-1-yl]-1H-pyrazolo[3,4-d]pyrimidine;

1-(3-ethoxybenzyl)-4-[4-[3-(dimethylamino)-2,2-dimethylpropyloxy]benzoyl]-piperazin-1-yl]-1H-pyrazolo[3,4-d]pyrimidine;

1-[(6-propylpyridin-2-yl)methyl]-4-[4-[3-(dimethylamino)-2,2-dimethylpropyloxy]-benzoyl]piperazin-1-yl]-1H-pyrazolo[3,4-d]pyrimidine;

1-(3-ethoxybenzyl)-4-[4-[4-[N-acetyl-N-[2-(1-pyrrolidinyl)ethyl]amino]benzoyl]-piperazin-1-yl]-1H-pyrazolo[3,4-d]pyrimidine;

1-(3-ethoxybenzyl)-4-[4-[4-[N-acetyl-N-[2-(dimethylamino)ethyl]amino]benzoyl]-piperazin-1-yl]-1H-pyrazolo[3,4-d]pyrimidine;

1-(3-ethoxybenzyl)-4-[4-[4-(ethylaminomethyl)benzoyl]piperazin-1-yl]-1H-pyrazolo[3,4-d]pyrimidine;

1-(3-ethoxybenzyl)-4-[4-[(trans-4-piperidinocyclohexyl)carbonyl]piperazin-1-yl]-1H-pyrazolo[3,4-d]pyrimidine;

1-(3-ethoxybenzyl)-4-[4-[[trans-4-((3S)-3-hydroxy-1-pyrrolidinyl)cyclohexyl]carbonyl]-piperazin-1-yl]-1H-pyrazolo[3,4-d]pyrimidine;

1-(3-ethoxybenzyl)-4-[4-[[trans-4-[N-acetyl-N-[2-(dimethylamino)ethyl]amino]-cyclohexyl]carbonyl]piperazin-1-yl]-1H-pyrazolo[3,4-d]pyrimidine;

1-(3-ethoxybenzyl)-4-[4-[[trans-4-[N-(2-furoyl)-N-[2-(dimethylamino)ethyl]amino]-cyclohexyl]carbonyl]piperazin-1-yl]-1H-pyrazolo[3,4-d]pyrimidine;

1-(3-ethoxybenzyl)-4-[4-[[trans-4-[N-(crotonoyl)-N-[2-(dimethylamino)ethyl]amino]-cyclohexyl]carbonyl]piperazin-1-yl]-1H-pyrazolo[3,4-d]pyrimidine;

1-(3-ethoxybenzyl)-4-[4-[[trans-4-[N-(methylthiocarbamoyl)-N-[2-(dimethylamino)-ethyl]amino]cyclohexyl]carbonyl]piperazin-1-yl]-1H-pyrazolo[3,4-d]pyrimidine;

1-[(2-propyl-1,3-thiazol-4-yl)methyl]-4-[4-[4-[N-crotonoyl-N-[2-(dimethylamino)ethyl]-amino]-benzoyl]piperazin-1-yl]-1H-pyrazolo[3,4-d]pyrimidine;

1-[(6-ethoxypyridin-2-yl)methyl]-4-[4-[[trans-4-(1-pyrrolidinyl)cyclohexyl]carbonyl]-piperazin-1-yl]-1H-pyrazolo[3,4-d]pyrimidine;

1-[(6-propylpyridin-2-yl)methyl]-4-[4-[[trans-4-(1-pyrrolidinyl)cyclohexyl]carbonyl]-piperazin-1-yl]-1H-pyrazolo[3,4-d]pyrimidine;

1-[(6-propylpyridin-2-yl)methyl]-4-[4-[[trans-4-(diethylaminomethyl)cyclohexyl]-carbonyl]piperazin-1-yl]-1H-pyrazolo[3,4-d]pyrimidine;

1-[(6-propylpyridin-2-yl)methyl]-4-[4-[[trans-4-[N-isopropyl-N-(2-methoxyethyl)amino-methyl]cyclohexyl]carbonyl]piperazin-1-yl]-1H-pyrazolo[3,4-d]pyrimidine;

1-[(2-propyl-1,3-thiazol-4-yl)methyl]-4-[4-[4-[2,2-dimethyl-3-(dimethylamino)propyloxy]benzoyl]piperazin-1-yl]-1H-pyrazolo[3,4-d]pyrimidine;

1-[(6-propylpyridin-2-yl)methyl]-4-[4-[[trans-4-(dipropylamino)cyclohexyl]carbonyl]-piperazin-1-yl]-1H-pyrazolo[3,4-d]pyrimidine;

1-[(2-propyl-1,3-thiazol-4-yl)methyl]-4-[4-[[trans-4-(dipropylamino)cyclohexyl]-carbonyl]piperazin-1-yl]-1H-pyrazolo[3,4-d]pyrimidine;

1-[(6-propylpyridin-2-yl)methyl]-4-[4-[[trans-4-(1-piperidyl)cyclohexyl]carbonyl]-piperazin-1-yl]-1H-pyrazolo[3,4-d]pyrimidine;

1-[(6-ethoxypyridin-2-yl)methyl]-4-[4-[[trans-4-(1-piperidyl)cyclohexyl]carbonyl]-piperazin-1-yl]-1H-pyrazolo[3,4-d]pyrimidine;

1-[(2-propyl-1,3-thiazol-4-yl)methyl]-4-[4-[[trans-4-(1-piperidyl)cyclohexyl]-carbonyl]piperazin-1-yl]-1H-pyrazolo[3,4-d]pyrimidine;

1-(3-ethoxybenzyl)-4-[4-[[trans-4-(ethylamino)cyclohexyl]carbonyl]piperazin-1-yl]-1H-pyrazolo [3,4-d]pyrimidine;

1-(3-ethoxybenzyl)-4-[4-[3-[2-(diisopropylamino)ethoxy]-4-[3-(dimethylamino)-2,2-(dimethyl)propyloxy]benzoyl]piperazin-1-yl]-1H-pyrazolo[3,4-d]pyrimidine;

1-(3-ethoxybenzyl)-4-[4-[4-[N-(cyclopropanecarbonyl)-N-[2-(dimethylamino)ethyl]-amino]piperidinocarbonyl]piperazin-1-yl]-1H-pyrazolo[3,4-d]pyrimidine;

1-(3-ethoxybenzyl)-4-[4-[4-(3,3-dimethylpiperadino)piperidinocarbonyl]piperazin-1-yl]-1H-pyrazolo[3,4-d]pyrimidine;

1-(3-ethoxybenzyl)-4-[4-[4-[N-ethyl-N-[2-(dimethylamino)ethyl]amino]piperidino-carbonyl]piperazin-1-yl]-1H-pyrazolo[3,4-d]pyrimidine;

1-[(6-propylpyridin-2-yl)methyl]-4-[4-[[trans-4-[[N-(t-butyl)-N-ethylamino]methyl]cyclohexyl]-carbonyl]piperazin-1-yl]-1H-pyrazolo[3,4-d]pyrimidine;

1-[(6-propylpyridin-2-yl)methyl]-4-[4-[[trans-4-[[N-(t-butyl)-N-[2-(methoxy)ethyl]amino]-methyl]cyclohexyl]carbonyl]piperazin-1-yl]-1H-pyrazolo[3,4-d]pyrimidine;

1-[(6-ethoxypyridin-2-yl)methyl]-4-[4-[[trans-4-[[N-(t-butyl)-N-[2-(methoxy)ethyl]amino]-methyl]cyclohexyl]carbonyl]piperazin-1-yl]-1H-pyrazolo[3,4-d]pyrimidine;

1-(3-ethoxybenzyl)-4-[4-[[trans-4-[[N-(t-butyl)-N-[2-(methoxy)ethyl]amino]methyl]-cyclohexyl]carbonyl]piperazin-1-yl]-1H-pyrazolo[3,4-d]pyrimidine;

1-[(2-propyl-1,3-thiazol-4-yl)methyl]-4-[4-[[trans-4-[[N-(t-butyl)-N-[2-(methoxy)ethyl]amino]-methyl]cyclohexyl]carbonyl]piperazin-1-yl]-1H-pyrazolo[3,4-d]pyrimidine;

1-(3-ethoxybenzyl)-4-[4-[[trans-4-[[N-(t-butyl)-N-[2-(hydroxy)ethyl]amino]methyl]-cyclohexyl]carbonyl]piperazin-1-yl]-1H-pyrazolo[3,4-d]pyrimidine;

1-[(6-propylpyridin-2-yl)methyl]-4-[4-[[trans-4-[N-[2-(dimethylamino)ethyl]-N-(methane-sulfonyl)amino]cyclohexyl]carbonyl]piperazin-1-yl]-1H-pyrazolo[3,4-d]pyrimidine;

1-[(6-ethoxypyridin-2-yl)methyl]-4-[4-[[trans-4-[N-[2-(dimethylamino)ethyl]-N-(methanesulfonyl)amino]cyclohexyl]carbonyl]piperazin-1-yl]-1H-pyrazolo[3,4-d]pyrimidine;

1-[(2-propyl-1,3-thiazol-4-yl)methyl]-4-[4-[[trans-4-[N-[2-(dimethylamino)ethyl]-N-(methanesulfonyl)amino]cyclohexyl]carbonyl]piperazin-1-yl]-1H-pyrazolo[3,4-d]pyrimidine;

1-[(6-propylpyridin-2-yl)methyl]-4-[4-[[trans-4-[[N-[2-(dimethylamino)ethyl]-N-pivaloylamino]methyl]cyclohexyl]carbonyl]piperazin-1-yl]-1H-pyrazolo[3,4-d]pyrimidine;

1-[(6-propylpyridin-2-yl)methyl]-4-[4-[[trans-4-[[N-(cyclopropanecarbonyl)-N-[2-(dimethylamino)ethyl]amino]methyl]cyclohexyl]carbonyl]piperazin-1-yl]-1H-pyrazolo[3,4-d]pyrimidine;

1-(3-ethoxybenzyl)-4-[4-[[trans-4-[N-[2-(dimethylamino)ethyl]-N-propionylamino]-cyclohexyl]carbonyl]piperazin-1-yl]-1H-pyrazolo[3,4-d]pyrimidine;

1-(3-ethoxy-2-fluorobenzyl)-4-[4-[(trans-4-piperidin-1-ylcyclohexyl)carbonyl]piperazin-1-yl]-1H-pyrazolo[3,4-d]pyrimidine;

1-(3-ethoxy-2-fluorobenzyl)-4-[4-[[trans-4-[[N-(t-butyl)-N-[2-(methoxy)ethyl]amino]-methyl]cyclohexyl]carbonyl]piperazin-1-yl]-1H-pyrazolo[3,4-d]pyrimidine;

1-(3-ethoxy-2-fluorobenzyl)-4-[4-[4-(ethylaminomethyl)benzoyl]piperazin-1-yl]-1H-pyrazolo[3,4-d]pyrimidine;

1-(3-ethoxy-2-fluorobenzyl)-4-[4-[4-[N-acetyl-N-[2-(dimethylamino)ethyl]amino]benzoyl]-piperazin-1-yl]-1H-pyrazolo[3,4-d]pyrimidine;

or a pharmaceutically acceptable salt thereof.

12. The compound according to claim 9 in which R² is 3-ethoxyphenyl group, 6-propylpyridin-2-yl group, 6-ethoxypyridin-2-yl group, 2-propyl-1,3-thiazol-4-yl group or 3-ethoxy-2-fluorophenyl group.

13. A pharmaceutical composition which comprises as an active ingredient a compound claimed in claim 8 or a pharmaceutically acceptable salt thereof and a pharamaceutically acceptable carrier therefore.

14. A pharmaceutical composition which comprises as an active ingredient a compound claimed in any one of claims 1, 2, 3, 4, 5, 6, 7, 9, 10, 11, or 13 or a pharmaceutically acceptable salt thereof and a pharmaceutically acceptable carrier therefor.

* * * * *